(12) United States Patent
Crane et al.

(10) Patent No.: US 12,269,883 B2
(45) Date of Patent: *Apr. 8, 2025

(54) BINDING AGENTS AND METHODS OF USING THE SAME

(71) Applicant: MOZART THERAPEUTICS, INC., Seattle, WA (US)

(72) Inventors: Courtney Crane, Seattle, WA (US); Kristine Swiderek, Seattle, WA (US); Susan Julien, Seattle, WA (US)

(73) Assignee: Mozart Therapeutics, Inc, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/907,087

(22) Filed: Oct. 4, 2024

(65) Prior Publication Data

US 2025/0026830 A1   Jan. 23, 2025

Related U.S. Application Data

(63) Continuation of application No. 18/264,056, filed as application No. PCT/US2022/014881 on Feb. 2, 2022.

(60) Provisional application No. 63/298,028, filed on Jan. 10, 2022, provisional application No. 63/209,949, filed on Jun. 11, 2021, provisional application No. 63/161,325, filed on Mar. 15, 2021, provisional application No. 63/148,016, filed on Feb. 10, 2021, provisional application No. 63/145,394, filed on Feb. 3, 2021.

(51) Int. Cl.
C07K 16/28 (2006.01)
A61K 39/00 (2006.01)
A61P 35/00 (2006.01)
A61P 37/06 (2006.01)

(52) U.S. Cl.
CPC .......... *C07K 16/2815* (2013.01); *A61P 35/00* (2018.01); *A61P 37/06* (2018.01); *C07K 16/2803* (2013.01); *A61K 2039/505* (2013.01); *C07K 2317/31* (2013.01); *C07K 2317/74* (2013.01); *C07K 2317/76* (2013.01); *C07K 2317/92* (2013.01)

(58) Field of Classification Search
CPC ............ C07K 16/2815; C07K 16/2803; C07K 2317/31; C07K 2317/74; C07K 2317/76; C07K 2317/92; A61P 35/00; A61P 37/06; A61K 2039/505
See application file for complete search history.

(56) References Cited

U.S. PATENT DOCUMENTS

| | | |
|---|---|---|
| 5,770,387 A | 6/1998 | Litwin et al. |
| 5,885,573 A | 3/1999 | Bluestone et al. |
| 5,929,212 A | 7/1999 | Jolliffe et al. |
| 8,119,775 B2 | 2/2012 | Moretta et al. |
| 8,551,478 B2 | 10/2013 | Mach et al. |
| 9,067,997 B2 | 6/2015 | Romagne et al. |
| 9,828,427 B2 | 11/2017 | Anfossi et al. |
| 9,879,082 B2 | 1/2018 | Wagtmann et al. |
| 9,902,936 B2 | 2/2018 | Moretta et al. |
| 10,253,095 B2 | 4/2019 | Romagne et al. |
| 10,377,826 B2 | 8/2019 | Ho et al. |
| 10,414,820 B2 | 9/2019 | Ho et al. |
| 10,596,195 B2 | 3/2020 | Cantor et al. |
| 10,668,180 B2 | 6/2020 | Thompson et al. |
| 11,117,964 B2 | 9/2021 | Hsu et al. |
| 11,254,744 B2 | 2/2022 | Chan et al. |
| 11,266,745 B2 | 3/2022 | Gudas et al. |
| 2001/0018041 A1 | 8/2001 | Hanna et al. |
| 2002/0168362 A1 | 11/2002 | Lazarovits et al. |
| 2003/0031668 A1 | 2/2003 | Kalled et al. |
| 2003/0232009 A1 | 12/2003 | Babcook et al. |
| 2005/0158305 A1 | 7/2005 | Ellis et al. |
| 2005/0266001 A1 | 12/2005 | Hadley |
| 2008/0254027 A1 | 10/2008 | Bernett et al. |
| 2009/0269787 A1 | 10/2009 | Tsukamoto |
| 2009/0304710 A1 | 12/2009 | Park et al. |
| 2010/0092482 A1 | 4/2010 | Grant et al. |
| 2010/0196359 A1 | 8/2010 | Kato et al. |
| 2010/0303828 A1 | 12/2010 | Levy et al. |
| 2011/0171215 A1 | 7/2011 | Davis et al. |
| 2011/0243929 A1 | 10/2011 | Coyle et al. |
| 2011/0250203 A1 | 10/2011 | Klitgaard et al. |
| 2011/0250213 A1 | 10/2011 | Tso et al. |
| 2013/0216540 A1 | 8/2013 | Justement et al. |

(Continued)

FOREIGN PATENT DOCUMENTS

| | | |
|---|---|---|
| EP | 3072522 A1 | 9/2016 |
| WO | WO 2005003168 A2 | 1/2005 |

(Continued)

OTHER PUBLICATIONS

Crane et al. U.S. Appl. No. 18/264,056. Published 2024 (US 2024/0101673 A1). Binding Agents and Methods of Using the Same. (Year: 2024).*

Brate et al., "Therapeutic intervention in relapsing autoimmune demyelinating disease through induction of myelin-specific regulatory CD8 T cell responses," *Journal of Translational Autoimmunity* 2:100010, Dec. 2019. (8 pages).

(Continued)

*Primary Examiner* — Brad Duffy
*Assistant Examiner* — Elizabeth A Shupe
(74) *Attorney, Agent, or Firm* — Fox Rothschild LLP

(57) ABSTRACT

The present invention provides binding agents that specifically bind to CD8+KIR+ T regulatory cells and their use in the treatment of diseases or disorders, such as an inflammatory disease, an autoimmune disease, cancer, or an infectious disease.

8 Claims, 33 Drawing Sheets

Specification includes a Sequence Listing.

(56) References Cited

U.S. PATENT DOCUMENTS

| | | |
|---|---|---|
| 2013/0236476 A1 | 9/2013 | Lee et al. |
| 2013/0251711 A1 | 9/2013 | Andre et al. |
| 2013/0251733 A1 | 9/2013 | Youd et al. |
| 2013/0273062 A1 | 10/2013 | Bensussan et al. |
| 2014/0308276 A1 | 10/2014 | Liu et al. |
| 2014/0348743 A1 | 11/2014 | Korman et al. |
| 2014/0377284 A1 | 12/2014 | Simons et al. |
| 2015/0086574 A1 | 3/2015 | Karsunky et al. |
| 2015/0232556 A1 | 8/2015 | Gauthier et al. |
| 2015/0290316 A1 | 10/2015 | Graziano et al. |
| 2015/0344580 A1 | 12/2015 | Abbasova et al. |
| 2016/0053014 A1 | 2/2016 | Huang et al. |
| 2016/0145350 A1 | 5/2016 | Lonberg et al. |
| 2016/0304610 A1 | 10/2016 | Sazinsky et al. |
| 2016/0355587 A1 | 12/2016 | West et al. |
| 2017/0198050 A1 | 7/2017 | Eckelman et al. |
| 2017/0306016 A1 | 10/2017 | Wang et al. |
| 2017/0313774 A1 | 11/2017 | Wang et al. |
| 2018/0072804 A1 | 3/2018 | Lifke et al. |
| 2018/0104308 A1 | 4/2018 | Mamonkin et al. |
| 2018/0237529 A1 | 8/2018 | Back et al. |
| 2018/0256710 A1 | 9/2018 | Tessier et al. |
| 2018/0355043 A1 | 12/2018 | Martinez et al. |
| 2018/0362655 A1 | 12/2018 | Wang et al. |
| 2019/0008955 A1 | 1/2019 | Swanson et al. |
| 2019/0062448 A1 | 2/2019 | Soros et al. |
| 2019/0071500 A1 | 3/2019 | Kley et al. |
| 2019/0071503 A1 | 3/2019 | Goldenberg et al. |
| 2019/0092868 A1 | 3/2019 | Lincecum et al. |
| 2019/0119391 A1 | 4/2019 | Youd et al. |
| 2019/0125832 A1 | 5/2019 | Kalergis Parra et al. |
| 2019/0169283 A1 | 6/2019 | Groth et al. |
| 2019/0256598 A1 | 8/2019 | Wang et al. |
| 2019/0276538 A1 | 9/2019 | Thudium et al. |
| 2019/0309069 A1 | 10/2019 | Yuan et al. |
| 2019/0322749 A1 | 10/2019 | Edwards et al. |
| 2019/0382488 A1 | 12/2019 | Ho et al. |
| 2020/0023045 A1 | 1/2020 | Shimamura et al. |
| 2020/0071403 A1 | 3/2020 | Fang et al. |
| 2020/0071404 A1 | 3/2020 | Sato et al. |
| 2020/0131272 A1 | 4/2020 | Beebe et al. |
| 2020/0148781 A1 | 5/2020 | Zeidler et al. |
| 2020/0199228 A1 | 6/2020 | Gauthier et al. |
| 2020/0216548 A1 | 7/2020 | Bender et al. |
| 2020/0247898 A1 | 8/2020 | Glennie et al. |
| 2020/0277372 A1 | 9/2020 | Codarri Deak et al. |
| 2020/0347144 A1 | 11/2020 | Pan et al. |
| 2020/0399391 A1 | 12/2020 | Chiron Blondel et al. |
| 2020/0408765 A1 | 12/2020 | Park et al. |
| 2021/0009687 A1 | 1/2021 | Triebel et al. |
| 2021/0009706 A1 | 1/2021 | Huang et al. |

FOREIGN PATENT DOCUMENTS

| | | |
|---|---|---|
| WO | WO 2005003172 A2 | 1/2005 |
| WO | WO 2006003179 A2 | 1/2006 |
| WO | WO 2007042573 A2 | 4/2007 |
| WO | WO 2008084106 A1 | 7/2008 |
| WO | WO 2010081890 A1 | 7/2010 |
| WO | WO 2012054509 A2 | 4/2012 |
| WO | WO 2012160448 A2 | 11/2012 |
| WO | WO 2014055648 A1 | 4/2014 |
| WO | WO 2014066532 A1 | 5/2014 |
| WO | WO 2014164553 A1 | 10/2014 |
| WO | WO 2016120789 A1 | 8/2016 |
| WO | WO 2016196912 A1 | 12/2016 |
| WO | WO 2017027325 A1 | 2/2017 |
| WO | WO 2017134306 A1 | 8/2017 |
| WO | WO 2018147960 A1 | 8/2018 |
| WO | WO 2018148223 A1 | 8/2018 |
| WO | WO 2018223004 A1 | 12/2018 |
| WO | WO 2019032661 A1 | 2/2019 |
| WO | WO 2020113164 A1 | 6/2020 |
| WO | WO 2021001289 A1 | 1/2021 |
| WO | WO 2021026233 A1 | 2/2021 |
| WO | WO 2023076876 A1 | 5/2023 |

OTHER PUBLICATIONS

Crucian et al., "Alterations in Levels of $CD28^-/CD8^+$ Suppressor Cell Precursor and $CD45RO^+/CD4^+$ Memory T Lymphocytes in the Peripheral Blood of Multiple Sclerosis Patients," *Clinical and Diagnostic Laboratory Immunology* 2(2):249-252, Mar. 1995. (4 pages).

Cunnusamy et al., "Disease Exacerbation of Multiple Sclerosis is Characterized by Loss of Terminally Differentiated Autoregulatory CD8+ T cells," *Clinical Immunology* 152(0):115-126, Mar. 2014 (NIH Public Access Author Manuscript, available in PMC May 1, 2015). (24 pages).

Gimeno et al., "KIR+ CD8+ T Lymphocytes in Cancer Immunosurveillance and Patient Survival: Gene Expression Profiling," *Cancers* 12:2991, Oct. 2020. (20 pages).

Karussis et al., "T Cell Vaccination Benefits Relapsing Progressive Multiple Sclerosis Patients: A Randomized, Double-Blind Clinical Trial," *PLoS One* 7(12):e50478, Dec. 2012. (10 pages).

Li et al., "Chapter 4: Characterization of KIR+CD8+ Regulatory T Cells in Humans by scRNA- and TCR-seq," T-Cell Repertoire Characterization, Part of the Methods in Molecular Biology book series, vol. 2574, pp. 41-121, Jan. 2022 [Published online Sep. 2022]. (81 pages).

Li et al., "Cytotoxic KLRG1 expressing lymphocytes invade portal tracts in primary biliary cholangitis," *Journal of Autoimmunity* 103:102293, Jun. 2019. (10 pages).

Li et al., "Human $KIR^+CD8^+$ T cells target pathogenic T cells in Celiac disease and are active in autoimmune diseases and COVID-19," bioRxiv pre-print, Dec. 2021. (35 pages).

Ménager-Marcq et al., "$CD8^+CD28^-$ Regulatory T Lymphocytes Prevent Experimental Inflammatory Bowel Disease in Mice," *Gastroenterology* 131(6):1775-1785, Dec. 2006. (11 pages).

Mishra et al., "$CD8^+$ Regulatory T Cell—A Mystery to Be Revealed," *Frontiers in Immunology* 12:708874, Aug. 2021. (7 pages).

Ortega et al., "The Disease-Ameliorating Function of Autoregulatory CD8 T Cells Is Mediated by Targeting of Encephalitogenic CD4 T Cells in Experimental Autoimmune Encephalomyelitis," *The Journal of Immunology* 191:117-126, Jul. 2013. (10 pages).

Pende et al., "Killer Ig-Like Receptors (KIRs): Their Role in NK Cell Modulation and Developments Leading to Their Clinical Exploitation," *Frontiers in Immunology* 10:1179, May 2019. (18 pages).

Ráki et al., "Tetramer visualization of gut-homing gluten-specific T cells in the peripheral blood of celiac disease patients," *PNAS* 104(8):2831-2836, Feb. 2007. (6 pages).

Saligrama et al., "Opposing T cell responses in experimental autoimmune encephalomyelitis," *Nature* 572:481-487, Aug. 2019 [with Extended Data]. (24 pages).

Zabinska et al., "$CD3^+CD8^+CD28^-$ T Lymphocytes in Patients with Lupus Nephritis," *Journal of Immunology Research* 2016:1058165, Jun. 2016. (7 pages).

Zhong et al., "TGF-ß-Induced $CD8^+CD103^+$ Regulatory T Cells Show Potent Therapeutic Effect on Chronic Graft-versus-Host Disease Lupus by Suppressing B Cells," *Frontiers in Immunology* 9:35, Jan. 2018. (14 pages).

\* cited by examiner

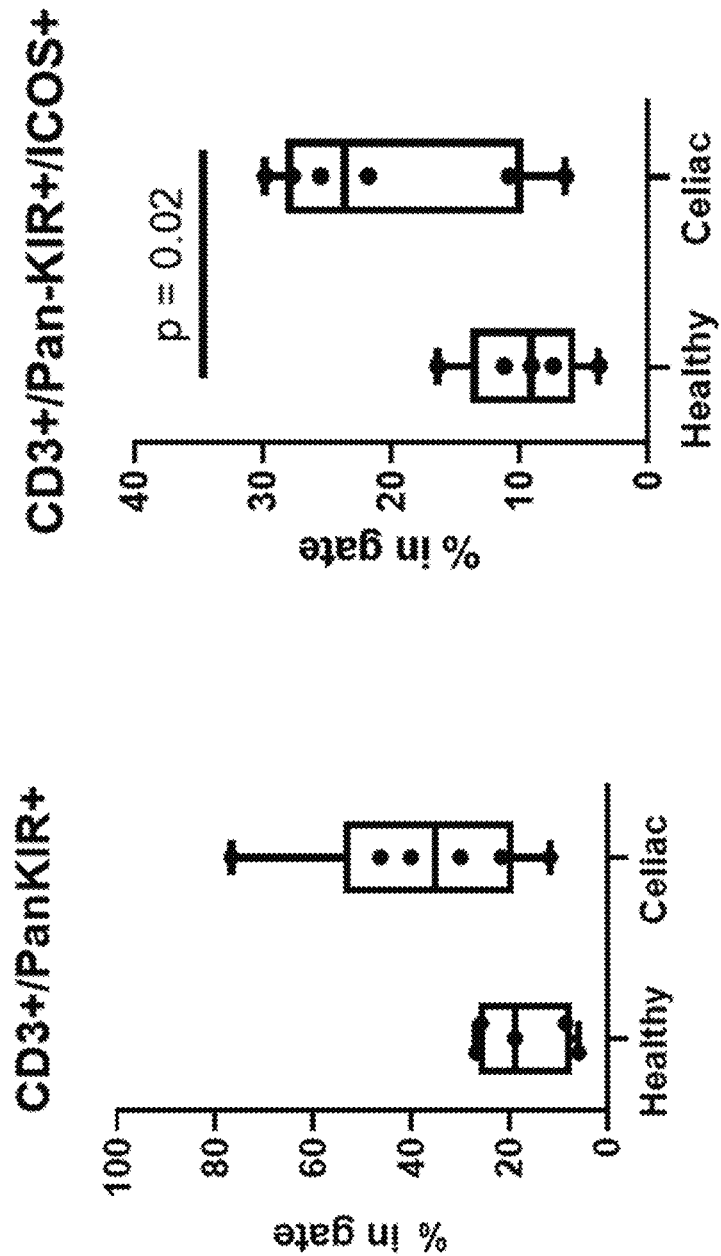

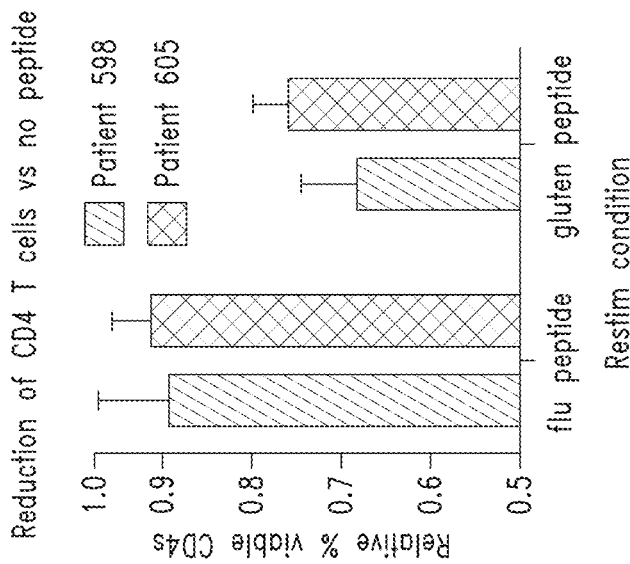
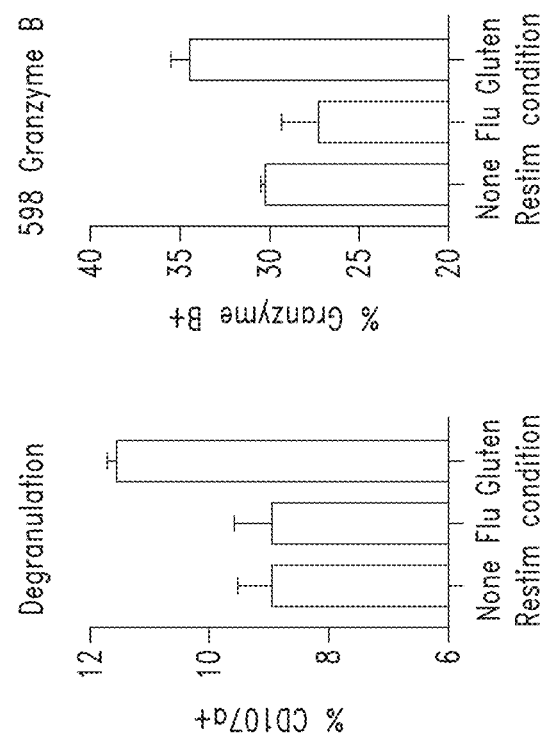
FIG. 9B
FIG. 9A

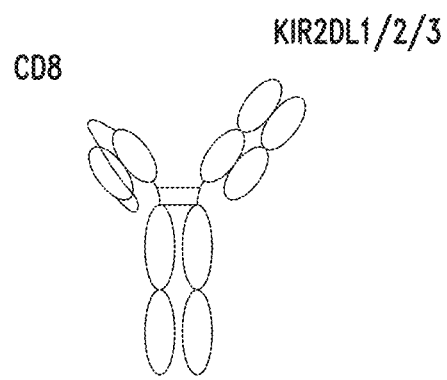
FIG. 29A
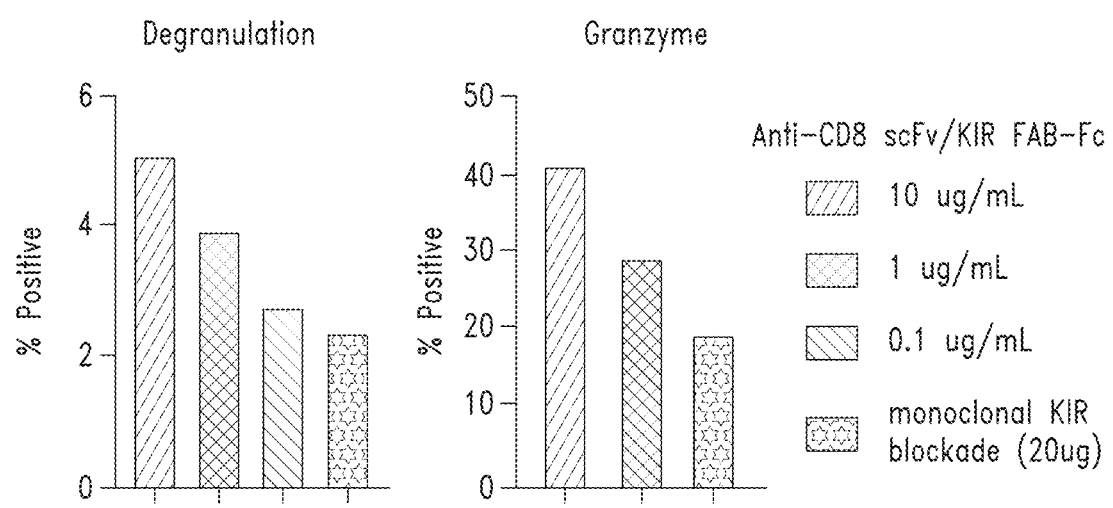
FIG. 29B
FIG. 29C

BINDING AGENTS AND METHODS OF USING THE SAME

REFERENCE TO AN ELECTRONIC SEQUENCE LISTING

This application contains a Sequence Listing which has been submitted electronically in xml format and is hereby incorporated by reference in its entirety. Said xml copy, created on Oct. 2, 2024, is named SeqList-368576-40311.xml and is 254,148 bytes in size.

BACKGROUND

The immune system includes the innate immune and the adaptive immune system. The adaptive immune system has a number of cell subtypes, including T cells subsets and B cell subsets. T cell subsets include a variety of types of T cells, including naïve T lymphocytes and effector T lymphocytes, such as cytotoxic T cells and helper T cells, and regulatory T cells. The activity of these T cells types is achieved by a balance between the activity of effector T cells and regulation by regulatory T cells. While effector T cells promote inflammation, regulatory T cells are generally thought to control it. Therefore, Tregs play an important role in autoimmune pathogenesis by maintaining self-tolerance, limiting autoimmunity and by controlling expansion and activation of autoreactive CD4+ T effector cells. Disruption of the balance between effector and regulatory T cells can lead to an inappropriate activation or suppression of an immune response, the loss of self-tolerance, autoimmune disorders, and cancer. The mechanisms and the regulation of regulatory T cells to maintain balance of the immune system is only beginning to be understood.

BRIEF SUMMARY

Provided herein are binding agents and their methods of use to modulate the activity of CD8+KIR+ regulatory T cells (Tregs). The binding agents are bispecific or multi-specific and specifically bind to antigens expressed on the surface of the CD8+KIR+ Tregs. In some embodiments, the CD8+KIR+ Tregs are MHC class I restricted. In some embodiments, the CD8+KIR+ Tregs are not MHC Qa-1 restricted. Also provided are methods of using the binding agents for the treatment of autoimmune disease, infectious disease, and cancer.

In some embodiments, a binding agent is provided that comprises a first binding domain that specifically binds to a first antigen, the first antigen selected from antigens expressed on CD8+KIR+ T regulatory cells (Tregs) other than a KIR protein; and a second binding domain that specifically binds to an inhibitory KIR protein expressed on the surface of the CD8+KIR+ Tregs, wherein the binding agent binds to CD8+KIR+ Tregs.

In some embodiments, the first antigen is selected from the group consisting of CD3, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some embodiments, the first antigen is selected from the group consisting of CD3, CD5, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some embodiments, the first antigen is selected from CD3, CD27, CD38, CD39, CD40L, CD45RA, CD45RB, CD45RO, CD73, CD122, ICOS, OX-40, 2B4, 41BB, and HLA-DR. In some embodiments, the first antigen is selected from CD3, CD5, CD27, CD38, CD39, CD40L, CD45RA, CD45RB, CD45RO, CD73, CD122, ICOS, OX-40, 2B4, 41BB, and HLA-DR. In some embodiments, the first antigen is selected from LAG-3/CD223, TIM-3, PD-1, S1000A8/9, and TLT2. In some embodiments, the first antigen is selected from CD103 (ITGAE), CD166, CD177, CXCR3, and S1000A8/9. In some embodiments, the first antigen is selected from CCR7, CXCR3, and CXCR5. In some embodiments, the first antigen is selected from PD-1, CXCR3, and ICOS. In some embodiments, the first antigen is selected from CD3, CD5, and CD8. In some embodiments, the first antigen is selected from CD3 and CD8.

In some embodiments, the binding agent is a bispecific antibody, a diabody, an antibody Fc fusion, an scFv1-ScFv2, an ScFv12-Fc-scFv22, an IgG-scFv, a DVD-Ig, a triomab/quadroma, a two-in-one IgG, a scFv2-Fc, a TandAb, an scFv-HSA-scFv, an scFv-VHH, a Fab-scFv-Fc, a Fab-VHH-Fc, a dAb-IgG, an IgG-VHH, a Tandem scFv-Fc, a (scFv1)$_2$-Fc-(VHH)$_2$, a BiTe, a DART, a crossmab, an anticalin, an affibody, an avimer, a DARPin, an adnectin, a scFv-Fc, a one-armed tandem scFv-Fc, or a DART-Fc. In some embodiments, either the first or second binding domain of the binding agent is selected from an antibody or antigen binding portion thereof, and the other binding domain is an antibody fragment. In some embodiments, the antigen binding portion is a Fab, Fab', F(ab')$_2$, Fv, scFv, or a single domain antibody (also referred to as a VHH, VNAR, sdAb, or NANOBODY®). In some embodiments, the first binding domain comprises a heavy chain variable region and a light chain variable region. In some embodiments, the second binding domain comprises a heavy chain variable region and a light chain variable region.

In some embodiments, the first binding domain specifically binds to CD3 or a subunit of CD3, optionally CD3epsilon. In some embodiments, the first binding domain comprises a heavy chain variable region (VH) and a light chain variable region (VL), the VH and VL having amino acid sequences selected from the pairs of amino acids sequences set forth in the group consisting of:
  a. SEQ ID NO: 1 and SEQ ID NO:2, respectively;
  b. SEQ ID NO:9 and SEQ ID NO: 10, respectively;
  c. SEQ ID NO: 17 and SEQ ID NO: 18, respectively;
  d. SEQ ID NO:25 and SEQ ID NO:26, respectively;
  e. SEQ ID NO:33 and SEQ ID NO:34, respectively;
  f. SEQ ID NO:41 and SEQ ID NO:34, respectively;
  g. SEQ ID NO:45 and SEQ ID NO:34, respectively;
  h. SEQ ID NO:49 and SEQ ID NO:50, respectively;
  i. SEQ ID NO:57 and SEQ ID NO:58, respectively;
  j. SEQ ID NO:65 and SEQ ID NO:66, respectively; and
  k. SEQ ID NO:65 and SEQ ID NO: 166, respectively.

In some embodiments, the first binding domain comprises a heavy chain variable region and a light chain variable region, the heavy and light chain variable regions comprising hCDR1, hCDR1, and hCDR3, and lCDR1, lCDR2, and lCDR3, respectively, the CDRs having amino acid sequences selected from the sets of amino acid sequences set forth in the group consisting:
  a. SEQ ID NO:3 to SEQ ID NO:8, respectively;
  b. SEQ ID NO: 11 to SEQ ID NO: 16, respectively;
  c. SEQ ID NO: 19 to SEQ ID NO:24, respectively;
  d. SEQ ID NO:27 to SEQ ID NO:32, respectively;
  e. SEQ ID NO:35 to SEQ ID NO:40, respectively;

f. SEQ ID NO:42 to SEQ ID NO:44 and SEQ ID NO:38 to SEQ ID NO:40, respectively;
g. SEQ ID NO:46 to SEQ ID NO:48 and SEQ ID NO:38 to SEQ ID NO:40, respectively;
h. SEQ ID NO:51 to SEQ ID NO:56, respectively;
i. SEQ ID NO:59 to SEQ ID NO:64, respectively;
j. SEQ ID NO:67 to SEQ ID NO:72, respectively; and
k. SEQ ID NOs: 67-69 and 167-169, respectively.

In some embodiments, the first binding domain specifically binds to CD8 or a subunit of CD8, optionally CD8alpha. In some embodiments, the first binding domain comprises a heavy chain variable region (VH) and a light chain variable region (VL), the VH and VL regions having the amino acid sequences selected from the pairs of amino acid sequences set forth in group consisting of:
a. SEQ ID NO:73 and SEQ ID NO:74, respectively; and
b. SEQ ID NO: 81 and SEQ ID NO:82, respectively;
or the first binding domain comprises a VHH chain, the VHH chain having the amino acid sequence selected from the amino acid sequences set forth in the group consisting of the following:
c. SEQ ID NO:89;
d. SEQ ID NO:93; and
e. SEQ ID NO:97.

In some embodiments, the first binding domain comprises a heavy chain variable region and a light chain variable region, the heavy and light chain variable regions comprising hCDR1, hCDR1, and hCDR3, and lCDR1, lCDR2, and lCDR3, respectively, the amino acid sequences of the CDRs selected from the amino acid sequences set forth in the group consisting of the following:
a. SEQ ID NO:75 to SEQ ID NO:80, respectively; or
b. SEQ ID NO:83 to SEQ ID NO:88, respectively;
or the first binding domain includes a VHH chain having hCDR1, hCDR2 and hCDR3, the amino acid sequences of the VHH CDRs selected from the amino acid sequences set forth in the group consisting of the following:
c. SEQ ID NO:90 to SEQ ID NO:92, respectively;
d. SEQ ID NO:94 to SEQ ID NO:96, respectively; and
e. SEQ ID NO:98 to SEQ ID NO: 100, respectively.

In some embodiments, the first binding domain specifically binds to ICOS or a subunit of ICOS. In some embodiments, the first binding domain comprises a heavy chain variable region (VH) and a light chain variable region (VL), the VH and VL having amino acid sequences of SEQ ID NO:170 and SEQ ID NO: 171, respectively.

In some embodiments, the first binding domain comprises a heavy chain variable region and a light chain variable region, the heavy and light chain variable regions comprising hCDR1, hCDR1, and hCDR3 having amino acid sequences of SEQ ID NOs: 172-174, respectively, and lCDR1, lCDR2, and lCDR3 having amino acid sequences of SEQ ID NOs: 175-177, respectively.

In some embodiments, the first binding domain specifically binds to PD-1 or a subunit of PD-1. In some embodiments, the first binding domain comprises a heavy chain variable region (VH) and a light chain variable region (VL), the VH and VL having amino acid sequences of SEQ ID NO: 178 and SEQ ID NO: 179, respectively.

In some embodiments, the first binding domain comprises a heavy chain variable region and a light chain variable region, the heavy and light chain variable regions comprising hCDR1, hCDR1, and hCDR3 having amino acid sequences of SEQ ID NOs: 180-182, respectively, and lCDR1, lCDR2, and lCDR3 having amino acid sequences of SEQ ID NOs: 183-185, respectively.

In some embodiments, the first binding domain specifically binds to CXCR3 or a subunit of CXCR3. In some embodiments, the first binding domain comprises a heavy chain variable region (VH) and a light chain variable region (VL), the VH and VL having amino acid sequences of SEQ ID NO: 186 and SEQ ID NO: 187, respectively.

In some embodiments, the first binding domain comprises a heavy chain variable region and a light chain variable region, the heavy and light chain variable regions comprising hCDR1, hCDR1, and hCDR3 having amino acid sequences of SEQ ID NOs: 188-190, respectively, and lCDR1, lCDR2, and lCDR3 having amino acid sequences of SEQ ID NOs: 191-193, respectively.

In some embodiments, the first binding domain specifically binds to CD5 or a subunit of CD5. In some embodiments, the first binding domain comprises a heavy chain variable region (VH) and a light chain variable region (VL), the VH and VL having amino acid sequences of SEQ ID NO: 194 and SEQ ID NO: 195, respectively.

In some embodiments, the first binding domain comprises a heavy chain variable region and a light chain variable region, the heavy and light chain variable regions comprising hCDR1, hCDR1, and hCDR3 having amino acid sequences of SEQ ID NOs: 196-198, respectively, and lCDR1, lCDR2, and lCDR3 having amino acid sequences of SEQ ID NOs: 199-201, respectively.

In some embodiments, the second binding domain specifically binds to an inhibitory KIR protein selected from KIR3DL1, KIR3DL2, KIR2DL1, KIR2DL2, and KIR2DL3 or a combination thereof. In some embodiments, the second binding domain specifically binds to KIR2DL1/2/3 or KIR2DL1/2. In some embodiments, the second binding domain comprises a heavy chain variable region (VH) and a light chain variable region (VL), the VH and VL having amino acid sequences selected from the pairs of amino acid sequences set forth in the group consisting of:
a. SEQ ID NO: 101 and SEQ ID NO: 102, respectively;
b. SEQ ID NO: 109 and SEQ ID NO:110, respectively;
c. SEQ ID NO: 117 and SEQ ID NO: 118, respectively;
d. SEQ ID NO: 125 and SEQ ID NO: 126, respectively;
e. SEQ ID NO: 133 and SEQ ID NO: 134, respectively;
f. SEQ ID NO: 141 and SEQ ID NO: 142, respectively;
g. SEQ ID NO: 149 and SEQ ID NO: 150, respectively; and
h. SEQ ID NO: 157 and SEQ ID NO: 158, respectively.

In some embodiments, the second binding domain comprises a heavy chain variable region and a light chain variable region, the heavy and light chain variable regions comprising hCDR1, hCDR1, and hCDR3, and lCDR1, lCDR2, and lCDR3, respectively, the CDRs having amino acid sequences selected from the sets of amino acid sequences set forth in from the group consisting of:
a. SEQ ID NO: 103 to SEQ ID NO: 108, respectively;
b. SEQ ID NO: 111 to SEQ ID NO: 116, respectively;
c. SEQ ID NO:119 to SEQ ID NO: 124, respectively;
d. SEQ ID NO: 127 to SEQ ID NO: 132, respectively;
e. SEQ ID NO: 135 to SEQ ID NO:140, respectively;
f. SEQ ID NO: 143 to SEQ ID NO: 148, respectively;
g. SEQ ID NO: 151 to SEQ ID NO: 156, respectively; and
h. SEQ ID NO: 159 and SEQ ID NO: 164, respectively.

In some embodiments, the binding agent does not contain an Fc domain. In some embodiments, the binding agent includes an Fc domain. In some embodiments, the Fc domain is selected from an IgG1 and an IgG4 Fc domain. In some embodiments, the binding agent has substantially no effector function activity. In some embodiments, the Fc domain is an IgG1 Fc domain. In some embodiments, the Fc domain is an IgG1 Fc null.

In some embodiments, the binding agent is bivalent or tetravalent. In some embodiments, the binding agent is bispecific.

Also provided is a pharmaceutical composition comprising the binding agent of any of the embodiments described herein and a pharmaceutically acceptable carrier.

Also provided are nucleic acids encoding the binding agent of any of the embodiments described herein. Further provided is a vector comprising any of the embodiments of nucleic acids described herein. Further also provided are cell lines comprising any of the embodiments of nucleic acids or vectors described herein.

In some embodiments, provided is a method of treating an autoimmune disease, comprising administering any of the embodiments of binding agents or pharmaceutical compositions described herein to a subject in need thereof in an amount effective to decrease the number or activity of pathogenic immune cells in the subject and thereby ameliorate a symptom of the autoimmune disease.

In some embodiments, provided is a method of suppressing an immune response mediated by pathogenic immune cells, comprising contacting CD8+KIR+ T regulatory cells (Tregs) with any of the embodiments of binding agents or pharmaceutical compositions described herein in an amount effective to activate or stimulate the CD8+KIR+ Tregs (activated Tregs), whereby the number or activity of pathogenic immune cells is decreased.

In some embodiments, provided is a method of suppressing an immune response to an autoantigen, comprising administering to a subject in need thereof any of the embodiments of binding agents or pharmaceutical compositions described herein in an amount effective to activate or stimulate the CD8+KIR+ Tregs, whereby the number or activity of pathogenic immune cells that are responsive to the autoantigen is decreased.

In some embodiments, provided is a method of suppressing an immune response to an antigen, comprising administering to a subject in need thereof any of the embodiments of binding agents or pharmaceutical compositions described herein in an amount effective to activate or stimulate the CD8+KIR+ Tregs, whereby the number or activity of pathogenic immune cells that are responsive to the antigen is decreased.

In some embodiments of these methods of treating autoimmune disease or suppressing an immune response, the CD8+KIR+ Tregs are contacted with the binding agent in vivo. In some embodiments, the CD8+KIR+ Tregs are contacted with the binding agent ex vivo. In some embodiments, the activated CD8+KIR+ Tregs are administered in an effective amount to a subject in need thereof. In some embodiments, the pathogenic immune cells are autoreactive CD4 T cells, autoantibody producing B cells or self antigen presenting dendritic cells. In some embodiments, the pathogenic immune cells are self antigen presenting cells. In some embodiments, the titer of autoantibodies is decreased in the subject.

In some embodiments, the subject has an autoimmune disease. In some embodiments, the autoimmune disease is selected from the group consisting of celiac disease, Crohn's disease, juvenile idiopathic arthritis, inflammatory bowel disease (IBD), insulin-dependent diabetes mellitus (IDDM or type 1 diabetes), lupus nephritis, myasthenia gravis, myocarditis, multiple sclerosis (MS), pemphigus/pemphigoid, rheumatoid arthritis (RA), scleroderma/systemic sclerosis, Sjögren's syndrome (SjS), systemic lupus erythematosus (SLE), and ulcerative colitis.

In some embodiments of the methods of treating autoimmune disease or suppressing an immune response, the binding agent specifically binds to CD8 and an inhibitory KIR protein on CD8+KIR+ Tregs. In some embodiments, the binding agent specifically binds to CD3 and an inhibitory KIR protein on CD8+KIR+ Tregs. In some embodiments, the binding agent specifically binds to CD5 and an inhibitory KIR protein on CD8+KIR+ Tregs. In some embodiments, the binding agent specifically binds to PD-1 and an inhibitory KIR protein on CD8+KIR+ Tregs. In some embodiments, the binding agent specifically binds to ICOS and an inhibitory KIR protein on CD8+KIR+ Tregs. In some embodiments, the binding agent specifically binds to CXCR3 and an inhibitory KIR protein on CD8+KIR+ Tregs. In some embodiments, the CD8+KIR+ Tregs are MHC class I restricted. In some embodiments, the CD8+KIR+ Tregs are not MHC HLA E (Qa-1b) restricted.

In some embodiments of the methods of treating autoimmune disease or suppressing an immune response, the methods further include administering an immunosuppressive agent to the subject. In some embodiments, the administration of the binding agent to the subject results in an improved treatment outcome in the subject. In some embodiments, the improved treatment outcome is a reduced frequency or severity disease flares, reduced systemic inflammatory cytokines, or reduced self reporting of symptoms associated with the autoimmune disease.

In some embodiments of the methods of treating autoimmune disease or suppressing an immune response, the binding agent is administered intravenously. In some embodiments, the binding agent is administered subcutaneously. In some embodiments, the binding agent is administered in a dose of about 0.01 mg/kg to about 20 mg/kg. In some embodiments, the binding agent has substantially no effector function activity.

In some embodiments, provided is the use of any of the embodiments of the binding agents or the pharmaceutical compositions described herein for the treatment of autoimmune disease in a subject by activating or stimulating CD8+KIR+ Tregs. In some embodiments, provided is the use of any of the embodiments of the binding agents or the pharmaceutical compositions described herein for the reduction of an immune response by pathogenic immune cells by activating or stimulating CD8+KIR+ Tregs. In some embodiments, provided is the use of any of the embodiments of the binding agents or the pharmaceutical compositions described herein for the reduction of autoantibody titer in a subject by activating or stimulating CD8+KIR+ Tregs.

In some embodiments, provided is a method of treating cancer, comprising administering any of the embodiments of the binding agents or the pharmaceutical compositions described herein, wherein the binding agent has substantially no effector function activity, to a subject in need thereof in an amount effective to activate or stimulate the CD8+KIR+ T regulatory cells (Tregs) and thereby ameliorate a symptom of the cancer.

In some embodiments, provided is a method of stimulating an immune response against an antigen associated with a cancer (cancer antigen), comprising contacting CD8+KIR+ T regulatory cells (Tregs) with any of the embodiments of the binding agents or the pharmaceutical compositions described herein, wherein the binding agent has substantially no effector function activity, in an amount effective to activate or stimulate the CD8+KIR+ Tregs (activated Tregs), whereby the immune response to the cancer antigen is increased.

In some embodiments, provided is a method of treating cancer, comprising administering any of the embodiments of the binding agents or the pharmaceutical compositions described herein, wherein the binding agent has effector function activity comprising at least ADCC, to a subject in need thereof in an amount effective to deplete the CD8+ KIR+ T regulatory cells (Tregs) and thereby ameliorate a symptom of the cancer.

In some embodiments, provided is a method of stimulating an immune response against an antigen associated with a cancer (cancer antigen), comprising contacting CD8+ KIR+ T regulatory cells (Tregs) with any of the embodiments of the binding agents or the pharmaceutical compositions described herein, wherein the binding agent has effector function activity comprising at least ADCC, in an amount effective to deplete the CD8+KIR+ Tregs, whereby the immune response to the cancer antigen is increased.

In some embodiments of the methods of treating cancer or stimulating an immune response to an antigen associated with cancer, the CD8+KIR+ Tregs are contacted with the binding agent in vivo. In some embodiments, the CD8+ KIR+ Tregs are contacted with the binding agent ex vivo. In some embodiments, the activated CD8+KIR+ Tregs are administered in an effective amount to a subject in need thereof. In some embodiments, the increased immune response comprises a reduction in cancer cells or depletion of immune suppressive immune cells. In some embodiments, the number of cancer cells in the subject are decreased.

In some embodiments, the cancer is selected from the group consisting of carcinomas, lymphomas, blastomas, sarcomas, and leukemias. In some embodiments, the cancer is selected from the group consisting of solid tumors such as breast, cervical, ovary, lung, colorectal (CRC) (and other cancers of the bowel), skin, esophageal, adenocarcinoma, bladder, and prostate cancers; and lymphomas.

In some embodiments, the binding agent specifically binds to CD8 and an inhibitory KIR protein on the CD8+ KIR+ Tregs. In some embodiments, the binding agent specifically binds to CD3 and an inhibitory KIR protein on the CD8+KIR+ Tregs. In some embodiments, the binding agent specifically binds to CD5 and an inhibitory KIR protein on CD8+KIR+ Tregs. In some embodiments, the binding agent specifically binds to PD-1 and an inhibitory KIR protein on CD8+KIR+ Tregs. In some embodiments, the binding agent specifically binds to CXCR3 and an inhibitory KIR protein on CD8+KIR+ Tregs. In some embodiments, the binding agent specifically binds to ICOS and an inhibitory KIR protein on CD8+KIR+ Tregs. In some embodiments, the CD8+KIR+ Tregs are MHC class I restricted. In some embodiments, the CD8+KIR+ Tregs are not MHC HLA E (Qa-1b) restricted.

In some embodiments, the methods further include administering a chemotherapeutic agent to the subject. In some embodiments, the methods further include administering an immunotherapy to the subject. In some embodiments, the methods further include administering an immunotherapy, such as a checkpoint inhibitor, to the subject. In some embodiments, the administration of the binding agent to the subject results in an improved treatment outcome in the subject. In some embodiments, the improved treatment outcome is a partial response or complete response. In some embodiments, the improved treatment outcome is remission.

In some embodiments, the binding agent is administered intravenously. In some embodiments, the binding agent is administered subcutaneously. In some embodiments, the binding agent is administered in a dose of about 0.01 mg/kg to about 20 mg/kg.

In some embodiments, provided is the use of any of the embodiments of the binding agents or the pharmaceutical compositions described herein, wherein the binding agent has substantially no effector function activity, for the treatment of cancer in a subject by activating or stimulating the CD8+KIR+ Tregs.

In some embodiments, provided is the use of any of the embodiments of the binding agents or the pharmaceutical compositions described herein, wherein the binding agent has substantially no effector function activity, for the reduction of immune suppression by immune suppressive immune cells by activating or stimulating the CD8+KIR+ Tregs.

In some embodiments, provided is the use of any of the embodiments of the binding agents or the pharmaceutical compositions described herein, wherein the binding agent has substantially no effector function activity, for the reduction of tumor burden in a subject by activating or stimulating CD8+KIR+ Tregs.

In some embodiments, provided is the use of any of the embodiments of the binding agents or the pharmaceutical compositions described herein, wherein the binding agent has effector function activity comprising at least ADCC, for the treatment of cancer in a subject by depleting CD8+KIR+ Tregs.

In some embodiments, provided is the use of any of the embodiments of the binding agents or the pharmaceutical compositions described herein, wherein the binding agent has effector function activity comprising at least ADCC, for the depletion of CD8+KIR+ Tregs.

In some embodiments, provided is the use of any of the embodiments of the binding agents or the pharmaceutical compositions described herein, wherein the binding agent has effector function activity comprising at least ADCC, for the reduction of tumor burden in a subject by depleting CD8+KIR+ Tregs.

In some embodiments, provided are methods of treating an infection, comprising administering any of the embodiments of the binding agents or the pharmaceutical compositions described herein to a subject in need thereof in an amount effective to activate or stimulate CD8+KIR+ Tregs and thereby ameliorate a symptom of the infection.

In some embodiments, provided are methods of stimulating an immune response against infected cells caused by an infection, comprising contacting CD8+KIR+ T regulatory cells (Tregs) with any of the embodiments of the binding agents or the pharmaceutical compositions described herein in an amount effective to activate or stimulate CD8+KIR+ Tregs (activated Tregs), whereby the immune response against the infected cells is increased.

In some embodiments, the CD8+KIR+ Tregs are contacted with the binding agent in vivo. In some embodiments, the CD8+KIR+ Tregs are contacted with the binding agent ex vivo. In some embodiments, the activated CD8+KIR+ Tregs are administered in an effective amount to a subject in need thereof.

In some of the embodiments of treating an infection or stimulating an immune response to infected cells, the immune response comprises a reduction in infected cells or immune suppressive immune cells selected from CD4 T regulatory cells and tolerizing DCs. In some embodiments, the number of infected cells in the subject is decreased. In some embodiments, the infection is selected from a bacterial disease, a systemic fungal disease, a rickettsial disease, a parasitic disease and a viral disease. In some embodiments, the infection is selected from the group consisting of an HIV infection, hepatitis C virus, (HCV) infection, human papillomavirus (HPV) infection, Epstein Bar Virus (EBV) infection, a coronavirus infection such as a SARS-COV2 infection (Covid-19), a cytomegalovirus (CMV) infection, and a flu virus infection.

In some embodiments, the binding agent specifically binds to CD8 and an inhibitory KIR protein on CD8+KIR+ Tregs. In some embodiments, the binding agent specifically binds to CD3 and an inhibitory KIR protein on CD8+KIR+ Tregs. In some embodiments, the binding agent specifically binds to CD5 and an inhibitory KIR protein on CD8+KIR+ Tregs. In some embodiments, the binding agent specifically binds to PD-1 and an inhibitory KIR protein on CD8+KIR+ Tregs. In some embodiments, the binding agent specifically binds to CXCR3 and an inhibitory KIR protein on CD8+KIR+ Tregs. In some embodiments, the binding agent specifically binds to ICOS and an inhibitory KIR protein on CD8+KIR+ Tregs. In some embodiments, the CD8+KIR+ Tregs are MHC class I restricted. In some embodiments, the CD8+KIR+ Tregs are not MHC HLA E (Qa-1b) restricted.

In some embodiments, the methods further include administering an anti-microbial or an anti-viral agent to the subject. In some embodiments, the administration of the binding agent to the subject results in an improved treatment outcome in the subject. In some embodiments, the improved treatment outcome is a reduction in infection. In some embodiments, the improved treatment outcome is a reduction in infected cells. In some embodiments, the binding agent is administered intravenously. In some embodiments, the binding agent is administered subcutaneously. In some embodiments, the binding agent is administered in a dose of about 0.01 mg/kg to about 20 mg/kg. In some embodiments, the binding agent has substantially no effector function activity.

In some embodiments, provided is the use of any of the embodiments of the binding agents or the pharmaceutical compositions described herein for the treatment of an infection in a subject by activating or stimulating CD8+KIR+ Tregs.

In some embodiments, provided is the use of any of the embodiments of the binding agents or the pharmaceutical compositions described herein for the stimulation of an immune response by activating or stimulating CD8+KIR+ Tregs and thereby suppressing immune suppressive immune cells.

In some embodiments, provided is the use of any of the embodiments of the binding agents or the pharmaceutical compositions described herein for the reduction of infection in a subject by activating or stimulating CD8+KIR+ Tregs.

In some embodiments, provided is a method of reducing or preventing onset of graft versus host disease (GVHD) following a transplant, comprising administering any of the binding agents or pharmaceutical compositions described herein to a subject in need thereof in an amount effective to activate or stimulate CD8+KIR+ Tregs and thereby reduce or ameliorate at least one symptom of GVHD. In some embodiments, the binding agent has substantially no effector function activity.

In some embodiments, provided herein is a method of treating a subject who has received a transplant, comprising contacting CD8+KIR+ T regulatory cells (Tregs) with any of the binding agents or the pharmaceutical compositions described herein in an amount effective to activate or stimulate CD8+KIR+ Tregs (activated Tregs), whereby GVHD is reduced or suppressed. In some embodiments, the binding agent has substantially no effector function activity.

In some embodiments, provided is a method of treating a subject who has received a transplant, comprising administering any of the binding agents or the pharmaceutical compositions described herein to a subject in need thereof in an amount effective to deplete CD8+KIR+ Tregs and thereby ameliorate a symptom of GVHD. In some embodiments, the binding agent has effector function activity comprising at least ADCC.

In some embodiments, provided is a method of suppressing GVHD against a transplant, comprising contacting CD8+KIR+ T regulatory cells (Tregs) with any of the binding agents or the pharmaceutical compositions described herein in an amount effective to deplete CD8+KIR+ Tregs, whereby GVHD or a symptom thereof is decreased. In some embodiments, the binding agent has effector function activity comprising at least ADCC.

In some embodiments, the CD8+KIR+ Tregs are contacted with the binding agent in vivo. In some embodiments, the CD8+KIR+ Tregs are contacted with the binding agent ex vivo. In some embodiments, the activated CD8+KIR+ Tregs are administered in an effective amount to a subject in need thereof.

In some embodiments, decreased GVHD comprises a reduction in CD4+ T cells active in GVHD. In some embodiments, the transplant is selected from the group consisting of an organ transplant, a hematopoietic stem cell transplant, an umbilical cord blood stem cell transplant, an inducible pluripotent stem cell-derived progenitor or differentiated cell transplant and a bone marrow transplant. In some embodiments, the transplant is a hematopoietic stem cell transplant, an umbilical cord blood stem cell transplant, an inducible pluripotent stem cell-derived progenitor or differentiated cell transplant or a bone marrow transplant. In some embodiments, the transplant is allogeneic.

In some embodiments, the binding agent specifically binds to CD8 and an inhibitory KIR protein on CD8+KIR+ Tregs. In some embodiments, the binding agent specifically binds to CD3 and an inhibitory KIR protein on CD8+KIR+ Tregs. In some embodiments, the binding agent specifically binds to CD5 and an inhibitory KIR protein on CD8+KIR+ Tregs. In some embodiments, the binding agent specifically binds to PD-1 and an inhibitory KIR protein on CD8+KIR+ Tregs. In some embodiments, the binding agent specifically binds to CXCR3 and an inhibitory KIR protein on CD8+KIR+ Tregs. In some embodiments, the binding agent specifically binds to ICOS and an inhibitory KIR protein on CD8+KIR+ Tregs. In some embodiments, the CD8+KIR+ Tregs are MHC class I restricted. In some embodiments, the CD8+KIR+ Tregs are not MHC HLA E (Qa-1b) restricted.

In some embodiments, an immunosuppressive agent is also administered to the subject.

In some embodiments, the administration of the binding agent to the subject results in an improved treatment outcome in the subject. In some embodiments, the improved treatment outcome is a reduction in a symptom associated with GVHD, reduced systemic inflammatory cytokines, reduced pathology in tissues impacted by GVHD, reduced self reporting of symptoms associated with an immune response associated with adverse effects on host tissues, improved or extended transplant engraftment, alleviation of one or more symptom(s), and/or prevention, delay, or slowing of onset or progression of rejection of the transplant, or extended transplant engraftment with decreased use of broad spectrum immunosuppressive agents, such as corticosteroids.

In some embodiments, the binding agent is administered intravenously. In some embodiments, the binding agent is administered subcutaneously.

In some embodiments, provided in the use of any of the binding agents or the pharmaceutical compositions described herein for the treatment of GVHD associated with transplant in a subject. In some embodiments, the binding agent has substantially no effector function activity.

In some embodiments, provided is the use of any of the binding agents or the pharmaceutical compositions described herein for the treatment of GVHD associated with transplant in a subject by activating or stimulating CD8+KIR+ Tregs. In some embodiments, the binding agent has substantially no effector function activity.

In some embodiments, provided is the use of any of the binding agents or the pharmaceutical compositions described herein for the reduction of GVHD associated with a transplant by activating or stimulating CD8+KIR+ Tregs. In some embodiments, the binding agent has substantially no effector function activity.

In some embodiments, provided herein is the use of any of the binding agents or the pharmaceutical compositions described herein for the reduction of GVHD to a transplant. In some embodiments, the binding agent has substantially no effector function activity.

In some embodiments, provided is the use of any of the binding agents of or the pharmaceutical compositions described herein for the treatment of GVHD associated with a transplant in a subject by depleting CD8+KIR+ Tregs. In some embodiments, the binding agent has effector function activity comprising at least ADCC.

In some embodiments, provided is the use of any of the binding agents or the pharmaceutical compositions described herein for the depletion of CD8+KIR+ Tregs. In some embodiments, the binding agent has effector function activity comprising at least ADCC.

In some embodiments, provided is the use of any of the binding agents or the pharmaceutical compositions described herein for the depletion of CD8+KIR+ Tregs in a subject who has received a transplant to reduce GVHD. In some embodiments, the binding agent has effector function activity comprising at least ADCC.

These and other aspects of the present invention may be more fully understood by reference to the following detailed description, non-limiting examples of specific embodiments and the appended drawings.

BRIEF DESCRIPTION OF THE DRAWINGS

FIGS. 8A to 8B show that Celiac patients have more CD8+KIR+ T cells (FIG. 8A) and CD8+KIR+ICOS+ T cells (FIG. 8B) compared to healthy controls.

FIGS. 9A to 9B show that gluten peptide restimulation of CD8+KIR+ T cells from Celiac patients increases degranulation (FIG. 9A, left) and Granzyme B levels (FIG. 9A, right), as compared to unstimulated cells or those stimulated with control flu peptides. Gluten peptide restimulation also leads to a reduction in reactive CD4+ T cells, as compared to unstimulated cells or those restimulated with control flu peptides (FIG. 9B).

FIG. 29A shows a bi-specific antibody having a CD8 binding domain and a binding domain that targets KIR2DL1/2/3. FIG. 29B shows degranulation and FIG. 29C shows granzyme B levels following administration of anti-CD8 scFv/KIR FAB-Fc (at doses of 10 µg/mL, 1 g/mL, or 0.1 µg/mL) or a monoclonal KIR blockade (at 20 µg).

DETAILED DESCRIPTION

Definitions

Figure 1:
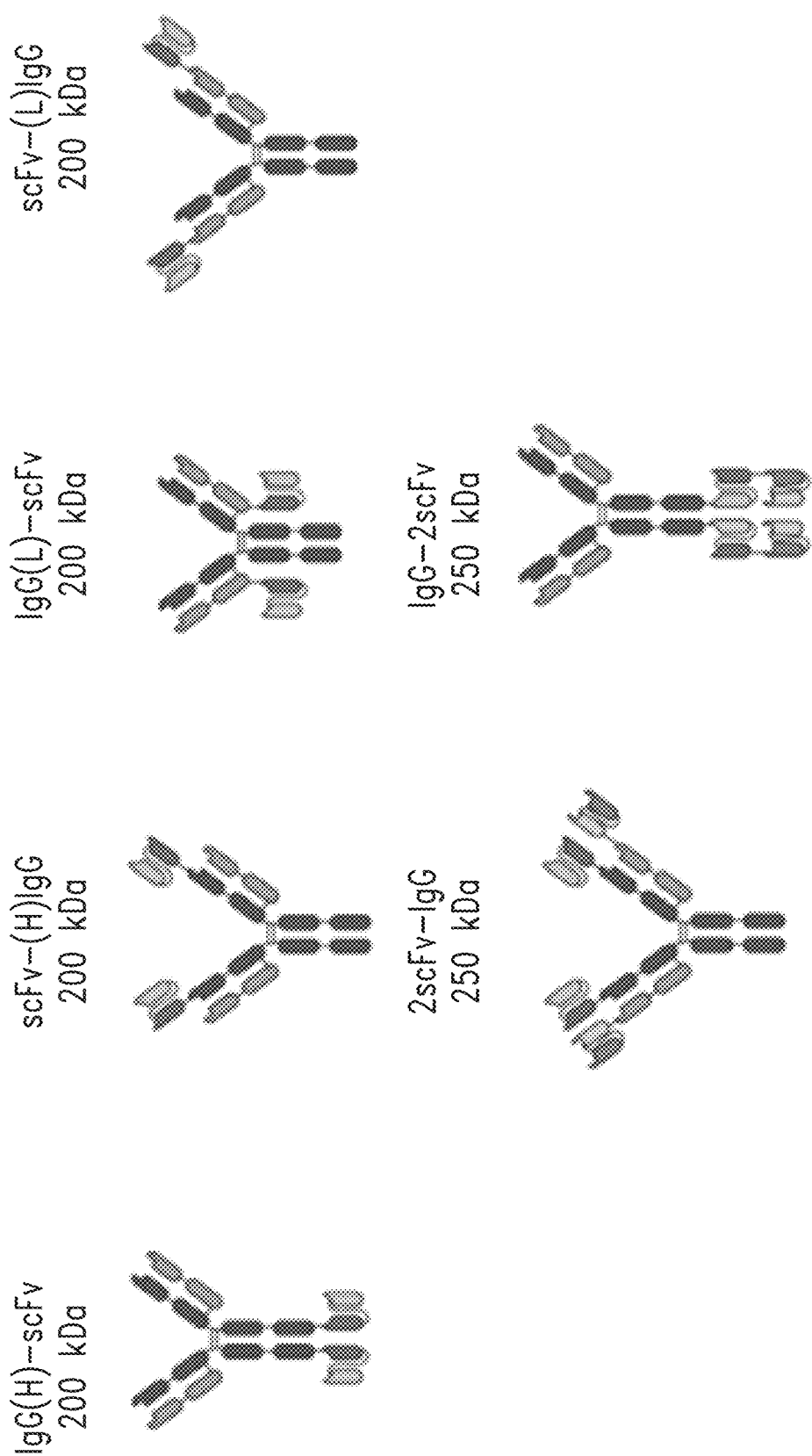
FIG. 1 shows various formats of IgG-scFv bispecific antibodies.

For convenience, certain terms in the specification, examples, and claims are defined here. Unless stated otherwise, or implicit from context, the following terms and phrases have the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein and unless otherwise indicated, the terms "a" and "an" are taken to mean "one", "at least one", or "one or more". Unless otherwise required by context, singular terms used herein shall include pluralities and plural terms shall include the singular.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The terms "decrease," "reduce," "reduced", "reduction", "decrease", and "inhibit" are all used herein generally to mean a decrease by a statistically significant amount relative to a reference.

The terms "increased", "increase", "enhance", or "activate" are all used herein to generally mean an increase by a statically significant amount relative to a reference.

The terms "isolated" or "partially purified" as used herein refer in the case of a nucleic acid, polypeptide or protein, to a nucleic acid, polypeptide or protein separated from at least one other component (e.g., nucleic acid or polypeptide or protein) that is present with the nucleic acid, polypeptide or protein as found in its natural source and/or that would be present with the nucleic acid, polypeptide or protein when expressed by a cell, or secreted in the case of secreted polypeptides and proteins. A chemically synthesized nucleic acid, polypeptide or protein, or one synthesized using in vitro transcription/translation, is considered "isolated." The terms "purified" or "substantially purified" refer to an isolated nucleic acid, polypeptide or protein that is at least 95% by weight the subject nucleic acid, polypeptide or protein, including, for example, at least 96%, at least 97%, at least 98%, at least 99%, or more.

As used herein, the terms "protein" and "polypeptide" are used interchangeably herein to designate a series of amino acid residues each connected to each other by peptide bonds between the alpha-amino and carboxyl groups of adjacent residues. The terms "protein" and "polypeptide" also refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing.

CD3epsilon is a protein that is expressed on T cells, including regulatory T cells. CD3epsilon polypeptides include, but are not limited to, those having the amino acid sequence set forth in NP000724.1; this sequence is incorporated by reference herein.

CD5 is a protein expressed on T cells and B cells. CD5 polypeptides include, but are not limited to, those having the amino acid sequence set forth in NP_055022.2 and NP_001333385.1; these sequences are incorporated by reference herein.

CD8alpha is a protein that is expressed on T cells, including regulatory T cells. CD8alpha polypeptides include, but are not limited to, those having the amino acid sequences set forth in NP_001759.3, NP001139345.1, NP_741969.1, NP_001369627.1, NP_757362.1, NP_001171571.1, NP_742100.1, NP_742099.1, and NP_004922; these sequences are incorporated by reference herein.

KIR3DL1 is a protein expressed on NK cells and on some T cells. It is also known as CD158E1, KIR, KIR2DL5B, KIR3DL1/S1, NKAT-3, NKAT3, NKB1, and NKB1B. KIR3DL1 polypeptides include, but are not limited to, those having the amino acid sequences set forth in NP_037421.2 and NP_001309097.1; these sequences are incorporated by reference herein.

KIR3DL2 is a protein expressed on NK cells and on some T cells. It is also known as 3DL2, CD158K, KIR-3DL2, NKAT-4, NKAT4, NKAT4B, and p140. KIR3DL2 polypeptides include, but are not limited to, those having the amino acid sequences set forth in NP_006728.2 and NP_001229796.1; these sequences are incorporated by reference herein.

KIR2DL1 is a protein expressed on NK cells and on some T cells. It is also known as CD158A, KIR-K64, KIR221, KIR2DL3, NKAT, NKAT-1, NKAT1, and p58.1. KIR2DL1 polypeptides include, but are not limited to, those having the amino acid sequence set forth in NP_055033.2; this sequence is incorporated by reference herein.

KIR2DL2 is a protein expressed on NK cells and on some T cells. It is also known as CD158B1, CD158b, NKAT-6, NKAT6, and p58.2. KIR2DL2 polypeptides include, but are not limited to, those having the amino acid sequence set forth in NP_055034.2; this sequence is incorporated by reference herein.

KIR2DL3 is a protein expressed on NK cells and on some T cells. It is also known as CD158B2, CD158b, GL183, KIR-023 GB, KIR-K7b, KIR-K7c, KIR2DL, KIR2DS5, KIRCL23, NKAT, NKAT2, NKAT2A, NKAT2B, and p58. KIR2DL3 polypeptides include, but are not limited to, those having the amino acid sequence set forth in NP_056952.2; this sequence is incorporated by reference herein.

CD27 is also referred to as TNF receptor superfamily member 7, S152, LPFS2, T14, TNFRSF7, and Tp55. CD27 polypeptides include, but are not limited to, those having the amino acid sequence set forth in NP_001233.2; this sequence is incorporated by reference herein.

CD38 is also referred to as ADP-ribosyl cyclase/cyclic ADP-ribose hydrolase 1, ADPRC1, and ADPRC 1. CD38 polypeptides include, but are not limited to, those having the amino acid sequence set forth in NP_001766.2; this amino acid sequence is incorporated by reference herein.

CD39 is also known as ectonucleoside triphosphate diphosphohydrolase 1, SPG64 ATPDase, and NTPDase-1. It encodes plasma membrane protein that hydrolyzes extracellular ATP and ADP to AMP. CD39 polypeptides include, but are not limited to, those having the amino acid sequences disclosed in NP_001307845.1, NP_001157651.1, NP_001157650.1, NP_001091645.1, NP_001767.3, NP_001299583.1, NP_001157655.1, NP_001157654.1, and NP_001157653.1; these amino acid sequences are incorporated by reference herein.

CD40L, or CD40 ligand, is also referred to as CD154, HIGM1, IGM, IMD3, T-BAM, TNFSF5, TRAP, gp39, and hCD40L. It is expressed on the surface of T cells. CD40L polypeptides include, but are not limited to, those having the amino acid sequence set forth in NP_000065.1; this sequence is incorporated by reference herein.

CD45 is referred to as protein tyrosine phosphatase receptor type C, B220, CD45R, GP180, L-CA, LCA, LY5, and T200. It has many isoforms, including CD45RA, CD45Rb, and CD45RO. CD45 RA and CD45Rb are expressed on naïve T cells. CD45RO is expressed on memory T cells. CD45RO polypeptides include, but are not limited to, those having the amino acid sequence disclosed in P08575-4. CD45RA polypeptides include, but are not limited to, those having the amino acid sequence disclosed in P08575-8. CD45RB polypeptides include, but are not limited to, those having the amino acid sequence disclosed in P08575-9. See UniProtKB database. These sequences are incorporated by reference herein.

CD73 is also referred to 5' nucleotidase ecto, CALJA, CD73, E5NT, NT, NT5, NTE, eN, and eNT. CD73 polypeptides include, but are not limited to, those disclosed in NP_001191742.1 and NP_002517.1; these amino acid sequences are incorporated by reference herein.

CD103, or integrin subunit alpha E (ITGAE), is also referred to as HUMINAE. CD103 polypeptides include, but are not limited to, those having the amino acid sequence disclosed in NP_002199.3; this amino acid sequence is incorporated by reference herein.

CD122, or interleukin 2 receptor subunit beta, is also referred to as IL15RB, IMD63, and P70-75. CD122 polypeptides include, but are not limited to, those having the amino acid sequences disclosed in NP_001333152.1, NP_001333151.1, and NP_000869.1; these amino acid sequences are incorporated by reference herein.

CD166, or activated leukocyte cell adhesion molecule (ALCAM), is also referred to as MEMD. CD166 polypeptides include, but are not limited to, those having the amino acid sequences set forth in NP_001618.2, NP_001230209.1, NP_001230210.1, and NP_001230212.1; these amino acid sequences are incorporated by reference herein.

CD177 is also referred to as HNA-2a, HNA2A, NB1, NB1 GP, PRV-1, and PRV1. CD177 polypeptides include, but are not limited to, those having the amino acid sequence set forth in NP_065139.2; this amino acid sequence is incorporated by reference herein.

CCR7, or C—C motif chemokine receptor 7, is also referred to as BLR2, CC-CKR-7, CCR-7, CD197, CDw197, CMKBR7, and EBI1. CCR7 polypeptides includes, but are not limited to, those having the amino acid sequences set forth in NP_001829.1, NP_001288643.1, NP_001288645.1, NP_001288646.1, and NP_001288647.1; these amino acid sequences are incorporated by reference herein.

CXCR3, or C—X—C motif chemokine receptor 3, is also referred to as GPR9, MigR, CD182, CD183, Mig-R, CKR-L2, CMKAR3, and IP10-R. CXCR3 polypeptides include, but are not limited to, those having the amino acid sequences set forth in NP_001495.1 and NP_001136269.1; these amino acid sequences are incorporated by reference herein.

CXCR5, or C—X—C motif chemokine 5, is also referred to as BLR1, CD185, and MDR15. CXCR5 polypeptides include, but are not limited to, those having the amino acid sequences set forth in NP_001707.1 and NP_116743.1; these amino acid sequences are incorporated by reference herein.

HLA-DR is a class II histocompatibility antigen composed of two chains. HLA-DR alpha chain polypeptides include, but are not limited to, those having the amino acid sequence set forth in NP_061984.2. HLA-DR beta chain polypeptides include, but are not limited to, those having the amino acid sequences set forth in NP_002116.2, NP_072049.2, NP_001346123.1, and NP_001346122.1. These amino acid sequences are incorporated by reference herein.

ICOS, or inducible T cell costimulatory, is also referred to as AILIM, CD278, and CVID1. ICOS polypeptides include, but are not limited to, those having the amino acid sequence set forth in NP_036224.1; this amino acid sequence is incorporated by reference herein.

LAG-3, or CD223, is also referred to as lymphocyte activating 3. LAG-3 polypeptides include, but are not limited to, those having the amino acid sequence set forth in NP_002277.4; this amino acid sequence is incorporated by reference herein.

OX-40 is also referred to as TNF receptor superfamily member 4 or TNFRSF4, ACT35, CD134, IMD16, and TXGP1L. OX-40 polypeptides include, but are not limited to, those having the amino acid sequence set forth in NP_003318.1; this amino acid sequence is incorporated by reference herein.

PD-1 is also referred to as programmed cell death protein 1. PD-1 polypeptides include, but are not limited to, those having the amino acid sequence set forth in NP_005009.2; this amino acid sequence is incorporated by reference herein.

S100A8/9, or S100A8 and S100A9, respectively, are $Ca^{2+}$ binding proteins belonging to the S100 family. S100A8 or S100-A8 is also referred to as 60B8AG, CAGA, CFAG, CGLA, CP-10, L1Ag, MA387, MIF, MRP8, NIF, and P8. S100A8 polypeptides include, but are not limited to, those having the amino acid sequences set forth in NP_001306125.1, NP_001306126.1, NP_001306127.1, NP_001306130.1, and NP_002955.2. S100A9, or S100-A9, is also referred to as 60B8AG, CAGB, CFAG, CGLB, L1AG, LIAG, MAC387, MIF, MRP14, NIF, and P14. S100A9 polypeptides include, but are not limited to, those having the amino acid sequence set forth in NP_002956.1. These amino acid sequences are incorporated by reference herein.

TIM-3, also referred to as Hepatitis A virus cellular receptor 2 (HAVCR2), is also known as CD366, HAVcr-2, KIM-3, SPTCL, TIM3, TIMD-3, and TIMD3. TIM-3 polypeptides include, but are not limited to, those having the amino acid sequence set forth in NP_116171.3; this amino acid sequence is incorporated by reference herein.

TLT-2, or triggering receptor expressed on myeloid cells like 2 (TREML2), is also referred to as C6orf76 or dJ238023.1. TLT-2 polypeptides include, but are not limited to, those having the amino acid sequence set forth in NP_079083.2; this amino acid sequence is incorporated by reference herein.

2B4, or CD244, is also referred to as NAIL, NKR2B4, Nmrk, and SLAMF4. 2B4 polypeptides include, but are not limited to, those having the amino acid sequences set forth in NP_057466.1, NP_001160135.1, or NP_001160136.1; these amino acid sequences are incorporated by reference herein.

41BB, or TNF receptor superfamily member 9 (TNFSF9), is also referred to as ILA, 4-1BB, CD137, and CDw137. 41BB polypeptides include, but are not limited to, those having the amino acid sequence set forth in NP_001552.2; this amino acid sequence is incorporated by reference herein.

As used herein, an "epitope" refers to the amino acids conventionally bound by an immunoglobulin VH/VL pair, such as the antibodies and other binding agents described herein. An epitope can be formed on a polypeptide from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An epitope defines the minimum binding site for an antibody or other binding agent, and thus represent the target of specificity of an antibody, antigen binding portion thereof or other immunoglobulin-based binding agent. In the case of a single domain antibody, an epitope represents the unit of structure bound by a variable domain in isolation.

As used herein, "specifically binds" refers to the ability of a binding agent (e.g., an antibody or antigen binding portion thereof) described herein to bind to a target with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the antibody or other binding agent and the concentration of target polypeptide. A person of ordinary skill in the art can determine appropriate conditions under which the antibodies and other binding agents described herein selectively bind to a target antigen using any suitable methods, such as titration of a binding agent in a suitable cell binding assay. A binding agent specifically bound to a target is not displaced by a non-similar competitor. In certain embodiments, a binding agent, such as an antibody or antigen-binding portion thereof is said to specifically bind to its target when it preferentially recognizes its target antigen in a complex mixture of proteins and/or macromolecules.

In some embodiments, a binding agent, such as an antibody or antigen-binding portion thereof or other binding agent as described herein specifically binds to a target polypeptide with a dissociation constant (KD) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an antibody or antigen-binding portion thereof or other binding agent as described herein specifically binds to a target polypeptide with a dissociation constant (KD) of from about $10^{-5}$ M to $10^{-6}$ M. In some embodiments, an antibody or antigen-binding portion thereof or other binding agent as described herein specifically binds to a target polypeptide with a dissociation constant (KD) of from about $10^{-6}$ M to $10^{-7}$ M. In some embodiments, an antibody or antigen-binding portion thereof or other binding agent as described herein specifically binds to a target polypeptide with a dissociation constant (KD) of from about $10^{-7}$ M to $10^{-8}$ M. In some embodiments, an antibody or antigen-binding portion thereof or other binding agent as described herein specifically binds to a target polypeptide with a dissociation constant (KD) of from about $10^{-8}$ M to $10^{-9}$ M. In some embodiments, an antibody or antigen-binding portion thereof or other binding agent as described herein specifically binds to a target polypeptide with a dissociation constant (KD) of from about $10^{-9}$ M to $10^{-10}$ M. In some embodiments, an antibody or antigen-binding portion thereof or other binding agent as described herein specifically binds to a target polypeptide with a dissociation constant (KD) of from about $10^{-10}$ M to $10^{-11}$ M. In some embodiments, an antibody or antigen-binding portion thereof or other binding agent as described herein specifically binds to a target polypeptide with a dissociation constant (KD) of from about $10^{-11}$ M to $10^{-12}$ M. In some embodiments, an antibody or antigen-binding portion thereof or other binding agent as described herein specifically binds to a target polypeptide with a dissociation constant (KD) of less than $10^{-12}$ M.

As used herein, the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

Other than in the examples, or where otherwise indicated, all numbers expressing quantities of ingredients or reaction conditions used herein should be understood as modified in all instances by the term "about". The term "about" when used in connection with percentages can mean+/−1%.

The term "statistically significant" or "significantly" refers to statistical significance and generally means a two standard deviation (2SD) difference, above or below a reference value.

Other terms are defined herein within the description of the various aspects of the invention.

Modulation of CD8+KIR+ Regulatory T Cells

Provided herein are binding agents comprising binding domains that specifically bind to antigens expressed on CD8+KIR+ regulatory T cells (Tregs). In some embodiments, the CD8+KIR+ Tregs are MHC class I restricted. In some embodiments, the CD8+KIR+ Tregs are not MHC Qa-1 (HLA-E) restricted. Also provided are methods of using the binding agents for the treatment of autoimmune disease, infectious disease, and cancer.

The binding agents include a first binding domain that specifically binds to a T cell antigen expressed on the CD8+KIR+ Tregs, other than a KIR protein, and a second binding domain that specifically binds to an inhibitory KIR protein expressed on the CD8+KIR+ Tregs. In some embodiments, the first binding domain specifically binds to an antigen selected from CD3, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, CD5, and 41BB. In some embodiments, the first binding domain specifically binds to an antigen selected from CD3, CD5, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some embodiments, the first binding domain specifically binds to a subunit of an antigen selected from CD3, CD8, CD40L, CD122, HLA-DR, OX-40, S1000A8/9, and 41BB/CD137.

In some embodiments, the first antigen is selected from a functional agonist that can activate the CD8 KIR+ Tregs. In some embodiments, such an antigen is, for example, CD3, CD27, CD38, CD39, CD40L, CD45RA, CD45RB, CD45RO, CD73, CD122, ICOS, OX-40, 2B4, 41BB, and HLA-DR. In some embodiments, such an antigen is, for example, CD3, CD5, CD27, CD38, CD39, CD40L, CD45RA, CD45RB, CD45RO, CD73, CD122, ICOS, OX-40, 2B4, 41BB, and HLA-DR. In some embodiments, the first binding domain has agonist activity when bound to such an antigen.

In some embodiments, the first antigen is selected from a functional antagonist to reduce functional inhibition of CD8 KIR+ Tregs. In some embodiments, such as antigen is, for example, LAG-3/CD223, TIM-3, PD-1, S1000A8/9, and TLT2. In some embodiments, the first binding domain has antagonist activity (e.g., blocking activity) when bound to such an antigen.

In some embodiments, the first antigen is a tethering moiety to enhance specificity of binding agent to CD8 KIR+ Tregs. In some embodiments, such an antigen is, for example, CD3, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some such an antigen is, for example, CD3, CD5, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some embodiments, the first binding domain specifically binds to such an antigen.

In some embodiments, the first antigen is a tethering moiety to enhance tissue specificity. In some embodiments, such an antigen is, for example, CD103 (ITGAE), CD166, CD177, CXCR3, and S1000A8/9. In some embodiments, the first binding domain specifically binds to such an antigen.

In some embodiments, the first antigen is an agonist to enhance CD8 KIR+ Treg cell migration. In some embodiments, such an antigen is, for example, CCR7, CXCR3, or CXCR5. In some embodiments, the first binding domain specifically binds to such an antigen.

In some embodiments, the first antigen is selected from PD-1, ICOS, and CXCR3. In some embodiments, the first binding domain specifically binds to such an antigen.

In some embodiments, the first antigen is selected from CD3 or CD8. In some embodiments, the first antigen is selected from CD3, CD5, or CD8. In some embodiments, the first antigen is selected from a subunit of CD3 or CD8. In some embodiments, the first antigen is CD3epsilon. In some embodiments, the first antigen is CD8alpha.

The second binding domain of the binding agent specifically binds to an inhibitory KIR protein (killer cell immunoglobulin like receptor protein). The inhibitory KIR protein can be, for example, KIR3DL1, KIR3DL2, KIR2DL1, KIR2DL2, or KIR2DL3 or a combination thereof, such as specifically binding to KIR2DL1/2/3 or KIR2DL1/2 proteins. In some embodiments, the KIR protein is selected from KIR3DL1, KIR3DL2, KIR2DL1, KIR2DL2, or KIR2DL3 or a combination thereof, such as KIR2DL1/2/3 or KIR2DL1/2 proteins. In some embodiments, the second binding domain is a KIR protein antagonist that blocks KIR protein interaction with its binding partner.

A binding agent can be any suitable agent that includes binding domains for both antigens. In some embodiments, a binding agent is bispecific (i.e., having binding domains for two different antigens). In some embodiments, a binding agent is bivalent (i.e., having two binding domains). In some embodiments, the binding agent is tetravalent (i.e., having four binding domains).

The binding domains of the binding agents can be derived from antibodies or from non-antibody formats. In some embodiments, a binding domain is derived from an antibody or antigen binding portions thereof (i.e., an antibody fragment). In some embodiments, the antibody fragment is a Fab, Fab', F(ab')2, Fv, scFv, or a single domain antibody (also referred to as a VHH, VNAR, sdAb, or NANOBODY®). In some embodiments, a binding domain is or is derived from an anticalin, affibody, avimer, DARPin, or adnectin.

Figure 2:
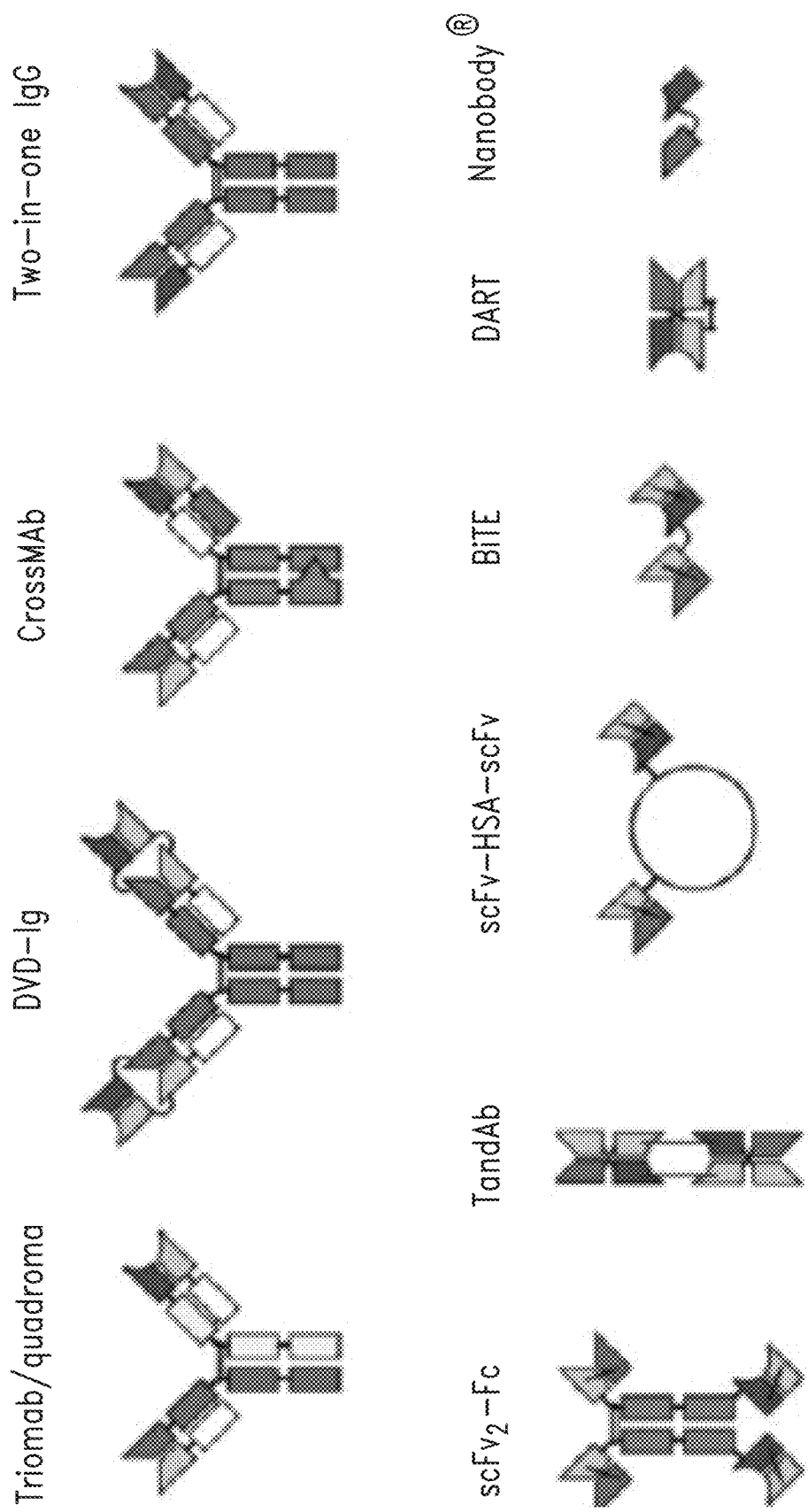
FIG. 2 shows various formats of certain bispecific antibodies.
Figure 3:
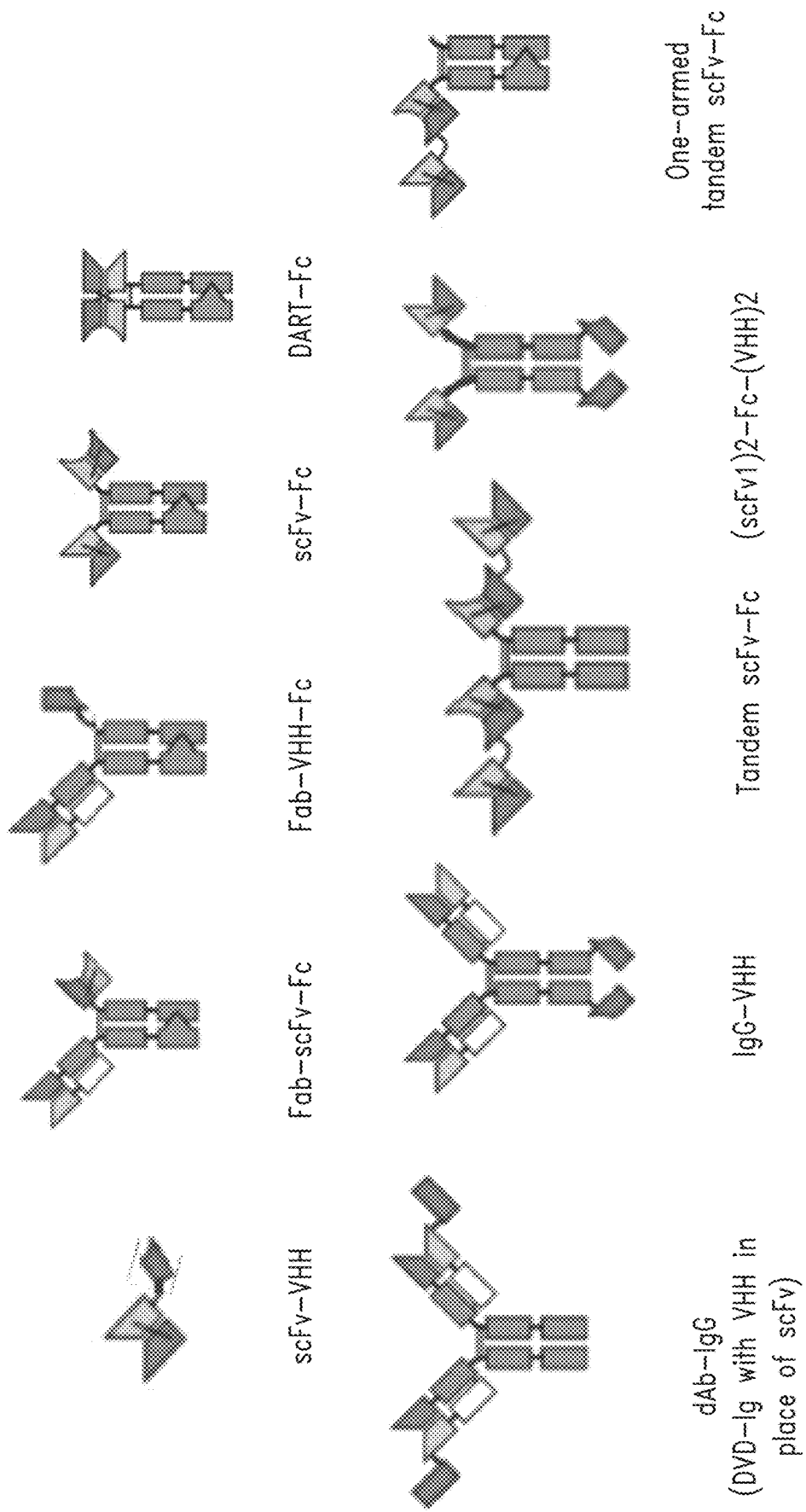
FIG. 3 shows various formats of additional bispecific antibodies.

In some embodiments, the binding agent is a bispecific antibody, a diabody, an antibody Fc fusion, scFv1-ScFv2, an ScFv12-Fc-scFv22, an IgG-scFv, a DVD-Ig, a triomab/quadroma, a two-in-one IgG, a scFv2-Fc, a TandAb, an scFv-HSA-scFv, an scFv-VHH, a Fab-scFv-Fc, a Fab-VHH-Fc, a dAb-IgG, an IgG-VHH, a Tandem scFv-Fc, a $(scFv1)_2$-Fc-$(VHH)_2$, a BiTe, a DART, a crossmab, an anticalin, an affibody, an avimer, a DARPin, an adnectin, a scFv-Fc, a one-armed tandem scFv-Fc, or a DART-Fc (see, e.g., FIGS. 2 and 3). In some embodiments, the IgG-scFv is an IgG (H)-scFv, scFv-(H) IgG, IgG (L)-scFv, scFv-(L) IgG, 2scFV-IgG, or IgG-2scFv (as shown in FIG. 1).

In some embodiments, the binding agent comprises a first binding domain comprising a heavy chain variable region and a light chain variable region. In some embodiments, the heavy and light chain variable regions of the first binding domain specifically bind to an antigen expressed on a CD8+KIR+ Treg, such as CD3, CD8, CD27, CD38, CD39, CD40L, CD45RA, CD45RB, CD45RO, CD73, CD103 (IT-GAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some embodiments, the heavy and light chain variable regions of the first binding domain specifically bind to an antigen expressed on a CD8+KIR+ Treg, such as CD3, CD5, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some embodiments, the heavy and light chain variable regions of the first binding domain specifically bind to a subunit of an antigen expressed on a CD8+KIR+ Treg, such as CD3, CD8, CD40L, CD122, HLA-DR, OX-40, S1000A8/9, and 41BB/CD137. In some embodiments, the heavy and light chain variable regions of the first binding domain specifically bind to a subunit of an antigen expressed on a CD8+KIR+ Treg, such as CD3, CD5, CD8, CD40L, CD122, HLA-DR, OX-40, S1000A8/9, and 41BB/CD137.

In some embodiments, the first antigen is selected from a functional agonist that can activate the CD8 KIR+ Tregs. In some embodiments, such an antigen is, for example, CD3, CD27, CD38, CD39, CD40L, CD45RA, CD45RB, CD45RO, CD73, CD122, ICOS, OX-40, 2B4, 41BB, and HLA-DR. In some embodiments, such an antigen is, for example, CD3, CD5, CD27, CD38, CD39, CD40L, CD45RA, CD45RB, CD45RO, CD73, CD122, ICOS, OX-40, 2B4, 41BB, and HLA-DR. In some embodiments, the first binding domain has agonist activity when bound to such an antigen.

In some embodiments, the first antigen is selected from a functional antagonist to reduce functional inhibition of CD8 KIR+ Tregs. In some embodiments, such as antigen is, for example, LAG-3/CD223, TIM-3, PD-1, S1000A8/9, and TLT2. In some embodiments, the first binding domain has antagonist activity (e.g., blocking activity) when bound to such an antigen.

In some embodiments, the first antigen is a tethering moiety to enhance specificity of binding agent to CD8 KIR+ Tregs. In some embodiments, such an antigen is, for example, CD3, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some embodiments, such an antigen is, for example, CD3, CD5, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some embodiments, the first binding domain specifically binds to such an antigen.

In some embodiments, the first antigen is a tethering moiety to enhance tissue specificity. In some embodiments, such an antigen is, for example, CD103 (ITGAE), CD166, CD177, CXCR3, and S1000A8/9. In some embodiments, the first binding domain specifically binds to such an antigen.

In some embodiments, the first antigen is an agonist to enhance CD8 KIR+ Tregs cell migration. In some embodiments, such an antigen is, for example, CCR7, CXCR3, or CXCR5. In some embodiments, the first binding domain specifically binds to such an antigen.

In some embodiments, the first antigen is selected from PD-1, ICOS, and CXCR3. In some embodiments, the first binding domain specifically binds to such an antigen.

In some embodiments, the first antigen is selected from CD3 or CD8. In some embodiments, the first antigen is selected from CD3, CD5, or CD8. In some embodiments, the first antigen is selected from a subunit of CD3 or CD8. In some embodiments, the first antigen is CD3epsilon. In some embodiments, the first antigen is CD8alpha.

Antibodies for use in the binding domains described herein are known in the art.

Antibodies to CD3 have been described in, for example, U.S. Pat. Nos. 5,929,212; 5,885,573; and 8,551,478 and in International Patent Publication WO2018223004.

Antibodies to CD8 have been described in, for example, Published U.S. patents application Nos. 20190382488 and 20190071500 and International Patent Publication WO2014164553 and WO2017134306.

Antibodies to CD5 have been described in, for example, Published US Patent Application Nos. 2018/0104308, 2011/0250203, and 2008/0254027.

Antibodies to CD27 have been described in, for example, Published U.S. patents application Nos. 20210009706, 20200247898, and 20200131272.

Antibodies to CD38 have been described in, for example, Published U.S. patents application Nos. 20200408765, 20200399391, 20090304710, and 20050158305.

Antibodies to CD39 have been described in, for example, Published U.S. patents application Nos. 20190062448, 20130273062, and 20100303828.

Antibodies to CD40L have been described in, for example, Published U.S. patents application Nos. 20190092868, 20100092482, 20030031668, and 20010018041.

Antibodies to CD45RA, CD45RB, and CD45RO have been described in, for example, Published U.S. patents application Nos. 20030232009 and 20020168362 and are available from commercial sources.

Antibodies to CD73 have been described in, for example, Published U.S. patents application Nos. 20200148781, 20200071404, 20190256598, and 20160145350.

Antibodies to CD103 (ITGAE) have been described in, for example, Published U.S. patent application No. 20050266001.

Antibodies to CD122 have been described in, for example, Published U.S. patents application Nos. 20180362655 and 20110250213.

Antibodies to CD166 have been described in, for example, Published U.S. patents application Nos. 20160355587 and 20090269787.

Antibodies to CD177 have been described in, for example, Published U.S. patent application No. 20190125832.

Antibodies to CCR7 have been described in, for example, Published U.S. patents application Nos. 20200216548, 20180237529, and 20150344580.

Antibodies to CXCR3 have been described in, for example, Published U.S. patents application Nos. 20190119391, 20190008955, and 20130251733.

Antibodies to CXCR5 have been described in, for example, Published U.S. patents application Nos. 20190169283, 20160053014, and 20130236476.

Antibodies to HLA-DR have been described in, for example, Published U.S. patents application Nos. 20180355043 and 20190071503.

Antibodies to ICOS have been described in, for example, Published U.S. patents application Nos. 20160304610 and 20110243929.

Antibodies to LAG-3/CD223 have been described in, for example, Published U.S. patents application Nos. 20210009687, 20200277372, 20200071403, and 20190276538.

Antibodies to OX40 have been described in, for example, Published U.S. patents application Nos. 20140377284, 20140308276, and 20100196359.

Antibodies to PD-1 have been described in, for example, Published U.S. patents application Nos. 20190322749, 20190309069, 20170313774, and 20110171215.

Antibodies to S1000A8/9 have been described in, for example, Published U.S. patents application Nos. 20180256710 and 20200023045.

Antibodies to TIM-3 have been described in, for example, Published U.S. patents application Nos. 20180072804, 20170306016, and 20150086574.

Antibodies to TLT-2 have been described in, for example, Published U.S. patent application No. 20130216540.

Antibodies to 2B4 are available, for example, from commercial vendors.

Antibodies to 41BB have been described in, for example, Published U.S. patents application Nos. 20170198050 and 20200347144.

In some embodiments, the first binding domain specifically binds to CD3epsilon and the heavy and light chain variable regions have the amino acid sequences set forth in SEQ ID NO:1 and SEQ ID NO:2, respectively; SEQ ID NO: 9 and SEQ ID NO:10, respectively; SEQ ID NO: 17 and SEQ ID NO: 18, respectively; SEQ ID NO:25 and SEQ ID NO:26, respectively; SEQ ID NO:33 and SEQ ID NO:34, respectively; SEQ ID NO:41 and SEQ ID NO:34, respectively; SEQ ID NO:45 and SEQ ID NO:34, respectively; SEQ ID NO:49 and SEQ ID NO:50, respectively; SEQ ID NO:57 and SEQ ID NO:58, respectively; SEQ ID NO:65 and SEQ ID NO:66, respectively; or SEQ ID NO:65 and SEQ ID NO: 166, respectively.

In some embodiments, the first binding domain specifically binds to CD3epsilon and the heavy and light chain variable regions have the amino acid sequences set forth in SEQ ID NO:1 and SEQ ID NO:2, respectively; SEQ ID NO: 9 and SEQ ID NO: 10, respectively; SEQ ID NO:17 and SEQ ID NO: 18, respectively; SEQ ID NO:25 and SEQ ID NO:26, respectively; SEQ ID NO:33 and SEQ ID NO:34, respectively; SEQ ID NO:41 and SEQ ID NO:34, respectively; SEQ ID NO:45 and SEQ ID NO:34, respectively; SEQ ID NO:49 and SEQ ID NO:50, respectively; SEQ ID NO:57 and SEQ ID NO:58, respectively; or SEQ ID NO:65 and SEQ ID NO:66, respectively; or SEQ ID NO: 65 and SEQ ID NO: 166, respectively; wherein the framework regions of the heavy and light chain variable regions are optionally modified with from 1 to 8, 1 to 6, 1 to 4, or 1 to 2 amino acid substitutions, deletions, or insertions, and wherein the CDRs of the heavy or light chain variable regions are not modified.

In some embodiments, the first binding domain comprises an amino acid sequence (e.g., a VH, VL, hCDR1, hCDR1, hCDR3, lCDR1, lCDR2, and/or lCDR3) according to any one or more of SEQ ID NOs: 1-72 and 166-169.

In some embodiments, the first binding domain specifically binds to CD8alpha and the heavy and light chain variable regions have the amino acid sequences set forth in SEQ ID NO:73 and SEQ ID NO:74, respectively; or SEQ ID NO:81 and SEQ ID NO:82, respectively; or the binding domain comprises a VHH chain having the amino acid sequence set forth in SEQ ID NO: 89, SEQ ID NO:93, or SEQ ID NO:97.

In some embodiments, the first binding domain specifically binds to CD8alpha and the heavy and light chain variable regions have the amino acid sequences set forth in SEQ ID NO:73 and SEQ ID NO:74, respectively; or SEQ ID NO:81 and SEQ ID NO:82, respectively; or the binding domain comprises a VHH chain having the amino acid sequence set forth in SEQ ID NO: 89, SEQ ID NO: 93, or SEQ ID NO:97, respectively; wherein the framework regions of the heavy and light chain variable regions or VHH chain are optionally modified with from 1 to 8, 1 to 6, 1 to 4, or 1 to 2 amino acid substitutions, deletions, or insertions, and wherein the CDRs of the heavy or light chain variable regions or the VHH chain are not modified.

In some embodiments, the first binding domain comprises an amino acid sequence (e.g., a VH, VL, hCDR1, hCDR1, hCDR3, lCDR1, lCDR2, and/or lCDR3) according to any one or more of SEQ ID NOs: 73-100.

In some embodiments, the first binding domain specifically binds to CD3epsilon and the heavy chain variable regions has complementarity determining regions hCDR1, hCDR2, and hCDR3, the light chain variable region lCDR1, lCDR2, and lCDR3, and the amino acid sequences of the heavy and light chain variable region CDRs are set forth in SEQ ID NO:3 to SEQ ID NO: 8, respectively; SEQ ID NO: 11 to SEQ ID NO: 16, respectively; SEQ ID NO: 19 to SEQ ID NO:24, respectively; SEQ ID NO:27 to SEQ ID NO:32, respectively; SEQ ID NO:35 to SEQ ID NO:40, respectively; SEQ ID NO:42 to SEQ ID NO:44 and SEQ ID NO:38 to SEQ ID NO:40, respectively; SEQ ID NO: 46 to SEQ ID NO:48 and SEQ ID NO:38 to SEQ ID NO:40, respectively; SEQ ID NO:51 to SEQ ID NO:56, respectively; SEQ ID NO:59 to SEQ ID NO: 64, respectively; or SEQ ID NO:67 to SEQ ID NO:72, respectively. In some embodiments, the first binding domain specifically binds to CD3epsilon and comprises light chain variable region lCDR1, lCDR2, and lCDR3 having the amino acid sequences set forth in SEQ ID NOs: 167, 168, and 169, respectively.

In some embodiments, the first binding domain specifically binds to CD8alpha and has heavy chain variable regions having complementarity determining regions hCDR1, hCDR2, and hCDR3 and the light chain variable region has lCDR1, lCDR2, and lCDR3, the amino acid sequences of the heavy and light chain variable region CDRs are set forth in SEQ ID NO:75 to SEQ ID NO: 80, respectively; or SEQ ID NO:83 to SEQ ID NO: 88, respectively; or the first binding domain includes a VHH chain having hCDR1, hCDR2, and hCDR3, and the amino acid sequences of the VHH CDRs are set forth in SEQ ID NO:90 to SEQ ID NO:92, respectively; SEQ ID NO:94 to SEQ ID NO:96, respectively; or SEQ ID NO:98 to SEQ ID NO: 100, respectively.

In some embodiments, the first binding domain specifically binds to ICOS and the heavy and light chain variable regions have the amino acid sequences set forth in SEQ ID NO: 170 and SEQ ID NO: 171, respectively.

In some embodiments, the first binding domain specifically binds to ICOS and the heavy and light chain variable regions have the amino acid sequences set forth in SEQ ID NO: 170 and SEQ ID NO:171, respectively; wherein the framework regions of the heavy and light chain variable regions are optionally modified with from 1 to 8, 1 to 6, 1 to 4, or 1 to 2 amino acid substitutions, deletions, or insertions, and wherein the CDRs of the heavy or light chain variable regions are not modified.

In some embodiments, the first binding domain comprises an amino acid sequence (e.g., a VH, VL, hCDR1, hCDR1, hCDR3, lCDR1, lCDR2, and/or lCDR3) according to any one or more of SEQ ID NOs: 170-177.

In some embodiments, the first binding domain specifically binds to PD-1 and the heavy and light chain variable regions have the amino acid sequences set forth in SEQ ID NO: 178 and SEQ ID NO: 179, respectively.

In some embodiments, the first binding domain specifically binds to PD-1 and the heavy and light chain variable regions have the amino acid sequences set forth in SEQ ID NO: 178 and SEQ ID NO:179, respectively; wherein the framework regions of the heavy and light chain variable regions are optionally modified with from 1 to 8, 1 to 6, 1 to 4, or 1 to 2 amino acid substitutions, deletions, or insertions, and wherein the CDRs of the heavy or light chain variable regions are not modified.

In some embodiments, the first binding domain comprises an amino acid sequence (e.g., a VH, VL, hCDR1, hCDR1, hCDR3, lCDR1, lCDR2, and/or lCDR3) according to any one or more of SEQ ID NOs: 178-185.

In some embodiments, the first binding domain specifically binds to CXCR3 and the heavy and light chain variable regions have the amino acid sequences set forth in SEQ ID NO: 186 and SEQ ID NO: 187, respectively.

In some embodiments, the first binding domain specifically binds to CXCR3 and the heavy and light chain variable regions have the amino acid sequences set forth in SEQ ID NO: 186 and SEQ ID NO: 187, respectively; wherein the framework regions of the heavy and light chain variable regions are optionally modified with from 1 to 8, 1 to 6, 1 to 4, or 1 to 2 amino acid substitutions, deletions, or insertions, and wherein the CDRs of the heavy or light chain variable regions are not modified.

In some embodiments, the first binding domain comprises an amino acid sequence (e.g., a VH, VL, hCDR1, hCDR1, hCDR3, lCDR1, lCDR2, and/or lCDR3) according to any one or more of SEQ ID NOs: 186-193.

In some embodiments, the first binding domain specifically binds to CD5 and the heavy and light chain variable regions have the amino acid sequences set forth in SEQ ID NO: 194 and SEQ ID NO: 195, respectively.

In some embodiments, the first binding domain specifically binds to CD5 and the heavy and light chain variable regions have the amino acid sequences set forth in SEQ ID NO: 194 and SEQ ID NO: 195, respectively; wherein the framework regions of the heavy and light chain variable regions are optionally modified with from 1 to 8, 1 to 6, 1 to 4, or 1 to 2 amino acid substitutions, deletions, or insertions, and wherein the CDRs of the heavy or light chain variable regions are not modified.

In some embodiments, the first binding domain comprises an amino acid sequence (e.g., a VH, VL, hCDR1, hCDR1, hCDR3, lCDR1, lCDR2, and/or lCDR3) according to any one or more of SEQ ID NOs: 194-201.

In some embodiments, the binding agent comprises a second binding domain comprising a heavy chain variable region and a light chain variable region. The second binding domain of the binding agent specifically binds to an inhibitory KIR protein (killer cell immunoglobulin like receptor protein). The inhibitory KIR protein can be KIR3DL1, KIR3DL2, KIR2DL1, KIR2DL2, or KIR2DL3 or a combination thereof, such as specifically binding to KIR2DL1/2/3 or KIR2DL1/2 proteins.

Antibodies to inhibitory KIR proteins are known in the art.

Antibodies to KIR3DL1 have been described in, for example, U.S. Pat. No. 5,770,387 and International Patent Publication WO2018148223.

Antibodies to KIR3DL2 have been described in, for example, Published U.S. application No. 20200199228 and 20150232556.

Antibodies to KIR2DL1, KIR2DL2, KIR2DL3, and combinations thereof have been describes in, for example, U.S. Pat. Nos. 10,668,180 and 10,253,095, International Patent Publication WO2006003179, Published U.S. application Nos. 20150290316 and 20130251711 and European Patent No. 3072522.

In some embodiments, the second binding domain specifically binds to KIR3DL1 and the heavy and light chain variable regions have the amino acid sequences set forth in SEQ ID NO: 133 and SEQ ID NO:134, respectively; SEQ ID NO:141 and SEQ ID NO: 142, respectively; or SEQ ID NO: 149 and SEQ ID NO: 150, respectively.

In some embodiments, the first binding domain specifically binds to KIR3DL1 and the heavy and light chain variable regions have the amino acid sequences set forth in SEQ ID NO:133 and SEQ ID NO: 134, respectively; SEQ ID NO: 141 and SEQ ID NO: 142, respectively; or SEQ ID NO: 149 and SEQ ID NO: 150, respectively; wherein the framework regions of the heavy and light chain variable regions are optionally modified with from 1 to 8, 1 to 6, 1 to 4, or 1 to 2 amino acid substitutions, deletions, or insertions, and wherein the CDRs of the heavy or light chain variable regions are not modified.

In some embodiments, the first binding domain specifically binds to KIR3DL2 and the heavy and light chain variable regions have the amino acid sequences set forth in the amino acid sequences set forth in SEQ ID NO: 157 and SEQ ID NO: 158, respectively.

In some embodiments, the first binding domain specifically binds to KIR3DL2 and the heavy and light chain variable regions have the amino acid sequences set forth in SEQ ID NO: 157 and SEQ ID NO: 158, respectively; wherein the framework regions of the heavy and light chain variable regions are optionally modified with from 1 to 8, 1 to 6, 1 to 4, or 1 to 2 amino acid substitutions, deletions, or insertions, and wherein the CDRs of the heavy or light chain variable regions are not modified.

In some embodiments, the first binding domain specifically binds to KIR2DL1/2/3 and the heavy and light chain variable regions have the amino acid sequences set forth in SEQ ID NO: 101 and SEQ ID NO:102, respectively; SEQ ID NO: 109 and SEQ ID NO:110, respectively; SEQ ID NO: 117 and SEQ ID NO: 118, respectively; or SEQ ID NO: 125 and SEQ ID NO: 126, respectively.

In some embodiments, the first binding domain specifically binds to KIR2DL1/2/3 and the heavy and light chain variable regions have the amino acid sequences set forth in SEQ ID NO:101 and SEQ ID NO: 102, respectively; SEQ ID NO: 109 and SEQ ID NO:110, respectively; SEQ ID NO: 117 and SEQ ID NO: 118, respectively; or SEQ ID NO: 125 and SEQ ID NO: 126, respectively; wherein the framework regions of the heavy and light chain variable regions are optionally modified with from 1 to 8, 1 to 6, 1 to 4, or 1 to 2 amino acid substitutions, deletions, or insertions, and wherein the CDRs of the heavy or light chain variable regions are not modified.

In some embodiments, the first binding domain specifically binds to KIR3DL1 and the heavy chain variable region has complementarity determining regions (CDR) hCDR1, hCDR2, and hCDR3, the light chain variable region has lCDR1, lCDR2, and lCDR3, and the amino acid sequences of the heavy and light chain variable region CDRs have the amino acid sequences set forth in SEQ ID NO: 135 to SEQ ID NO: 140, respectively; SEQ ID NO: 143 to SEQ ID NO: 148, respectively; or SEQ ID NO: 151 to SEQ ID NO: 156, respectively.

In some embodiments, the first binding domain specifically binds to KIR3DL2 and the heavy chain variable region has complementarity determining regions hCDR1, hCDR2, and hCDR3, the light chain variable region has lCDR1, lCDR2, and lCDR3, and the amino acid sequences of the heavy and light chain variable region CDRs are set forth in the amino acid sequences of SEQ ID NO: 159 to SEQ ID NO: 164, respectively.

In some embodiments, the first binding domain specifically binds to KIR2DL1/2/3 and the heavy chain variable region has complementarity determining regions hCDR1, hCDR2, and hCDR3, the light chain variable region has lCDR1, lCDR2, and lCDR3, the amino acid sequences of the heavy and light chain variable region CDRs are set forth in SEQ ID NO: 103 to SEQ ID NO: 108, respectively; SEQ ID NO: 111 to SEQ ID NO: 116, respectively; SEQ ID NO: 119 to SEQ ID NO: 124, respectively; or SEQ ID NO: 127 to SEQ ID NO: 132, respectively.

Binding Agents

The binding agent can be any suitable agent that includes at least a first binding domain and a second binding domain, wherein the first binding domain that specifically binds to a first antigen that is selected from antigens expressed on CD8+KIR+ T regulatory cells (Tregs), other than a KIR protein; and a second binding domain that specifically binds to an inhibitory KIR protein, wherein the binding agent binds to CD8+KIR+ Tregs.

In some embodiments, a binding agent is bispecific (i.e., having binding domains for two different antigens). In some embodiments, a binding agent is bivalent (i.e., having two binding domains). In some embodiments, the binding agent is tetravalent (i.e., having four binding domains). In some embodiments, the binding agent is trivalent, hexavalent, or octavalent.

The binding domains of the binding agents can be derived from antibodies or from non-antibody formats. In some embodiments, a binding domain is derived from an antibody or antigen binding portion thereof (i.e., an antigen binding antibody fragment). In some embodiments, the antibody fragment is a Fab, Fab', F(ab')2, Fv, scFv, or a single domain antibody (also referred to as a VHH, VNAR, sdAb, or NANOBODY®). In some embodiments, a binding domain is derived from an anticalin, affibody, avimer, DARPin, adnectin, or a receptor ectodomain Fc fusion protein.

In some embodiments, the binding agent is a bispecific antibody, a diabody, an antibody Fc fusion, scFv1-ScFv2, an ScFv12-Fc-scFv22, an IgG-scFv, a DVD-Ig, a triomab/quadroma, a two-in-one IgG, a scFv2-Fc, a TandAb, an scFv-HSA-scFv, an scFv-VHH, a Fab-scFv-Fc, a Fab-VHH-Fc, a dAb-IgG, an IgG-VHH, a Tandem scFv-Fc, a (scFv1)$_2$-Fc-(VHH)$_2$, a BiTe, a DART, a crossmab, an anticalin, an affibody, an avimer, a DARPin, an adnectin, a scFv-Fc, a one-armed tandem scFv-Fc, or a DART-Fc. In some embodiments, the IgG-scFv is an IgG (H)-scFv, scFv-(H) IgG, IgG (L)-scFv, scFv-(L) IgG, 2scFV-IgG, or IgG-2scFv (as shown in FIG. 1).

As used herein, the term "antibody" refers to immunoglobulin molecules and immunologically active portions of immunoglobulin molecules, i.e., molecules that contain an antigen binding site (antigen binding portion) that specifically binds to a target antigen. The term generally refers to antibodies comprised of two immunoglobulin heavy chain variable regions and two immunoglobulin light chain variable regions including full length antibodies (having heavy and light chain constant regions) and antigen-binding portions thereof; including, for example, an intact monoclonal antibody, a Fab, a Fab', a F(ab')$_2$, a Fv, a disulfide linked Fv, a scFv, a single domain antibody (dAb), a diabody, a multi-specific antibody, a dual specific antibody, a bispecific antibody, and single chain antibodies (see, e.g., Huston et al., Proc. Natl. Acad. Sci. U.S.A., 85, 5879-5883 (1988) and Bird et al., Science 242, 423-426 (1988), which are incorporated herein by reference).

In an antibody, each heavy chain is composed of a variable region (abbreviated as VH) and a constant region. The heavy chain constant region may include three domains CH1, CH2, and CH3 and optionally a fourth domain, CH4. Each of these domains is referred to as an "Fc domain". As used herein, when a binding agent includes an Fc domain, it can include one or more Fc domains, or an entire Fc region, unless otherwise specified by context. Each light chain is composed of a variable region (abbreviated as VL) and a constant region or constant domain. The light chain constant region is a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs that are arranged from the N terminus to the C terminus in the following order: FR1, CDR1, FR2, CDR2, FR3, CDR3, and FR4. This structure is well known to those skilled in the art.

As used herein, an "antigen-binding portion" of an antibody refers to the portions of an antibody as described herein having the VH and VL sequences or the heavy and light chain variable region CDRs. In accordance with the term "antigen-binding portion" of an antibody, examples of antigen binding portions include a Fab, a Fab', a F(ab')$_2$, a Fv, a disulfide linked Fv, a scFv, a single domain antibody (dAb), a diabody, and single chain antibodies. As used herein, the terms Fab, F(ab')$_2$ and Fv refer to the following: (i) an Fab fragment, i.e. a monovalent fragment composed of the VL, VH, CL and CH1 domains; (ii) an F(ab')$_2$ fragment, i.e. a bivalent fragment comprising two Fab fragments linked to one another in the hinge region via a disulfide bridge; and (iii) an Fv fragment composed of the VL and VH domains of an antibody. Although the two domains of the Fv fragment, namely VL and VH, are encoded by separate coding regions, they may further be linked to one another using a synthetic linker, e.g. a poly-G4S amino acid sequence ((G4S) n' disclosed as SEQ ID NO: 165, wherein n=1 to 5), making it possible to prepare them as a single protein chain in which the VL and VH regions combine in order to form monovalent molecules (known as single chain Fv (ScFv)). The term "antigen-binding portion" of an antibody is also intended to include such single chain antibodies.

Other forms of single chain antibodies such as "diabodies" are likewise included here. Diabodies are bivalent, bispecific antibodies in which VH and VL domains are expressed on a single polypeptide chain, but using a linker connecting the VH and VL domains that is too short for the two domains to be able to combine on the same chain, thereby forcing the VH and VL domains to pair with complementary domains of a different chain (VL and VH, respectively), and to form two antigen-binding sites (see, for example, Holliger, R, et al. (1993) Proc. Natl. Acad. Sci. USA 90:64446448; Poljak, R. J, et al. (1994) Structure 2:1121-1123).

An immunoglobulin constant region, or Fc region, refers to a heavy or light chain constant region. Human heavy chain and light chain constant region amino acid sequences are known in the art. A constant region can be of any suitable type, which can be selected from the classes of immunoglobulins, IgA, IgD, IgE, IgG, and IgM. Several immunoglobulin classes can be further divided into isotypes, e.g., IgGI, IgG2, IgG3, IgG4, or IgA1, and IgA2. The heavy-chain constant regions (Fc) that corresponds to the different classes of immunoglobulins can be α, β, ε, γ, and μ, respectively. The light chains can be one of either kappa (or κ) and lambda (or λ).

In some embodiments the binding agent lacks an Fc region or domains thereof. In some embodiments, the binding agent has an entire Fc region or an Fc domain thereof. In some embodiments, the binding agent has an Fc region or Fc domain of an IgG1 isotype. In some embodiments, the binding agent has an Fc region or Fc domain of an IgG2 isotype. In some embodiments, the binding agent has an Fc region or Fc domain of an IgG3 isotype. In some embodiments, the binding agent has an Fc region or Fc domain of an IgG4 isotype. In some embodiments, an Fc domain can have a hybrid isotype comprising constant regions from two or more isotypes. In some embodiments, an Fc region or Fc domain can be an IgG1 or IgG4 constant region.

In some embodiments, the C-terminus of an Fc domain (e.g., the heavy chain) can be a complete C-terminus ending with the amino acid residues PGK. In some embodiments, the C-terminus of the Fc domain also can be a shortened C-terminus in which one or two of the C terminal amino acid residues have been removed. In some embodiments, the C-terminus of the Fc domain is a shortened C-terminus ending PG. In some embodiments, a binding agent comprising a heavy chain including a C-terminal CH3 domain comprises the C-terminal glycine-lysine dipeptide (G446 and K447, numbering according to Kabat EU index). In some embodiments, a binding agent comprising a heavy chain including a C-terminal CH3 domain comprises a C-terminal glycine residue (G446, numbering according to Kabat EU index).

The binding agents as described herein are multispecific, typically bispecific binding agents. In some embodiments, the binding agents are multispecific antibodies or antibody-like molecules, such as bispecific antibodies. Multispecific antibodies are monoclonal antibodies that have binding specificities for at least two different sites or antigens. The binding agents described herein typically have binding specificities for different antigens. Bispecific antibodies can be prepared as full length antibodies or antibody fragments. Bispecific and multi-specific antibodies include the following: an scFv1-ScFv2, an ScFv12-Fc-scFv22, an IgG-scFv, a DVD-Ig, a triomab/quadroma, a two-in-one IgG, a scFv2-Fc, a TandAb, an scFv-HSA-scFv, an scFv-VHH, a Fab-scFv-Fc, a Fab-VHH-Fc, a dAb-IgG, an IgG-VHH, a Tandem scFv-Fc, a (scFv1)$_2$-Fc-(VHH)$_2$, a scFv-Fc, a one-armed tandem scFv-Fc, and a DART-Fc In some embodiments, the IgG-scFv is an IgG (H)-scFv, scFv-(H) IgG, IgG (L)-scFv, svFc-(L) IgG, 2scFV-IgG, or IgG-2scFv (as shown in FIG. 1).

Techniques for making multispecific antibodies include, but are not limited to, recombinant co-expression of two immunoglobulin heavy chain-light chain pairs having different specificities (see Milstein and Cuello, Nature 305:537 (1983), WO 93/08829, and Traunecker et al., EMBO J. 10:3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking of two or more antibodies or fragments (see, e.g., U.S. Pat. No. 4,676,980, and Brennan et al., Science, 229:81 (1985)); using leucine zippers to produce bi-specific antibodies (see, e.g., Kostelny et al., J. Immunol., 148 (5): 1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147:60 (1991).

Engineered antibodies with three or more functional antigen binding sites, including "Octopus antibodies", are also included herein (see, e.g. US 2006/0025576A1).

The binding agents (e.g., antibodies or antigen binding fragments) herein also include a "Dual Acting FAb" or "DAF" comprising an antigen binding site that binds to two different antigens (see, e.g., US 2008/0069820 and Bostrom et al., 2009, Science 323:1610-14). "Crossmab" antibodies are also included herein (see, e.g., WO 2009/080251, WO 2009/080252, WO2009/080253, WO2009/080254, and WO2013/026833).

In some embodiments, the binding agents comprise different antigen-binding sites, fused to one or the other of the two subunits of the Fc domain; thus, the two subunits of the Fc domain may be comprised in two non-identical polypeptide chains. Recombinant co-expression of these polypeptides and subsequent dimerization leads to several possible combinations of the two polypeptides. To improve the yield and purity of the bispecific molecules in recombinant production, it will thus be advantageous to introduce in the Fc domain of the binding agent a modification promoting the association of the desired polypeptides.

Accordingly, in particular aspects relates to a binding agent comprising (a) at least a first binding domain, (b) a second binding domain, and (c) a Fc domain composed of a first and a second subunit capable of stable association, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect, the Fc modification is a so-called "knob-into-hole" modification, comprising a "knob" modification in one of the two subunits of the Fc domain and a "hole" modification in the other one of the two subunits of the Fc domain. In a particular aspect, the first subunit of the Fc domain comprises the amino acid substitutions S354C and T366W (EU numbering) and the second subunit of the Fc domain comprises the amino acid substitutions Y349C, T366S, and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in some embodiments, in a CH3 domain of an Fc domain an amino acid residue is replaced with an amino acid residue having a larger side chain volume, thereby generating a protuberance within the CH3 domain which is positionable in a cavity within a CH3 domain of a second Fc domain, and in the CH3 domain of the second Fc domain an amino acid residue is replaced with an amino acid residue having a smaller side chain volume, thereby generating a cavity within the CH3 domain of the second Fc domain within which the protuberance within the CH3 domain of the first Fc domain is positionable. The protuberance and cavity can be made by altering the nucleic acid encoding the polypeptides, e.g., by site-specific mutagenesis, or by peptide synthesis. In a specific embodiment, in the CH3 domain of the first Fc domain the threonine residue at position 366 is replaced with a tryptophan residue (T366W), and in the CH3 domain of the second Fc domain the tyrosine residue at position 407 is replaced with a valine residue (Y407V). In another embodiment, in the second Fc domain additionally the threonine residue at position 366 is replaced with a serine residue (T366S) and the leucine residue at position 368 is replaced with an alanine residue (L368A).

In yet a further aspect, in the first Fc domain additionally the serine residue at position 354 is replaced with a cysteine residue (S354C), and in the second Fc domain additionally the tyrosine residue at position 349 is replaced by a cysteine residue (Y349C). Introduction of these two cysteine residues results in the formation of a disulfide bridge between the two Fc domains that further stabilizes the dimer (Carter (2001), J Immunol Methods 248, 7-15). In some embodiments, the first Fc domain comprises the amino acid substitutions S354C and T366W (EU numbering) and the second Fc domain comprises the amino acid substitutions Y349C, T366S, and Y407V (numbering according to Kabat EU index).

In some embodiments, a modification promoting association of the first and the second Fc domains comprises a modification mediating electrostatic steering effects, e.g. as described in PCT publication WO 2009/089004. Generally, this method involves replacement of one or more amino acid residues at the interface of the two Fc domains by charged amino acid residues so that homodimer formation becomes electrostatically unfavorable but heterodimerization electrostatically favorable.

In some embodiments, a binding agent comprises one or more scFvs or "single-chain variable fragments". An scFv is a fusion protein of the variable regions of the heavy (VH) and light chain (VL) variable regions of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. scFv antibodies are, e.g., described in Houston, J. S., Methods in Enzymol. 203 (1991) 46-96. Methods for making scFv molecules and designing suitable peptide linkers are described in, for example, U.S. Pat. Nos. 4,704,692; 4,946,778; Raag and Whitlow, FASEB 9:73-80 (1995) and Bird and Walker, TIBTECH, 9:132-137 (1991).

Binding agents that are scFv-Fcs have been described by Sokolowska-Wedzina et al., Mol. Cancer Res. 15 (8): 1040-1050, 2017.

In some embodiments, a binding agent is a "bispecific T cell engager" or BiTE (see, e.g., WO2004/106381, WO2005/061547, WO2007/042261, and WO2008/119567). This approach utilizes two antibody variable domains arranged on a single polypeptide. For example, a single polypeptide chain can include two single chain Fv (scFv) fragments, each having a variable heavy chain (VH) and a variable light chain (VL) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different proteins, such that both proteins are bound by the BiTE.

As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species. In some embodiments, a binding agent that is a bispecific antibody is composed of a single polypeptide chain comprising two single chain FV fragments (scFV) fused to each other by a peptide linker.

A single-domain antibody is an antibody fragment consisting of a single monomeric variable antibody domain. Single domains antibodies can be derived from the variable domain of the antibody heavy chain from camelids (e.g., NANOBODIES® or VHH fragments). Furthermore, the term single-domain antibody includes an autonomous human heavy chain variable domain (aVH) or VNAR fragments derived from sharks (see, e.g., Hasler et al., Mol. Immunol. 75:28-37, 2016).

Techniques for producing single domain antibodies (DABs or VHH) are known in the art, as disclosed for example in Cossins et al. (2006, Prot Express Purif 51:253-259 and Li et al., Immunol. Lett. 188:89-95, 2017). Single domain antibodies may be obtained, for example, from camels, alpacas or llamas by standard immunization techniques. (See, e.g., Muyldermans et al., TIBS 26:230-235, 2001; Yau et al., J Immunol Methods 281:161-75, 2003; and Maass et al., J Immunol Methods 324:13-25, 2007.) A VHH may have potent antigen-binding capacity and can interact with novel epitopes that are inaccessible to conventional VH-VL pairs (see, e.g., Muyldermans et al., 2001). Alpaca serum IgG contains about 50% camelid heavy chain only IgG antibodies (HCAbs) (see, e.g., Maass et al., 2007). Alpacas may be immunized with antigens and VHHs can be isolated that bind to and neutralize the target antigen (see, e.g., Maass et al., 2007). PCR primers that amplify alpaca VHH coding sequences have been identified and may be used to construct alpaca VHH phage display libraries, which can be used for antibody fragment isolation by standard biopanning techniques well known in the art (see, e.g., Maass et al., 2007).

In some embodiments, a binding agent is a IgG-scFV. IgG-scFv formats include IgG (H)-scFv, scFv-(H) IgG, IgG (L)-scFv, svFc-(L) IgG, 2scFV-IgG, and IgG-2scFv. These and other bispecific antibody formats and methods of making them have been described in for example, Brinkmann and Kontermann, MAbs 9 (2): 182-212 (2017); Wang et al., Antibodies, 2019, 8, 43; Dong et al., 2011, MAbs 3:273-88; Natsume et al., J. Biochem. 140 (3): 359-368, 2006; Cheal et al., Mol. Cancer Ther. 13 (7): 1803-1812, 2014; and Bates and Power, Antibodies, 2019, 8, 28.

Igg-like dual-variable domain antibodies (DVD-Ig) have been described by Wu et al., 2007, Nat Biotechnol 25:1290-97; Hasler et al., Mol. Immunol. 75:28-37, 2016 and in WO 08/024188 and WO 07/024715. Triomabs have been described by Chelius et al., MAbs 2 (3): 309-319, 2010. 2-in-1-IgGs have been described by Kontermann et al., Drug Discovery Today 20 (7): 838-847, 2015. Tanden antibody or TandAb have been described by Kontermann et al., id. ScFv-HSA-scFv antibodies have also been described by Kontermann et al. (id.).

In some embodiments, the binding agent is a scaffold antigen binding protein, such as for example, fibronectin and designed ankyrin repeat proteins (DARPins) which have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13:695-701 (2008). In some embodiments, a scaffold antigen binding protein is selected from the group consisting of Lipocalins (Anticalin), a Protein A-derived molecule such as Z-domain of Protein A (Affibody), an A-domain (Avimer/Maxibody), a serum transferrin (transbody); a designed ankyrin repeat protein (DARPin), a fibronectin (AdNectin), a C-type lectin domain (Tetranectin); a variable domain of a new antigen receptor beta-lactamase (VNAR fragments), a human gamma-crystallin or ubiquitin (Affilin molecules); a kunitz type domain of human protease inhibitors, and microbodies such as the proteins from the knottin family, peptide aptamers and fibronectin (adnectin).

Lipocalins are a family of extracellular proteins which transport small hydrophobic molecules such as steroids, bilins, retinoids, and lipids. They have a rigid beta-sheet secondary structure with a number of loops at the open end of the conical structure which can be engineered to bind to different target antigens. Anticalins are between 160-180 amino acids in size, and are derived from lipocalins. For further details, see Biochim Biophys Acta 1482:337-350 (2000), U.S. Pat. No. 7,250,297B1, and US20070224633.

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details, see J. Mol. Biol. 332, 489-503 (2003), PNAS 100 (4), 1700-1705 (2003) and J. Mol. Biol. 369, 1015-1028 (2007), and US20040132028A1.

Fc Domain Modifications to Alter Effector Function

In some embodiments, an Fc region or Fc domain has substantially no binding to at least one Fc receptor selected from FcγRI (CD64), FcγRIIA (CD32a), FcγRIIB (CD32b), FcγRIIIA (CD16a), and FcγRIIIB (CD16b). In some embodiments, an Fc region or domain exhibits substantially no binding to any of the Fc receptors selected from FcγRI (CD64), FcγRIIA (CD32a), FcγRIIB (CD32b), FcγRIIIA (CD16a), and FcγRIIIB (CD16b). As used herein, "substantially no binding" refers to weak to no binding to a selected Fcgamma receptor or receptors. In some embodiments, "substantially no binding" refers to a reduction in binding affinity (e.g., increase in Kd) to a Fc gamma receptor of at least 1000-fold. In some embodiments, an Fc domain or region is an Fc null. As used herein, an "Fc null" refers to an Fc region or Fc domain that exhibits weak to no binding to any of the Fcgamma receptors. In some embodiments, an Fc null domain or region exhibits a reduction in binding affinity (e.g., increase in Kd) to Fc gamma receptors of at least 1000-fold.

In some embodiments, an Fc domain has reduced or substantially no effector function activity. As used herein, "effector function activity" refers to antibody dependent cellular cytotoxicity (ADCC), antibody dependent cellular phagocytosis (ADCP) and/or complement dependent cytotoxicity (CDC). In some embodiments, an Fc domain exhibits reduced ADCC, ADCP, or CDC activity, as compared to a wildtype Fc domain. In some embodiments, an Fc domain exhibits a reduction in ADCC, ADCP, and CDC, as compared to a wildtype Fc domain. In some embodiments, an Fc domain exhibits substantially no effector function (i.e., the ability to stimulate ADCC, ADCP, or CDC). As used herein, "substantially no effector function" refers to a reduction in effector function activity of at least 1000-fold, as compared to a wildtype Fc domain.

In some embodiments, an Fc domain has reduced or no ADCC activity. As used herein reduced or no ADCC activity refers to a decrease in ADCC activity of an Fc domain by of a factor of at least 10, at least 20, at least 30, at least 50, at least 100, or at least 500.

In some embodiments, an Fc domain has reduced or no CDC activity. As used herein reduced or no CDC activity refers to a decrease in CDC activity of an Fc domain by of a factor of at least 10, at least 20, at least 30, at least 50, at least 100, or at least 500.

In vitro and/or in vivo cytotoxicity assays can be conducted to confirm the reduction/depletion of ADCC and/or CDC activity. For example, Fc receptor (FcR) binding assays can be conducted to ensure that the antibody lacks Fcgamma receptor (hence likely lacking ADCC activity). The primary cells for mediating ADCC, NK cells, express FcgammaRIII only, whereas monocytes express FcgammaRI, FcgammaRII, and FcgammaRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest are described in U.S. Pat. No. 5,500,362 (see, e.g., Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166: 1351-1361 (1987)). Alternatively, non-radioactive assays methods may be employed (see, e.g., ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc. Nat'l Acad. Sci. USA 95:652-656 (1998).

C1q binding assays may also be carried out to confirm that an antibody or Fc domain or region is unable to bind C1q and hence lacks CDC activity or has reduced CDC activity.

See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)).

In some embodiments, an Fc domain has reduced or no ADCP activity. As used herein reduced or no ADCP activity refers to a decrease in ADCP activity of an Fc domain by of a factor of at least 10, at least 20, at least 30, at least 50, at least 100, or at least 500.

ADCP binding assays may also be carried out to confirm that an antibody or Fc domain or region lacks ADCP activity or has reduced ADCP activity. See, e.g., US20190079077 and US20190048078 and the references disclosed therein.

Antibodies with reduced effector function activity include those with substitution of one or more of Fc region residues 238, 265, 269, 270, 297, 327, and 329 (see U.S. Pat. No. 6,737,056). Such Fc mutants include Fc mutants with substitutions at two or more of amino acid positions 265, 269, 270, 297, and 327, including the so-called "DANA" Fc mutant with substitution of residues 265 and 297 to alanine (see U.S. Pat. No. 7,332,581). Certain antibody variants with diminished binding to FcRs are also known. (See, e.g., U.S. Pat. No. 6,737,056; WO 2004/056312, and Shields et al., J. Biol. Chem. 9 (2): 6591-6604 (2001).)

In certain embodiments, a binding agent comprises an Fc domain or region with one or more amino acid substitutions which diminish FcgammaR binding, e.g., substitutions at positions 234 and 235 of the Fc region (EU numbering of residues). In some embodiments, the substitutions are L234A and L235A (LALA). In some embodiments, the Fc domain further comprises D265A and/or P329G in an Fc region derived from a human IgG1 Fc region. In some embodiments, the substitutions are L234A, L235A, and P329G (LALA-PG) in an Fc region derived from a human IgG1 Fc region. (See, e.g., WO 2012/130831). In some embodiments, the substitutions are L234A, L235A, and D265A (LALA-DA) in an Fc region derived from a human IgG1 Fc region.

In some embodiments, alterations are made in the Fc region that result in altered (i.e., either diminished) C1q binding and/or Complement Dependent Cytotoxicity (CDC), e.g., as described in U.S. Pat. No. 6,194,551, WO 99/51642, and Idusogie et al. J. Immunol. 164:4178-4184 (2000).

Modification of Binding Domains

In some embodiments, a binding domain may be modified by a conservative substitution or substitutions. For conservative amino acid substitutions, a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative amino acid substitutions, e.g., substitutions of entire regions having similar hydrophobicity characteristics, are well known. Polypeptides comprising conservative amino acid substitutions can be tested in any one of the assays described herein to confirm that a desired activity, e.g., antigen-binding activity and specificity of a native or reference polypeptide is retained.

For conservative substitutions, amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser(S), Thr (T), Cys (C), Tyr (Y), Asn (N), Gln (Q); (3) acidic: Asp (D), Glu (E); and (4) basic: Lys (K), Arg (R), His (H).

Alternatively, for conservative substitutions naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. Non-conservative substitutions will entail exchanging a member of one of these classes or another class.

Particular conservative substitutions include, for example; Ala to Gly or to Ser; Arg to Lys; Asn to Gln or to His; Asp to Glu; Cys to Ser; Gln to Asn; Glu to Asp; Gly to Ala or to Pro; His to Asn or to Gln; Ile to Leu or to Val; Leu to Ile or to Val; Lys to Arg, to Gln or to Glu; Met to Leu, to Tyr or to Ile; Phe to Met, to Leu or to Tyr; Ser to Thr; Thr to Ser; Trp to Tyr; Tyr to Trp; and/or Phe to Val, to Ile or to Leu.

In some embodiments, a conservatively modified variant of a binding domain preferably is at least 90%, at least 91%, at least 92%, at least 93%, at least 94%, at least 95%, at least 96%, at least 97%, at least 98%, at least 99%, or more, identical to the reference VH or VL sequence, wherein the VH and VL CDRs are not modified. The degree of homology (percent identity) between the reference and modified sequence can be determined, for example, by comparing the two sequences using freely available computer programs commonly employed for this purpose on the world wide web (e.g., BLASTp or BLASTn with default settings).

Modification of a native (or reference) amino acid sequence can be accomplished by any of a number of techniques known to one of skill in the art. Mutations can be introduced, for example, at particular sites by synthesizing oligonucleotides containing the desired mutant sequence, flanked by restriction sites enabling ligation to fragments of the native sequence. Following ligation, the resulting reconstructed sequence encodes a variant having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion desired. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

CD8+KIR+ Regulatory T Cells

The regulatory T cells are characterized by the phenotype of being CD8+KIR+ and are typically MHC Class I restricted. In humans, the CD8+Kir+ regulatory T cells express inhibitory KIR proteins. In some embodiments, the KIR proteins expressed by the cells can include one or more of the inhibitory KIR proteins, e.g., KIR2DL1, KIR2DL2, KIR2DL3, KIR2DL5, KIR3DL1, and KIR3DL2; and may specifically include one or more of KIR2DL2, KIR2DL3, and KIR3DL1. In some embodiments, the CD8+KIR+ regulatory T cells are not HLA E (Qa-1b) restricted. (See, e.g., Lohwasser et al., International Immunology 13:321-327 (2001) and Sarantopoulos et al., J. Clin. Invest. 114 (9): 1218-1221 (2004) for a general explanation of murine Qa-1b and human HLA E restriction.) In some embodiments, the CD8+KIR+ regulatory T cells can also be characterized as being CD44+, CD122+, and are not HLA E (Qa-1b) restricted. In some embodiments, the CD8+KIR+ regulatory T cells can also be characterized as being CD28−. In some embodiments, the CD8+KIR+ regulatory T cells can also be characterized as being CD28−, CD44+, and CD122+. In some embodiments, the CD8+KIR+ regulatory T cells can also be characterized as being CD28−, CD44+, and CD122+, and are not HLA E (Qa-1b) restricted.

In some embodiments, the CD8+KIR+ Tregs express the following antigens: CD3, CD8, PD-1, CD16, CD122, CD39, CXCR3, ICOS, CD103, and inhibitory KIR proteins.

In some embodiments, CD8+KIR+ Tregs express one or more of the following antigens: CD3, CD27, CD38, CD39, CD40L, CD45RA, CD45RB, CD45RO, CD73, CD103 (IT-GAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB. In some embodiments, CD8+KIR+ Tregs express one or more of the following antigens: CD3, CD5, CD16, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, KLRB1, KLRG1, LAG-3/CD223, NKG2C, NKG2D, OX-40, PD-1, S1000A8/9, TIM-3, TLT-2, 2B4, and 41BB. In some embodiments, CD8+KIR+ Tregs express one or more of the following antigens: CD39, KLRB1, KLRG1, NKG2C, NKG2D, CXCR3, and CD122.

Production of Binding Agents

In various embodiments, binding agents can be produced in human, murine, or other animal-derived cells lines. Recombinant DNA expression can be used to produce the binding agents. This allows the production of antibodies as well as a spectrum of antigen binding portions and other binding agents (including fusion proteins) in a host species of choice. The production of antibodies, antigen binding portions thereof and other binding agents in bacteria, yeast, transgenic animals, and chicken eggs are also alternatives for cell-based production systems. The main advantages of transgenic animals are potential high yields from renewable sources.

As used herein, the term "nucleic acid" or "nucleic acid sequence" or "polynucleotide sequence" or "nucleotide" refers to a polymeric molecule incorporating units of ribonucleic acid, deoxyribonucleic acid, or an analog thereof. The nucleic acid can be either single-stranded or double-stranded. A single-stranded nucleic acid can be one strand nucleic acid of a denatured double-stranded DNA. In some embodiments, the nucleic acid can be a cDNA, e.g., a nucleic acid lacking introns.

Nucleic acid molecules encoding the amino acid sequence of an antibody, or antigen binding portion thereof, as well as other binding agents can be prepared by a variety of methods known in the art. These methods include, but are not limited to, preparation of synthetic nucleotide sequences encoding of an antibody, antigen binding portion or other binding agent(s). In addition, oligonucleotide-mediated (or site-directed) mutagenesis, PCR-mediated mutagenesis, and cassette mutagenesis can be used to prepare nucleotide sequences encoding an antibody or antigen binding portion as well as other binding agents. A nucleic acid sequence encoding at least an antibody, antigen binding portion thereof, binding agent, or a polypeptide thereof, as described herein, can be recombined with vector DNA in accordance with conventional techniques, such as, for example, blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel et al., Current Protocols in Molecular Biology (John Wiley & Sons), 1987-1993, and can be used to construct nucleic acid sequences and vectors that encode an antibody or antigen binding portion thereof or a VH and/or VL polypeptide thereof. Where the binding agent comprises antibodies or antigen binding portions thereof, in some embodiments, a VH polypeptide is encoded by a first nucleic acid. In some embodiments, a VL polypeptide is encoded by a second nucleic acid. In some embodiments, the VH and VL polypeptides are encoded by one nucleic acid.

A nucleic acid molecule, such as DNA, is said to be "capable of expressing" a polypeptide if it contains nucleotide sequences that contain transcriptional and translational regulatory information and such sequences are "operably linked" to nucleotide sequences that encode the polypeptide. An operable linkage is a linkage in which the regulatory DNA sequences and the DNA sequence sought to be expressed (e.g., an antibody or antigen binding portion thereof) are connected in such a way as to permit gene expression of a polypeptide(s) or antigen binding portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an antibody or antigen-binding portion thereof or other binding agent as described herein can occur in either prokaryotic or eukaryotic cells. Suitable hosts include bacterial or eukaryotic hosts, including yeast, insects, fungi, bird, and mammalian cells either in vivo or in situ, or host cells of mammalian, insect, bird, or yeast origin. The mammalian cell or tissue can be of human, primate, hamster, rabbit, rodent, cow, pig, sheep, horse, goat, dog, or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or antigen binding portion thereof as described herein with a specified amino terminus sequence. Moreover, problems associated with retention of initiation codon-derived methionine residues in direct yeast (or bacterial) expression may be avoided. (See, e.g., Sabin et al., 7 Bio/Technol. 705 (1989); Miller et al., 7 Bio/Technol. 698 (1989).) Any of a series of yeast gene expression systems incorporating promoter and termination elements from the actively expressed genes coding for glycolytic enzymes produced in large quantities when yeast are grown in medium rich in glucose can be utilized to obtain recombinant antibodies or antigen-binding portions thereof or other binding agents. Known glycolytic genes can also provide very efficient transcriptional control signals. For example, the promoter and terminator signals of the phosphoglycerate kinase gene can be utilized.

Production of antibodies or antigen-binding portions thereof and other binding agents in insects can be achieved, for example, by infecting an insect host with a baculovirus engineered to express a polypeptide by methods known to those of ordinary skill in the art. See Ausubel et al., 1987-1993.

In some embodiments, the introduced nucleic acid sequence (encoding an antibody or antigen binding portion thereof or a polypeptide thereof or other binding agent) is incorporated into a plasmid or viral vector capable of autonomous replication in a recipient host cell. Any of a wide variety of vectors can be employed for this purpose and are known and available to those of ordinary skill in the art. See, e.g., Ausubel et al., 1987-1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Exemplary prokaryotic vectors known in the art include plasmids such as those capable of replication in *E. coli*. Other gene expression elements useful for the expression of DNA encoding antibodies or antigen-binding portions thereof and other binding agents include, but are not limited to (a) viral transcription promoters and their enhancer elements, such as the SV40 early promoter, (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983). Immunoglobulin-encoding DNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin encoding nucleotide sequences, the transcriptional promoter can be, for example, human cytomegalovirus, the promoter enhancers can be cytomegalovirus and mouse/human immunoglobulin.

In some embodiments, for expression of DNA coding regions in rodent cells, the transcriptional promoter can be a viral LTR sequence, the transcriptional promoter enhancers can be either or both the mouse immunoglobulin heavy chain enhancer and the viral LTR enhancer, and the polyadenylation and transcription termination regions. In other embodiments, DNA sequences encoding other proteins are combined with the above-recited expression elements to achieve expression of the proteins in mammalian cells.

Each coding region or gene fusion is assembled in, or inserted into, an expression vector. Recipient cells capable of expressing the variable region(s) or antigen binding portions thereof are then transfected singly with nucleotides encoding an antibody or an antibody polypeptide or antigen-binding portion thereof, or are co-transfected with a polynucleotide(s) encoding VH and a VL chain coding regions. The transfected recipient cells are cultured under conditions that permit expression of the incorporated coding regions and the expressed antibody chains or intact antibodies or antigen binding portions are recovered from the culture.

In some embodiments, the nucleic acids containing the coding regions encoding an antibody or antigen-binding portion thereof are assembled in separate expression vectors that are then used to co-transfect a recipient host cell. Each vector can contain one or more selectable genes. For example, in some embodiments, two selectable genes are used, a first selectable gene designed for selection in a bacterial system and a second selectable gene designed for selection in a eukaryotic system, wherein each vector has a set of coding regions. This strategy results in vectors which first direct the production, and permit amplification, of the nucleotide sequences in a bacterial system. The DNA vectors so produced and amplified in a bacterial host are subsequently used to co-transfect a eukaryotic cell, and allow selection of a co-transfected cell carrying the desired transfected nucleic acids (e.g., encoding antibody heavy and light chains). Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused nucleotide sequences encoding VH and VL chains can be assembled on the same expression vector.

For transfection of the expression vectors and production of the antibodies or antigen binding portions thereof or other binding agents, the recipient cell line can be a Chinese Hamster ovary cell line (e.g., DG44) or a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0. SP2/0 cells only produce immunoglobulins encoded by the transfected genes. Myeloma cells can be grown in culture or in the peritoneal cavity of a mouse, where secreted immunoglobulin can be obtained from ascites fluid.

An expression vector encoding an antibody or antigen-binding portion thereof or other binding agent can be introduced into an appropriate host cell by any of a variety of suitable means, including such biochemical means as transformation, transfection, protoplast fusion, calcium phosphate-precipitation, and application with polycations such as diethylaminoethyl (DEAE) dextran, and such mechanical means as electroporation, direct microinjection and microprojectile bombardment. Johnston et al., 240 Science 1538 (1988), as known to one of ordinary skill in the art.

Yeast provides certain advantages over bacteria for the production of immunoglobulin heavy and light chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes polypeptides bearing leader sequences (i.e., pre-polypeptides). See, e.g., Hitzman et al., 11th Intl. Conf. Yeast, Genetics & Molec. Biol. (Montpelier, France, 1982).

Yeast gene expression systems can be routinely evaluated for the levels of production, secretion and the stability of antibodies, and assembled antibodies and antigen binding portions thereof. Various yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. Another example is the translational elongation factor 1alpha promoter. A number of approaches can be taken for evaluating optimal expression plasmids for the expression of immunoglobulins in yeast. See II DNA Cloning 45, (Glover, ed., IRL Press, 1985) and e.g., U.S. Publication No. US 2006/0270045 A1.

Bacterial strains can also be utilized as hosts for the production of the antibody molecules or antigen binding portions thereof or other binding agents described herein. *E. coli* K12 strains such as *E. coli* W3110, *Bacillus* species, enterobacteria such as *Salmonella typhimurium* or *Serratia marcescens*, and various *Pseudomonas* species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of antibodies and antigen binding portions thereof in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin molecules including leader peptide removal, folding and assembly of VH and VL chains, glycosylation of the antibody molecules, and secretion of functional antibody and/or antigen binding portions thereof.

Mammalian cells which can be useful as hosts for the production of antibody proteins, in addition to the cells of lymphoid origin described above, include cells of fibroblast origin, such as Vero or CHO-K1 cells. Exemplary eukaryotic cells that can be used to express immunoglobulin polypeptides include, but are not limited to, COS cells, including COS 7 cells; 293 cells, including 293-6E cells; CHO cells, including CHO-S, CHO-K1, and DG44 cells; PERC6™ cells (Crucell); and NS0 cells. In some embodiments, a particular eukaryotic host cell is selected based on its ability to make desired post-translational modifications to the heavy chains and/or light chains. For example, in some embodiments, CHO cells produce polypeptides that have a higher level of sialylation than the same polypeptide produced in 293 cells.

In some embodiments, one or more antibodies or antigen-binding portions thereof or other binding agents can be produced in vivo in an animal that has been engineered or transfected with one or more nucleic acid molecules encoding the polypeptides, according to any suitable method.

In some embodiments, an antibody or antigen-binding portion thereof is produced in a cell-free system. Non-limiting exemplary cell-free systems are described, e.g., in Sitaraman et al., Methods Mol. Biol. 498:229-44 (2009); Spirin, Trends Biotechnol. 22:538-45 (2004); and Endo et al., Biotechnol. Adv. 21:695-713 (2003).

Many vector systems are available for the expression of the VH and VL chains in mammalian cells (see Glover, 1985). Various approaches can be followed to obtain intact antibodies. As discussed above, it is possible to co-express VH and VL chains and optionally the associated constant regions in the same cells to achieve intracellular association and linkage of VH and VL chains into complete tetrameric $H_2L_2$ antibodies or antigen-binding portions thereof. The co-expression can occur by using either the same or different plasmids in the same host. Nucleic acids encoding the VH and VL chains or antigen binding portions thereof can be placed into the same plasmid, which is then transfected into cells, thereby selecting directly for cells that express both chains. Alternatively, cells can be transfected first with a plasmid encoding one chain, for example the VL chain, followed by transfection of the resulting cell line with a VH chain plasmid containing a second selectable marker. Cell lines producing antibodies, antigen-binding portions thereof or other binding agents via either route could be transfected with plasmids encoding additional copies of peptides, VH, VL, or VH plus VL chains in conjunction with additional selectable markers to generate cell lines with enhanced properties, such as higher production of assembled antibodies or antigen binding portions thereof or enhanced stability of the transfected cell lines.

Additionally, plants have emerged as a convenient, safe, and economical alternative expression system for recombinant antibody production, which are based on large scale culture of microbes or animal cells. Antibodies or antigen binding portions can be expressed in plant cell culture, or plants grown conventionally. The expression in plants may be systemic, limited to sub-cellular plastids, or limited to seeds (endosperms). See, e.g., U.S. Patent Pub. No. 2003/0167531; U.S. Pat. Nos. 6,080,560; 6,512,162; and WO 0129242. Several plant-derived antibodies have reached advanced stages of development, including clinical trials (see, e.g., Biolex, N.C.).

For intact antibodies, the variable regions (VH and VL) of the antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (see, e.g., WO 87/02671; which is incorporated by reference herein in its entirety). An antibody can contain both light chain and heavy chain constant regions. The heavy chain constant region can include CH1, hinge, CH2, CH3, and, sometimes, CH4 regions. In some embodiments, the CH2 domain can be deleted or omitted.

Alternatively, techniques described for the production of single chain antibodies (see, e.g., U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989); which are incorporated by reference herein in their entireties) can be adapted to produce single chain antibodies that specifically bind to the desired antigen. Single chain antibodies are formed by linking the heavy and light chain variable regions of the Fv region via an amino acid bridge, resulting in a single chain polypeptide. Techniques for the assembly of functional Fv fragments in *E. coli* can also be used (see, e.g., Skerra et al., Science 242:1038-1041 (1988); which is incorporated by reference herein in its entirety). Method of making other binding agents are described supra.

Intact (e.g., whole) antibodies, their dimers, individual light and heavy chains, or antigen binding portions thereof can be recovered and purified by known techniques, e.g., immunoadsorption or immunoaffinity chromatography, chromatographic methods such as HPLC (high performance liquid chromatography), ammonium sulfate precipitation, gel electrophoresis, or any combination of these. See generally, Scopes, Protein Purification (Springer-Verlag, N.Y., 1982). Substantially pure antibodies or antigen binding portions thereof of at least about 90% to 95% homogeneity are advantageous, as are those with 98% to 99% or more homogeneity, particularly for pharmaceutical uses. Once purified, partially or to homogeneity as desired, an intact antibody or antigen binding portions thereof can then be used therapeutically or in developing and performing assay procedures, immunofluorescent staining, and the like. See generally, Vols. I & II Immunol. Meth. (Lefkovits & Pernis, eds., Acad. Press, NY, 1979 and 1981).

Pharmaceutical Formulations

In some aspects the binding agents relate to compositions comprising active ingredients (i.e., including a binding agent as described herein or a nucleic acid encoding an antibody or antigen-binding portion thereof or other binding agent as described herein). In some embodiments, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on any particular formulation. Typically such compositions are prepared as injectable either as liquid solutions or suspensions; however, solid forms suitable for rehydration, or suspensions, in liquid prior to use can also be prepared. A preparation can also be emulsified or presented as a liposome composition. An antibody or antigen binding portion thereof or other binding agent can be mixed with excipients that are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, a pharmaceutical composition can contain minor amounts of auxiliary substances such as wetting or emulsifying agents, pH buffering agents and the like which enhance or maintain the effectiveness of the active ingredient (e.g., an antibody or antigen binding portion thereof or other binding agent). The pharmaceutical compositions as described herein can include pharmaceutically acceptable salts of the components therein. Pharmaceutically acceptable salts include the acid addition salts (formed with the free amino groups of a polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Physiologically tolerable carriers are well known in the art. Exemplary liquid carriers are sterile aqueous solutions that contain the active ingredients (e.g., an antibody and/or antigen binding portions thereof or other binding agent) and water, and may contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent that will be effective in the treatment of a particular disorder or condition will depend on the nature of the disorder or condition, and can be determined by standard clinical techniques.

In some embodiments, a pharmaceutical composition comprising an antibody or antigen-binding portion thereof or other binding agent or a nucleic acid encoding an antibody or antigen-binding portion thereof or other binding agent as described herein can be a lyophilisate.

In some embodiments, a syringe comprising a therapeutically effective amount of a binding agent, or a pharmaceutical composition described herein is provided.

Treatment of Inflammatory and Autoimmune Disease

In some aspects, the binding agents as described herein can be used in a method(s) comprising administering a binding agent or a pharmaceutical composition as described herein to a subject having an inflammatory disease. In some aspects, the binding agents as described herein can be used in a method(s) comprising administering a binding agent or a pharmaceutical composition as described herein to a subject having an autoimmune disease or having an immune response to an autoantigen or having an immune response to an antigen that causes or results in the onset of an autoimmune disorder (which may be collectively referred to as an autoimmune disease herein). In some embodiments, the subject is in need of treatment for an autoimmune disease. In some embodiments, provided are methods of treating an autoimmune disease, comprising administering any of the binding agents described herein or the pharmaceutical compositions described herein to a subject in need thereof in an amount effective to decrease the number or activity of pathogenic immune cells in the subject and thereby ameliorate a symptom of the autoimmune disease. In some embodiments, provided are methods for suppressing an immune response mediated by pathogenic immune cells, comprising contacting CD8+KIR+ T regulatory cells (Tregs) with any of the binding agents as described herein or the pharmaceutical compositions as described herein in an amount effective to activate or stimulate the CD8+KIR+ Tregs (activated Tregs), whereby the number or activity of pathogenic immune cells is decreased. In some embodiments, provided are methods for suppressing an immune response to an autoantigen, comprising administering to a subject in need thereof any of the binding agents described herein or the pharmaceutical compositions described herein in an amount effective to activate or stimulate CD8+KIR+ Tregs, whereby the number or activity of pathogenic immune cells that are responsive to the autoantigen is decreased. In some embodiments, provided are methods for preventing an immune response to an autoantigen that causes or results in the onset of an autoimmune disorder, comprising administering to a subject in need thereof any of the binding agents described herein or the pharmaceutical compositions described herein in an amount effective to activate or stimulate CD8+KIR+ Tregs, whereby the number or activity of pathogenic immune cells that are responsive to the autoantigen is decreased or the titer of autoantibodies is decreased in the subject. In some embodiments, provided are methods for suppressing an immune response to an autoantigen, that causes or results in the onset of an autoimmune disorder, comprising administering to a subject in need thereof any of the binding agents described herein or the pharmaceutical compositions described herein in an amount effective to activate or stimulate CD8+KIR+ Tregs, whereby the number or activity of pathogenic immune cells that are responsive to the autoantigen is decreased or the titer of autoantibodies is decreased in the subject. In some embodiments, provided are methods for suppressing an immune response to an antigen or autoantigen that causes or results in the onset of an autoimmune disorder, comprising administering to a subject in need thereof any of the binding agents described herein or the pharmaceutical compositions described herein in an amount effective to activate or stimulate CD8+KIR+ Tregs, whereby the immune response to the antigen or autoantigen is decreased or suppressed in the subject.

As used herein, the term "autoantigen" refers to an antigen (e.g., a cell surface protein or other antigen) that is normally recognized by the immune system (e.g., a healthy human immune system) as self. An antigen or autoantigen becomes the target of a humoral or cell mediated immune response in an autoimmune disease or condition or it triggers an excessive immune response (collectively "autoimmune disease"). As used herein, to "activate or stimulate" CD8+KIR+ Tregs, or activated CD8+KIR+ Tregs, refer to an increase of the regulatory T cell functions of such cells, such as the ability to suppress an immune response, and in particular an immune response to an autoantigen or to suppressing an immune response to an autoantigen that causes or results in the onset of an autoimmune disorder. Activation or stimulation of CD8+KIR+ Tregs may include removal of a suppressive effect on such cells, so as to restore the CD8+KIR+ Tregs (e.g., restore balance to the immune system or restore balanced immune activity in a subject or in the subject needing treatment prior to the onset of disease). Activation or stimulation of CD8+KIR+ Tregs may also include removal of CD4+ cells, B cells, or other cells mediating an immune response, such as by elimination, for example, cytolysis, of such cells.

As used herein, pathogenic immune cells refer to immune cells that are reactive with an autoantigen or that induce a response to an autoantigen. Examples of such pathogenic immune cells include autoreactive CD4+ T cells, autoantibody producing B cells, self antigen presenting dendritic cells, and other self antigen presenting cells, as are known in the art.

In some embodiments, the CD8+KIR+ Tregs are contacted with the binding agent in vivo. In some embodiments, the CD8+KIR+ Tregs are contacted with the binding agent ex vivo. The activated CD8+KIR+ Tregs can then be administered in an effective amount to a subject in need thereof.

In some embodiments, the activated CD8+KIR+ Tregs exert a suppressive effect on pathogenic immune cells, such as autoreactive CD4+ T cells, autoantibody producing B cells, self antigen presenting dendritic cells, or self antigen presenting cells. In some embodiments, the activated CD8+KIR+ Tregs exert a suppressive effect on pathogenic immune cells, such as autoreactive CD4+ T cells, autoantibody producing B cells, and self antigen presenting dendritic cells. In some embodiments, the activated CD8+KIR+ Tregs deplete pathogenic immune cells, such as autoreactive CD4+ T cells, autoantibody producing B cells, and self antigen presenting dendritic cells. In some embodiments, the activated CD8+KIR+ Tregs modulate the pathogenic effect of pathogenic immune cells and decrease the titer of autoantibodies in the subject. In some embodiments, the activated CD8+KIR+ Tregs decrease the titer of autoantibodies in the subject.

In some embodiments, the binding agent is selected from any of the binding agents described herein, in each case that has reduced effector function activity or has substantially no effector function activity. In some embodiments, the reduced effector function activity is reduced or no ADCC, ADCP, or CDC effector function activity. In some embodiments, having substantially no effector function activity means having substantially no ADCC, ADCP, and CDC effector function activity. In some embodiments, a binding agent lacks an Fc domain or region and has reduced effector function or substantially no effector function. In some embodiments, a binding agent has an Fc domain or region with reduced effector function or substantially no effector function due to amino acid substitutions in the Fc domain or region. In some embodiments, a binding agent has an Fc domain or region with reduced effector function or substantially no effector function due to amino acid substitutions in the Fc domain or region, such as Fc null substitutions. In some embodiments, a binding agent lacks an Fc domain or region or has an Fc domain or region with reduced binding to one or more Fcgamma receptors or is an Fc null domain. In some embodiments, a binding agent lacks an Fc domain or region. In some embodiments, a binding agent has an Fc domain or region with reduced binding to one or more Fcgamma receptors or is an Fc null domain. In some embodiments, a binding agent has an Fc domain or region with reduced binding to one or more Fcgamma receptors due to amino acid substitutions in the Fc domain or region.

Without intending to be bound by any particular theory, the reduction or absence of effector function activity by a binding agent may limit the interaction of the binding agent with other cell types (i.e., non-CD8+KIR+ Tregs) and/or limit depletion of the CD8+KIR+ Tregs bound by the binding agent.

In some embodiments, the subject in need of treatment has an autoimmune disease. In some embodiments, the subject in need of treatment has an autoimmune disease, such as for example, autoimmune-induced hepatitis, Addison's Disease, Alopecia Areata, Alport's Syndrome, Ankylosing Spondylitis, Anti-phospholipid Syndrome, Arthritis, Ascariasis, Aspergillosis Atopic Allergy, Atopic Dermatitis, Atopic Rhinitis, Autoimmune Hemolytic Anemia, Autoimmune Hepatitis, Autoimmune Myositis, Behcet's Disease, Bird-Fancier's Lung, Bronchial Asthma, Caplan's Syndrome, Cardiomyopathy, Celiac Disease, Chagas' Disease, Chronic Glomerulonephritis, Chronic Graft versus Host Disease, Cogan's Syndrome, Cold Agglutinin Disease, CREST Syndrome, Crohn's Disease, Cryoglobulinemia, Cushing's Syndrome, Dermatomyositis, Discoid Lupus, Dressier's Syndrome, Eaton-Lambert Syndrome, Encephalomyelitis, Endocrine ophthalmopathy, Erythematosus, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease (Syndrome), Hashimoto's Thyroiditis, Hemolytic Anemia, Henoch-Schonlein Purpura, Hyperviscosity Syndrome, Idiopathic Adrenal Atrophy, Idiopathic Pulmonary Fibrosis, Idiopathic Thrombocytopenia Purpura, IgA Nephropathy, Inflammatory Bowel Disease (Syndrome), Insulin-Dependent Diabetes Mellitus (IDDM or Type I), Juvenile Arthritis, Juvenile Idiopathic Arthritis, Juvenile Diabetes Mellitus (Type I), Lambert-Eaton Syndrome Laminitis, Lichen Planus, Lupoid Hepatitis, Lupus, Lupus Nephritis, Lymphopenia, Macroglobulinemia, Meniere's Disease, Mixed Connective Tissue Disease, Monoclonal Gammopathy of Undermined Origin, Multiple Sclerosis, Myasthenia Gravis, Myocarditis, Pemphigus/Pemphigoid, Pernicious Anemia, POEMS syndrome, Polyglandular Syndromes, Polyarteritis Nodosa, Polymyositis, Presenile Dementia, Primary Agammaglobulinemia, Primary Biliary Cirrhosis/Cholangitis, Psoriasis, Psoriatic Arthritis, Raynauds Phenomenon, Reiter's Syndrome, Rheumatic Fever, Rheumatoid Arthritis, Sampter's Syndrome, Schmidt's Syndrome, Scleroderma/Systemic Sclerosis, Shulman's Syndrome, Sjörgen's Syndrome, Stiff-Man Syndrome, Sympathetic Ophthalmia, Systemic Lupus Erythematosus, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulinemia, and/or Wegener's Granulomatosis.

In some embodiments the autoimmune disease is autoimmune hepatitis, celiac disease, Crohn's disease, juvenile idiopathic arthritis, inflammatory bowel disease (IBD), insulin-dependent diabetes mellitus (IDDM or type 1 diabetes), lupus nephritis, myasthenia gravis, myocarditis, multiple sclerosis (MS), pemphigus/pemphigoid, primary biliary cirrhosis/cholangitis, rheumatoid arthritis (RA), scleroderma/systemic sclerosis, Sjögren's syndrome (SjS), systemic lupus erythematosus (SLE), or ulcerative colitis.

In some embodiments, the autoimmune disease is selected from autoimmune hepatitis, celiac disease, Crohn's disease, inflammatory bowel disease (IBD), insulin-dependent diabetes mellitus (IDDM or type 1 diabetes), multiple sclerosis (MS), rheumatoid arthritis (RA), systemic lupus erythematosus (SLE), or ulcerative colitis.

The methods described herein include administering a therapeutically effective amount of a binding agent to a subject having an autoimmune disease. As used herein, the phrases "therapeutically effective amount", "amount effective", "effective amount", and "effective dose" may refer to an amount of the binding agent as described herein that provides a therapeutic benefit in the treatment of, management of, prevention of relapse, delay of, or prevention of onset of an autoimmune disease, e.g., an amount that provides a statistically significant decrease in at least one symptom, sign, or marker of an autoimmune disease. Determination of a therapeutically effective amount is well within the capability of those skilled in the art. Generally, a therapeutically effective amount can vary with the subject's history, age, condition, and sex, as well as the severity and type of the medical condition in the subject, and administration of other pharmaceutically active agents.

It is contemplated that the methods herein reduce symptoms, pathology, disease progression, or disease flares in a subject. As used herein, a "subject" refers to a human or animal. Usually the animal is a vertebrate such as a primate, rodent, domestic animal, or game animal. Primates include chimpanzees, cynomolgus monkeys, spider monkeys, and macaques, e.g., Rhesus. Rodents include mice, rats, woodchucks, ferrets, rabbits, and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments, the subject is a mammal, e.g., a primate, e.g., a human. The terms, "patient", "individual", and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used, for example, as subjects that represent animal models of, for example, various autoimmune diseases. In addition, the methods described herein can be used to treat domesticated animals and/or pets. A subject can be male or female. In certain embodiments, the subject is a human.

A subject can be one who has been previously diagnosed with or identified as suffering from an autoimmune disease and in need of treatment, but need not have already undergone treatment for the autoimmune disease. Alternatively, a subject can also be one who has not been previously diagnosed as having an autoimmune disease in need of treatment. A subject can be one who exhibits one or more risk factors for a condition or one or more complications related to an autoimmune disease who does not exhibit risk factors. A "subject in need" of treatment for an autoimmune disease can be a subject having that disease or diagnosed as having that disease. In some embodiments, the subject is in need of treatment if the subject is at risk for developing an immune response to an antigen or autoantigen that may cause or result in the onset of an autoimmune disorder. In other embodiments, a subject "at risk of developing" an autoimmune disease refers to a subject diagnosed as being at risk for developing the disease or condition.

As used herein, the terms "treat", "treatment", "treating", or "amelioration" when used in reference to a disease, disorder, or medical condition (e.g., autoimmune disease), refer to therapeutic treatments for a condition, wherein the object is to reverse, alleviate, ameliorate, inhibit, slow down, or stop the progression or severity of a symptom or condition. The term "treating" includes reducing or alleviating at least one adverse effect or symptom of a condition or disease. Treatment is generally "effective" if one or more symptoms or clinical markers are reduced. Alternatively, treatment is "effective" if the progression of a condition is reduced or halted. That is, "treatment" may include not just the improvement of symptoms or markers, but also a cessation or at least slowing of progress or worsening of symptoms that would be expected in the absence of treatment. Beneficial or desired clinical results include, but are not limited to, reduction in one or more symptoms, reducing disease flares in the subject, alleviation of one or more symptom(s), diminishment of extent of the deficit, stabilized (i.e., not worsening) state of an autoimmune disease, or a prevention, delay, or slowing of onset or progression of the autoimmune disease. As used herein, the term "administering" refers to contacting a binding agent as described herein or a nucleic acid encoding the binding agent as described herein (e.g., by administration to a subject) by a method or route which results in binding of the binding agent to the CD8+KIR+ Tregs. Similarly, a pharmaceutical composition comprising a binding agent as described herein or a nucleic acid encoding the binding agent as described herein disclosed herein can be administered by any appropriate route which results in an effective treatment in the subject.

The dosage ranges for a binding agent depend upon the potency, and encompass amounts large enough to produce the desired effect, e.g., reduction in one or more symptoms, reducing disease flares in the subject, alleviation of one or more symptom(s), diminishment of extent of the deficit, stabilized (i.e., not worsening) state of an autoimmune disease, or a prevention, delay, or slowing of onset or progression of the autoimmune disease. The dosage should not be so large as to cause unacceptable adverse side effects. Generally, the dosage will vary with the age, condition, and sex of the subject and can be determined by one of skill in the art. The dosage can also be adjusted by the individual physician in the event of any complication. In some embodiments, the dosage ranges from about 0.01 mg/kg body weight to about 20 mg/kg body weight. In some embodiments, the dosage ranges from about 0.5 mg/kg body weight to about 15 mg/kg body weight. In some embodiments, the dose range is from about 0.5 mg/kg body weight to about 5 mg/kg body weight. Alternatively, the dose range can be titrated to maintain serum levels between 1 μg/mL and 1000 μg/mL.

In some embodiments, a subject receives a single dose of any of the binding agents described herein, such as for treatment of an acute autoimmune disease or condition. In some embodiments, a subject receives a single dose of any of the binding agents described herein, such as for prevention of an immune response that may lead to an autoimmune disease or condition. In some embodiments, a subject receives repeated doses of any of the binding agents described herein, such as for treatment of a chronic autoimmune disease or condition. In some embodiments, a subject receives repeated doses of any of the binding agents described herein, such as for prevention of an immune response that may lead to an autoimmune disease or condition. In some embodiments, the doses are administered weekly, biweekly, every three weeks, monthly, bi-monthly, or every 6 months for several weeks, months, or years. The duration of treatment depends upon the subject's clinical progress and responsiveness to treatment.

In some embodiments, a dose can be administered intravenously. In some embodiments, an intravenous administration can be an infusion occurring over a period of from about 10 minutes to about 4 hours. In some embodiments, an intravenous administration can be an infusion occurring over a period of from about 30 minutes to about 90 minutes. In some embodiments, a dose can be administered subcutaneously.

Pharmaceutical compositions containing any of the binding agents described herein can be administered in a unit dose. The term "unit dose" when used in reference to a pharmaceutical composition refers to physically discrete units suitable as unitary dosage for the subject, each unit containing a predetermined quantity of active material (e.g., a binding agent), calculated to produce the desired therapeutic effect in association with the required physiologically acceptable diluent, i.e., carrier, or vehicle.

In some embodiments, administration of any of the binding agents described herein can result in an improved treatment outcome, such as reduced systemic inflammatory cytokines, reduced pathology in tissues impacted by disease, reduced flare frequency and/or severity, reduced self reporting of symptoms associated with disease, alleviation of one or more symptom(s), and/or prevention, delay, or slowing of onset or progression of the autoimmune disease.

In some embodiments, a binding agent or a pharmaceutical composition of any of the binding agents described herein, is administered with an immunotherapy. As used herein, "immunotherapy" refers to therapeutic strategies designed to modulate the subject's own immune system. Examples of an immunotherapy include, but are not limited to, antibodies such as check point inhibitors and modulators and immunosuppressive agents, such as cyclosporine, cyclosporine A, mycophenylate mofetil, sirolimus, tacrolimus, etanercept, prednisone, azathioprine, methotrexate cyclophosphamide, prednisone, aminocaproic acid, chloroquine, hydroxychloroquine, hydrocortisone, dexamethasone, chlorambucil, DHEA, danazol, bromocriptine, meloxicam, infliximab, abatacept, belatacept, and adalimumab.

Treatment of Transplant Complications

In some embodiments, provided are methods of treating complications of a transplant associated with graft versus host disease or GVHD. In some embodiments, provided are methods for reducing complications of GVHD in a subject, comprising administering a binding agent or a pharmaceutical composition as described herein to a subject who has received a transplant to suppress a host immune response to the transplant. In some embodiments, provided are methods for reducing complications of GVHD in a subject, comprising administering a binding agent or a pharmaceutical composition as described herein to a subject who has received a transplant to suppress an immune response associated with the transplant. In some embodiments, provided are methods of reducing GVHD comprising administering a binding agent or a pharmaceutical composition as described herein to a subject who has received a transplant and is experiencing GVHD, whereby a symptom of GVHD is reduced. In some embodiments, provided are methods of suppressing GVHD comprising administering a binding agent or a pharmaceutical composition as described herein to a subject who has received a transplant and is experiencing GVHD, whereby GVHD is suppressed or reduced. In some embodiments, provided are methods of suppressing or reducing GVHD comprising contacting a binding agent or a pharmaceutical composition as described herein with CD8+KIR+ T regulatory cells (Tregs) from a subject who has received a transplant, whereby the CD8+KIR+ T regulatory cells (Tregs) are activated. In some embodiments, provided are methods of suppressing or reducing GVHD comprising contacting a binding agent or a pharmaceutical composition as described herein with CD8+KIR+ T regulatory cells (Tregs) from a subject who has received a transplant, whereby the CD8+KIR+ T regulatory cells (Tregs) of the transplant are depleted. In some embodiments, provided are methods of suppressing or reducing GVHD comprising contacting a binding agent or a pharmaceutical composition as described herein with CD8+KIR+ T regulatory cells (Tregs) from a subject who has received a transplant, whereby the CD8+KIR+ T regulatory cells (Tregs) are depleted.

In some embodiments, the subject has received a hematopoietic stem cell transplant, an umbilical cord blood stem cell transplant, an inducible pluripotent stem cell-derived progenitor or differentiated cell transplant, a bone marrow transplant or a solid organ transplant. The transplant is typically an allogeneic transplant. In some embodiments, the subject has received a hematopoietic stem cell transplant, an umbilical cord blood stem cell transplant, an inducible pluripotent stem cell-derived progenitor or differentiated cell transplant, a bone marrow transplant or a solid organ transplant and is experiencing GVHD. In some embodiments, the subject has received a hematopoietic stem cell transplant, an umbilical cord blood stem cell transplant, an inducible pluripotent stem cell-derived progenitor or differentiated cell transplant, a bone marrow transplant or a solid organ transplant and is at risk of experiencing GVHD. In some embodiments, the subject has received a hematopoietic stem cell transplant and is experiencing GVHD. In some embodiments, the subject has received a hematopoietic stem cell transplant and is at risk of experiencing GVHD. In some embodiments, the subject has received an umbilical cord blood stem cell transplant and is experiencing GVHD. In some embodiments, the subject has received an umbilical cord blood stem cell transplant and is at risk of experiencing GVHD. In some embodiments, the subject has received an inducible pluripotent stem cell-derived progenitor or differentiated cell transplant and is experiencing GVHD. In some embodiments, the subject has received an inducible pluripotent stem cell-derived progenitor or differentiated cell transplant and is at risk of experiencing GVHD. In some embodiments, the subject has received a bone marrow transplant and is experiencing GVHD. In some embodiments, the subject has received a bone marrow transplant and is at risk of experiencing GVHD. In some embodiments, the subject has received a solid organ transplant and is experiencing GVHD. In some embodiments, the subject has received a solid organ transplant and is at risk of experiencing GVHD.

In some embodiments, GVHD is suppressed or reduced by depletion of pathogenic immune cells, such as CD4 T cells. In some embodiments, GVHD is suppressed or reduced by depletion of pathogenic immune cells, such as CD8+KIR+ Tregs from the transplant. In some embodiments, the CD8+KIR+ Tregs are contacted with the binding agent in vivo. In some embodiments, the CD8+KIR+ Tregs are contacted with the binding agent ex vivo. The activated CD8+KIR+ Tregs can then be administered in an effective amount to a subject in need thereof.

In some embodiments, the binding agent is selected from any of the binding agents described herein, in each case that has reduced effector function activity or has substantially no effector function activity. In some embodiments, the reduced effector function activity is reduced or no ADCC, ADCP, or CDC effector function activity. In some embodiments, having substantially no effector function activity means having substantially no ADCC, ADCP, and CDC effector function activity. In some embodiments, a binding agent lacks an Fc domain or region and has reduced effector function or substantially no effector function. In some embodiments, a binding agent has an Fc domain or region with reduced effector function or substantially no effector function due to amino acid substitutions in the Fc domain or region. In some embodiments, a binding agent has an Fc domain or region with reduced effector function or substantially no effector function due to amino acid substitutions in the Fc domain or region, such as Fc null substitutions. In some embodiments, a binding agent lacks an Fc domain or region or has an Fc domain or region with reduced binding to one or more Fcgamma receptors or is an Fc null domain. In some embodiments, a binding agent lacks an Fc domain or region. In some embodiments, a binding agent has an Fc domain or region with reduced binding to one or more Fcgamma receptors or is an Fc null domain. In some embodiments, a binding agent has an Fc domain or region with reduced binding to one or more Fcgamma receptors due to amino acid substitutions in the Fc domain or region.

In some embodiments, the binding agent is selected from any of the binding agents described herein, in each case that has effector function activity comprising at least ADCC. In some embodiments, the effector function activity is ADCC in combination with ADCP and/or CDC effector function activity. In some embodiments, having effector function activity means having ADCC, ADCP, and CDC effector function activity. In various embodiments, such a binding agent has an Fc domain or has an Fc domain that binds to one or more Fcgamma receptors.

Without intending to be bound by any particular theory, the reduction or absence of effector function activity by a binding agent may limit the interaction of the binding agent with other cell types (i.e., non CD8+KIR+ Tregs) and/or limits depletion of the CD8+KIR+ Tregs. In contrast, the presence of effector function activity by a binding agent is believed to bias the immune response towards depletion of CD8+KIR+ Tregs.

In some embodiments, the transplant is a stem cell transplant, a bone marrow transplant or a solid organ transplant. As used herein, the term "transplant" mean refers to an organ, tissue, or cell that has been transplanted from one subject to a different subject, or transplanted within the same subject (e.g., to a different area within the subject). Organs such as liver, kidney, heart, or lung, or other body parts, such as bone or skeletal matrix such as bone marrow, tissue, such as skin, cornea, intestines, endocrine glands, or stem cells or various types, or hematopoietic cells including hematopoietic stem and progenitor cells, umbilical cord blood stem cells and inducible pluripotent stem cell-derived progenitor or differentiated cells, are all examples of transplants. In some embodiments, the solid organ transplant is a liver, kidney, lung, pancreas, and/or heart transplant. The term transplant includes a graft. The transplant can be an allograft (or allogeneic graft) or xenograft. The term "allograft" refers to a graft between two genetically non-identical members of a species. The term "xenograft" refers to a graft between members of different species.

In some embodiments, the transplant is a bone marrow transplant. In some embodiments, the transplant is a hematopoietic stem cell transplant. In some embodiments, the transplant is an umbilical cord blood stem cell transplant. In some embodiments, the transplant is an inducible pluripotent stem cell-derived progenitor or differentiated cell transplant.

In some embodiments, the subject has graft versus host disease or GVHD. In some embodiments, the subject is at risk of having GVHD.

The methods described herein include administering a therapeutically effective amount of a binding agent to a subject receiving a transplant. As used herein, the phrases "therapeutically effective amount", "amount effective", "effective amount", and "effective dose" may refer to an amount of the binding agent as described herein that provides a therapeutic benefit in the management of GVHD associated with a transplant. In some embodiments, the therapeutic benefit is delay of or prevention of onset of a GVHD. In some embodiments, the therapeutic benefit is a statistically significant decrease in at least one symptom, sign, or marker of GVHD. Determination of a therapeutically effective amount is well within the capability of those skilled in the art. Generally, a therapeutically effective amount can vary with the subject's history, age, condition, and sex, as well as the severity and type of the medical condition in the subject, and administration of other pharmaceutically active agents.

It is contemplated that the methods herein reduce symptoms of, reduce, or prevent GVHD in a subject who has received a transplant. As used herein, a "subject" refers to a human or animal. Usually the animal is a vertebrate such as a primate, rodent, domestic animal, or game animal. Primates include chimpanzees, cynomolgus monkeys, spider monkeys, and macaques, e.g., Rhesus. Rodents include mice, rats, woodchucks, ferrets, rabbits, and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish, and salmon. In certain embodiments, the subject is a mammal, e.g., a primate, e.g., a human. The terms, "patient", "individual", and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used, for example, as subjects that represent animal models of, for example, various autoimmune diseases. In addition, the methods described herein can be used to treat domesticated animals, and/or pets. A subject can be male or female. In certain embodiments, the subject is a human.

A subject can be one who will receive a transplant. Alternatively, a subject can be one who has already received a transplant. A subject can be one who will receive a transplant and is at risk of GVHD. A subject can be one who has received a transplant and is at risk of having GVHD. A subject can be one who has received a transplant and has GVHD.

As used herein, the terms "treat", "treatment", "treating", or "amelioration" when used in reference to a disease, disorder, or medical condition (e.g., GVHD), refer to therapeutic treatments for a condition, wherein the object is to reverse, alleviate, ameliorate, inhibit, slow down, or stop the progression or severity of a symptom or condition of GVHD. The term "treating" includes reducing or alleviating at least one adverse effect or symptom of a condition or disease. Treatment is generally "effective" if one or more symptoms or clinical markers are reduced. Alternatively, treatment is "effective" if the progression of a condition is reduced or halted. That is, "treatment" may include not just the improvement of symptoms or markers, but also a cessation or at least slowing of progress or worsening of symptoms that would be expected in the absence of treatment. Beneficial or desired clinical results include, but are not limited to, reduction in one or more symptoms associated with GVHD.

As used herein, the term "administering" refers to contacting a binding agent as described herein or a nucleic acid encoding the binding agent as described herein (e.g., by administration to a subject) by a method or route which results in binding of the binding agent to the CD8+KIR+ Tregs. Similarly, a pharmaceutical composition comprising a binding agent as described herein or a nucleic acid encoding the binding agent as described herein disclosed herein can be administered by any appropriate route which results in an effective treatment in the subject.

The dosage ranges for a binding agent depend upon the potency, and encompass amounts large enough to produce the desired effect, e.g., reduction in one or more symptoms of GVHD or reducing or preventing GVHD. The dosage should not be so large as to cause unacceptable adverse side effects. Generally, the dosage will vary with the age, condition, and sex of the subject and can be determined by one of skill in the art. The dosage can also be adjusted by the individual physician in the event of any complication. In some embodiments, the dosage ranges from about 0.01 mg/kg body weight to about 20 mg/kg body weight. In some embodiments, the dosage ranges from about 0.5 mg/kg body weight to about 15 mg/kg body weight. In some embodiments, the dose range is from about 0.5 mg/kg body weight to about 5 mg/kg body weight. Alternatively, the dose range can be titrated to maintain serum levels between 1 µg/mL and 1000 µg/mL.

In some embodiments, a subject receives a single dose of any of the binding agents described herein, such as for treatment of acute GVHD following a transplant. In some embodiments, a subject receives repeated doses of any of the binding agents described herein, such as for treatment of a chronic GVHD. In some embodiments, the doses are administered weekly, biweekly, every three weeks, monthly, bimonthly, or every 6 months for several weeks, months, or years. The duration of treatment depends upon the subject's clinical progress and responsiveness to treatment.

In some embodiments, a dose can be administered intravenously. In some embodiments, an intravenous administration can be an infusion occurring over a period of from about 10 minutes to about 4 hours. In some embodiments, an intravenous administration can be an infusion occurring over a period of from about 30 minutes to about 90 minutes. In some embodiments, a dose can be administered subcutaneously.

Pharmaceutical compositions containing any of the binding agents described herein can be administered in a unit dose. The term "unit dose" when used in reference to a pharmaceutical composition refers to physically discrete units suitable as unitary dosage for the subject, each unit containing a predetermined quantity of active material (e.g., a binding agent), calculated to produce the desired therapeutic effect in association with the required physiologically acceptable diluent, i.e., carrier, or vehicle.

In some embodiments, administration of any of the binding agents described herein can result in an improved treatment outcome, such as reduced systemic inflammatory cytokines, reduced pathology in tissues impacted by disease, reduced self reporting of symptoms associated with an immune response associated with adverse effects on host tissues, improved or extended transplant engraftment, alleviation of one or more symptom(s), and/or prevention, delay, or slowing of onset or progression of rejection of the transplant, or extended transplant engraftment with decreased use of broad spectrum immunosuppressive agents, such as corticosteroids.

In some embodiments, a binding agent or a pharmaceutical composition of any of the binding agents described herein, is administered with an immunosuppressive agent, such as a corticosteroid(s).

Treatment of Infectious Disease

In some aspects, the binding agents as described herein can be used in a method(s) comprising administering a binding agent or pharmaceutical composition as described herein to a subject having an infection. In some embodiments, the subject is in need of treatment for an infection. In some embodiments, provided is a method of treating an infection by administering any of the binding agents or pharmaceutical compositions described herein to a subject in need thereof in an amount effective to activate or stimulate CD8+KIR+ Tregs and thereby ameliorate a symptom of the infection. In some embodiments, the method comprises stimulating an immune response against an infectious agent by contacting CD8+KIR+ T regulatory cells (Tregs) with any of the binding agents or pharmaceutical compositions described herein in an amount effective to activate or stimulate CD8+KIR+ Tregs (activated Tregs), whereby the immune response against an infectious agent is stimulated. In some embodiments, the method comprises stimulating an immune response against a cell(s) infected with an infectious agent by contacting CD8+KIR+ T regulatory cells (Tregs) with any of the binding agents or pharmaceutical compositions described herein in an amount effective to activate or stimulate CD8+KIR+ Tregs (activated Tregs), whereby infected cells are depleted. In some embodiments, the method comprises stimulating an immune response against a cell infected with an infectious agent by contacting CD8+KIR+ T regulatory cells (Tregs) with any of the binding agents or pharmaceutical compositions described herein in an amount effective to activate or stimulate CD8+ KIR+ Tregs (activated Tregs), whereby the immune response against the infected cell is stimulated.

In some embodiments of the methods of treating infection, the CD8+KIR+ Tregs are contacted with any of the binding agents described herein in vivo. In some embodiments, the CD8+KIR+ Tregs are contacted with any of the binding agents described herein ex vivo. The activated CD8+KIR+ Tregs are subsequently administered in an effective amount to a subject in need thereof. In some embodiments, the immune response comprises a reduction in immune suppressive immune cells. As used herein, immune suppressive immune cells include CD4 Tregs and tolerizing DCs. In some embodiments, the number of infected cells in the subject is decreased.

In some embodiments, the binding agent is selected from any of the binding agents described herein, in each case that has reduced effector function activity or has substantially no effector function activity. In some embodiments, the reduced effector function activity is reduced or no ADCC, ADCP, or CDC effector function activity. In some embodiments, having substantially no effector function activity means having substantially no ADCC, ADCP, and CDC effector function activity. In some embodiments, a binding agent lacks an Fc domain or region and has reduced effector function or substantially no effector function. In some embodiments, a binding agent has an Fc domain or region with reduced effector function or substantially no effector function due to amino acid substitutions in the Fc domain or region. In some embodiments, a binding agent has an Fc domain or region with reduced effector function or substantially no effector function due to amino acid substitutions in the Fc domain or region, such as Fc null substitutions. In some embodiments, a binding agent lacks an Fc domain or region or has an Fc domain or region with reduced binding to one or more Fcgamma receptors or is an Fc null domain. In some embodiments, a binding agent lacks an Fc domain or region. In some embodiments, a binding agent has an Fc domain or region with reduced binding to one or more Fcgamma receptors or is an Fc null domain. In some embodiments, a binding agent has an Fc domain or region with reduced binding to one or more Fcgamma receptors due to amino acid substitutions in the Fc domain or region.

Without intending to be bound by any particular theory, the reduction or absence of effector function activity by a binding agent may limit the interaction of the binding agent with other cell types (i.e., non-CD8+KIR+ Tregs) and/or limits depletion of the CD8+KIR+ Tregs bound by the binding agent.

In some embodiments, the subject is in need of treatment for an infectious disease or is infected with an infectious agent, such as for example, a bacterial disease, a systemic fungal disease, rickettsial disease, a parasitic disease, or a viral disease. In some embodiments, the infection is a bacterial disease, such as Diphtheria, Pertussis, Occult Bacteremia, Urinary Tract Infection, Gastroenteritis, Cellulitis, Epiglottitis, Tracheitis, Adenoid Hypertrophy, Retropharyngeal Abscess, Impetigo, Ecthyma, Pneumonia, Endocarditis, Septic Arthritis, Pneumococcal Pneumonia, Peritonitis, Bacteremia, Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, *Salmonella*, Typhoid Fever, Dysentery, Conjunctivitis, Sinusitis, Brucellosis Tularemia, Cholera, Bubonic Plague, Tetanus, Necrotizing Enteritis, Actinomycosis, Mixed Anaerobic Infections, Syphilis, Relapsing Fever, Leptospirosis, Lyme Disease, Rat Bite Fever, Tuberculosis, including *Mycobacterium tuberculosis*, Lymphadenitis, Leprosy, *Chlamydia*, Chlamydial Pneumonia, Trachoma, or Inclusion Conjunctivitis; a systemic fungal disease such as Histoplasmosis, Coccicidoidomycosis, Blastomycosis, Sporotrichosis, Cryptococcosis, Systemic Candidiasis, Aspergillosis, Mucormycosis, Mycetoma, or Chromomycosis; a rickettsial disease, such as Typhus, Rocky Mountain Spotted Fever Ehrlichiosis, Eastern Tick-Borne Rickettsioses, Rickettsialpox, Q Fever, or Bartonellosis; a parasitic disease such as Malaria, Babesiosis, African Sleeping Sickness, Chagas' Disease, Leishmaniasis, Dum-Dum Fever, Toxoplasmosis Meningoencephalitis, Keratitis, Dientamebiasis, Giardiasis, Cryptosporidiosis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic Filariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease, and Alveolar Hydatid Disease; and Viral Disease such as Measles, Subacute sclerosing panencephalitis, Common Cold, Mumps, Rubella, Roseola, Fifth Disease, Chickenpox, Coronavirus Infection, Covid19 Disease, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis Myocarditis, Echovirus Infection, Epstein-Barr Virus Pericarditis, Gastroenteritis, Hepatitis A infection, Hepatitis B infection, Hepatitis C infection, HIV infection, human papillomavirus (HPV) infection, Reye's Syndrome, Kawasaki Syndrome, Influenza, Bronchitis, Viral "Walking" Pneumonia, Acute Febrile Respiratory Disease, Acute pharyngoconjunctival fever, Epidemic keratoconjunctivitis, Herpes Simplex Virus 1 (HSV-1) infection, Herpes Simples Virus 2 (HSV-2) infection, Shingles, Cytomegalic inclusion Disease, Rabies, Progressive Multifocal Leukoencephalopathy, Kuru, Fatal Familial Insomnia, Creutzfeldt-Jakob Disease, Gerstmann-Sfraussler-Scheinker Disease, Tropical Spastic Paraparesis, Western Equine Encephalitis, California Encephalitis, St. Louis Encephalitis, Yellow Fever, Dengue, Lymphocytic choriomeningitis, Lassa Fever, Hemorrhagic Fever, Hantavirus Pulmonary Syndrome, Marburg Virus Infections, Ebola Virus Infections, and Smallpox.

In some embodiments, the infection is a viral infection. In some embodiments, the infection is a viral infection, such as an HIV infection, Hepatitis A infection, Hepatitis B infection, Hepatitis C infection, an Epstein Bar Virus infection, a coronavirus infection such as a SARS-COV2 infection (Covid-19), and flu virus infection (influenza). In some embodiments, an infection is cause by an infectious agent, such as a coronavirus, diphtheria, ebola, flu (influenza), HIV, human papillomavirus (HPV), Hepatitis A, Hepatitis B, Hepatitis C, measles virus, respiratory syncytial virus, rotavirus, and herpes virus.

The methods described herein include administering a therapeutically effective amount of a binding agent to a subject having an infection or having cells infected by an infectious agent. As used herein, the phrases "therapeutically effective amount", "amount effective", "effective amount", or "effective dose" may refer to an amount of any of the binding agents or pharmaceutical compositions as described herein that provide a therapeutic benefit in the treatment of, management of or prevention of relapse of an infectious disease, e.g., an amount that provides a statistically significant decrease in at least one symptom, sign, or marker of an infection. Determination of a therapeutically effective amount is well within the capability of those skilled in the art. Generally, a therapeutically effective amount can vary with the subject's history, age, condition, and sex, as well as the severity and type of the medical condition in the subject, and administration of other pharmaceutically active agents.

As used herein, a "subject" refers to a human or animal. Usually the animal is a vertebrate such as a primate, rodent, domestic animal, or game animal. Primates include chimpanzees, cynomolgus monkeys, spider monkeys, and macaques, e.g., Rhesus. Rodents include mice, rats, woodchucks, ferrets, rabbits, and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish, and salmon. In certain embodiments, the subject is a mammal, e.g., a primate, e.g., a human. The terms, "patient", "individual", and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used, for example, as subjects that represent animal models of, for example, various infections. In addition, the methods described herein can be used to treat domesticated animals and/or pets. A subject can be male or female. In certain embodiments, the subject is a human.

A subject can be one who has been previously diagnosed with or identified as suffering from an infection and in need of treatment, but need not have already undergone treatment for the infection. Alternatively, a subject can also be one who has not been previously diagnosed as having an infection, but is in need of treatment. A subject can be one who exhibits one or more risk factors for a condition or one or more complications related to an infection or a subject who does not exhibit such risk factors. A "subject in need" of treatment for an infection can be a subject having that infection or diagnosed as having that infection. In other embodiments, a subject "at risk of developing" an infection refers to a subject diagnosed as being at risk for developing the infection.

As used herein, the terms "treat", "treatment", "treating", or "amelioration" when used in reference to a disease, disorder, or medical condition (e.g., an infection), refer to therapeutic treatments for a condition, wherein the object is to reverse, alleviate, ameliorate, inhibit, prevent, slow down, or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, reduction in infected cells in the subject, alleviation of one or more symptom(s), diminishment of extent of the deficit, stabilized (i.e., not worsening) state of the infection, or a delay or slowing of the infection or progression of the infection as compared to that expected in the absence of treatment. As used herein, the term "administering" refers to providing a binding agent as described herein or a nucleic acid encoding the binding agent as described herein into contact (e.g., by administration to a subject) by a method or route which results in binding to the binding agent to the CD8+KIR+ Tregs. Similarly, a pharmaceutical composition comprising a binding agent as described herein or a nucleic acid encoding the binding agent as described herein disclosed herein can be administered by any appropriate route which results in an effective treatment in the subject.

The dosage ranges for a binding agent depend upon the potency, and encompass amounts large enough to produce the desired effect, e.g., stimulation of an immune response against infected cells, reducing the number of infected cells, or slow or preventing progression of the infection. The dosage should not be so large as to cause unacceptable adverse side effects. Generally, the dosage will vary with the age, condition, and sex of the subject and can be determined by one of skill in the art. The dosage can also be adjusted by the individual physician in the event of any complication. In some embodiments, the dosage ranges from about 0.01 mg/kg body weight to about 20 mg/kg body weight. In some embodiments, the dosage ranges from about 0.01 mg/kg body weight to about 10 mg/kg body weight. In some embodiments, the dosage ranges from about 0.1 mg/kg body weight to about 10 mg/kg body weight. In some embodiments, the dosage ranges from about 0.5 mg/kg body weight to about 10 mg/kg body weight. In some embodiments, the dose range is from about 0.5 mg/kg body weight to about 5 mg/kg body weight. Alternatively, the dose range can be titrated to maintain serum levels between 1 μg/mL and 1000 μg/mL.

In some embodiments, a subject receives a single dose of any of the binding agents or pharmaceutical compositions as described herein, such as for treatment of an acute infection. In some embodiments, a subject receives a single dose of any of the binding agents or pharmaceutical compositions as described herein, such as for prevention of an immune response to an infection that may lead to an autoimmune disease or condition. In some embodiments, a subject receives repeated doses of any of the binding agents or pharmaceutical compositions as described herein, such as for treatment of a chronic infection. In some embodiments, the doses are administered weekly, biweekly, every three weeks, monthly, bi-monthly, or every 6 months for several weeks, months, or years. The duration of treatment depends upon the subject's clinical progress and responsiveness to treatment.

In some embodiments, a dose can be administered intravenously. In some embodiments, an intravenous administration can be an infusion occurring over a period of from about 10 minutes to about 4 hours. In some embodiments, an intravenous administration can be an infusion occurring over a period of from about 30 minutes to about 90 minutes. In some embodiments, a dose can be administered subcutaneously.

In some embodiments, a total of from about 2 to about 10 doses are administered to a subject. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, a total of 9 doses are administered. In some embodiments, a total of 10 doses are administered. In some embodiments, a total of more than 10 doses are administered.

Pharmaceutical compositions containing a binding agent can be administered in a unit dose. The term "unit dose" when used in reference to a pharmaceutical composition refers to physically discrete units suitable as unitary dosage for the subject, each unit containing a predetermined quantity of active material (e.g., binding agent), calculated to produce the desired therapeutic effect in association with the required physiologically acceptable diluent, i.e., carrier, or vehicle.

In some embodiments, administration of any of the binding agents described herein can result in an improved treatment outcome such as amelioration of clinical symptoms, or reduction of viral load, or elimination or reduction of pathogen or reduction in infected cells.

In some embodiments, a binding agent or a pharmaceutical composition of any of the embodiments described herein is administered with an infectious disease control agent, such as an anti-bacterial, anti-fungal, or an antiviral agent. Antibacterial gents can be, for example, Lactam Antibiotics, such as Penicillin G, Penicillin V, Cloxacillin, Dicloxacillin, Methicillin, Nafcillin, Oxacillin, Ampicillin, Amoxicillin, Bacampicillin, Azlocillin, Carbenicillin, Mezlocillin, Piperacillin or Ticarcillin; Aminoglycosides such as Amikacin, Gentamicin, Kanamycin, Neomycin, Netilmicin, Streptomycin, or Tobramycin; Macrolides such as Azithromycin, Clarithromycin, Erythromycin, Lincomycin or Clindamycin; Tetracyclines such as Demeclocycline, Doxycycline, Minocycline, Oxytetracycline or Tetracycline; Quinolones such as Cinoxacin or Nalidixic Acid; Fluoroquinolones such as Ciprofloxacin, Enoxacin, Grepafloxacin, Levofloxacin, Lomefloxacin, Norfloxacin, Ofloxacin, Sparfloxacin, or Trovafloxacin; Polypeptides such as Bacitracin, Colistin or Polymyxin B; Sulfonamides such as Sulfisoxazole, Sulfamethoxazole, Sulfadiazine, Sulfamethizole, or Sulfacetamide; and other Antibacterial Agents such as Trimethoprim, Sulfamethazole, Chloramphenicol, Vancomycin, Metronidazole, Quinupristin, Dalfopristin, Rifampin, Spectinomycin, or Nitrofurantoin; and Antiviral Agents, such as for example, General Antiviral Agents such as Idoxuridine, Vidarabine, Trifluridine, Acyclovir, Famciclovir, Penciclovir, Valacyclovir, Ganciclovir, Foscarnet, Ribavirin, Amantadine, Rimantadine, or Cidofovir; Antisense Oligonucleotides; Immunoglobulins; Interferons; and other drugs, such as Zidovudine, Didanosine, Zalcitabine, Stavudine, Lamivudine, Nevirapine, Delavirdine, Saquinavir, Oseltamivir and Peramivir, Ritonavir, Indinavir, or Nelfinavir.

Treatment of Cancer

In some aspects, the binding agents or pharmaceutical compositions as described herein can be used in a method(s) for the treatment of cancer comprising administering a binding agent or pharmaceutical compositions as described herein to a subject in need thereof. In some embodiments, provided are methods of treating cancer, comprising administering any of the binding agents described herein or any of the pharmaceutical compositions described herein, wherein the binding agent has substantially no effector function activity, to a subject in need thereof in an amount effective to activate or stimulate CD8+KIR+ Tregs and thereby ameliorate a symptom of the cancer. In some embodiments, provided are methods of stimulating an immune response against an antigen associated with a cancer (cancer antigen; e.g., an antigen expressed on a cancer cell), comprising contacting CD8+KIR+ T regulatory cells (Tregs) with any of the binding agents described herein or any of the pharmaceutical compositions described herein, wherein the binding agent has substantially no effector function activity, in an amount effective to activate or stimulate CD8+KIR+ Tregs (activated Tregs), whereby the immune response to the cancer antigen is increased.

In some embodiments, the binding agent is selected from any of the binding agents described herein, in each case that has reduced effector function activity or has substantially no effector function activity. In some embodiments, the reduced effector function activity is reduced or no ADCC, ADCP, or CDC effector function activity. In some embodiments, having substantially no effector function activity means having substantially no ADCC, ADCP, and CDC effector function activity. In some embodiments, a binding agent lacks an Fc domain or region and has reduced effector function or substantially no effector function. In some embodiments, a binding agent has an Fc domain or region with reduced effector function or substantially no effector function due to amino acid substitutions in the Fc domain or region. In some embodiments, a binding agent has an Fc domain or region with reduced effector function or substantially no effector function due to amino acid substitutions in the Fc domain or region, such as Fc null substitutions. In some embodiments, a binding agent lacks an Fc domain or region or has an Fc domain or region with reduced binding to one or more Fcgamma receptors or is an Fc null domain. In some embodiments, a binding agent lacks an Fc domain or region. In some embodiments, a binding agent has an Fc domain or region with reduced binding to one or more Fcgamma receptors or is an Fc null domain. In some embodiments, a binding agent has an Fc domain or region with reduced binding to one or more Fcgamma receptors due to amino acid substitutions in the Fc domain or region.

In some embodiments, provided are methods of treating cancer, comprising administering any of the binding agents described herein or any of the pharmaceutical compositions described herein, wherein the binding agent has effector function activity comprising at least ADCC, to a subject in need thereof in an amount effective to deplete CD8+KIR+ Tregs and thereby ameliorate a symptom of the cancer. In some embodiments, provided are methods of stimulating an immune response against a cancer, comprising contacting CD8+KIR+ T regulatory cells (Tregs) with any of the binding agents described herein or any of the pharmaceutical compositions described herein, wherein the binding agent has effector function activity comprising at least ADCC, in an amount effective to deplete CD8+KIR+ Tregs, whereby the immune response to the cancer is increased. In some embodiments, provided are methods of stimulating an immune response against an antigen associated with a cancer (cancer antigen), comprising contacting CD8+KIR+ T regulatory cells (Tregs) with any of the binding agents described herein or any of the pharmaceutical compositions described herein, wherein the binding agent has effector function activity comprising at least ADCC, in an amount effective to deplete CD8+KIR+ Tregs, whereby the immune response to the cancer antigen is increased.

In some embodiments, the binding agent is selected from any of the binding agents described herein, in each case that has effector function activity comprising at least ADCC. In some embodiments, the effector function activity is ADCC in combination with ADCP and/or CDC effector function activity. In some embodiments, having effector function activity means having ADCC, ADCP, and CDC effector function activity. In various embodiments, such a binding agent has an Fc domain or has an Fc domain that binds to one or more Fcgamma receptors.

In some embodiments, wherein the CD8+KIR+ Tregs are contacted with the binding agent in vivo. In some embodiments, the CD8+KIR+ Tregs are contacted with the binding agent ex vivo. In some embodiments, the activated CD8+KIR+ Tregs are administered in an effective amount to a subject in need thereof.

Without intending to be bound by any particular theory, the reduction or absence of effector function activity by a binding agent may limit the interaction of the binding agent with other cell types (i.e., non CD8+KIR+ Tregs) and/or limits depletion of the CD8+KIR+ Tregs. In contrast, the presence of effector function activity by a binding agent is believed to bias the immune response towards depletion of CD8+KIR+ Tregs.

In some embodiments, an increased immune response comprises a reduction in cancer cells or depletion of immune suppressive immune cells. In this context, immune suppressive immune cells refers to, for example, tumor associated macrophages, CD4+ Tregs, and/or tolerizing dendritic cells (DCs). In some embodiments, the number of cancer cells in the subject is decreased. In some embodiments, the number of immune suppressive immune cells in the subject is decreased.

The terms "cancer" and "malignancy" refer to an uncontrolled growth of cells which interferes with the normal functioning of the bodily organs and systems. A cancer or malignancy may be primary or metastatic, i.e., it has become invasive, seeding tumor growth in tissues remote from the original tumor site. A "tumor" refers to an uncontrolled growth of cells which interferes with the normal functioning of the bodily organs and systems. As used herein, the term cancer includes malignancies and tumors, unless otherwise indicated by context. A subject that has a cancer is a subject having objectively measurable cancer cells present in the subject's body. Included in this definition are benign tumors and malignant cancers, as well as potentially dormant tumors and micro-metastases. Cancers that migrate from their original location and seed other vital organs can eventually lead to the death of the subject through the functional deterioration of the affected organs. Hematologic malignancies (hematopoietic cancers), such as leukemias and lymphomas, are able to for example out-compete the normal hematopoietic compartments in a subject, thereby leading to hematopoietic failure (in the form of anemia, thrombocytopenia and neutropenia) ultimately causing death.

Examples of cancers include, but are not limited to, carcinomas, lymphomas, blastomas, sarcomas, myelomas, and leukemias. More particular examples of such cancers include, but are not limited to, basal cell carcinoma, biliary tract cancer, bladder cancer, bone cancer, brain and CNS cancer, breast cancer (e.g., triple negative breast cancer), cancer of the peritoneum, cervical cancer; cholangiocarcinoma, choriocarcinoma, chondrosarcoma, colon and rectum cancer (colorectal cancer), connective tissue cancer, cancer of the digestive system, endometrial cancer, esophageal cancer, eye cancer, cancer of the head and neck, gastric cancer (including gastrointestinal cancer and stomach cancer), glioblastoma (GBM), hepatic carcinoma, hepatoma, intra-epithelial neoplasm, kidney or renal cancer (e.g., clear cell kidney cancer or non-clear cell kidney cancer), larynx cancer, leukemia, liver cancer, lung cancer (e.g., small-cell lung cancer, non-small cell lung cancer, adenocarcinoma of the lung, and squamous carcinoma of the lung), lymphoma including Hodgkin's and non-Hodgkin's lymphoma, melanoma, mesothelioma, myelomas, neuroblastoma, oral cavity cancer (e.g., lip, tongue, mouth, and pharynx), ovarian cancer, pancreatic cancer, prostate cancer, retinoblastoma, rhabdomyosarcoma, cancer of the respiratory system, salivary gland carcinoma, sarcoma, skin cancer, squamous cell cancer, testicular cancer, thyroid cancer, uterine or endometrial cancer, uterine serious carcinoma, cancer of the urinary system, vulval cancer; as well as other carcinomas and sarcomas, as well as B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia), chronic lymphocytic leukemia (CLL), acute lymphoblastic leukemia (ALL), Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome; and myelomas, such as multiple myeloma.

In some embodiments, the cancer is selected from a solid tumor, including but not limited to, hepatocellular carcinoma, lung carcinoma such as small cell lung cancer and large cell lung cancer, colorectal carcinoma, esophageal carcinoma, cervical carcinoma, ovarian carcinoma, renal cell carcinoma, prostate carcinoma, and bladder carcinoma.

The methods described herein include administering a therapeutically effective amount of a binding agent or a pharmaceutical composition as described herein to a subject having a cancer or malignancy. As used herein, the phrases "therapeutically effective amount", "effective amount" "amount effective", or "effective dose" may refer to an amount of the binding agent or pharmaceutical composition as described herein that provides a therapeutic benefit in the treatment of, management of, or prevention of relapse of a cancer or malignancy, e.g., an amount that provides a statistically significant decrease in at least one symptom, sign, or marker of a cancer, tumor, or malignancy. Determination of a therapeutically effective amount is well within the capability of those skilled in the art. Generally, a therapeutically effective amount can vary with the subject's history, age, condition, and sex, as well as the severity and type of the medical condition in the subject, and administration of other pharmaceutically active agents.

In some embodiments, the methods described herein reduce tumor size or tumor burden in the subject, and/or reduce metastasis in the subject. In various embodiments, tumor size in the subject is decreased by about 25-50%, about 40-70%, or about 50-90% or more. In various embodiments, the methods reduce the tumor size by 10%, 20%, 30%, or more. In various embodiments, the methods reduce tumor size by 10%, 15%, 20%, 25%, 30%, 35%, 40%, 45%, 50%, 55%, 60%, 65%, 70%, 75%, 80%, 85%, 90%, 95%, or 100%.

As used herein, a "subject" refers to a human or animal. Usually the animal is a vertebrate such as a primate, rodent, domestic animal, or game animal. Primates include chimpanzees, cynomolgus monkeys, spider monkeys, and macaques, e.g., Rhesus. Rodents include mice, rats, woodchucks, ferrets, rabbits, and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish, and salmon. In certain embodiments, the subject is a mammal, e.g., a primate, e.g., a human. The terms, "patient", "individual", and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used, for example, as subjects that represent animal models of, for example, various cancers. In addition, the methods described herein can be used to treat domesticated animals and/or pets. A subject can be male or female. In certain embodiments, the subject is a human.

A subject can be one who has been previously diagnosed with or identified as suffering from a cancer and in need of treatment, but need not have already undergone treatment for the cancer. Alternatively, a subject can also be one who has not been previously diagnosed as having a cancer in need of treatment. A subject can be one who exhibits one or more risk factors for a condition or one or more complications related to a cancer or a subject who does not exhibit risk factors. A "subject in need" of treatment for a particular cancer can be a subject having that condition or diagnosed as having that condition. In other embodiments, a subject "at risk of developing" a condition refers to a subject diagnosed as being at risk for developing the condition.

As used herein, the terms "treat", "treatment", "treating", or "amelioration" when used in reference to a disease, disorder, or medical condition (e.g., a cancer), refer to therapeutic treatments for a condition, wherein the object is to reverse, alleviate, ameliorate, inhibit, slow down, or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, reduction in cancer cells in the subject, alleviation of one or more symptom(s), diminishment of extent of the deficit, stabilized (i.e., not worsening) state of a cancer or malignancy, delay, or slowing of tumor growth and/or metastasis, and an increased lifespan as compared to that expected in the absence of treatment. As used herein, the term "administering" refers to contacting a binding agent or pharmaceutical composition as described herein or a nucleic acid encoding the binding agent as described herein (e.g., by administration to a subject) by a method or route which results in binding to the binding agent to the CD8+KIR+ Tregs. Similarly, a pharmaceutical composition comprising a binding agent as described herein or a nucleic acid encoding the binding agent as described herein disclosed herein can be administered by any appropriate route which results in an effective treatment in the subject.

The dosage ranges for a binding agent depend upon the potency, and encompass amounts large enough to produce the desired effect, e.g., slowing of tumor growth or a reduction in tumor size. The dosage should not be so large as to cause unacceptable adverse side effects. Generally, the dosage will vary with the age, condition, and sex of the subject and can be determined by one of skill in the art. The dosage can also be adjusted by the individual physician in the event of any complication. In some embodiments, the dosage ranges from about 0.01 mg/kg body weight to about 20 mg/kg body weight. In some embodiments, the dosage ranges from about 0.01 mg/kg body weight to about 10 mg/kg body weight. In some embodiments, the dosage ranges from about 0.1 mg/kg body weight to about 10 mg/kg body weight. In some embodiments, the dosage ranges from about 0.5 mg/kg body weight to about 10 mg/kg body weight. In some embodiments, the dose range is from about 0.5 mg/kg body weight to about 5 mg/kg body weight. Alternatively, the dose range can be titrated to maintain serum levels between 1 µg/mL and 1000 µg/mL.

Administration of the doses recited above can be repeated. In a preferred embodiment, the doses recited above are administered weekly, biweekly, every three weeks, or monthly for several weeks or months. The duration of treatment depends upon the subject's clinical progress and responsiveness to treatment.

In some embodiments, a dose can be administered intravenously. In some embodiments, an intravenous administration can be an infusion occurring over a period of from about 10 minutes to about 4 hours. In some embodiments, an intravenous administration can be an infusion occurring over a period of from about 30 minutes to about 90 minutes. In some embodiments, a dose can be administered subcutaneously.

Pharmaceutical compositions containing a binding agent can be administered in a unit dose. The term "unit dose" when used in reference to a pharmaceutical composition refers to physically discrete units suitable as unitary dosage for the subject, each unit containing a predetermined quantity of active material (e.g., binding agent), calculated to produce the desired therapeutic effect in association with the required physiologically acceptable diluent, i.e., carrier, or vehicle.

In some embodiments, administration of any of the binding agents described herein can result in an improved treatment outcome as an objective response selected from stable disease, a partial response, or a complete response as determined by standard medical criteria for the cancer being treated. In some embodiments, the improved treatment outcome is reduced tumor burden. In some embodiments, the improved treatment outcome is progression-free survival or disease-free survival.

In some embodiments, a binding agent or a pharmaceutical composition of any of the embodiments described herein is administered with an immunotherapy or a chemotherapy. As used herein, "immunotherapy" refers to therapeutic strategies designed to induce or augment the subject's own immune system to fight the cancer or malignancy. Examples of an immunotherapy include, but are not limited to, antibodies such as check point inhibitors. In some embodiments, the chemotherapy is, for example, alkylating agents, such as for example, Nitrogen mustards such as cyclophosphamide, Ifosfamide, trofosfamide, or Chlorambucil; Nitrosoureas such as carmustine (BCNU) and Lomustine (CCNU); Alkylsulphonates such as busulfan and Treosulfan; Triazenes such as Dacarbazine; Platinum containing compounds such as Cisplatin and carboplatin; Plant Alkaloids such as Vinca alkaloids such as vincristine, Vinblastine, Vindesine and Vinorelbine; Taxoids such as paclitaxel and Docetaxol; DNA Topoisomerase Inhibitors; Epipodophyllins such as etoposide, Teniposide, Topotecan, 9-aminocamptothecin, camptothecin, exatecan, and crisnatol; mitomycins such as Mitomycin C; Anti-metabolites such as Anti-folates such as DHFR inhibitors such as methotrexate and Trimetrexate; IMP dehydrogenase Inhibitors such as mycophenolic acid, Tiazofurin, Ribavirin and EICAR; Ribonucleotide reductase Inhibitors such as hydroxyurea, and deferoxamine; and Pyrimidine analogs such as Uracil analogs such as 5-Fluorouracil, Floxuridine, Doxifluridine and Ratitrexed; Cytosine analogs such as cytarabine (ara C), Cytosine arabinoside, and fludarabine; Purine analogs such as mercaptopurine and Thioguanine; Hormonal therapies such as Receptor antagonists such as Anti-estrogens such as Tamoxifen, Raloxifene and megestrol; LHRH agonists such as goscrclin and Leuprolide acetate; Anti-androgens such as flutamide and bicalutamide; Retinoids/Deltoids; Vitamin D3 analogs such as EB 1089, CB 1093 and KH 1060; Photodynamic therapies such as vertoporfm (BPD-MA), Phthalocyanine, photosensitizer Pc4, Demethoxy-hypocrellin A and (2BA-2-DMHA); Cytokines such as Interferon-alpha and Interferon-gamma; Tumor necrosis factor; and others such as Isoprenylation inhibitors such as Lovastatin; Dopaminergic neurotoxins such as I-methyl-4-phenylpyridinium ion; Cell cycle inhibitors such as staurosporine; Actinomycins such as Actinomycin D, and Dactinomycin; Bleomycins such as bleomycin A2, Bleomycin B2, and Peplomycin; Anthracyclines such as daunorabicin, Doxorubicin (adriamycin), Idarubicin, Epirabicin, Pirarabicin, Zorabicin, and Mitoxantrone; MDR inhibitors such as verapamil and Ca2+ ATPase inhibitors such as thapsigargin.

EXEMPLARY EMBODIMENTS

The present invention is further illustrated by the following embodiments which should not be construed as limiting.

1. A binding agent comprising:
   a first binding domain that specifically binds to a first antigen, the first antigen selected from antigens expressed on CD8+KIR+ T regulatory cells (Tregs) other than a KIR protein; and
   a second binding domain that specifically binds to an inhibitory KIR protein, wherein the binding agent binds to CD8+KIR+ Tregs.
2. The binding agent of the preceding embodiment, wherein the first antigen is selected from the group consisting of CD3, CD5, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB.
3. The binding agent of any of the preceding embodiments, wherein the first antigen is selected from the group consisting of CD3, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB.
4. The binding domain of any of the preceding embodiments, wherein the first antigen is selected from the following groups of antigens:
   a. CD3, CD5, CD27, CD38, CD39, CD40L, CD45RA, CD45RB, CD45RO, CD73, CD122, ICOS, OX-40, 2B4, 41BB, and HLA-DR;
   b. LAG-3/CD223, TIM-3, PD-1, S1000A8/9, and TLT2;
   c. CD3, CD5, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB;
   d. CD103 (ITGAE), CD166, CD177, CXCR3, and S1000A8/9;
   e. CCR7, CXCR3, and CXCR5;
   f. PD-1, ICOS, and CXCR3;
   g. CD3, CD5, and CD8; and
   h. CD3 and CD8.
5. The binding domain of any of the preceding embodiments, wherein the first antigen is selected from the following groups of antigens:
   a. CD3, CD27, CD38, CD39, CD40L, CD45RA, CD45RB, CD45RO, CD73, CD122, ICOS, OX-40, 2B4, 41BB, and HLA-DR;
   b. LAG-3/CD223, TIM-3, PD-1, S1000A8/9, and TLT2;
   c. CD3, CD8, CD27, CD38, CD39, CD40L, CD45RA, CD45RB, CD45RO, CD73, CD103 (ITGAE), CD122, CD166, CD177, CCR7, CXCR3, CXCR5, HLA-DR, ICOS, LAG-3/CD223, OX-40, PD-1, S1000A8/9, TIM-3, TLT-2, 2B4, and 41BB;
   d. CD103 (ITGAE), CD166, CD177, CXCR3, and S1000A8/9;
   e. CCR7, CXCR3, and CXCR5; and
   f. CD3 and CD8.
6. The binding agent of any of the preceding embodiments, wherein the binding agent is a bispecific antibody, a diabody, an antibody Fc fusion, an scFv1-ScFv2, an ScFv12-Fc-scFv22, an IgG-scFv, a DVD-Ig, a triomab/quadroma, a two-in-one IgG, a scFv2-Fc, a TandAb, an scFv-HSA-scFv, an scFv-VHH, a Fab-scFv-Fc, a Fab-VHH-Fc, a dAb-IgG, an IgG-VHH, a Tandem scFv-Fc, a (scFv1)2-Fc-(VHH)2, a BiTe, a DART, a CrossMab, a scFv-Fc, a one-armed tandem scFv-Fc, a DART-Fc, an anticalin, an affibody, an avimer, a DARPin, or an adnectin.
7. The binding agent of any of the preceding embodiments, wherein either the first or second binding domain is selected from an antibody or antigen binding portion thereof, and the other binding domain is an antibody fragment.
8. The binding agent of embodiment 7, wherein the antigen binding portion is a Fab, Fab', F(ab')2, Fv, scFv, or a single domain antibody, such as a VHH, VNAR, sdAb, or NANOBODY®.
9. The binding agent of any of the preceding embodiments, wherein the first binding domain comprises a heavy chain variable region and a light chain variable region.
10. The binding agent of any of the preceding embodiments, wherein the second binding domain comprises a heavy chain variable region, and a light chain variable region.
11. The binding agent of any of the preceding embodiments, wherein the first binding domain specifically binds to CD3 or a subunit of CD3, optionally CD3epsilon.
12. The binding agent of embodiment 11, wherein the first binding domain comprises a heavy chain variable region (VH) and a light chain variable region (VL), the VH and VL amino acid sequences selected from the pairs of amino acid sequences set forth in the group consisting of:
   a. SEQ ID NO:1 and SEQ ID NO:2, respectively;
   b. SEQ ID NO:9 and SEQ ID NO: 10, respectively;
   c. SEQ ID NO: 17 and SEQ ID NO: 18, respectively;
   d. SEQ ID NO:25 and SEQ ID NO:26, respectively;
   e. SEQ ID NO:33 and SEQ ID NO:34, respectively;
   f. SEQ ID NO:41 and SEQ ID NO:34, respectively;
   g. SEQ ID NO:45 and SEQ ID NO:34, respectively;
   h. SEQ ID NO:49 and SEQ ID NO:50, respectively;
   i. SEQ ID NO:57 and SEQ ID NO:58, respectively;
   j. SEQ ID NO:65 and SEQ ID NO:66, respectively; and
   k. SEQ ID NO:65 and SEQ ID NO: 166, respectively.
13. The binding agent of embodiment 11, wherein the first binding domain comprises a heavy chain variable region (VH) having the amino acid sequence set forth in SEQ ID NO:1 and a light chain variable region (VL) having the amino acid sequence set forth in SEQ ID NO:2.
14. The binding agent of embodiment 11, wherein the first binding domain comprises a heavy chain variable region (VH) having the amino acid sequence set forth in SEQ ID NO:9 and a light chain variable region (VL) having the amino acid sequence set forth in SEQ ID NO:10.
15. The binding agent of embodiment 11, wherein the first binding domain comprises a heavy chain variable region (VH) having the amino acid sequence set forth in SEQ ID NO:17 and a light chain variable region (VL) having the amino acid sequence set forth in SEQ ID NO:18.
16. The binding agent of embodiment 11, wherein the first binding domain comprises a heavy chain variable region (VH) having the amino acid sequence set forth in SEQ ID NO:25 and a light chain variable region (VL) having the amino acid sequence set forth in SEQ ID NO:26.
17. The binding agent of embodiment 11, wherein the first binding domain comprises a heavy chain variable region (VH) having the amino acid sequence set forth in SEQ ID NO:33 and a light chain variable region (VL) having the amino acid sequence set forth in SEQ ID NO:34.

18. The binding agent of embodiment 11, wherein the first binding domain comprises a heavy chain variable region (VH) having the amino acid sequence set forth in SEQ ID NO:41 and a light chain variable region (VL) having the amino acid sequence set forth in SEQ ID NO:34.

19. The binding agent of embodiment 11, wherein the first binding domain comprises a heavy chain variable region (VH) having the amino acid sequence set forth in SEQ ID NO:45 and a light chain variable region (VL) having the amino acid sequence set forth in SEQ ID NO:34.

20. The binding agent of embodiment 11, wherein the first binding domain comprises a heavy chain variable region (VH) having the amino acid sequence set forth in SEQ ID NO:49 and a light chain variable region (VL) having the amino acid sequence set forth in SEQ ID NO:50.

21. The binding agent of embodiment 11, wherein the first binding domain comprises a heavy chain variable region (VH) having the amino acid sequence set forth in SEQ ID NO:57 and a light chain variable region (VL) having the amino acid sequence set forth in SEQ ID NO:58.

22. The binding agent of embodiment 11, wherein the first binding domain comprises a heavy chain variable region (VH) having the amino acid sequence set forth in SEQ ID NO:65 and a light chain variable region (VL) having the amino acid sequence set forth in SEQ ID NO:66.

23. The binding agent of embodiment 11, wherein the first binding domain comprises a heavy chain variable region (VH) having the amino acid sequence set forth in SEQ ID NO:65 and a light chain variable region (VL) having the amino acid sequence set forth in SEQ ID NO: 166.

24. The binding agent of embodiment 11, wherein the first binding domain comprises a heavy chain variable region and a light chain variable region, the heavy and light chain variable regions comprising hCDR1, hCDR1, and hCDR3, and lCDR1, lCDR2, and lCDR3, respectively, the CDRs having amino acid sequences selected from the sets of amino acid sequences set forth in the group consisting of:
a. SEQ ID NO:3 to SEQ ID NO:8, respectively;
b. SEQ ID NO: 11 to SEQ ID NO: 16, respectively;
c. SEQ ID NO: 19 to SEQ ID NO:24, respectively;
d. SEQ ID NO:27 to SEQ ID NO:32, respectively;
e. SEQ ID NO:35 to SEQ ID NO:40, respectively;
f. SEQ ID NO:42 to SEQ ID NO:44 and SEQ ID NO:38 to SEQ ID NO:40, respectively;
g. SEQ ID NO:46 to SEQ ID NO:48 and SEQ ID NO:38 to SEQ ID NO:40, respectively;
h. SEQ ID NO:51 to SEQ ID NO:56, respectively;
i. SEQ ID NO:59 to SEQ ID NO:64, respectively;
j. SEQ ID NO:67 to SEQ ID NO:72, respectively; and
k. SEQ ID NOs: 67-69 and 167-169, respectively.

25. The binding agent of any of embodiments 1 to 10, wherein the first binding domain specifically binds to CD8 or a subunit of CD8, optionally CD8alpha.

26. The binding agent of embodiment 25, wherein the first binding domain comprises a heavy chain variable region (VH) and a light chain variable region (VL), the VH and VL regions having amino acid sequences selected from the pairs of amino acid sequences set forth in the group consisting of:
a. SEQ ID NO:73 and SEQ ID NO:74, respectively; and
b. SEQ ID NO:81 and SEQ ID NO:82, respectively;
or the first binding domain comprises a VHH chain, the VHH chain having the amino acid sequence selected from the amino acid sequences set forth in the group consisting of:
c. SEQ ID NO:89;
d. SEQ ID NO:93; and
e. SEQ ID NO:97.

27. The binding agent of embodiment 25, wherein the first binding domain comprises a heavy chain variable region (VH) having the amino acid sequence set forth in SEQ ID NO:73 and a light chain variable region (VL) having the amino acid sequence set forth in SEQ ID NO:74.

28. The binding agent of embodiment 25, wherein the first binding domain comprises a heavy chain variable region (VH) having the amino acid sequence set forth in SEQ ID NO:81 and a light chain variable region (VL) having the amino acid sequence set forth in SEQ ID NO:82.

29. The binding agent of embodiment 25, wherein the first binding domain comprises a VHH chain having the amino acid sequence set forth in SEQ ID NO: 89.

30. The binding agent of embodiment 25, wherein the first binding domain comprises a VHH chain having the amino acid sequence set forth in SEQ ID NO: 93.

31. The binding agent of embodiment 25, wherein the first binding domain comprises a VHH chain having the amino acid sequence set forth in SEQ ID NO: 97.

32. The binding agent of embodiment 25, wherein the first binding domain comprises a heavy chain variable region and a light chain variable region, the heavy and light chain variable regions comprising hCDR1, hCDR1, and hCDR3, and lCDR1, lCDR2, and lCDR3, respectively, the CDRs having amino acid sequences selected from the sets of amino acid sequences set forth in the group consisting of:
a. SEQ ID NO:75 to SEQ ID NO:80, respectively; and
b. SEQ ID NO:83 to SEQ ID NO:88, respectively;
or the first binding domain includes a VHH chain having hCDR1, hCDR2, and hCDR3, the amino acid sequences of the VHH CDRs selected from the sets of amino acid sequences set forth in the group consisting of:
c. SEQ ID NO:90 to SEQ ID NO:92, respectively;
d. SEQ ID NO:94 to SEQ ID NO:96, respectively; and
e. SEQ ID NO:98 to SEQ ID NO: 100, respectively.

33. The binding agent of any of embodiments 1 to 10, wherein the first binding domain specifically binds to ICOS.

34. The binding agent of embodiment 33, wherein the first binding domain comprises a heavy chain variable region (VH) having the amino acid sequence of SEQ ID NO:170 and a light chain variable region (VL) having the amino acid sequence of SEQ ID NO:171.

35. The binding agent of embodiment 33, wherein the first binding domain comprises a heavy chain variable region and a light chain variable region, the heavy and light chain variable regions comprising hCDR1, hCDR1, and hCDR3 amino acid sequences according to SEQ ID NOs: 172, 173, and 174, respectively, and lCDR1, lCDR2, and lCDR3 amino acid sequences according to SEQ ID NOs: 175, 176, and 177, respectively.

36. The binding agent of any of embodiments 1 to 10, wherein the first binding domain specifically binds to PD-1.
37. The binding agent of embodiment 36, wherein the first binding domain comprises a heavy chain variable region (VH) having the amino acid sequence of SEQ ID NO: 178 and a light chain variable region (VL) having the amino acid sequence of SEQ ID NO: 179.
38. The binding agent of embodiment 36, wherein the first binding domain comprises a heavy chain variable region and a light chain variable region, the heavy and light chain variable regions comprising hCDR1, hCDR1, and hCDR3 amino acid sequences according to SEQ ID NOs: 180, 181, and 182, respectively, and lCDR1, lCDR2, and lCDR3 amino acid sequences according to SEQ ID NOs: 183, 184, and 185, respectively.
39. The binding agent of any of embodiments 1 to 10, wherein the first binding domain specifically binds to CXCR3.
40. The binding agent of embodiment 39, wherein the first binding domain comprises a heavy chain variable region (VH) having the amino acid sequence of SEQ ID NO: 186 and a light chain variable region (VL) having the amino acid sequence of SEQ ID NO: 187.
41. The binding agent of embodiment 39, wherein the first binding domain comprises a heavy chain variable region and a light chain variable region, the heavy and light chain variable regions comprising hCDR1, hCDR1, and hCDR3 amino acid sequences according to SEQ ID NOs: 188, 189, and 190, respectively, and lCDR1, lCDR2, and lCDR3 amino acid sequences according to SEQ ID NOs: 191, 192, and 193, respectively.
42. The binding agent of any of embodiments 1 to 10, wherein the first binding domain specifically binds to CD5.
43. The binding agent of embodiment 42, wherein the first binding domain comprises a heavy chain variable region (VH) having the amino acid sequence of SEQ ID NO: 194 and a light chain variable region (VL) having the amino acid sequence of SEQ ID NO: 195.
44. The binding agent of embodiment 42, wherein the first binding domain comprises a heavy chain variable region and a light chain variable region, the heavy and light chain variable regions comprising hCDR1, hCDR1, and hCDR3 amino acid sequences according to SEQ ID NOs: 196, 197, and 198, respectively, and lCDR1, lCDR2, and lCDR3 amino acid sequences according to SEQ ID NOs: 199, 200, and 201, respectively.
45. The binding agent of any of the preceding embodiments, wherein the inhibitory KIR protein is selected from KIR3DL1, KIR3DL2, KIR2DL1, KIR2DL2, and KIR2DL3 or a combination thereof.
46. The binding agent of embodiment 45, wherein the second binding domain specifically binds to KIR2DL1/2/3 or KIR2DL1/2.
47. The binding agent of any of the preceding embodiments, wherein the second binding domain comprises a heavy chain variable region (VH) and a light chain variable region (VL), the VH and VL regions having amino acid sequences selected from the pairs of amino acid sequences set forth in the group consisting of:
a. SEQ ID NO:101 and SEQ ID NO:102, respectively;
b. SEQ ID NO: 109 and SEQ ID NO: 110, respectively;
c. SEQ ID NO:117 and SEQ ID NO: 118, respectively;
d. SEQ ID NO: 125 and SEQ ID NO: 126, respectively;
e. SEQ ID NO: 133 and SEQ ID NO: 134, respectively;
f. SEQ ID NO: 141 and SEQ ID NO: 142, respectively;
g. SEQ ID NO: 149 and SEQ ID NO: 150, respectively; and
h. SEQ ID NO: 157 and SEQ ID NO: 158, respectively.
48. The binding agent of any of the preceding embodiments, wherein the second binding domain comprises a heavy chain variable region (VH) having the amino acid sequence set forth in SEQ ID NO: 101 and a light chain variable region (VL) having the amino acid sequence set forth in SEQ ID NO: 102.
49. The binding agent of any of claims 1 to 47, wherein the second binding domain comprises a heavy chain variable region (VH) having the amino acid sequence set forth in SEQ ID NO:109 and a light chain variable region (VL) having the amino acid sequence set forth in SEQ ID NO: 110.
50. The binding agent of any of claims 1 to 47, wherein the second binding domain comprises a heavy chain variable region (VH) having the amino acid sequence set forth in SEQ ID NO:117 and a light chain variable region (VL) having the amino acid sequence set forth in SEQ ID NO: 118.
51. The binding agent of any of claims 1 to 47, wherein the second binding domain comprises a heavy chain variable region (VH) having the amino acid sequence set forth in SEQ ID NO: 125 and a light chain variable region (VL) having the amino acid sequence set forth in SEQ ID NO: 126.
52. The binding agent of any of claims 1 to 47, wherein the second binding domain comprises a heavy chain variable region (VH) having the amino acid sequence set forth in SEQ ID NO: 133 and a light chain variable region (VL) having the amino acid sequence set forth in SEQ ID NO: 134.
53. The binding agent of any of claims 1 to 47, wherein the second binding domain comprises a heavy chain variable region (VH) having the amino acid sequence set forth in SEQ ID NO: 141 and a light chain variable region (VL) having the amino acid sequence set forth in SEQ ID NO: 142.
54. The binding agent of any of claims 1 to 47, wherein the second binding domain comprises a heavy chain variable region (VH) having the amino acid sequence set forth in SEQ ID NO: 149 and a light chain variable region (VL) having the amino acid sequence set forth in SEQ ID NO: 150.
55. The binding agent of any of claims 1 to 47, wherein the second binding domain comprises a heavy chain variable region (VH) having the amino acid sequence set forth in SEQ ID NO: 157 and a light chain variable region (VL) having the amino acid sequence set forth in SEQ ID NO: 158.
56. The binding agent of any of claims 1 to 47, wherein the second binding domain comprises a heavy chain variable region and a light chain variable region, the heavy and light chain variable regions comprising hCDR1, hCDR1, and hCDR3, and lCDR1, lCDR2, and lCDR3, respectively, the CDRs having amino acid sequences selected from the sets of amino acid sequences set forth in the group consisting of the CDRs having amino acid sequence selected from the sets of amino acid sequences set forth in the group consisting of:
a. SEQ ID NO: 103 to SEQ ID NO:108, respectively;
b. SEQ ID NO: 111 to SEQ ID NO:116, respectively;

c. SEQ ID NO: 119 to SEQ ID NO: 124, respectively;
d. SEQ ID NO: 127 to SEQ ID NO:132, respectively;
e. SEQ ID NO: 135 to SEQ ID NO:140, respectively;
f. SEQ ID NO: 143 to SEQ ID NO: 148, respectively;
g. SEQ ID NO: 151 to SEQ ID NO: 156, respectively; and
h. SEQ ID NO: 159 and SEQ ID NO: 164, respectively.

57. The binding agent of any of the preceding embodiments, where the binding agent does not contain an Fc domain.
58. The binding agent of any of embodiments 1 to 56, further comprising an Fc domain.
59. The binding agent of embodiment 58, wherein the Fc domain is selected from an IgG1 and an IgG4 Fc domain.
60. The binding agent of embodiment 59, wherein the binding agent has substantially no effector function activity.
61. The binding agent of any of embodiments 58 to 60, wherein the Fc domain is an IgG1 Fc domain.
62. The binding agent of any of embodiments 58 to 61, wherein the Fc domain is an IgG1 Fc null.
63. The binding agent of any of the preceding embodiments, wherein the binding agent is bivalent or tetravalent.
64. The binding agent of any of the preceding embodiments, wherein the binding agent is bispecific.
65. A pharmaceutical composition comprising the binding agent of any of embodiments 1 to 64 and a pharmaceutically acceptable carrier.
66. A nucleic acid encoding the binding agent of any of embodiments 1 to 64.
67. A vector comprising the nucleic acid of embodiment 66.
68. A cell line comprising the vector of embodiment 67.
69. A method of treating an autoimmune disease, comprising administering the binding agent of any of embodiments 1 to 64 or the pharmaceutical composition of embodiment 65 to a subject in need thereof in an amount effective to decrease the number or activity of pathogenic immune cells in the subject and thereby ameliorate a symptom of the autoimmune disease.
70. A method of suppressing an immune response mediated by pathogenic immune cells, comprising contacting CD8+KIR+ T regulatory cells (Tregs) with the binding agent of any of embodiments 1 to 64 or the pharmaceutical composition of embodiment 65 in an amount effective to activate or stimulate CD8+KIR+ Tregs (activated Tregs), whereby the number or activity of pathogenic immune cells is decreased.
71. A method of suppressing an immune response to an antigen, such as an autoantigen, comprising administering to a subject in need thereof the binding agent of any of embodiments 1 to 64 or the pharmaceutical composition of embodiment 65 in an amount effective to activate or stimulate CD8+KIR+ Tregs, whereby the number or activity of pathogenic immune cells that are responsive to the antigen or autoantigen is decreased.
72. The method of embodiment 70, wherein the CD8+KIR+ Tregs are contacted with the binding agent in vivo.
73. The method of embodiment 70, wherein the CD8+KIR+ Tregs are contacted with the binding agent ex vivo.
74. The method of embodiment 73, wherein the activated CD8+KIR+ Tregs are administered in an effective amount to a subject in need thereof.
75. The method of any of embodiments 69 to 74, wherein the pathogenic immune cells are autoreactive CD4 T cells, autoantibody producing B cells, or self antigen presenting dendritic cells.
76. The method of any of embodiments 69 to 74, wherein the pathogenic immune cells are self antigen presenting cells.
77. The method of embodiment 71, whereby the titer of autoantibodies is decreased in the subject.
78. The method of any of embodiments 69 and 74 to 77, wherein the subject has an autoimmune disease selected from the group consisting of celiac disease, Crohn's disease, juvenile idiopathic arthritis, inflammatory bowel disease (IBD), insulin-dependent diabetes mellitus (IDDM or type 1 diabetes), lupus nephritis, myasthenia gravis, myocarditis, multiple sclerosis (MS), pemphigus/pemphigoid, rheumatoid arthritis (RA), scleroderma/systemic sclerosis, Sjögren's syndrome (SjS), systemic lupus erythematosus (SLE), and ulcerative colitis.
79. The method of embodiment 78, wherein the autoimmune disease is selected from the group consisting of celiac disease, Crohn's disease, inflammatory bowel disease (IBD), insulin-dependent diabetes mellitus (IDDM or type 1 diabetes), lupus nephritis, multiple sclerosis (MS), rheumatoid arthritis (RA), scleroderma/systemic sclerosis, Sjögren's syndrome (SjS), systemic lupus erythematosus (SLE), and ulcerative colitis.
80. The method of any of embodiments 69 to 79, wherein the binding agent specifically binds to CD8 and the inhibitory KIR protein on CD8+KIR+ Tregs.
81. The method of any of embodiments 69 to 79, wherein the binding agent specifically binds to CD3 and the inhibitory KIR protein on CD8+KIR+ Tregs.
82. The method of any of embodiments 69 to 79, wherein the binding agent specifically binds to CD5 and the inhibitory KIR protein on CD8+KIR+ Tregs.
83. The method of any of embodiments 69 to 79, wherein the binding agent specifically binds to PD-1 and the inhibitory KIR protein on CD8+KIR+ Tregs.
84. The method of any of embodiments 69 to 79, wherein the binding agent specifically binds to ICOS and the inhibitory KIR protein on CD8+KIR+ Tregs.
85. The method of any of embodiments 69 to 79, wherein the binding agent specifically binds to CXCR3 and the inhibitory KIR protein on CD8+KIR+ Tregs.
86. The method of any of embodiments 69 to 85 wherein the CD8+KIR+ Tregs are MHC class I restricted.
87. The method of any of embodiments 69 to 86, wherein the CD8+KIR+ Tregs are not MHC HLA E (Qa-1b) restricted.
88. The method of any of embodiments 69 to 87, further comprising administering an immunosuppressive agent to the subject.
89. The method of any of embodiments 69 to 88, wherein the administration of the binding agent to the subject results in an improved treatment outcome in the subject.
90. The method of embodiment 89, wherein the improved treatment outcome is reduced frequency or severity disease flares, reduced systemic inflammatory cytokines, or reduced self reporting of symptoms associated the autoimmune disease.
91. The method of any of embodiments 69 to 90, wherein the binding agent is administered intravenously.
92. The method of any of embodiments 69 to 91, wherein the binding agent is administered subcutaneously.

93. The method of any of embodiments 69 to 92, wherein the binding agent is administered in a dose of about 0.01 mg/kg to about 20 mg/kg.

94. The method of any of embodiments 69 to 93, wherein the binding agent has substantially no effector function activity.

95. Use of the binding agent of any of embodiments 1 to 64 or the pharmaceutical composition of embodiment 65 for the treatment of autoimmune disease in a subject by activating or stimulating CD8+KIR+ Tregs.

96. Use of the binding agent of any of embodiments 1 to 64 or the pharmaceutical composition of embodiment 65 for the reduction of an immune response by pathogenic immune cells by activating or stimulating CD8+KIR+ Tregs.

97. Use of the binding agent of any of embodiments 1 to 64 or the pharmaceutical composition of embodiment 65 for the reduction of autoantibody titer in a subject by activating or stimulating CD8+KIR+ Tregs.

98. A method of treating cancer, comprising administering the binding agent of any of embodiments 1 to 64 or the pharmaceutical composition of embodiment 65, wherein the binding agent has substantially no effector function activity, to a subject in need thereof in an amount effective to activate or stimulate CD8+KIR+ Tregs and thereby ameliorate a symptom of the cancer.

99. A method of stimulating an immune response against an antigen associated with a cancer (cancer antigen), comprising contacting CD8+KIR+ T regulatory cells (Tregs) with the binding agent of any of embodiments 1 to 64 or the pharmaceutical composition of embodiment 65, wherein the binding agent has substantially no effector function activity, in an amount effective to activate or stimulate CD8+KIR+ Tregs (activated Tregs), whereby the immune response to the cancer antigen is increased.

100. A method of treating cancer, comprising administering the binding agent of any of embodiments 1 to 64 or the pharmaceutical composition of embodiment 65, wherein the binding agent has effector function activity comprising at least ADCC, to a subject in need thereof in an amount effective to deplete CD8+KIR+ Tregs and thereby ameliorate a symptom of the cancer.

101. A method of stimulating an immune response against an antigen associated with a cancer (cancer antigen), comprising contacting CD8+KIR+ T regulatory cells (Tregs) with the binding agent of any of embodiments 1 to 64 or the pharmaceutical composition of embodiment 65, wherein the binding agent has effector function activity comprising at least ADCC, in an amount effective to deplete CD8+KIR+ Tregs, whereby the immune response to the cancer antigen is increased.

102. The method of embodiment 99 or 101, wherein the CD8+KIR+ Tregs are contacted with the binding agent in vivo.

103. The method of embodiment 99, wherein the CD8+KIR+ Tregs are contacted with the binding agent ex vivo.

104. The method of embodiment 103, wherein the activated CD8+KIR+ Tregs are administered in an effective amount to a subject in need thereof.

105. The method of any of embodiments 99 and 101 to 104, wherein the increased immune response comprises a reduction in cancer cells or depletion of immune suppressive immune cells.

106. The method of any of embodiments 98 to 105, whereby the cancer cells in the subject are decreased.

107. The method of any of embodiments 98 to 106, wherein the cancer is selected from the group consisting of carcinomas, lymphomas, blastomas, sarcomas, myelomas and leukemias.

108. The method of any of embodiments 98 to 107, wherein the cancer is selected from the group consisting of solid tumors such as breast, cervical, ovary, lung, CRC (and other cancers of the bowel), skin, esophageal, adenocarcinoma, bladder, and prostate; and lymphomas.

109. The method of any of embodiments 98 to 108, wherein the binding agent specifically binds to CD8 and the inhibitory KIR protein on CD8+KIR+ Tregs.

110. The method of any of embodiments 98 to 108, wherein the binding agent specifically binds to CD3 and the inhibitory KIR protein on CD8+KIR+ Tregs.

111. The method of any of embodiments 98 to 108, wherein the binding agent specifically binds to CD5 and the inhibitory KIR protein on CD8+KIR+ Tregs.

112. The method of any of embodiments 98 to 108, wherein the binding agent specifically binds to PD-1 and the inhibitory KIR protein on CD8+KIR+ Tregs.

113. The method of any of embodiments 98 to 108, wherein the binding agent specifically binds to ICOS and the inhibitory KIR protein on CD8+KIR+ Tregs.

114. The method of any of embodiments 98 to 108, wherein the binding agent specifically binds to CXCR3 and the inhibitory KIR protein on CD8+KIR+ Tregs.

115. The method of any of embodiments 98 to 114 wherein the CD8+KIR+ Tregs are MHC class I restricted.

116. The method of any of embodiments 98 to 115, wherein the CD8+KIR+ Tregs are not MHC HLA E (Qa-1b) restricted.

117. The method of any of embodiments 98 to 116, further comprising administering a chemotherapeutic agent or an immunotherapy, such as a check point inhibitor, to the subject.

118. The method of any of embodiments 98 to 117, wherein the administration of the binding agent to the subject results in an improved treatment outcome in the subject.

119. The method of embodiment 118, wherein the improved treatment outcome is a partial response or complete response.

120. The method of embodiment 118, wherein the improved treatment outcome is remission.

121. The method of any of embodiments 98 to 120, wherein the binding agent is administered intravenously.

122. The method of any of embodiments 98 to 120, wherein the binding agent is administered subcutaneously.

123. The method of any of embodiments 98 to 122, wherein the binding agent is administered in a dose of about 0.01 mg/kg to about 20 mg/kg.

124. Use of the binding agent of any of embodiments 1 to 64 or the pharmaceutical composition of embodiment 65, wherein the binding agent has substantially no effector function activity, for the treatment of cancer in a subject by activating or stimulating CD8+KIR+ Tregs.

125. Use of the binding agent of any of embodiments 1 to 64 or the pharmaceutical composition of embodiment 65, wherein the binding agent has substantially no effector function activity, for the reduction of immune 125. (cont.) suppression by immune suppressive immune cells by activating or stimulating CD8+KIR+ Tregs.

126. Use of the binding agent of any of embodiments 1 to 64 or the pharmaceutical composition of embodiment 65, wherein the binding agent has substantially no effector function activity, for the reduction of tumor burden in a subject by activating or stimulating CD8+KIR+ Tregs.

127. Use of the binding agent of any of embodiments 1 to 64 or the pharmaceutical composition of embodiment 65, wherein the binding agent has effector function activity comprising at least ADCC, for the treatment of cancer in a subject by depleting CD8+KIR+ Tregs.

128. Use of the binding agent of any of embodiments 1 to 64 or the pharmaceutical composition of embodiment 65, wherein the binding agent has effector function activity comprising at least ADCC, for the depletion of CD8+KIR+ Tregs.

129. Use of the binding agent of any of embodiments 1 to 64 or the pharmaceutical composition of embodiment 65, wherein the binding agent has effector function activity comprising at least ADCC, for the reduction of tumor burden in a subject.

130. A method of treating an infection, comprising administering the binding agent of any of embodiments 1 to 64 or the pharmaceutical composition of embodiment 65 to a subject in need thereof in an amount effective to activate or stimulate CD8+KIR+ Tregs and thereby ameliorate a symptom of the infection.

131. A method of stimulating an immune response against infected cells caused by an infection, comprising contacting CD8+KIR+ T regulatory cells (Tregs) with the binding agent of any of embodiments 1 to 64 or the pharmaceutical composition of embodiment 65 in an amount effective to activate or stimulate CD8+KIR+ Tregs (activated Tregs), whereby the immune response against the infected cells.

132. The method of embodiment 131, wherein the CD8+KIR+ Tregs are contacted with the binding agent in vivo.

133. The method of embodiment 131, wherein the CD8+KIR+ Tregs are contacted with the binding agent ex vivo.

134. The method of embodiment 133, wherein the activated CD8+KIR+ Tregs are administered in an effective amount to a subject in need thereof.

135. The method of any of embodiments 131 to 134, wherein the immune response comprises a reduction in infected cells or reduction in immune suppressive immune cells selected from CD4+ T regulatory cells and tolerizing DCs.

136. The method of embodiment 135, whereby the number of infected cells in the subject is decreased.

137. The method of any of embodiments 130 to 136, wherein the infection is selected from a bacterial disease, a systemic fungal disease, rickettsial disease, a parasitic disease, and a viral disease.

138. The method of embodiment 137, wherein the infection is selected from the group consisting of an HIV infection, hepatitis C virus (HCV) infection, human papillomavirus (HPV) infection, Epstein Bar Virus (EBV) infection, coronavirus infection such as a SARS-COV2 infection (Covid-19), cytomegalovirus (CMV) infection, and flu virus infection.

139. The method of any of embodiments 130 to 138, wherein the binding agent specifically binds to CD8 and the inhibitory KIR protein on CD8+KIR+ Tregs.

140. The method of any of embodiments 130 to 138, wherein the binding agent specifically binds to CD3 and the inhibitory KIR protein on CD8+KIR+ Tregs.

141. The method of any of embodiments 130 to 138, wherein the binding agent specifically binds to CD5 and the inhibitory KIR protein on CD8+KIR+ Tregs.

142. The method of any of embodiments 130 to 138, wherein the binding agent specifically binds to PD-1 and the inhibitory KIR protein on CD8+KIR+ Tregs.

143. The method of any of embodiments 130 to 138, wherein the binding agent specifically binds to ICOS and the inhibitory KIR protein on CD8+KIR+ Tregs.

144. The method of any of embodiments 130 to 138, wherein the binding agent specifically binds to CXCR3 and the inhibitory KIR protein on CD8+KIR+ Tregs.

145. The method of any of embodiments 130 to 144 wherein the CD8+KIR+ Tregs are MHC class I restricted.

146. The method of any of embodiments 130 to 145, wherein the CD8+KIR+ Tregs are not MHC HLA E (Qa-1b) restricted.

147. The method of any of embodiments 130 to 146, further comprising administering an anti-microbial or an anti-viral agent to the subject.

148. The method of any of embodiments 130 to 147, wherein the administration of the binding agent to the subject results in an improved treatment outcome in the subject.

149. The method of embodiment 148, wherein the improved treatment outcome is a reduction in infection or infected cells.

150. The method of any of embodiments 130 to 149, wherein the binding agent is administered intravenously.

151. The method of any of embodiments 130 to 149, wherein the binding agent is administered subcutaneously.

152. The method of any of embodiments 130 to 151, wherein the binding agent is administered in a dose of about 0.01 mg/kg to about 20 mg/kg.

153. The method of any of embodiments 130 to 149, wherein he binding agent has substantially no effector function activity.

154. Use of the binding agent of any of embodiments 1 to 64 or the pharmaceutical composition of embodiment 65 for the treatment of an infection in a subject by activating or stimulating CD8+KIR+ Tregs.

155. Use of the binding agent of any of embodiments 1 to 64 or the pharmaceutical composition of embodiment 65 for the stimulation of an immune response by activating or stimulating CD8+KIR+ Tregs and thereby suppressing immune suppressive immune cells.

156. Use of the binding agent of any of embodiments 1 to 64 or the pharmaceutical composition of embodiment 65 for the reduction of infection or infected cells in a subject by activating or stimulating CD8+KIR+ Tregs.

157. A method of reducing or preventing onset of graft versus host disease (GVHD) following a transplant, comprising administering the binding agent of any of embodiments 1 to 64 or the pharmaceutical composition of embodiment 65, wherein the binding agent has substantially no effector function activity, to a subject in need thereof in an amount effective to activate or stimulate CD8+KIR+ Tregs and thereby reduce or ameliorate at least one symptom of GVHD.

158. A method of treating a subject who has received a transplant, comprising contacting CD8+KIR+ T regulatory cells (Tregs) with the binding agent of any of embodiments 1 to 64 or the pharmaceutical composition of embodiment 65, wherein the binding agent has substantially no effector function activity, in an amount effective to activate or stimulate CD8+KIR+ Tregs (activated Tregs), whereby GVHD is reduced or suppressed.
159. A method of treating a subject who has received a transplant, comprising administering the binding agent of any of embodiments 1 to 64 or the pharmaceutical composition of embodiment 65, wherein the binding agent has effector function activity comprising at least ADCC, to a subject in need thereof in an amount effective to deplete CD8+KIR+ Tregs and thereby ameliorate a symptom of GVHD.
160. A method of suppressing GVHD against a transplant, comprising contacting CD8+KIR+ T regulatory cells (Tregs) with the binding agent of any of embodiments 1 to 64 or the pharmaceutical composition of embodiment 65, wherein the binding agent has effector function activity comprising at least ADCC, in an amount effective to deplete CD8+KIR+ Tregs, whereby GVHD or a symptom thereof is decreased.
161. The method of embodiment 158 or 160, wherein the CD8+KIR+ Tregs are contacted with the binding agent in vivo.
162. The method of embodiment 158, wherein the CD8+KIR+ Tregs are contacted with the binding agent ex vivo.
163. The method of embodiment 162, wherein the activated CD8+KIR+ Tregs are administered in an effective amount to a subject in need thereof.
164. The method of any of embodiments 157 and 160 to 163, wherein the decreased GVHD comprises a reduction in CD4+ T cells active in GVHD.
165. The method of any of embodiments 157 to 164, wherein the transplant is selected from the group consisting of an organ transplant, a hematopoietic stem cell transplant, an umbilical cord blood stem cell transplant, an inducible pluripotent stem cell-derived progenitor or differentiated cell transplant, and a bone marrow transplant.
166. The method of any of embodiment 165, wherein the transplant is a hematopoietic stem cell transplant, an umbilical cord blood stem cell transplant, an inducible pluripotent stem cell-derived progenitor or differentiated cell transplant, or a bone marrow transplant.
167. The method of any of embodiments 157 to 166, wherein the transplant is allogeneic.
168. The method of any of embodiments 157 to 167, wherein the binding agent specifically binds to CD8 and the inhibitory KIR protein on CD8+KIR+ Tregs.
169. The method of any of embodiments 157 to 167, wherein the binding agent specifically binds to CD3 and the inhibitory KIR protein on CD8+KIR+ Tregs.
170. The method of any of embodiments 157 to 167, wherein the binding agent specifically binds to CD5 and the inhibitory KIR protein on CD8+KIR+ Tregs.
171. The method of any of embodiments 157 to 167, wherein the binding agent specifically binds to PD-1 and the inhibitory KIR protein on CD8+KIR+ Tregs.
172. The method of any of embodiments 157 to 167, wherein the binding agent specifically binds to ICOS and the inhibitory KIR protein on CD8+KIR+ Tregs.
173. The method of any of embodiments 157 to 167, wherein the binding agent specifically binds to CXCR3 and the inhibitory KIR protein on CD8+KIR+ Tregs.
174. The method of any of embodiments 157 to 173 wherein the CD8+KIR+ Tregs are MHC class I restricted.
175. The method of any of embodiments 157 to 174, wherein the CD8+KIR+ Tregs are not MHC HLA E (Qa-1b) restricted.
176. The method of any of embodiments 157 to 175, further comprising administering an immunosuppressive agent to the subject.
177. The method of any of embodiments 157 to 176, wherein the administration of the binding agent to the subject results in an improved treatment outcome in the subject.
178. The method of embodiment 177, wherein the improved treatment outcome is a reduction in a symptom associated with GVHD, reduced systemic inflammatory cytokines, reduced pathology in tissues impacted by GVHD, reduced self reporting of symptoms associated with an immune response associated with adverse effects on host tissues, improved or extended transplant engraftment, alleviation of one or more symptom(s), and/or prevention, delay, or slowing of onset or progression of rejection of the transplant, or extended transplant engraftment with decreased use of broad spectrum immunosuppressive agents, such as corticosteroids.
179. The method of any of embodiments 157 to 178, wherein the binding agent is administered intravenously.
180. The method of any of embodiments 157 to 178, wherein the binding agent is administered subcutaneously.
181. Use of the binding agent of any of embodiments 1 to 64 or the pharmaceutical composition of embodiment 65, wherein the binding agent has substantially no effector function activity, for the treatment of GVHD associated with transplant in a subject.
182. Use of the binding agent of any of embodiments 1 to 64 or the pharmaceutical composition of embodiment 65, wherein the binding agent has substantially no effector function activity, for the treatment of GVHD associated with transplant in a subject by activating or stimulating CD8+KIR+ Tregs.
183. Use of the binding agent of any of embodiments 1 to 64 or the pharmaceutical composition of embodiment 65, wherein the binding agent has substantially no effector function activity, for the reduction of GVHD associated with a transplant by activating or stimulating CD8+KIR+ Tregs.
184. Use of the binding agent of any of embodiments 1 to 64 or the pharmaceutical composition of embodiment 65, wherein the binding agent has substantially no effector function activity, for the reduction of GVHD to a transplant.
185. Use of the binding agent of any of embodiments 1 to 64 or the pharmaceutical composition of embodiment 65, wherein the binding agent has effector function activity comprising at least ADCC, for the treatment of GVHD associated with a transplant in a subject by depleting CD8+KIR+ Tregs.
186. Use of the binding agent of any of embodiments 1 to 64 or the pharmaceutical composition of embodiment 65, wherein the binding agent has effector function activity comprising at least ADCC, for the depletion of CD8+KIR+ Tregs.
187. Use of the binding agent of any of embodiments 1 to 64 or the pharmaceutical composition of embodiment 65, wherein the binding agent has effector function activity comprising at least ADCC, for the depletion of CD8+KIR+ Tregs in a subject who has received a transplant to reduce GVHD.

188. Use of the binding agent of any of embodiments 1 to 64 or the pharmaceutical composition of embodiment 65, in any of the methods of embodiments 69 to 94, 98 to 123, 130 to 153, and 157 to 180.

189. Use of the binding agent of any of embodiments 1 to 64 or the pharmaceutical composition of embodiment 65, in the manufacture of a medicament for use in any of the methods of embodiments 69 to 94, 98 to 123, 130 to 153, and 157 to 180.

Sequences

The sequence listing of the present application is submitted electronically in ST.26 format. The original sequence listing submitted in the parent application PCT/US2022/014881, filed Feb. 2, 2022, was submitted electronically in ST.25 format. Sequences from the original sequence listing having a length that is below the minimum length permitted under ST.26 format are provided in the following table.

| SEQ ID NO | Sequence |
|---|---|
| 139 | DVS |
| 155 | DNN |
| 192 | DTS |

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Example 1: Testing of Mono and Bispecific Molecules on CD8+KIR+ Treg Cell Activation and Cytotoxicity Against Pathogenic Immune Cells in an Autoimmune Disorder To test a panel of monospecific and bispecific molecules (including inhibitory KIR blockers) for the functional recovery of CD8 KIR+ Treg cell activation and cytotoxicity-mediated elimination of pathogenic immune cells, such as autoreactive CD4 T cells, primary CD8+KIR+ T cells will be incubated with escalating concentrations of a CD3 agonist antibody, which will mimic peptide/MHC binding of CD8 KIR+ T cell receptors in the presence of increasing concentrations of inhibitory KIR blocking molecules. It can be expected that blockade of the inhibitory KIR signal will reduce the activation threshold of TCR engagement required for CD8 KIR+ Treg cell activation resulting in a specific and increased activation status of CD8 KIR+ T cells. The increased activation of CD8+KIR+ Treg cells will be confirmed by the increase of secretion of certain cytokines (e.g., IFNgamma, IL-10, TNFalpha, IL-35 or subunits thereof, etc), the increase of expression markers associated with activation (e.g., CD69, CD25, CD62L, CD44, CD45) and an increase of proliferation.

The panel of mono- and bi-specific molecules will be examined based on their potency by inducing CD8 KIR+ Treg cell mediated functional consequences, and will be subsequently tested using Celiac patient peripheral blood mononuclear cell-derived CD8 KIR+ Treg cells in response to gluten restimulated CD4 T cells. Increased activation and enhanced activity toward pathogenic immune cells by CD8KIR+ Treg cells will be confirmed by an increase of secretion of certain cytokines (e.g., IFNgamma, IL-10, TNFalpha, and/or IL-35 or subunits thereof, etc.), an increase of expression markers (e.g., CD69, CD25, CD62L, CD44, and/or CD45), a decrease in inhibitory molecules (LAG-3, TIM-3, and/or PD-1), an increase of proliferation, increased inhibition of autoreactive CD4+ T cells and other pathogenic immune cells, such as autoantibody producing B cells, self-antigen presenting dendritic cells and self-APC.

Example 2: Testing of Mono and Bispecific Molecules on CD8+KIR+ Treg Cell Activation and Cytotoxicity in an Infection Model A panel of monospecific and bispecific molecules, (including inhibitory KIR blockers) will be tested for the functional recovery of CD8 KIR+ Treg cell activation and cytotoxicity mediated direct and indirect elimination of pathogen infected cells. Human CMV specific T cells (Cellero) will be cultured with increasing doses of a virally derived dominant epitope (pp65), which binds the MHC class I molecule HLA-A2. Peptides will be loaded onto an HLA-A2 expressing lymphoma cell line T2. For testing of specific inhibitory KIR molecule functions, either the MHC I deficient lymphoma T1 cell line or the K562 cell line will be transfected with relevant cognate MHC class I molecules (e.g., HLA-C2 when blocking KIR2DL1). To confirm that KIR blockade specifically and effectively reestablishes the elimination of pathogen infected cells, CD8 Treg cell activation, cytotoxicity, cytokine production, and proliferation will be examined. The degree of target cell elimination and apoptosis using Annexin V staining and proliferation will also be determined. As controls we will use, for example, irrelevant influenza hemaglutinin peptides (negative control), CD3 antibody bead activation (positive control), or the MHC deficient lymphoma T1 cell line or parent K562 cells (negative controls). To detect activation with greater sensitivity we will transfect, for example, Jurkat cells with SHP1/2 or NFAT reporter to show enhanced activation upon inhibitory KIR blockade and/or agonist binding to prioritize molecules for use.

Example 3: Testing of Mono and Bispecific Molecules on CD8+KIR+ Treg Cell Activation and Cytotoxicity in a Cancer Model CD8 KIR+ Treg cells will be tested against a panel of tumor cell lines with high antigenic burden in the presence of a panel of KIR bispecific molecules to determine if KIR blockade improves CD8 KIR Treg cell activation and target cell killing. KIR bispecific molecules will be tested alone or in combination with other KIR bispecific molecules and in combination with other immune checkpoint inhibitors. As an example, studies will test anti-CD3 agonist antibody dose escalation in conjunction with KIR molecule dose escalation in coculture with tumor cell lines to include, for example: A549 (NSCLC), H1229 (NSCLC), A375 (Melanoma), SK-Mel 3 (Melanoma), Caki-1 (RCC), and/or 786-O (RCC). Dependence of haplotype on responses will be determined using for example primary NY-ESO-1 specific T cells (Cellero) vs NY-ESO1 peptide pulsed T2 (HLA-A2 restricted cell line) and/or HLA-A2 K562. To assess if a subset of HLA expression by tumor cell targets is required for optimal responses (e.g., HLA-B binding KIR3DL1 or KIR2DL1/2/3 binding HLA-C), the relevant HLA molecules will be overexpressed in either K562 or T1 cells and pulsed with relevant dominant epitopes (antibodies.cancer.gov/detail/MajorHistocompatibilityComplexClassICPeptide1).

Example 4: Testing of Mono- and Bispecific Molecules on CD8+KIR+ Treg Cell Activation and Cytotoxicity in a GVHD Transplantation Model Following hematopoietic stem cell transplant and other transplant procedures, a serious and life threatening complication can occur in which donor-derived cells recognize allogeneic host tissues as foreign and become activated, destroying healthy cells of the recipient, which is known as graft vs. host disease (GVHD). Alloreactive GVHD results in transplant associated morbidity in up to 50% of transplant recipients, and accounts for approximately 20% of deaths following transplant. KIR blockade on CD8+KIR+ Tregs may reduce the severity of graft vs host disease in the event that transplanted cells destroy healthy tissues and recognize it as foreign. To test the impact of KIR blockade on GVHD severity, a well-characterized GVHD model will be used, in which human immune cells are injected into NOD/SCID/gamma chain (NSG) deficient mice, and subsequent multiorgan acute pathology observed as a result of human cell activation and destruction of mouse tissues. KIR blocking mono- and bispecific molecules will be injected every 72 hours for the duration of the 30-45 day study, and endpoint analysis will include serum pro-inflammatory cytokines, activation marker expression of human T cells, disease scoring (including survival and body weight), and histopathological analysis of gut tissues for inflammation and epithelial cell killing. This study will support the utility of KIR blockade as a method to reduce severity of GVHD while preserving transplant engraftment, as well as determine the effect of KIR blockade on systemic diseases that may impact multiple organs and tissues.

Example 5: Ly49 Blockade Increases the Activity of CD8+Ly49+ T Regulatory Cells The effects of Ly49 blockade on CD8+Ly49+ Tregs were confirmed in vitro. Briefly, cells were isolated from the spleens and lymph nodes of C57BL/6 mice 10 days after EAE induction using a standard MOG peptide protocol at day 10 (see Saligrama et al., Nature 572:481-487 (2019)). CD4+ T cells, CD8+CD28− regulatory T cells, and CD8+CD28+ were isolated using magnetic separation and stimulated with CD3/CD28 in the presence of no blocking antibody (control) or F(ab')$_2$ fragments of blocking antibody LY49 C/I (clone 5e6; lacking the Fc portion of the antibody) (anti-Ly49) and cultured 1:1 with CD4 T cells.

Figure 4A:
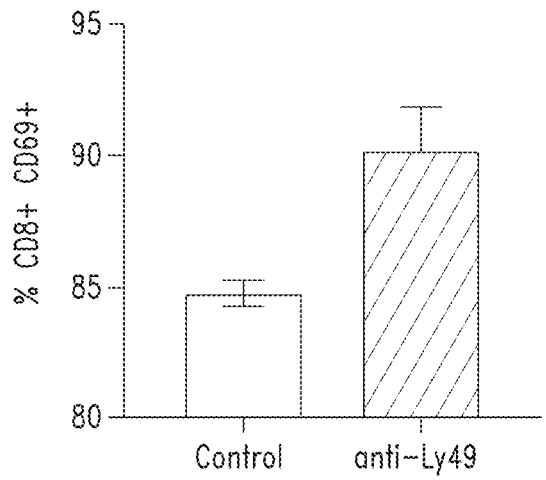
FIGS. 4A to 4D show the effects of Ly49 blockade on CD8+KIR+ T regulatory cells.
Figure 4B:
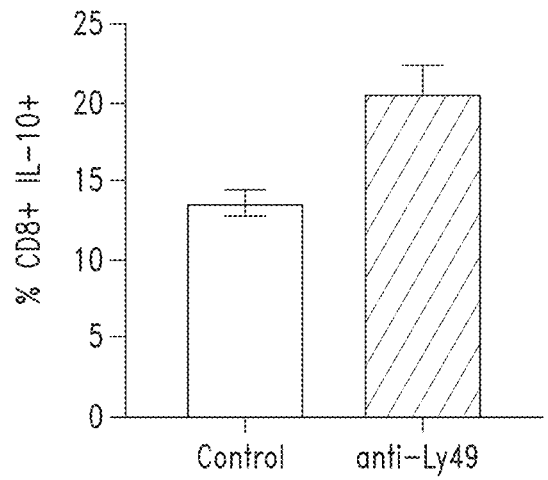
Figure 4C:
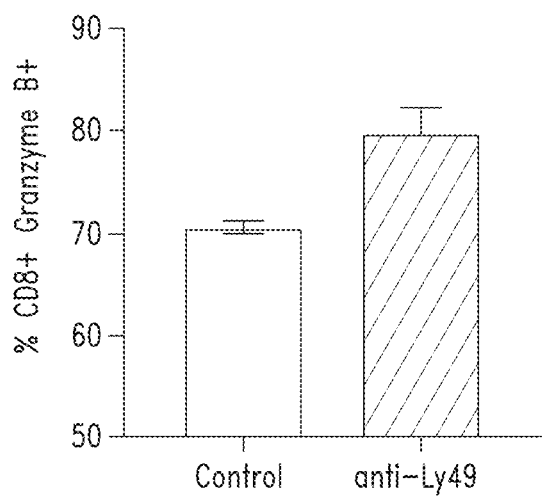
Figure 4D:
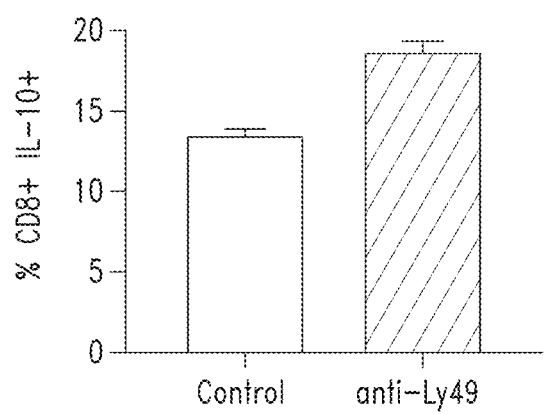

Referring to FIGS. 4A to 4D, in the presence of Ly49 blockade there was a statistically significant increase in CD8+ Treg activation (FIG. 4A), production of immunosuppressive cytokines (FIG. 4B), cytolytic activity (Granzyme B) (FIG. 4C), and an increase in CD4 T cell production of anti-inflammatory IL-10 cytokine (FIG. 4D). Similar results were observed with cells stimulated with CD3/CD28 in the presence of full length Ly49 C/I blocking antibody (clone 5E6) (data not shown). These results confirm that CD8+Ly49+ T cells exhibit an increase in activation by Ly49/KIR blockade.

Supernatants from the cells (above) were collected at 48 hours after the initiation of the co-culture and analyzed for a variety of analytes (cytokines) using a Bioplex assay.

The results of this analysis indicated that Ly49 blockade suppresses the following proinflammatory cytokines in samples from mice treated with MOG and suppressor peptide as compared to mice treated with MOG peptide alone: RANTES, IL-6, IL-18, GM-CSF, TNFalpha, and IFN-gamma (data not shown). In addition, IL-2 and IL-15 levels were decreased in samples from mice treated with MOG and suppressor peptide as compared to mice treated with MOG peptide (data not shown). Levels of the anti-inflammatory cytokines IL-22 and MCP-3 were decreased in samples from mice treated with MOG and suppressor peptide as compared to mice treated with MOG peptide (data not shown).

Figure 5:
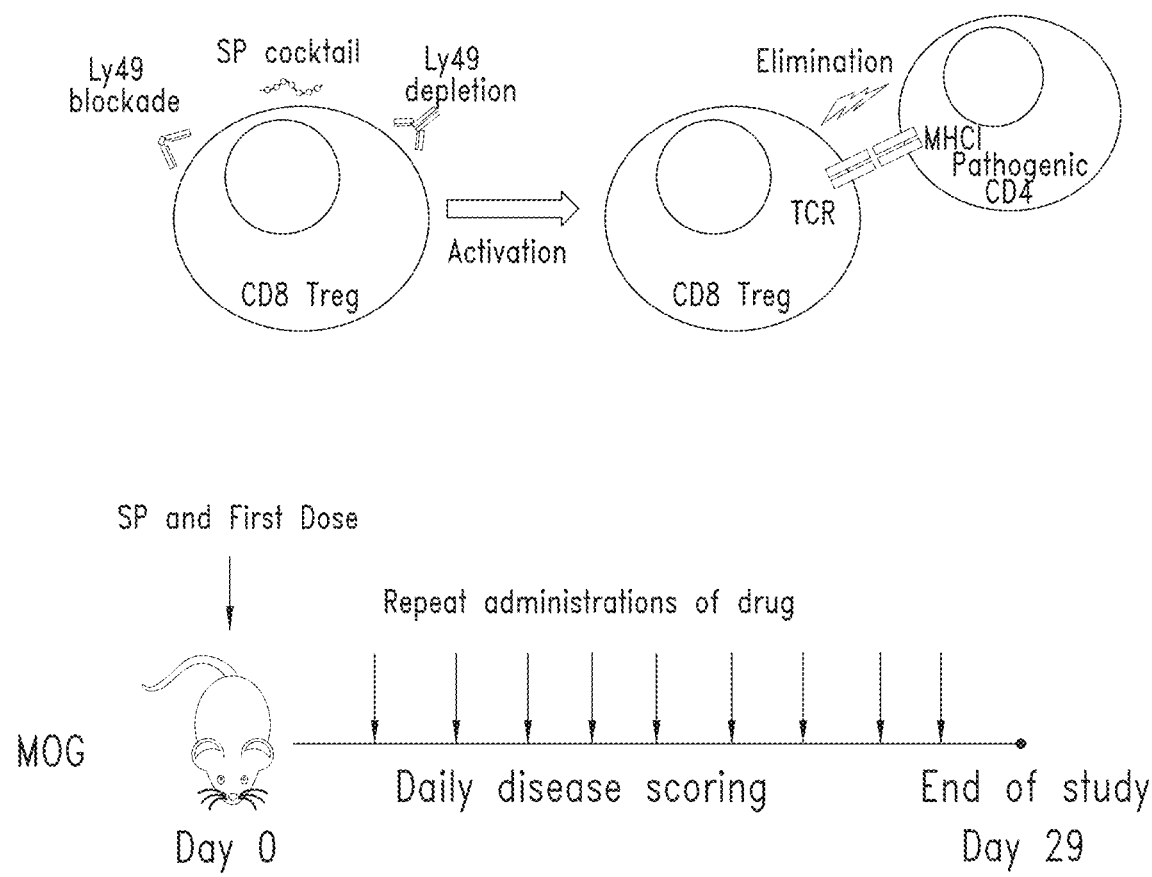
FIG. 5 shows the experimental design for assessing the effects of Ly49 blockade in a murine experimental autoimmune encephalomyelitis (EAE) model.
Figure 6:
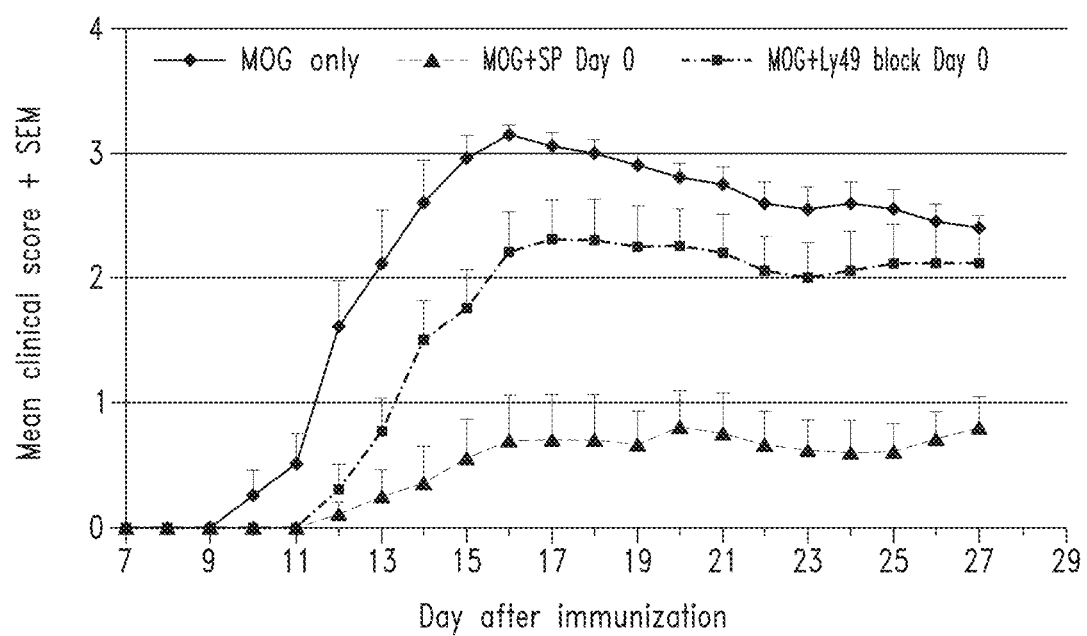
FIG. 6 shows disease severity (as measured by clinical score) at 7 to 27 days following immunization with MOG only, MOG+SP, MOG+Ly49 blockade. (MOG=myelin oligodendrocyte glycoprotein; see Saligrama et al., Nature 572:481-487 (2019).)

The effects of Ly49 blockade were assessed in vivo in a murine EAE model. Briefly, EAE was induced in C57BL/6 mice using a standard MOG injection protocol (see Saligrama et al., Nature 572:481-487 (2019)). Mice were administered MOG alone or in combination with a "surrogate peptide" cocktail ("SP") or F(ab')2 fragments of blocking antibody LY49 C/I (clone 5E6; lacking the Fc portion of the antibody) (anti-Ly49 or "Ly49 blockade") (FIG. 5). Ly49 blockade delayed onset of disease and diminished severity of disease (FIG. 6), suggesting that CD8+ Treg mobilization at the time of autoimmune trigger contributed to control of disease.

Example 6: CD8 KIR+ T Cells have Greater Cytolytic Potential than CD8 T Cells Negative for KIR Expression in Celiac Patients Peripheral blood mononuclear cells (PBMCs) were obtained from Celiac patients and from healthy donors. The PBMCs were enriched for CD8+ T cells, and then stained for several surface markers, including CD8 and a mix of pan-inhibitory KIR reactive peptides, and sorted to obtain CD8+KIR+ T cells and CD8+KIR-cells. After sorting, the PBMCs were stimulated with gluten peptides. Six days after stimulation, the CD8 Treg cells were evaluated for intracellular Granzyme, perforin, and IFNgamma levels.

Figures 7A, 7B, 7C:
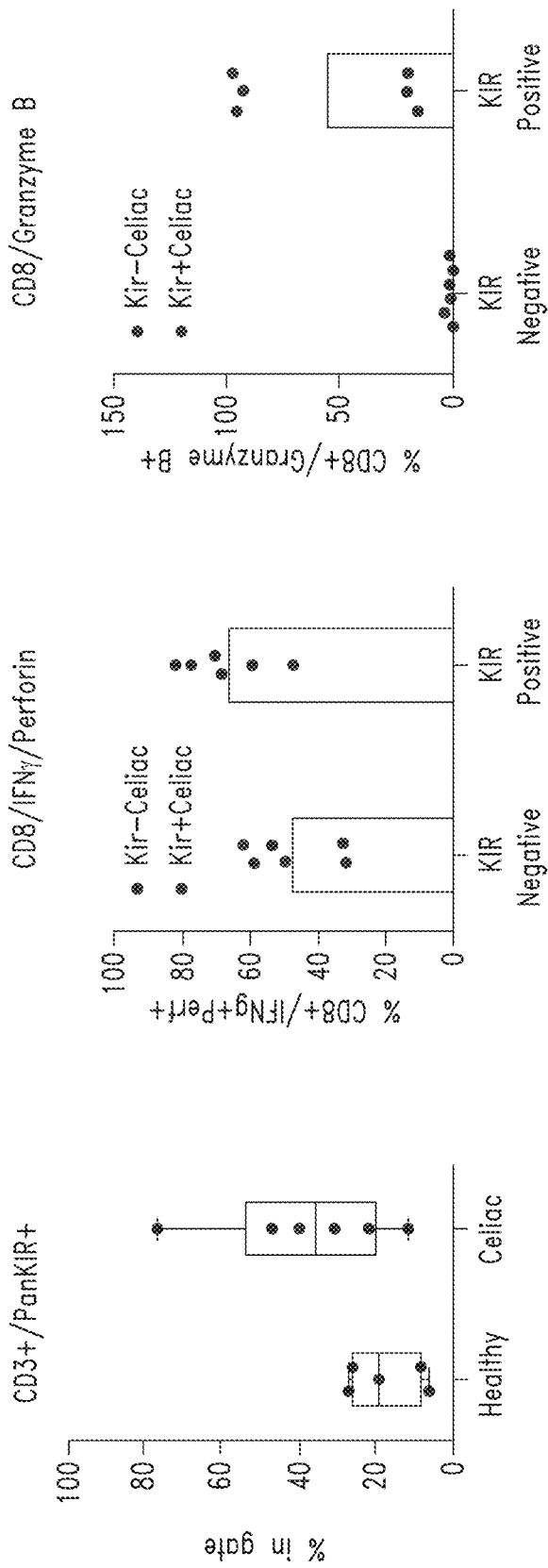
FIGS. 7A to 7C show characteristics of T cells prevalent in Celiac patients. Celiac patients have an increased prevalence of CD8+KIR+ T cells (FIG. 7A); have an increase in percentage of CD8+ T cells with intracellular IFNgamma and perforin (FIG. 7B); and have an increase in percentage of CD8+ T cells with intracellular Granzyme B (FIG. 7C).

PBMCs from Celiac patients had a greater percentage of CD8+KIR+ Treg cells (FIG. 7A). The KIR+CD8+ T cells had a greater percentage of cells with perforin, and intracellular IFNgamma and Granzyme B as compared to CD8+ KIR-T cells (FIGS. 7 B and 7C). These results indicate that Celiac patients harbor CD8+KIR+ T cells with greater cytolytic potential than CD8+ T cells negative for KIR.

Example 7: Celiac Patients have More KIR+CD8+ T Cells and More ICOS Expression on KIR+CD8+ T Cells than from Healthy Controls PBMCs from Celiac patients (six) or healthy donors were analyzed by flow cytometry and gated on CD8+ T cells. PBMCs from Celiac patients had more CD3+/PanKIR+ T cells than PBMCs from healthy donors (FIG. 8A). PBMCs from Celiac patients had more CD3+/PanKIR+/ICOS+ cells than PBMCs from healthy donors (FIG. 8B). These results indicate that Celiac patients have more ICOS expression on KIR+CD8+ T cells.

Example 8: Gluten Restimulation Increases Granzyme B Levels and Degranulation of CD8+KIR+ Tregs and Loss of CD4+ T Cells To determine the effects of the gluten restimulation on the CD8+KIR+ T cells, PMBCs from Celiac patients were stimulated with gluten peptides for 12 days to enrich for both CD4 reactive cells and CD8+ Treg cells in the presence of IL-7 and 15. CD8 Tregs and CD4 T cells were then selected and combined 1:1 with autologous APCs pulsed with no peptide, flu peptides, or gluten peptides. 48 hours later, the cells were analyzed by flow cytometry Restimulation with the gluten peptides increased degranulation, as measured by CD107 (FIG. 9A, left), and Granzyme B levels (FIG. 9A, right), as compared to restimulation with control flu peptides or unstimulated cells. (598 refers to PBMCs from patient 598.) Restimulation with gluten peptides also caused a reduction of the percentage of viable CD4+ cells, while restimulation with flu peptide did not (FIG. 9B). These results indicate that the antigenic response by CD8+KIR+ Tregs is specific, consistent with the source of the Tregs from Celiac patients, and are rapid and sustained. These results show that CD8+ Treg cells are upregulated and CD4+ T cell activation is down-regulated, and that pathogenic CD4+ T cells are eliminated.

Figure 10B:
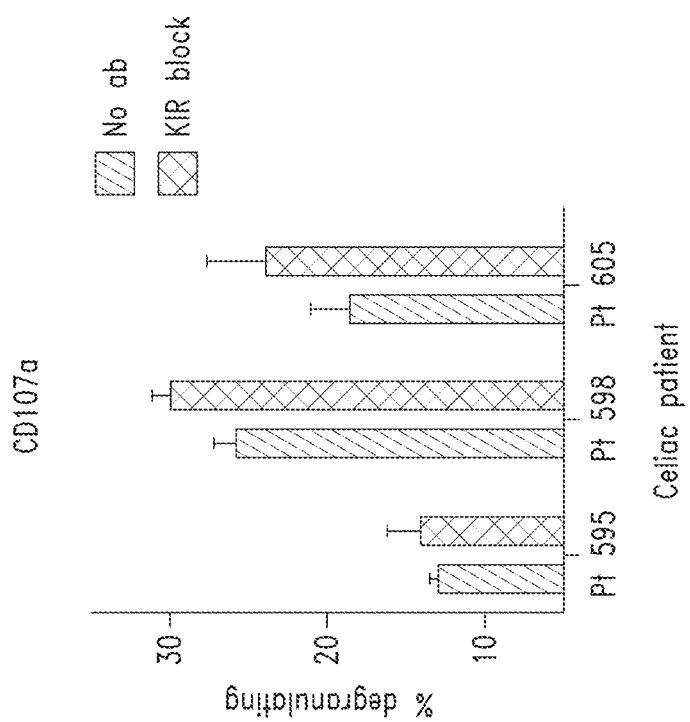
FIGS. 10A to 10B show that KIR blockade ("KIR block") of CD8+ Tregs results in increased intracellular Granzyme B levels (FIG. 10A) and increased degranulation (CD107) (FIG. 10B).
Figure 10A:
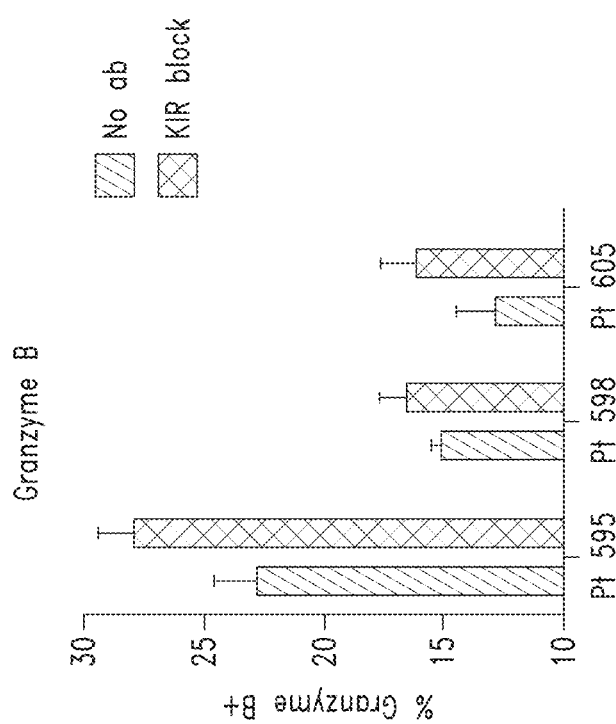

Example 9: KIR Blockade Increases Granzyme B Content and Degranulation of CD8+ T Cells CD8+CD16+ T cells were selected from 3 patients diagnosed with Celiac disease and cultured 1:1 with CD4+ T cells and 1 ug/ml anti-CD3 agonist antibody (clone OKT3) in the presence or absence of 100 ug/ml KIR2DL1/2/3 and KIR3DL1 antagonist antibodies (50 ug each). 48 hours later, CD8+ Treg cells were analyzed using flow cytometry. KIR blockade ("KIR block") increased intracellular Granzyme B levels (FIG. 10A) and degranulation (CD107) (FIG. 10B).

Figure 11:
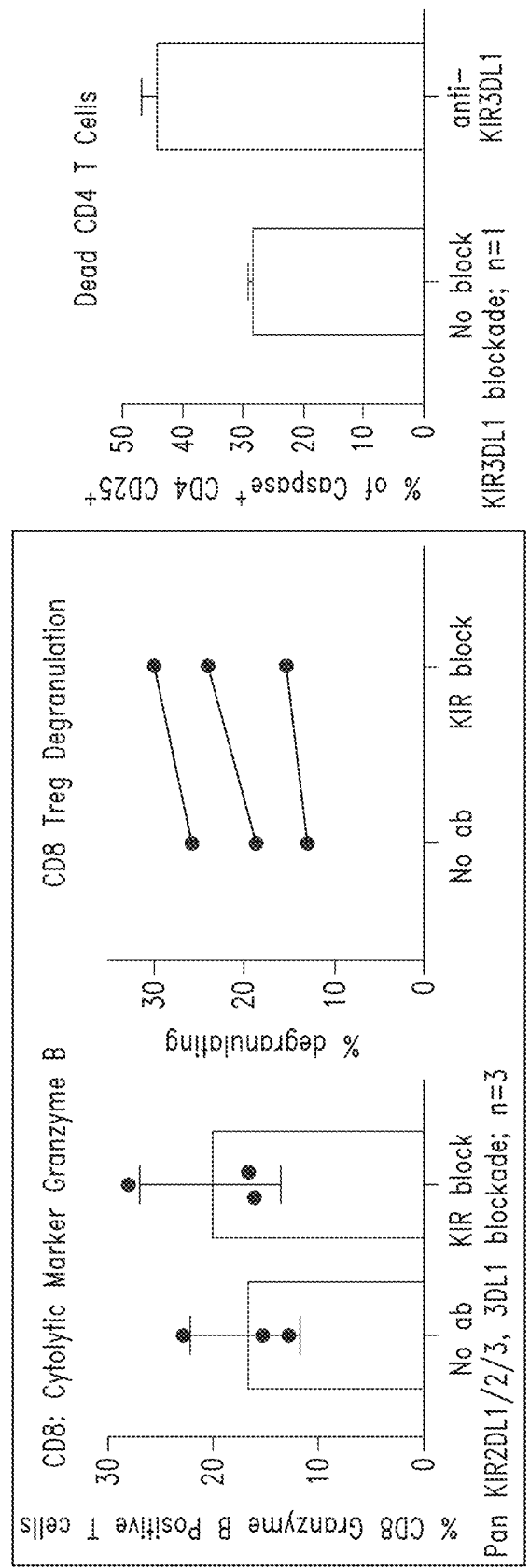
FIG. 11 shows an increase in cytolytic activity of CD8+ T cells, a decrease in CD4+ T cell activation, and an increase in CD4+ T cell death in PBMCs from celiac patients treated with KIR blockade and gluten restimulation.

The effects of KIR blockade were assessed in vitro in another experiment using PBMCs from celiac patients. Briefly, CD8+ Treg were enriched from Celiac patient PBMCs and cultured with autologous CD4 T cells and antigen presenting cells pulsed with a gliadin peptide cocktail, and analyzed using flow cytometry. Upon restimulation, cells administered anti-inhibitory KIR antibodies (anti-KIR2DL1/2/3, anti-KIR3DL1 or a cocktail of anti-KIR2DL1/2/3 and KIR3DL1) exhibited an induction of cytolytic activity of CD8+ T cells, a decrease in CD4+ T cell activation, and an increase in CD4+ T cell death (FIG. 11). These results were consistently observed across several patient samples upon mono- and bi-specific KIR blockade.

Example 10: KIR Blockade Decreases CD4+ T Cell Activation

Figure 12:
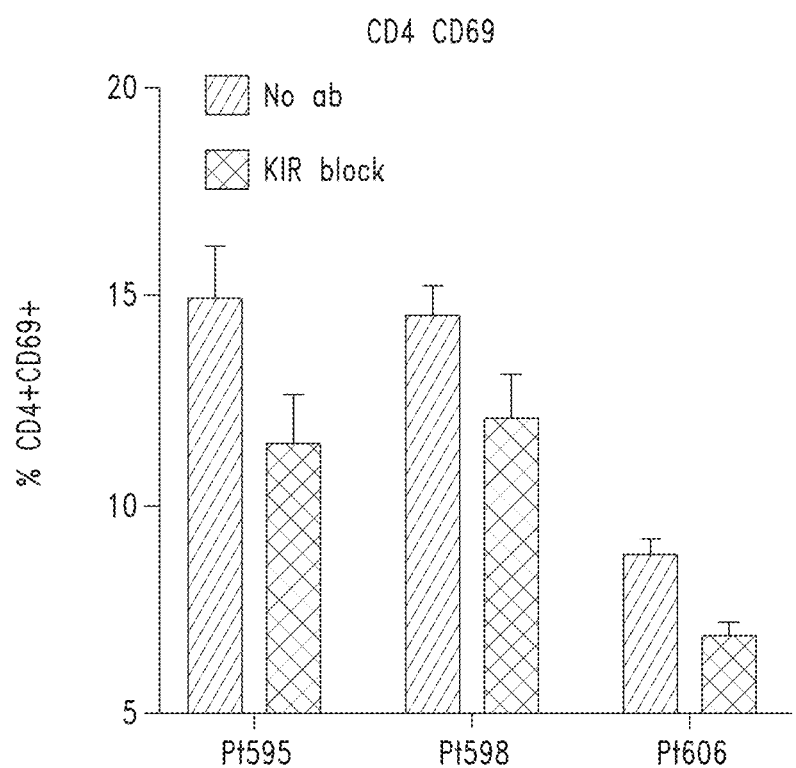
FIG. 12 shows that KIR blockade of CD8+CD16+ T cells reduced CD4 T cell activation and proliferation (CD69) in samples from three Celiac patients.

CD8+CD16+ T cells were selected from 3 patients diagnosed with Celiac disease and cultured 1:1 with CD4+ T cells and 1 ug/ml anti-CD3 agonist antibody (clone OKT3) in the presence or absence of 100 ug/ml KIR2DL1/2/3 and KIR3DL1 antagonist antibodies (50 ug each). 48 hours later, CD8+ Treg cells were analyzed using flow cytometry. KIR blockade reduced CD4+ T cell activation and proliferation (CD69) in samples from all three patients (FIG. 12).

Example 11: Association Between Select KIR Proteins and HLA Ligand Expression in CD8+ Treg Cells in Celiac Disease Celiac patient PBMCs were stained with antibodies directed toward KIR2DL1/2/3 and KIR3DL1. After gating on CD8 T cells, the percentage positivity of the cells for the KIR ligands and HLA haplotype was determined. (HLA and KIR typing were performed in collaboration with Scisco Genetics.)

CD8 T cells from patients expressed KIRs as follows: 3 of 3 expressed KIR2DL and 2 of 3 expressed KIR3DL in peripheral blood. HLA ligands for the select KIRs are overrepresented in the Celiac patient samples. 9 of 10 patients had at least one copy of HLA-C 07:01:01 and 10 of 10 patients had at least one copy of HLA-B 08:01:01.

Example 12: Characterization of Bispecific Molecules that Co-Bind to CD8 and KIR2DL A CrossMab was prepared using a Fab that binds to KIR2L1/2/3 (prepared from IPH2102 IgG1r mAb (parental antibody VH and VL sequences, SEQ ID NOs: 101 and 102, respectively)) and an scFv that binds to CD8alpha (prepared from Mb1b IgG1r mAb (parental antibody VH and VL sequences, SEQ ID NOs: 81 and 82)). The Fab and scFv were attached to an IgG1 hinge-CH2-CH3 in which the CH3 domain was engineered to contain the "knobs-into-holes" mutations to enforce correct association of the two heterodimeric heavy chains. The "knob" heavy chain included mutations S354C and T366W. The "hole" heavy chain included mutations Y349C, T366S, L368A, and Y407V.

The KIR2L1/2/3-CD8alpha CrossMAb was tested for co-binding to KIR2DL1 or KIR2DL3 and CD8alpha by biolayer interferometry using an Octet instrument. For the co-binding studies, the CrossMAb was captured to AHC (anti-human Fc) biosensors using 2-fold dilutions ranging from 0.3125 ug/ml to 20 µg/ml. The analytes (KIR2DL1, KIR2DL3, and CD8alpha) were kept constant at 100 nM. Analyte co-binding following capture was analyzed in two ways: first the association of KIR2DL1 or KIR2DL3 followed directly by the association of CD8alpha, or the association of CD8alpha followed by the direct association of KIRDL1 or KIR2DL3. KIR2DL1, KIR2DL3, and CD8alpha were tagged with a hexahistidine peptide. The CrossMab was able to co-bind targets KIR2DL1 or KIR2DL3 and CD8alpha.

CrossMAb affinity for KIR2DL1, KIR2DL3, and CD8alpha ligands was measured and compared to the anti-CD8alpha and anti-KIR2DL1/L2/L3 parental antibodies using the Octet instrument. For kinetic analysis, the CrossMAb was captured to AHC (anti-human Fc) biosensors using a load concentration of 1.25 ug/ml. Each analyte (KIR2DL1, KIR2DL3, and CD8alpha) concentration ranged from 6.25 nM to 200 nM. Analyte binding following capture was analyzed first for the association of KIR2DL1, KIR2DL3, or CD8alpha followed by the dissociation of each analyte independently. This ensured that ka (on rate), kd (off rate), and KD values could be obtained and directly compared to the parental antibodies. The kinetic analysis revealed that the CrossMab retained affinity for targets KIR2DL1, KIR2DL3, and CD8alpha.

The affinities of the parental antibodies anti-KIR2DL1/L2/L3 IPH2102 IgG1r mAb and anti-CD8alpha Mb1b IgG1r mAb were also analyzed. For kinetic analysis, the parental antibodies were separately captured to AHC (anti-human Fc) biosensors using a load concentration of 1.25 ug/ml. For IPH2102 IgG1r mAb, the KIR2DL1, or KIR2DL3 analytes ranged from 6.25 nM to 200 nM. Analyte binding following capture was analyzed first for association of KIR2DL1 or KIR2DL3 followed by the dissociation of each analyte independently. Likewise, for the Mb1b IgG1r mAb, the CD8alpha analyte ranged from 6.25 nM to 200 nM. Analyte binding following capture was analyzed first for association followed by the dissociation of CD8alpha.

TABLE 1

Comparison of affinities between the parental antibodies and the CrossMAb

| Protein | Target | Affinity KD (nM) |
|---|---|---|
| IPH2102 parental antibody | KIR2DL1/L2/L3 | KIR2DL1: 1.38 nM<br>KIR2DL3: 0.78 nM |
| Mb1b parental antibody | CD8alpha | CD8alpha: 2.6 nm |
| IPH2102/Mb1b CrossMAb | KIR2DL1/L2/L3 and CD8alpha | KIR2DL1: 1.52 nM<br>KIR2DL3: 0.88 nM<br>CD8alpha: 2.07 nM |

Figure 13:
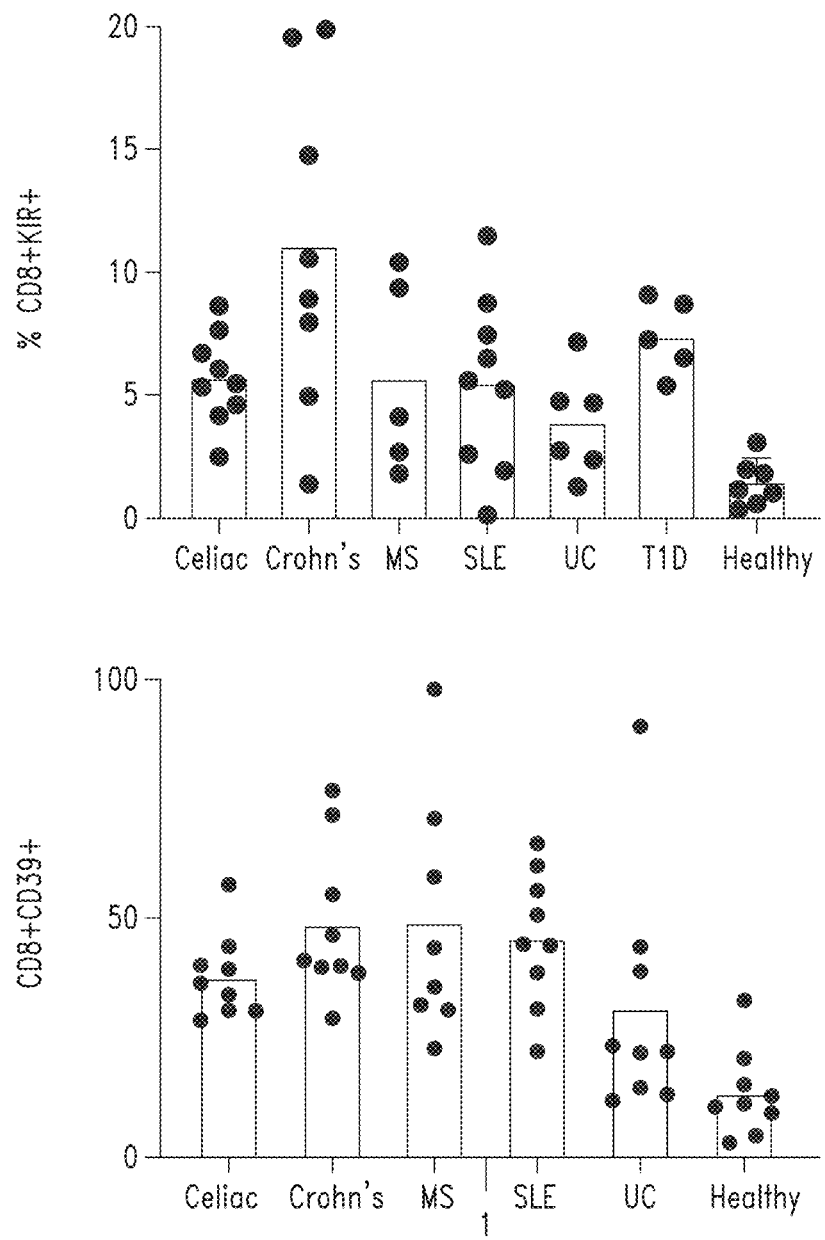
FIG. 13 shows the presence of CD8+KIR+ Treg cells (upper panel) and CD8+CD39+ Treg cells (lower panel) in samples from patients having celiac disease, Crohn's disease, multiple sclerosis (MS), systemic lupus erythematosus (SLE), ulcerative colitis (UC), or type 1 diabetes (T1D), or in healthy subjects.

Example 13: Analyses of PBMC Samples from Patients Diagnosed with Other Autoimmune Diseases PBMCs from patients having Lupus, Ulcerative colitis, Crohn's Disease, Multiple Sclerosis, and Type 1 Diabetes were analyzed using flow cytometry and bioplex assays. CD8+KIR+ Treg cells were identified in these patient samples using a cocktail of antibodies directed toward a subset of inhibitory KIR surface receptors, KIR2DL1/2/3 and KIR3DL1 (FIG. 13). The Tregs were found to express CXCR3, CD39, and other cells surface markers, consistent with the CD8+ Tregs from Celiac disease patients (data not shown). The CD8+ Tregs were found to produce soluble analytes associated with CD8+ Treg cell function, including IFNgamma and IL-22 (data not shown).

Figure 14:
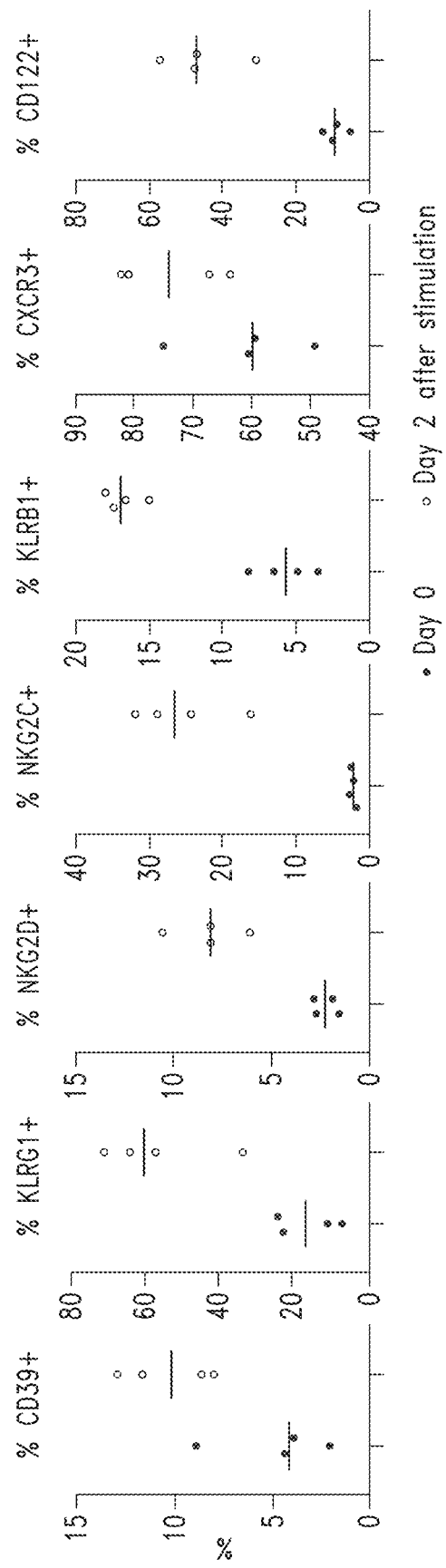
FIG. 14 shows expression of surface markers CD39, KLRG1, NKG2D, NKG2C, KLRB, CXCR3, and CD122 on CD8+KIR+ Treg cells isolated from celiac patient PBMC samples.

Example 14: Phenotypic and Functional Characterization of CD8+KIR+ Treg Cells PBMCs from individuals with celiac disease and the HLA DQ2.5 haplotype were analyzed using flow cytometry and bioplex assays to detect soluble analytes in supernatant. CD8+KIR+ Treg cells were identified in these patient samples, and were found to express the surface markers CD39, KLRG1, NKG2D, NKG2C, KLRB, CXCR3, and CD122 (FIG. 14).

Figure 15:
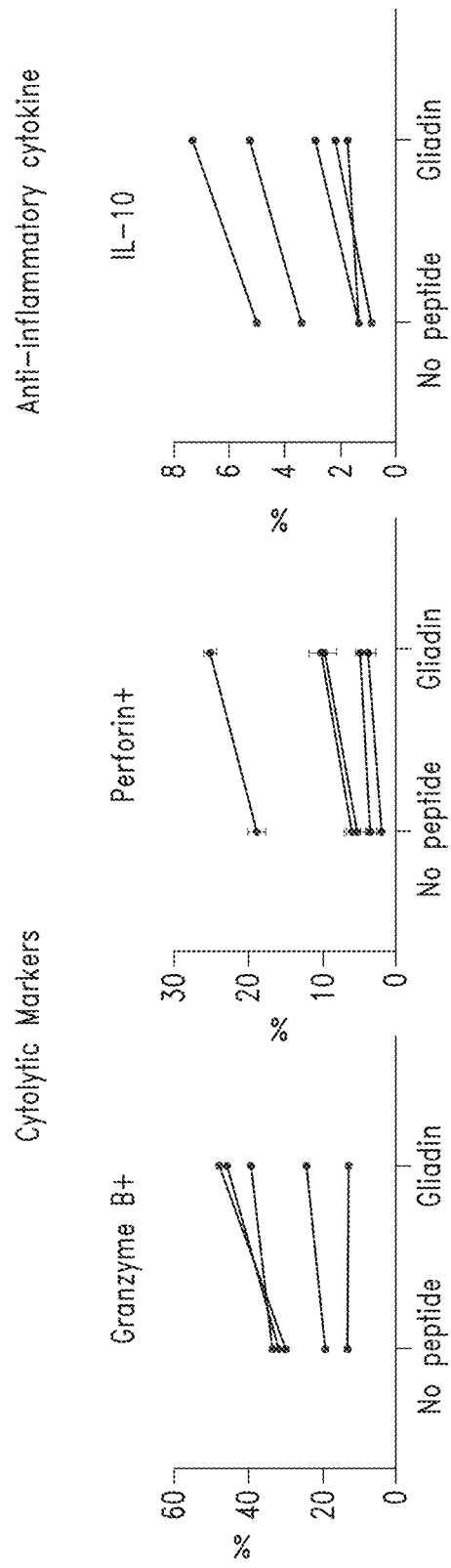
FIG. 15 shows granzyme B, perforin, and IL-10 production by CD8+ Treg cells isolated from celiac patient PBMC samples.
Figure 16:
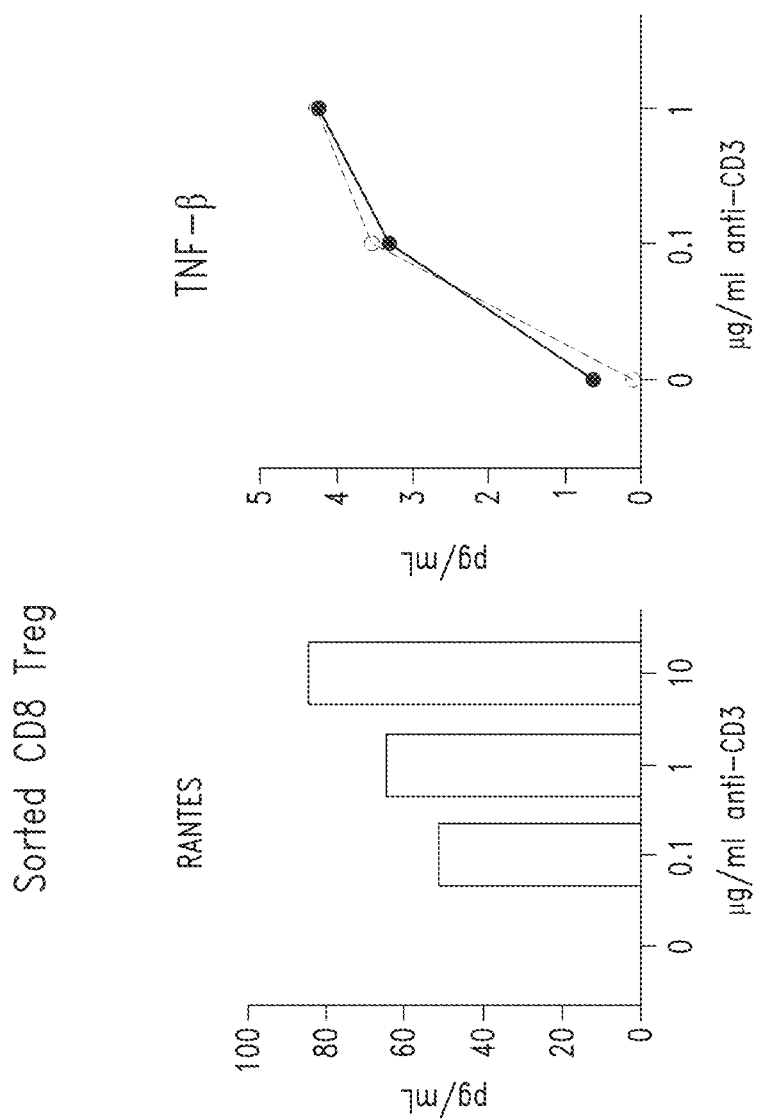
FIG. 16 shows production of RANTES and TNFβ by CD8+KIR+ Treg cells isolated from celiac patient PBMC samples, following stimulation with anti-CD3 antibodies.
Figure 17:
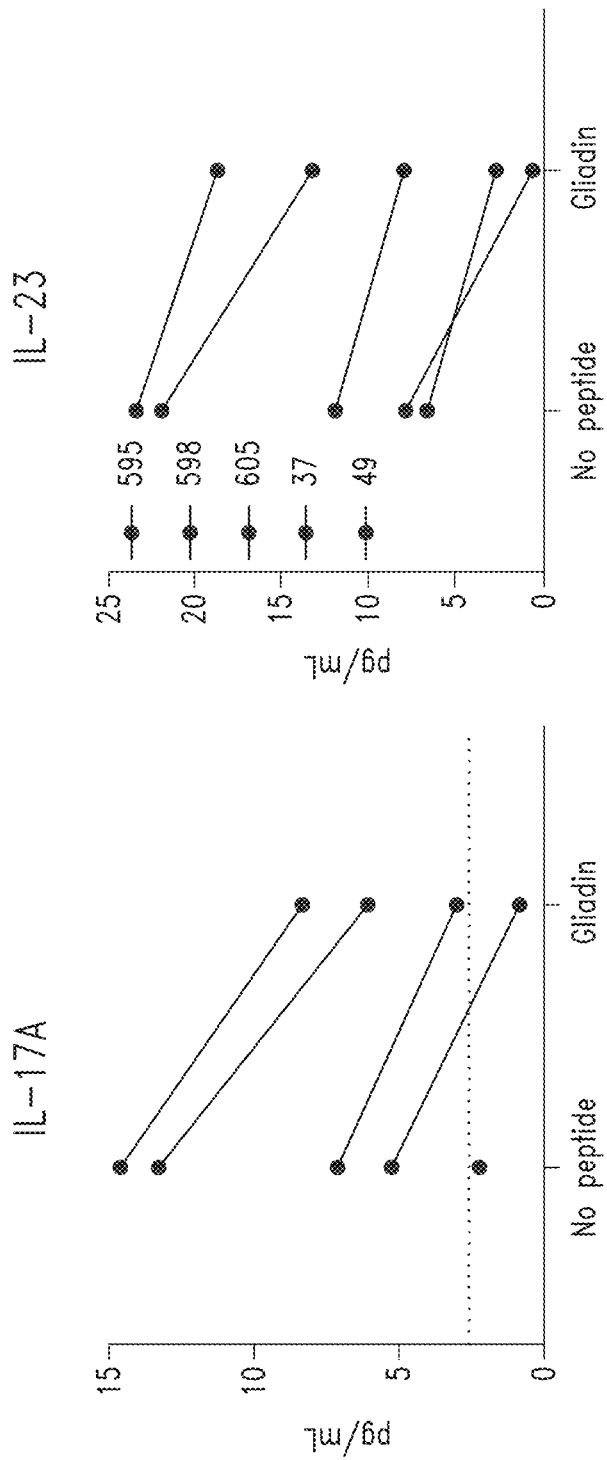
FIG. 17 shows a decrease in IL-17A and IL-23 production by CD4+ T cells co-cultured with CD8+KIR+ Treg cells following gliadin stimulation.
Figure 18:
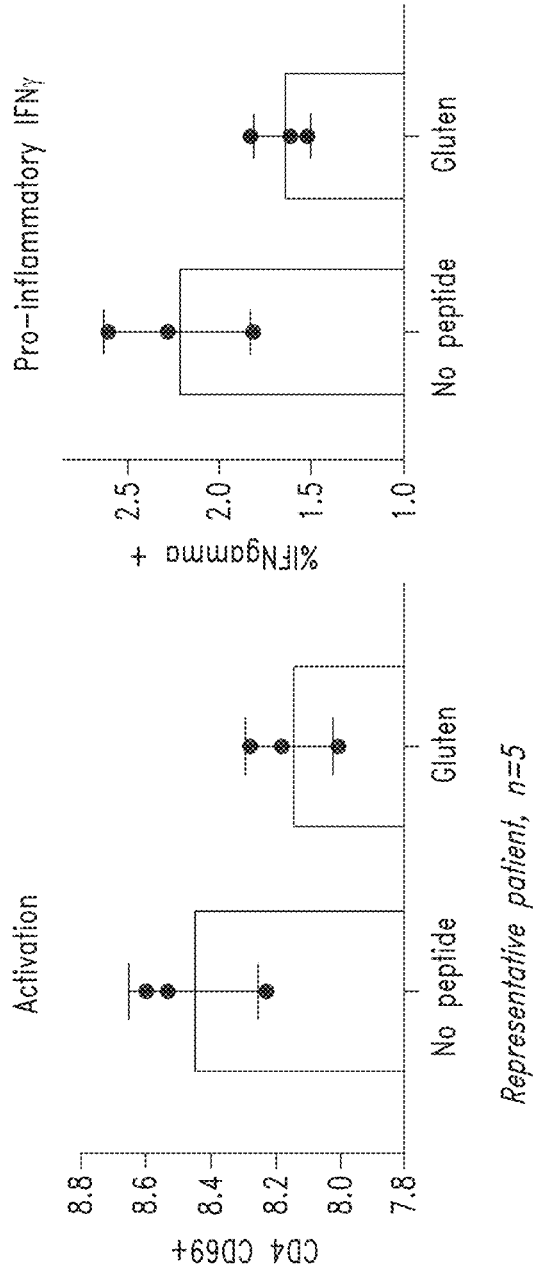
FIG. 18 shows changes in activation and IFNγ by CD4+ T cells co-cultured with CD8+KIR+ Treg cells and stimulated with gluten.
Figure 19:
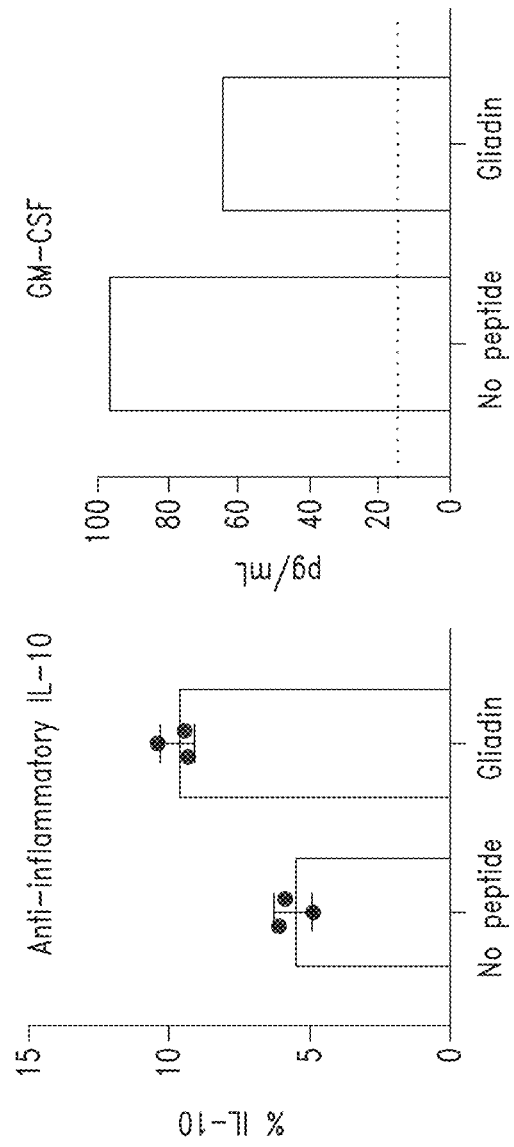
FIG. 19 shows an increase in anti-inflammatory cytokines in CD4+ T cells co-cultured with CD8+KIR+ Treg cells and stimulated with gliadin. IL-10 produced by CD4+ T cells is indicated using intracellular cytokine staining.

When cultured under optimized conditions with autologous CD4 T cells and antigen presenting cells pulsed with gliadin peptides, the CD8+KIR+ Tregs produced soluble analytes associated with CD8+ Treg cell function, including the cytolytic markers granzyme B, perforin, and CD107a, the intracellular anti-inflammatory cytokines IL-10, IFNγ, and TNFα, and secreted cytokines (see, e.g., FIG. 15). Stimulation of isolated CD8+KIR+ Treg cells with increasing doses of anti-CD3 antibodies produced a number of cytokines and chemokines in a dose-dependent manner, including RANTES and TNFβ that titrated with the strength of TCR signal delivered (FIG. 16). When co-cultured with CD4+ T cells restimulated with gliadin, CD8+KIR+ Treg cells controlled CD4+ T cell activation and decreased proinflammatory cytokines produced by CD4+ cells (FIGS. 17-19). CD4+ T cell markers of activation show that addition of CD8+KIR+ Treg cells during gliadin restimulation specifically decreases gliadin-reactive CD4+ T cell activation (FIG. 18). Anti-inflammatory cytokines produced by CD4 T cells also increased (FIG. 19) and certain inflammatory cytokines and chemokines detected in the co-culture supernatant were down-regulated. These data indicate that CD8+KIR+ Tregs isolated from PBMCs derived from celiac patients are able to survive, expand, and function when cultured under optimized conditions, and thus functional defects in celiac patients appear to be reversible.

Figure 20:
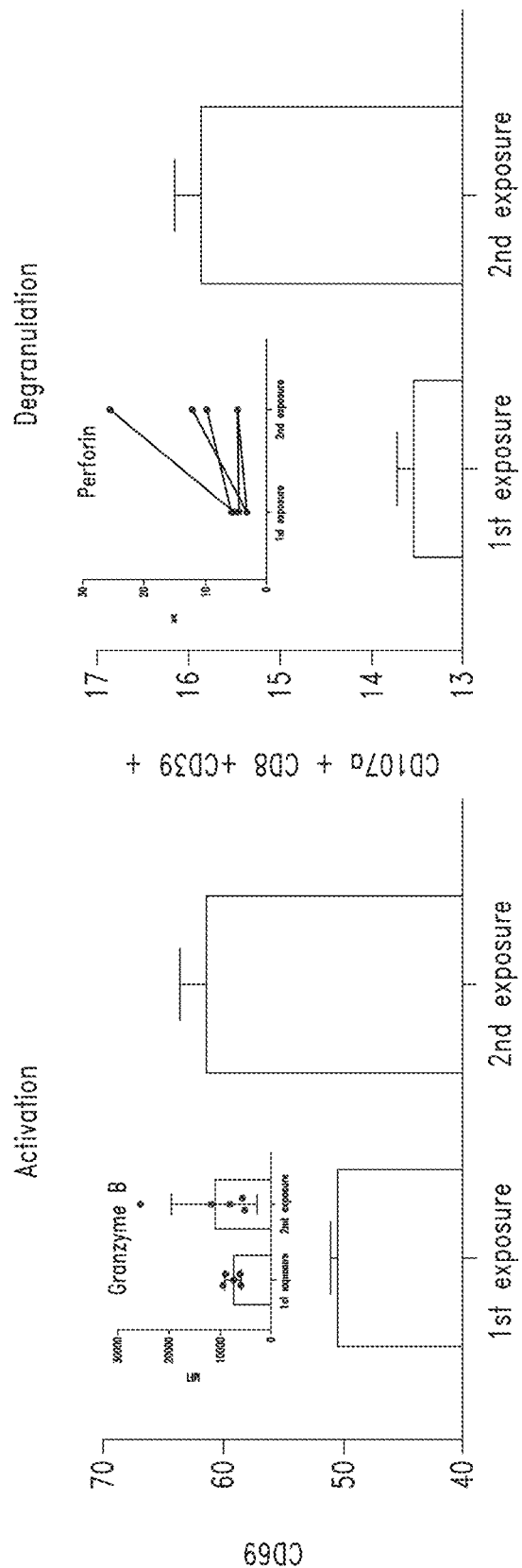
FIG. 20 shows an increased CD8+ Treg cell response upon repeated antigenic exposure.

Additionally, enriched recall of the CD8+ Treg cell response and prevalence was observed upon repeated antigenic exposure, suggesting a potentially long lasting and disease-modifying effect (FIG. 20). Although patient-to-patient variability was observed, consistent effects on the functional response of CD8+ Treg cells over repeated antigenic exposure were observed across multiple data readouts. These findings suggest a possible induced memory function of CD8+ Treg cells.

Figure 21:
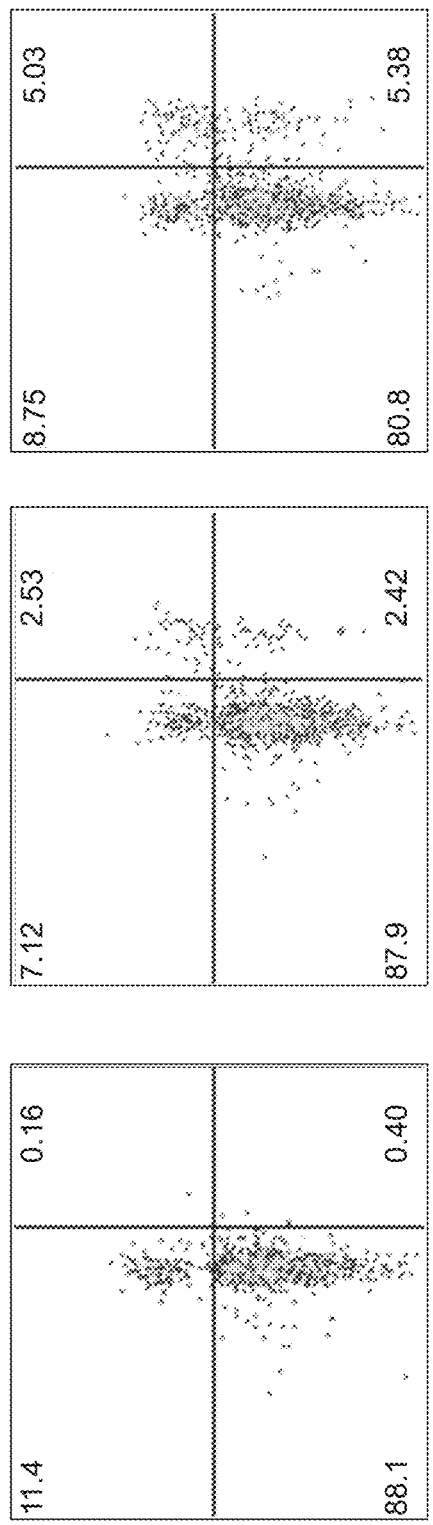
FIG. 21 shows selective expression of inhibitory KIR proteins KIR2DL1/2/3 and KIR3DL1 by CD8+ Treg cells from celiac patient PBMCs.

Example 15: Association Between Select KIR Proteins and HLA Ligand Expression in CD8+ Treg Cells in Celiac Disease Celiac patient PBMCs were stained with antibodies directed toward KIR2DL1/2/3 and KIR3DL1 and analyzed using flow cytometry. Narrow expression of particular inhibitory KIR proteins on CD8+ Treg cells was observed, with patients selectively expressing KIR2DL1/2/3, KIR3DL1, or both KIR2DL1/2/3 and KIR3DL1 (FIG. 21), an observation that extended to patients with other AI indications, including having Systemic Lupus Erythematosus, Ulcerative colitis, Crohn's Disease, Multiple Sclerosis, and Type 1 Diabetes (FIG. 13). This expression pattern was associated with nearly ubiquitous genomic expression of inhibitory KIR proteins, and overrepresented haplotype expression of their respective HLA ligands across celiac patients relative to a healthy control population (Table 2).

TABLE 2

Receptor-Ligand Pairings are Over-Represented in Celiac Patients

| Receptor/Ligand Pair | | Celiac Patients | Prevalence* |
|---|---|---|---|
| Inhibitory KIR | KIR3DL1 | 14 out of 15 | |
| Ligand | HLA-B | 42 out of 53 | US: ~25% |

TABLE 2-continued

Receptor-Ligand Pairings are Over-Represented in Celiac Patients

| Receptor/Ligand Pair | | Celiac Patients | Prevalence* |
|---|---|---|---|
| Haplotype | 08:01:01 | | (<<in other countries) |
| Inhibitory KIR | KIR2DL1 | 15 out of 15 | |
| Ligand | HLA-C | 43 out of 53 | US: ~30% |
| Haplotype | 07:01:01 | | |

*http://www.allelefrequencies.net/hla.asp

Example 16: T Cell Expression and Interaction Patterns in PBMC and Gut Tissue from Celiac Patients Pre- and Post-Challenge with Gluten Formalin fixed, paraffin embedded celiac patient duodenal biopsies were sectioned and stained using a proprietary platform and custom antibody cocktail that detects eight cell markers simultaneously in fixed tissues (developed in collaboration with Ultivue, Inc.). The antibody cocktail included antibodies directed toward CD3, CD4, CD8, CD28, PD-1, Ki-67, Granzyme B, and KIR2DL1/2/3.

Figure 22:
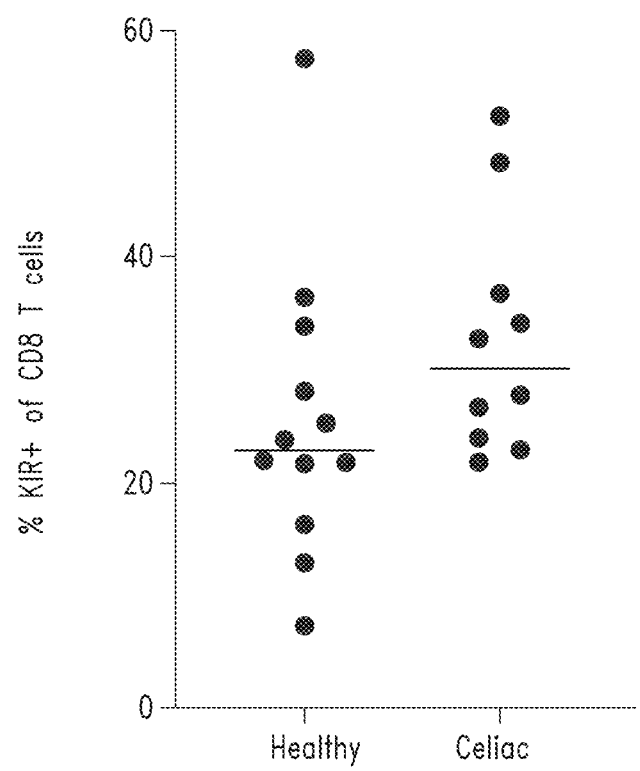
FIG. 22 shows increases in CD8+KIR+ T cells in celiac patients.
Figure 23:
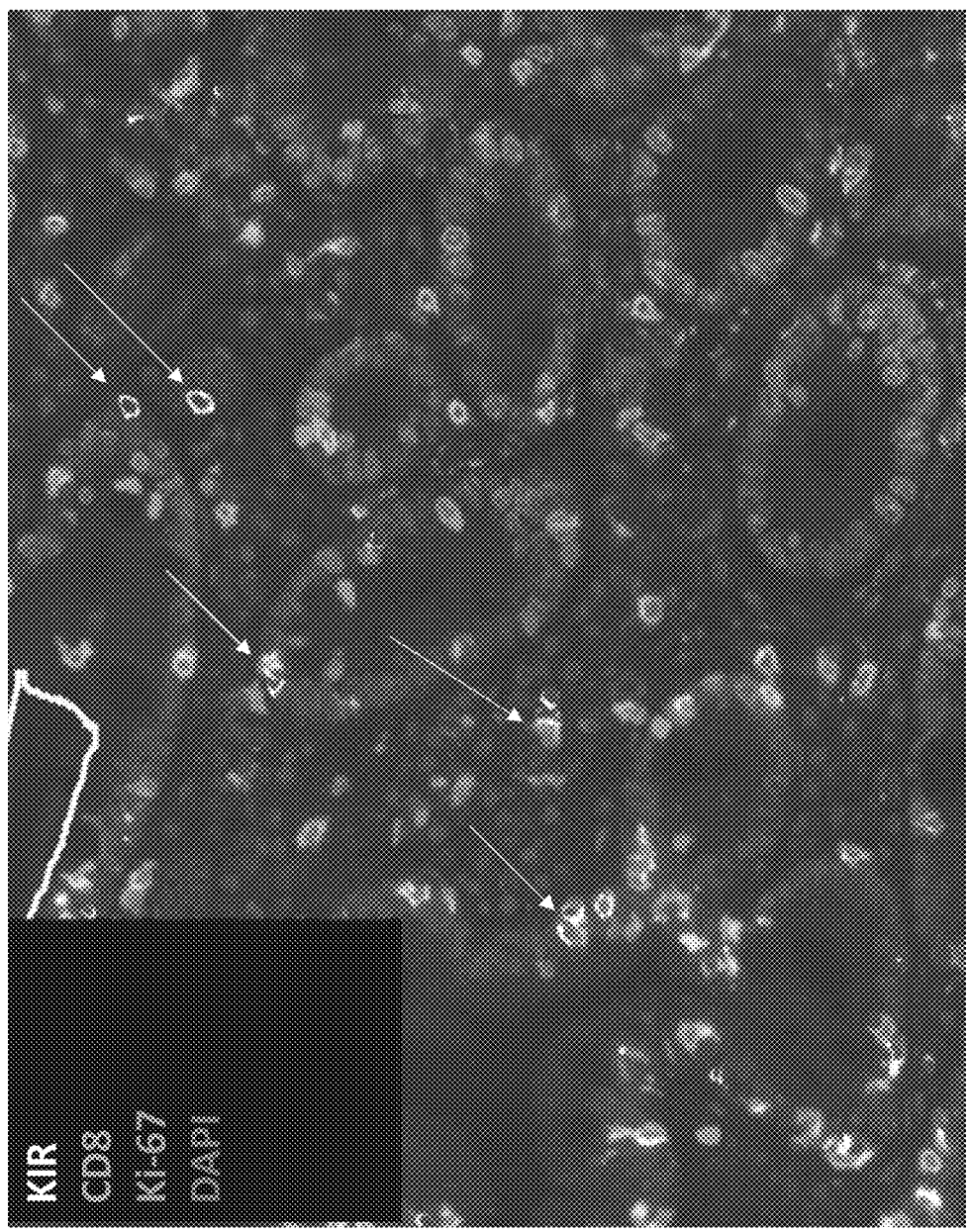
FIG. 23 shows the presence of CD8+KIR+ T cells in the gut tissue of a celiac patient.

CD8+KIR+ Treg cells are increased in celiac disease (FIG. 22). Expression of inhibitory KIR was confirmed in celiac patient peripheral blood and tissue and is a marker of CD8+ Treg cells (FIG. 23). Only a subset of CD8+ T cells co-localize with KIR expression, so KIR and CD8 co-expression is indicative of CD8+ Treg cells in gut tissue.

Figure 24:
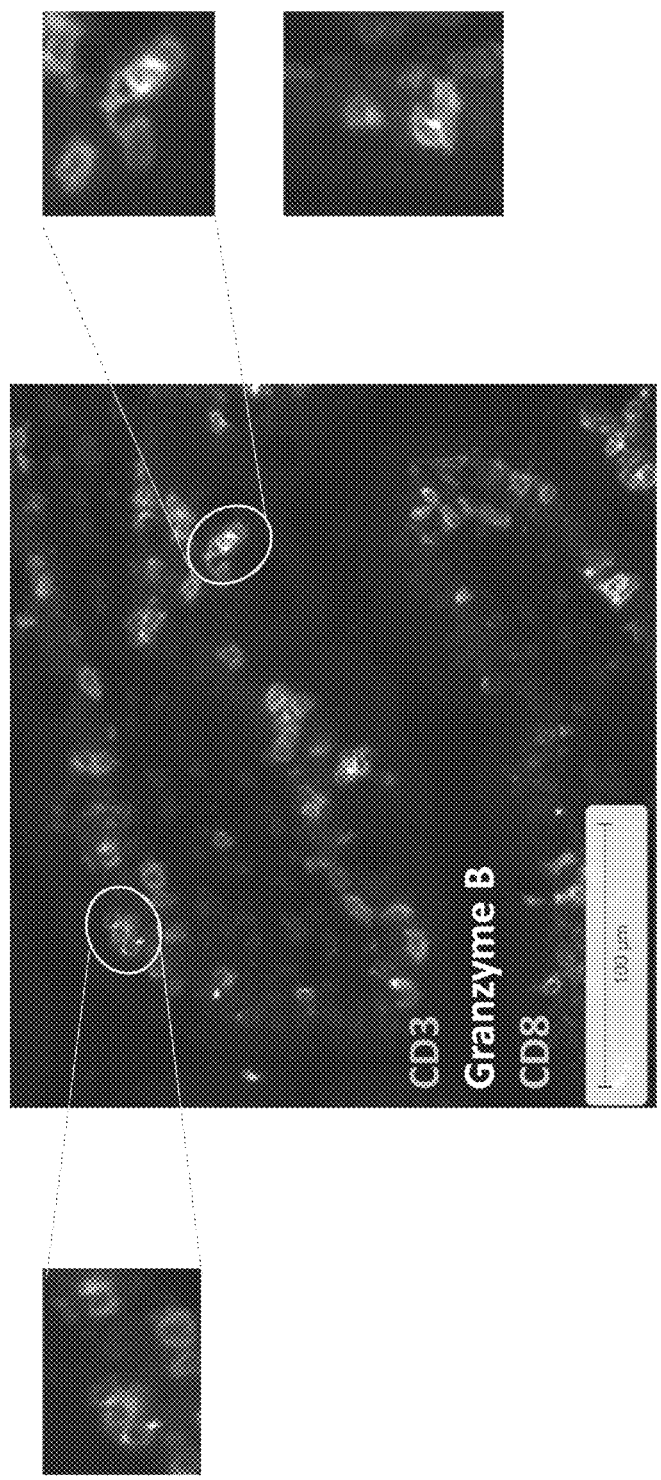
FIG. 24 shows the interaction of granzyme-positive CD8+ T cells with CD4+ T cells in the gut tissue of a celiac patient. Granzyme B is shown as white, CD8+ T cells are shown as green, CD4+ T cells are shown as ochre, and the interaction between CD8+ T cells and CD4+ T cells is shown as yellow.

Duodenal tissue samples from a celiac patient on a gluten-free diet, and prior to challenge with gluten, were analyzed for T cell markers. Granzyme-positive CD8+ T cells were observed interacting directly with CD4+ T cells (see FIG. 24, in which granzyme B is shown as white, CD8+ T cells are shown as green, CD4+ T cells are shown as ochre, and the interaction between CD8+ T cells and CD4+ T cells is shown as yellow).

Figure 25:
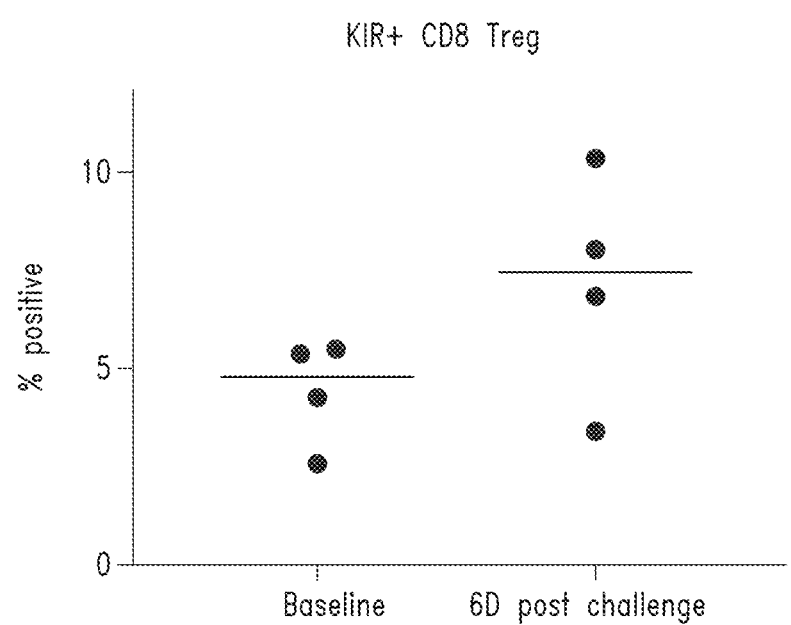
FIG. 25 shows an increase in CD8+ Treg cells in peripheral blood 6 days (6D) after challenge with gluten.
Figure 26:
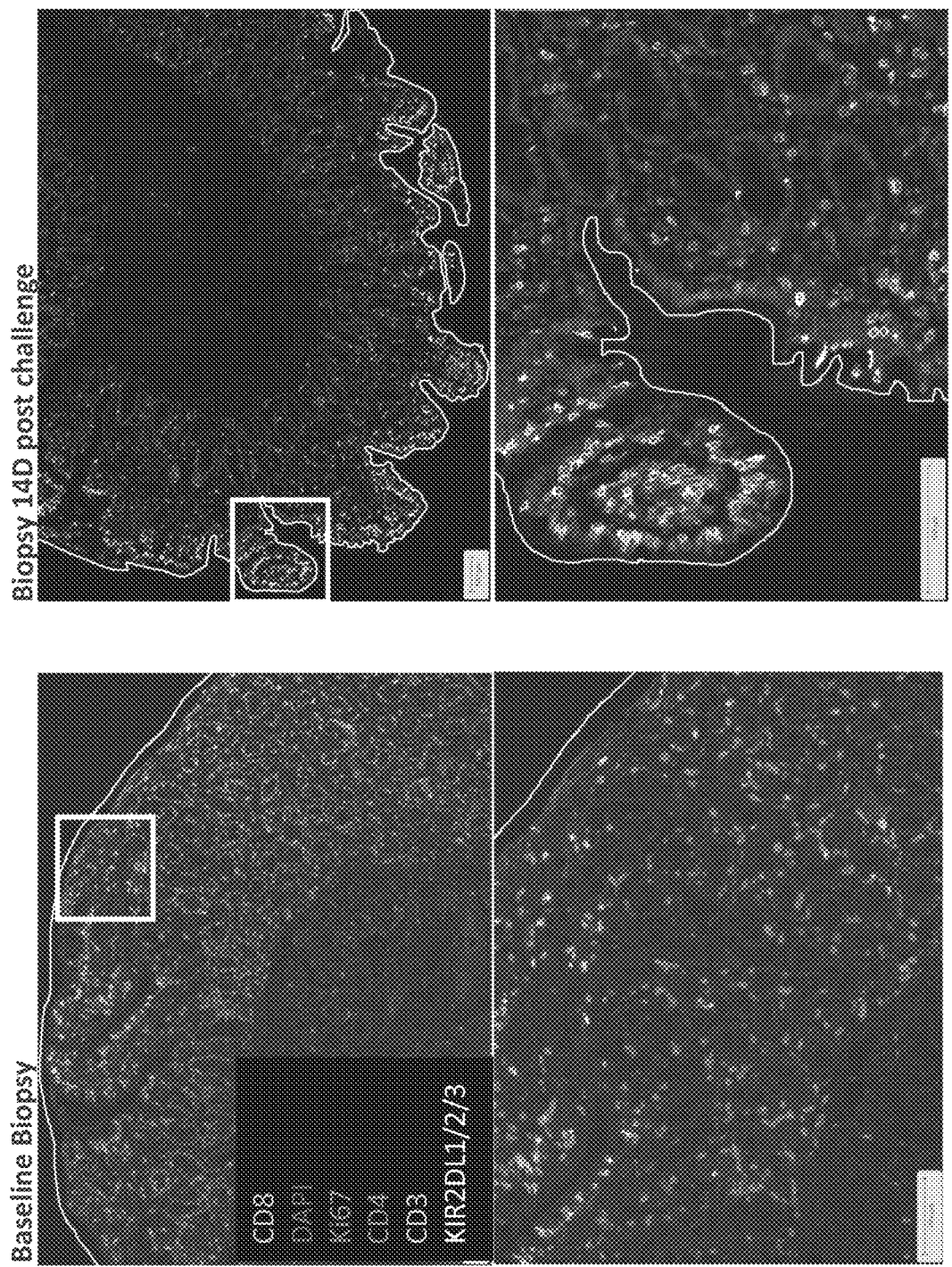
FIG. 26 shows an increase in CD8+ Treg cells in tissue biopsies 14 days (14D) following challenge with gluten.
Figure 27:
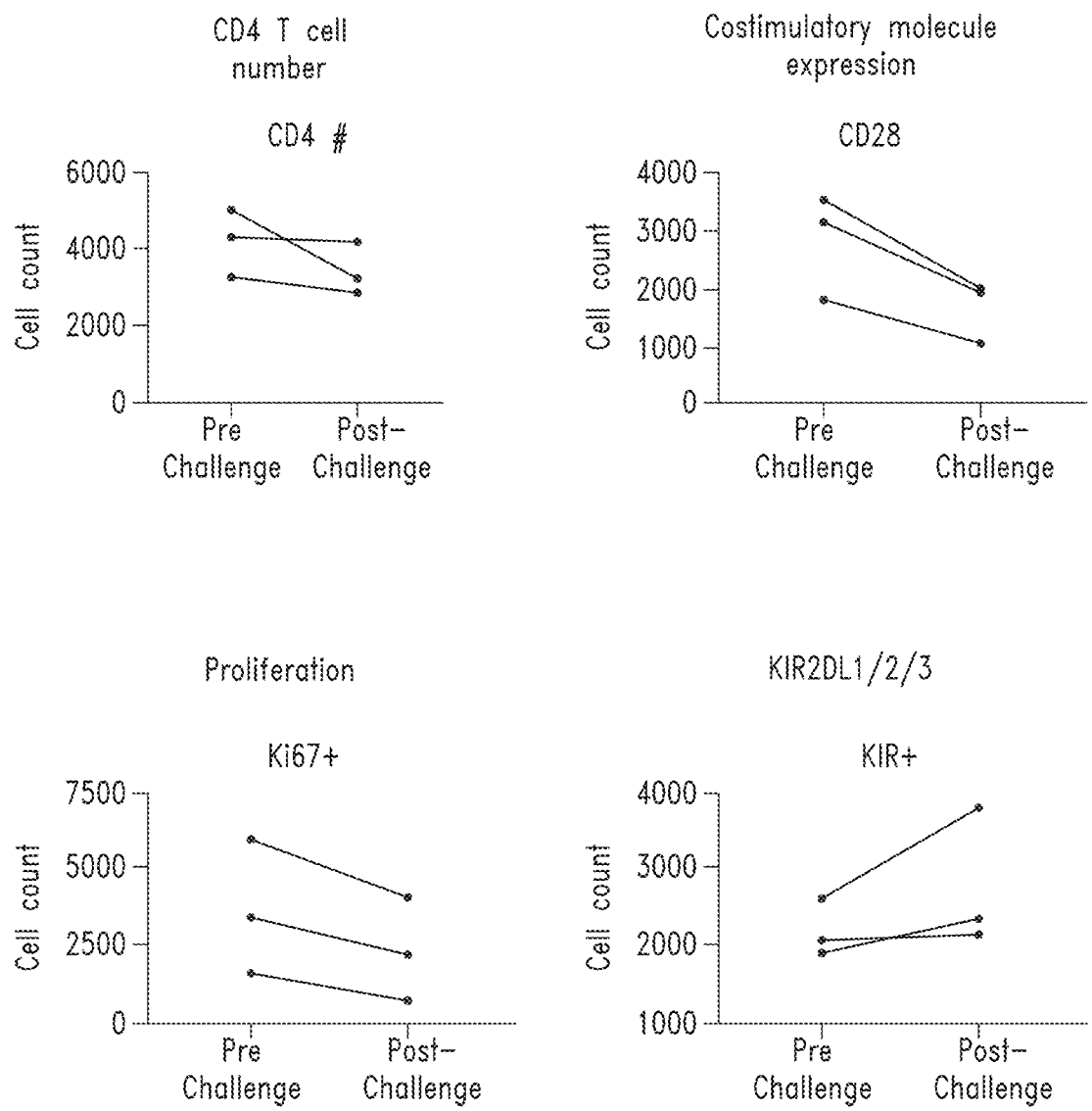
FIG. 27 shows CD4+ T cell number, costimulatory molecule expression, and proliferation, and KIR2DL expressing T cells, in celiac patient tissue samples fourteen days after gluten challenge (relative to matched patient tissues pre-gluten challenge).

Upon challenge with gluten, CD8+ Treg cells increased in peripheral blood (FIG. 25) and tissue in celiac patients (FIG. 26). Fourteen days after gluten challenge, CD4+ T cell number, costimulatory molecule expression, and proliferation in tissue decreased, while inhibitory KIR2DL expressing T cells increased (relative to matched patient tissues pre-gluten challenge) (FIG. 27).

Example 17: Bi-specific KIR Binders

Figure 28:
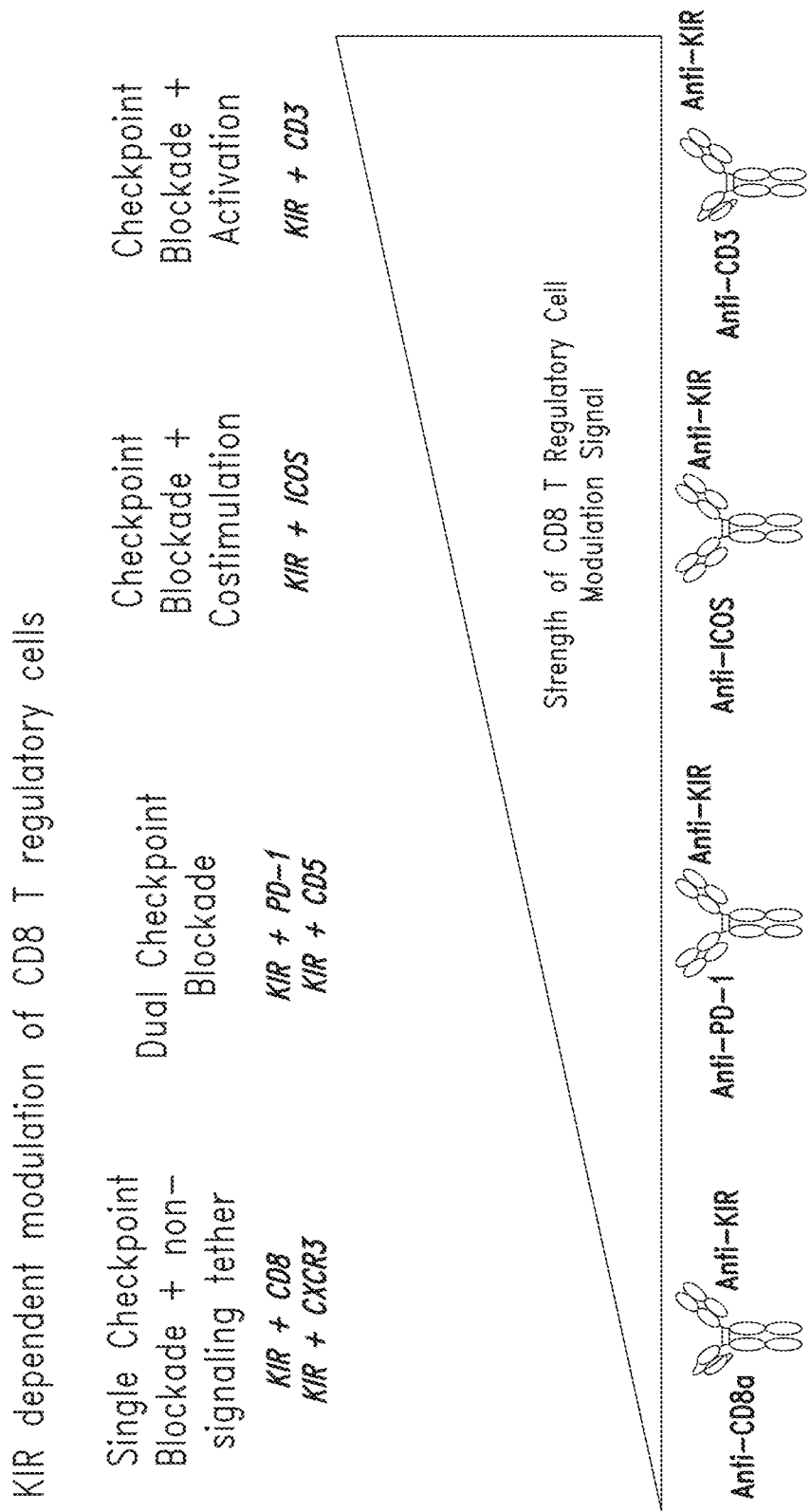
FIG. 28 shows examples of bi-specific KIR binders and their expected impacts on activation signal strength.

Bi-specific KIR binders, such as bi-specific antibodies or fragments thereof that have binding domains targeting KIR and another molecule, can be used to engineer signal strength to reach a functional threshold of activation and to achieve function without toxicity (FIG. 28).

Figure 30:
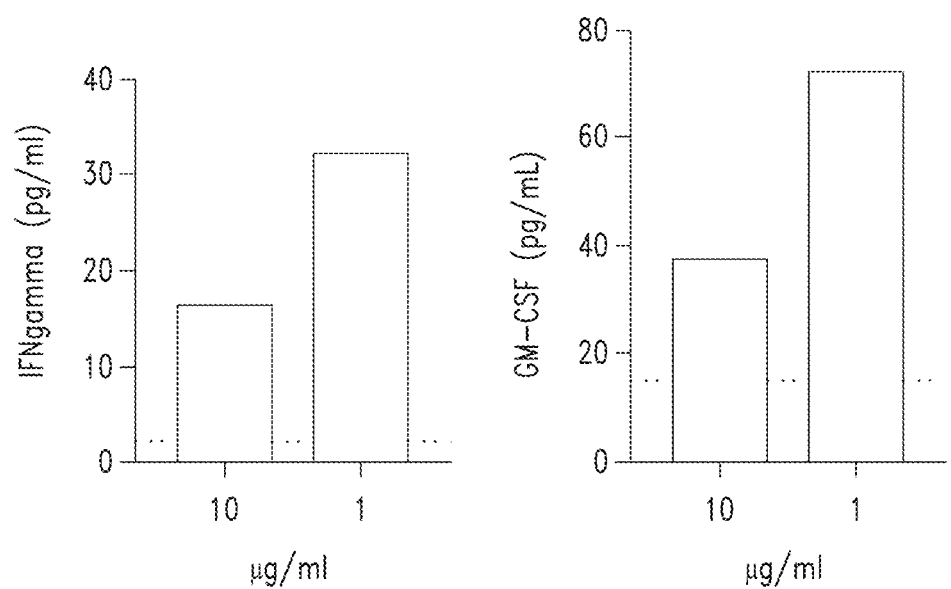
FIG. 30 shows dose-dependent reductions in proinflammatory cytokines following administration of anti-CD8 scFv/KIR FAB-Fc (at doses of 10 µg/mL or 1 µg/mL).
Figure 31:
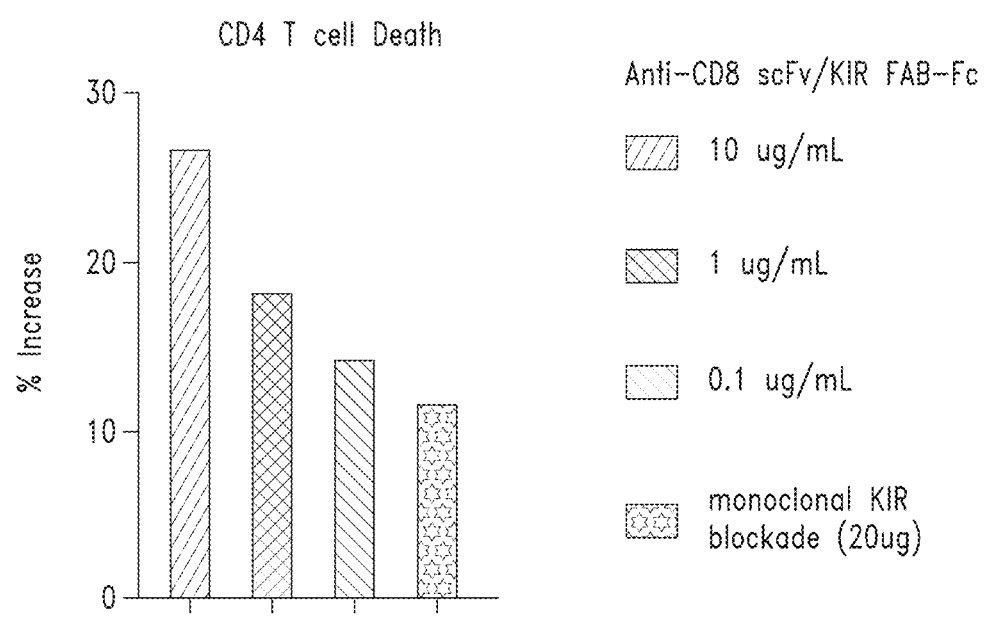
FIG. 31 shows CD4+ T cell death following administration of anti-CD8 scFv/KIR FAB-Fc (at doses of 10 µg/mL, 1 µg/mL, or 0.1 µg/mL) or a monoclonal KIR blockade (at 20 µg).
Figure 32:
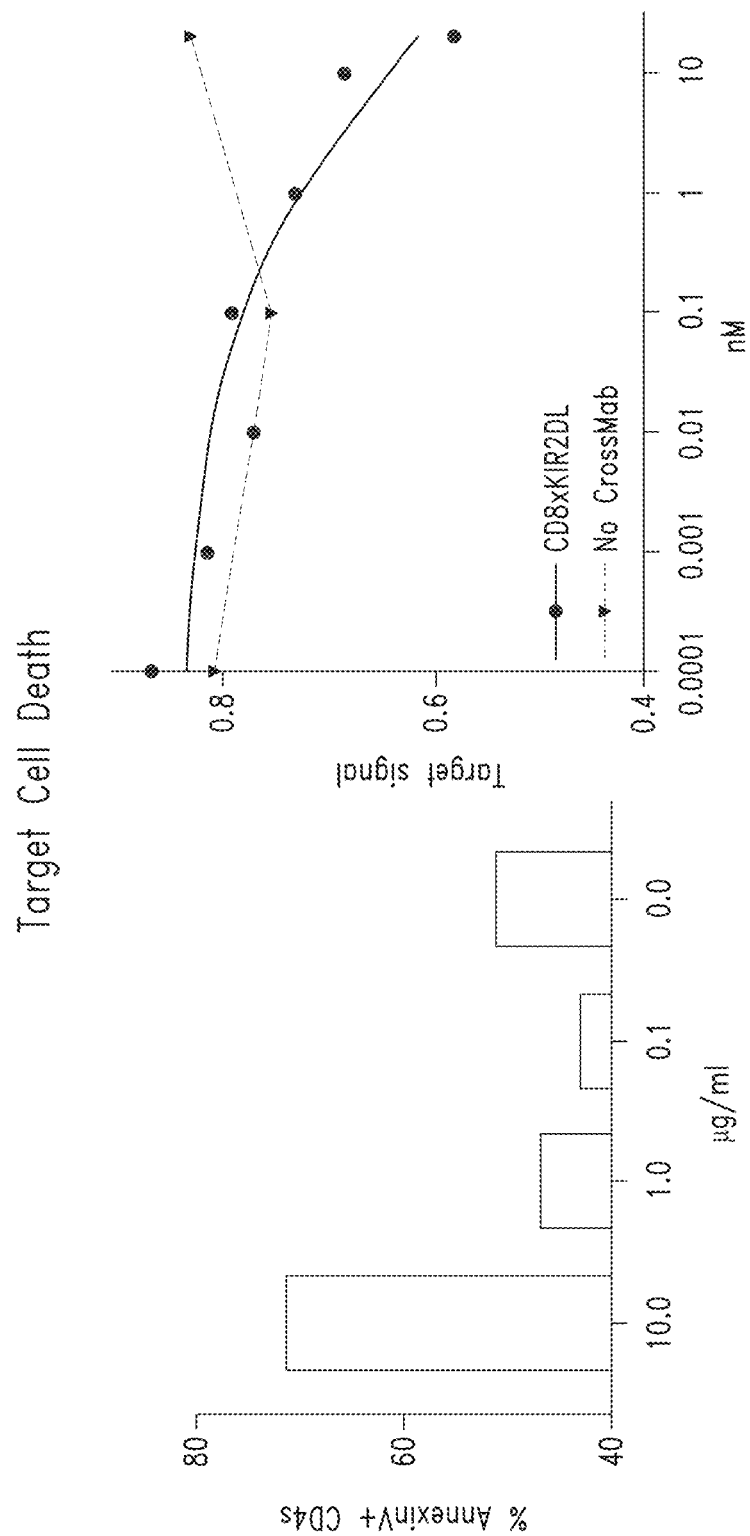
FIG. 32 shows CD4+ T cell death following administration of anti-CD8 scFv/KIR FAB-Fc (at doses of 10 µg/mL, 1 µg/mL, or 0.1 µg/mL).
Figure 33:
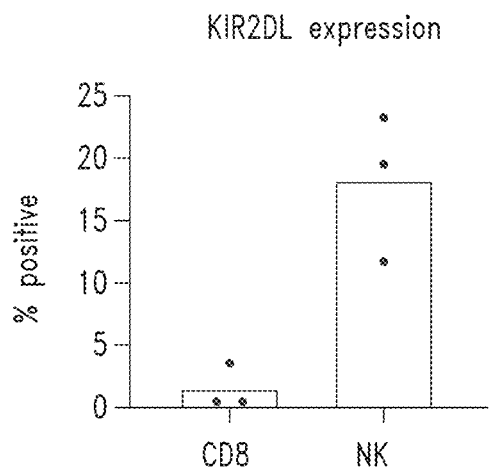
FIG. 33 shows preferential binding of the bi-specific blocker (anti-KIR2DL1/2/3 and anti-CD8) to CD8+ T cells relative to NK cells.
Figure 34:
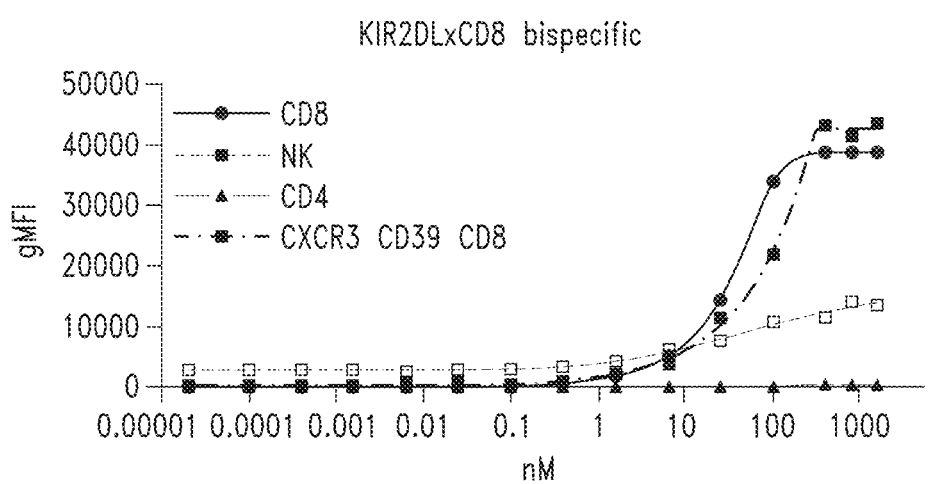
FIG. 34 shows preferential binding of the bi-specific blocker (anti-KIR2DL1/2/3 and anti-CD8) to CD8+ T cells relative to NK cells and CD4+ T cells.

Briefly, CD8 Treg were enriched from Celiac patient PBMCs and cultured with autologous CD4 T cells and antigen presenting cells pulsed with a gliadin peptide cocktail and analyzed using flow cytometry (FIGS. 29A, 29B, and 29C), bioplex assay detecting 34 analytes (ProCarta Plex; FIG. 30), and longitudinal imaging using incucyte, followed by flow cytometry (FIG. 31). Gluten restimulation of celiac patient-derived PBMCs in the presence of a bi- and mono-specific KIR blockade indicated that the bi-specific blockade (anti-KIR2DL1/2/3 and anti-CD8) resulted in greater effects on CD8+ Treg cell activity than blocking KIR alone (FIGS. 29A, 29B, and 29C). These effects were also dose-dependent (FIGS. 29B and 29C). Dose-dependent reductions were also observed for an extensive panel of proinflammatory cytokines (FIG. 30) and chemokines. Bi-specific KIR-CD8 blockade was also associated with greater and dose-dependent effects on CD4+ T cell survival (FIGS. 31 and 32). Bi-specifics binding KIR3DL1 and CD8 were similarly effective (data not shown). Preferential binding of the bi-specific blocker (anti-KIR2DL1/2/3 and anti-CD8) to CD8+ T cells was demonstrated, despite 10-fold fewer CD8+ T cells expressing KIR compared to NK cells (FIGS. 33 and 34). Similar preferential binding was observed for bi-specifics targeting KIR3DL1 rather than KIR2DL1/2/3 (data not shown).

While specific embodiments have been illustrated and described, it will be readily appreciated that the various embodiments described above can be combined to provide further embodiments, and that various changes can be made therein without departing from the spirit and scope of the invention.

All of the U.S. patents, U.S. patent application publications, U.S. patent applications, foreign patents, foreign patent applications, and non-patent publications referred to in this specification or listed in the Application Data Sheet, including U.S. patent application Ser. No. 18/264,056 filed Aug. 2, 2023, U.S. Provisional Patent Application No. 63/145,394 filed Feb. 3, 2021, U.S. Provisional Patent Application No. 63/148,016 filed Feb. 10, 2021, U.S. Provisional Patent Application No. 63/161,325 filed Mar. 15, 2021, U.S. Provisional Patent Application No. 63/209,949 filed Jun. 11, 2021, and U.S. Provisional Patent Application No. 63/298,028 filed Jan. 10, 2022, are incorporated herein by reference, in their entirety, unless explicitly stated otherwise. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

```
Sequence total quantity: 201
SEQ ID NO: 1           moltype = AA  length = 119
FEATURE                Location/Qualifiers
REGION                 1..119
                       note = CD3epsilon VH
source                 1..119
                       mol_type = protein
```

```
                          organism = synthetic construct
SEQUENCE: 1
DIKLQQSGAE LARPGASVKM SCKTSGYTFT RYTMHWVKQR PGQGLEWIGY INPSRGYTNY    60
NQKFKDKATL TTDKSSSTAY MQLSSLTSED SAVYYCARYY DDHYCLDYWG QGTTLTVSS    119

SEQ ID NO: 2              moltype = AA   length = 106
FEATURE                   Location/Qualifiers
REGION                    1..106
                          note = CD3epsilon VL
source                    1..106
                          mol_type = protein
                          organism = synthetic construct
SEQUENCE: 2
DIQLTQSPAI MSASPGEKVT MTCRASSSVS YMNWYQQKSG TSPKRWIYDT SKVASGVPYR    60
FSGSGSGTSY SLTISSMEAE DAATYYCQQW SSNPLTFGAG TKLELK                 106

SEQ ID NO: 3              moltype = AA   length = 7
FEATURE                   Location/Qualifiers
REGION                    1..7
                          note = CD3epsilon VH HCDR1
source                    1..7
                          mol_type = protein
                          organism = synthetic construct
SEQUENCE: 3
FTRYTMH                                                               7

SEQ ID NO: 4              moltype = AA   length = 17
FEATURE                   Location/Qualifiers
REGION                    1..17
                          note = CD3epsilon VH HCDR2
source                    1..17
                          mol_type = protein
                          organism = synthetic construct
SEQUENCE: 4
YINPSRGYTN YNQKFKD                                                   17

SEQ ID NO: 5              moltype = AA   length = 10
FEATURE                   Location/Qualifiers
REGION                    1..10
                          note = CD3epsilon VH HCDR3
source                    1..10
                          mol_type = protein
                          organism = synthetic construct
SEQUENCE: 5
YYDDHYCLDY                                                           10

SEQ ID NO: 6              moltype = AA   length = 10
FEATURE                   Location/Qualifiers
REGION                    1..10
                          note = CD3epsilon VL LCDR1
source                    1..10
                          mol_type = protein
                          organism = synthetic construct
SEQUENCE: 6
RASSSVSYMN                                                           10

SEQ ID NO: 7              moltype = AA   length = 7
FEATURE                   Location/Qualifiers
REGION                    1..7
                          note = CD3epsilon VL LCDR2
source                    1..7
                          mol_type = protein
                          organism = synthetic construct
SEQUENCE: 7
DTSKVAS                                                               7

SEQ ID NO: 8              moltype = AA   length = 9
FEATURE                   Location/Qualifiers
REGION                    1..9
                          note = CD3epsilon VL LCDR3
source                    1..9
                          mol_type = protein
                          organism = synthetic construct
SEQUENCE: 8
QQWSSNPLT                                                             9

SEQ ID NO: 9              moltype = AA   length = 119
FEATURE                   Location/Qualifiers
REGION                    1..119
```

```
                        note = CD3epsilon VH muromonab
source                  1..119
                        mol_type = protein
                        organism = synthetic construct
SEQUENCE: 9
QVQLQQSGAE LARPGASVKM SCKASGYTFT RYTMHWVKQR PGQGLEWIGY INPSRGYTNY    60
NQKFKDKATL TTDKSSSTAY MQLSSLTSED SAVYYCARYY DDHYCLDYWG QGTTLTVSS    119

SEQ ID NO: 10           moltype = AA  length = 106
FEATURE                 Location/Qualifiers
REGION                  1..106
                        note = CD3epsilon VL
source                  1..106
                        mol_type = protein
                        organism = synthetic construct
SEQUENCE: 10
QIVLTQSPAI MSASPGEKVT MTCSASSSVS YMNWYQQKSG TSPKRWIYDT SKLASGVPAH    60
FRGSGSGTSY SLTISGMEAE DAATYYCQQW SSNPFTFGSG TKLEIN                 106

SEQ ID NO: 11           moltype = AA  length = 7
FEATURE                 Location/Qualifiers
REGION                  1..7
                        note = CD3epsilon VH muromonab HCDR1
source                  1..7
                        mol_type = protein
                        organism = synthetic construct
SEQUENCE: 11
FTRYTMH                                                              7

SEQ ID NO: 12           moltype = AA  length = 17
FEATURE                 Location/Qualifiers
REGION                  1..17
                        note = CD3epsilon VH muromonab HCDR2
source                  1..17
                        mol_type = protein
                        organism = synthetic construct
SEQUENCE: 12
YINPSRGYTN YNQKFKD                                                  17

SEQ ID NO: 13           moltype = AA  length = 10
FEATURE                 Location/Qualifiers
REGION                  1..10
                        note = CD3epsilon VH muromonab HCDR3
source                  1..10
                        mol_type = protein
                        organism = synthetic construct
SEQUENCE: 13
YYDDHYCLDY                                                          10

SEQ ID NO: 14           moltype = AA  length = 10
FEATURE                 Location/Qualifiers
REGION                  1..10
                        note = CD3epsilon VL LCDR1
source                  1..10
                        mol_type = protein
                        organism = synthetic construct
SEQUENCE: 14
SASSSVSYMN                                                          10

SEQ ID NO: 15           moltype = AA  length = 7
FEATURE                 Location/Qualifiers
REGION                  1..7
                        note = CD3epsilon VL LCDR2
source                  1..7
                        mol_type = protein
                        organism = synthetic construct
SEQUENCE: 15
DTSKLAS                                                              7

SEQ ID NO: 16           moltype = AA  length = 7
FEATURE                 Location/Qualifiers
REGION                  1..7
                        note = CD3epsilon VL LCDR3
source                  1..7
                        mol_type = protein
                        organism = synthetic construct
SEQUENCE: 16
WSSNPFT                                                              7
```

-continued

```
SEQ ID NO: 17              moltype = AA   length = 125
FEATURE                    Location/Qualifiers
REGION                     1..125
                           note = CD3epsilon VH XmAb13676
source                     1..125
                           mol_type = protein
                           organism = synthetic construct
SEQUENCE: 17
EVQLVESGGG LVQPGGSLRL SCAASGFTFS TYAMNWVRQA PGKGLEWVGR IRSKYNNYAT     60
YYADSVKGRF TISRDDSKNT LYLQMNSLRA EDTAVYYCVR HGNFGDSYVS WFAYWGQGTL    120
VTVSS                                                                125

SEQ ID NO: 18              moltype = AA   length = 109
FEATURE                    Location/Qualifiers
REGION                     1..109
                           note = CD3epsilon VL
source                     1..109
                           mol_type = protein
                           organism = synthetic construct
SEQUENCE: 18
QAVVTQEPSL TVSPGGTVTL TCGSSTGAVT TSNYANWVQQ KPGKSPRGLI GGTNKRAPGV     60
PARFSGSLLG GKAALTISGA QPEDEADYYC ALWYSNHWVF GGGTKLTVL                109

SEQ ID NO: 19              moltype = AA   length = 5
FEATURE                    Location/Qualifiers
REGION                     1..5
                           note = CD3epsilon VH XmAb13676 HCDR1
source                     1..5
                           mol_type = protein
                           organism = synthetic construct
SEQUENCE: 19
TYAMN                                                                  5

SEQ ID NO: 20              moltype = AA   length = 19
FEATURE                    Location/Qualifiers
REGION                     1..19
                           note = CD3epsilon VH XmAb13676 HCDR2
source                     1..19
                           mol_type = protein
                           organism = synthetic construct
SEQUENCE: 20
RIRSKYNNYA TYYADSVKG                                                  19

SEQ ID NO: 21              moltype = AA   length = 14
FEATURE                    Location/Qualifiers
REGION                     1..14
                           note = CD3epsilon VH XmAb13676 HCDR3
source                     1..14
                           mol_type = protein
                           organism = synthetic construct
SEQUENCE: 21
HGNFGDSYVS WFAY                                                       14

SEQ ID NO: 22              moltype = AA   length = 14
FEATURE                    Location/Qualifiers
REGION                     1..14
                           note = CD3epsilon LCDR1
source                     1..14
                           mol_type = protein
                           organism = synthetic construct
SEQUENCE: 22
GSSTGAVTTS NYAN                                                       14

SEQ ID NO: 23              moltype = AA   length = 7
FEATURE                    Location/Qualifiers
REGION                     1..7
                           note = CD3epsilon LCDR2
source                     1..7
                           mol_type = protein
                           organism = synthetic construct
SEQUENCE: 23
GTNKRAP                                                                7

SEQ ID NO: 24              moltype = AA   length = 9
FEATURE                    Location/Qualifiers
REGION                     1..9
                           note = CD3epsilon LCDR3
source                     1..9
                           mol_type = protein
```

```
                          organism = synthetic construct
SEQUENCE: 24
ALWYSNHWV                                                                       9

SEQ ID NO: 25             moltype = AA   length = 119
FEATURE                   Location/Qualifiers
REGION                    1..119
                          note = CD3epsilon VH gOKT3-5
source                    1..119
                          mol_type = protein
                          organism = synthetic construct
SEQUENCE: 25
QVQLVQSGGG VVQPGRSLRL SCKASGYTFT RYTMHWVRQA PGKGLEWIGY INPSRGYTNY              60
NQKVKDRFTI STDKSKSTAF LQMDSLRPED TAVYYCARYY DDHYCLDYWG QGTPVTVSS              119

SEQ ID NO: 26             moltype = AA   length = 107
FEATURE                   Location/Qualifiers
REGION                    1..107
                          note = CD3epsilon VL
source                    1..107
                          mol_type = protein
                          organism = synthetic construct
SEQUENCE: 26
DIQMTQSPSS LSASVGDRVT ITCSASSSVS YMNWYQQTPG KAPKRWIYDT SKLASGVPSR              60
FSGSGSGTDY TFTISSLQPE DIATYYCQQW SSNPFTFGQG TKLQITR                           107

SEQ ID NO: 27             moltype = AA   length = 5
FEATURE                   Location/Qualifiers
REGION                    1..5
                          note = CD3epsilon VH gOKT3-5 HCDR1
source                    1..5
                          mol_type = protein
                          organism = synthetic construct
SEQUENCE: 27
RYTMH                                                                           5

SEQ ID NO: 28             moltype = AA   length = 17
FEATURE                   Location/Qualifiers
REGION                    1..17
                          note = CD3epsilon VH gOKT3-5 HCDR2
source                    1..17
                          mol_type = protein
                          organism = synthetic construct
SEQUENCE: 28
YINPSRGYTN YNQKVKD                                                             17

SEQ ID NO: 29             moltype = AA   length = 10
FEATURE                   Location/Qualifiers
REGION                    1..10
                          note = CD3epsilon VH gOKT3-5 HCDR3
source                    1..10
                          mol_type = protein
                          organism = synthetic construct
SEQUENCE: 29
YYDDHYCLDY                                                                     10

SEQ ID NO: 30             moltype = AA   length = 10
FEATURE                   Location/Qualifiers
REGION                    1..10
                          note = CD3epsilon VL LCDR1
source                    1..10
                          mol_type = protein
                          organism = synthetic construct
SEQUENCE: 30
SASSSVSYMN                                                                     10

SEQ ID NO: 31             moltype = AA   length = 7
FEATURE                   Location/Qualifiers
REGION                    1..7
                          note = CD3epsilon VL LCDR2
source                    1..7
                          mol_type = protein
                          organism = synthetic construct
SEQUENCE: 31
DTSKLAS                                                                         7

SEQ ID NO: 32             moltype = AA   length = 9
FEATURE                   Location/Qualifiers
REGION                    1..9
```

```
                        note = CD3epsilon VL LCDR3
source                  1..9
                        mol_type = protein
                        organism = synthetic construct
SEQUENCE: 32
QQWSSNPFT                                                            9

SEQ ID NO: 33           moltype = AA  length = 119
FEATURE                 Location/Qualifiers
REGION                  1..119
                        note = CD3epsilon VH JA185
source                  1..119
                        mol_type = protein
                        organism = synthetic construct
SEQUENCE: 33
QVQLVQSGGG VVQPGRSLRL SCKASGYTFT RYTMHWVRQA PGKGLEWIGY INPSRGYTNY     60
NQKVKDRFTI STDKSKSTAF LQMDSLRPED TAVYYCARYY DDHYCLDYWG QGTTLTVSS     119

SEQ ID NO: 34           moltype = AA  length = 107
FEATURE                 Location/Qualifiers
REGION                  1..107
                        note = CD3epsilon VL
source                  1..107
                        mol_type = protein
                        organism = synthetic construct
SEQUENCE: 34
DIQMTQSPSS LSASVGDRVT ITCSASSSVS YMNWYQQTPG KAPKRWIYDT SKLASGVPSR     60
FSGSGSGTDY TFTISSLQPE DIATYYCQQW SSNPFTFGQG TKLQITR                  107

SEQ ID NO: 35           moltype = AA  length = 12
FEATURE                 Location/Qualifiers
REGION                  1..12
                        note = CD3epsilon VH JA185 HCDR1
source                  1..12
                        mol_type = protein
                        organism = synthetic construct
SEQUENCE: 35
KASGYTFTRY TM                                                        12

SEQ ID NO: 36           moltype = AA  length = 14
FEATURE                 Location/Qualifiers
REGION                  1..14
                        note = CD3epsilon VH JA185 HCDR2
source                  1..14
                        mol_type = protein
                        organism = synthetic construct
SEQUENCE: 36
YINPSRGYTN YNQK                                                      14

SEQ ID NO: 37           moltype = AA  length = 8
FEATURE                 Location/Qualifiers
REGION                  1..8
                        note = CD3epsilon VH JA185 HCDR3
source                  1..8
                        mol_type = protein
                        organism = synthetic construct
SEQUENCE: 37
YYDDHYCL                                                             8

SEQ ID NO: 38           moltype = AA  length = 10
FEATURE                 Location/Qualifiers
REGION                  1..10
                        note = CD3epsilon VL LCDR1
source                  1..10
                        mol_type = protein
                        organism = synthetic construct
SEQUENCE: 38
SASSSVSYMN                                                           10

SEQ ID NO: 39           moltype = AA  length = 7
FEATURE                 Location/Qualifiers
REGION                  1..7
                        note = CD3epsilon VL LCDR2
source                  1..7
                        mol_type = protein
                        organism = synthetic construct
SEQUENCE: 39
DTSKLAS                                                              7
```

```
SEQ ID NO: 40             moltype = AA  length = 8
FEATURE                   Location/Qualifiers
REGION                    1..8
                          note = CD3epsilon VL LCDR3
source                    1..8
                          mol_type = protein
                          organism = synthetic construct
SEQUENCE: 40
QQWSSNPF                                                                    8

SEQ ID NO: 41             moltype = AA  length = 117
FEATURE                   Location/Qualifiers
REGION                    1..117
                          note = CD3epsilon VH JA198
source                    1..117
                          mol_type = protein
                          organism = synthetic construct
SEQUENCE: 41
QVQLVQSGGG VVQPGRSLRL SCKASGYTFT RYTMHWVRQA PGKGLEWIGK ASGYTFTRYT           60
MVKDRFTIST DKSKSTAFLQ MDSLRPEDTG VYFCARYYQD HYCLDYWGQG TTLTVSS              117

SEQ ID NO: 42             moltype = AA  length = 12
FEATURE                   Location/Qualifiers
REGION                    1..12
                          note = CD3epsilon VH JA198 HCDR1
source                    1..12
                          mol_type = protein
                          organism = synthetic construct
SEQUENCE: 42
KASGYTFTRY TM                                                               12

SEQ ID NO: 43             moltype = AA  length = 12
FEATURE                   Location/Qualifiers
REGION                    1..12
                          note = CD3epsilon VH JA198 HCDR2
source                    1..12
                          mol_type = protein
                          organism = synthetic construct
SEQUENCE: 43
KASGYTFTRY TM                                                               12

SEQ ID NO: 44             moltype = AA  length = 8
FEATURE                   Location/Qualifiers
REGION                    1..8
                          note = CD3epsilon VH JA198 HCDR3
source                    1..8
                          mol_type = protein
                          organism = synthetic construct
SEQUENCE: 44
YYQDHYCL                                                                    8

SEQ ID NO: 45             moltype = AA  length = 119
FEATURE                   Location/Qualifiers
REGION                    1..119
                          note = CD3epsilon VH JA207
source                    1..119
                          mol_type = protein
                          organism = synthetic construct
SEQUENCE: 45
QVQLVQSGGG VVQPGRSLRL SCKASGYTFT RYTMHWVRQA PGKGLEWIGY INPSRGYTNY           60
NQKVKDRFTI STDKSKNTAF LQMDSLRPED TGVYFCARYY DDHYCLDYWG QGTTLTVSS            119

SEQ ID NO: 46             moltype = AA  length = 12
FEATURE                   Location/Qualifiers
REGION                    1..12
                          note = CD3epsilon VH JA207 HCDR1
source                    1..12
                          mol_type = protein
                          organism = synthetic construct
SEQUENCE: 46
KASGYTFTRY TM                                                               12

SEQ ID NO: 47             moltype = AA  length = 14
FEATURE                   Location/Qualifiers
REGION                    1..14
                          note = CD3epsilon VH JA207 HCDR2
source                    1..14
                          mol_type = protein
                          organism = synthetic construct
```

```
SEQUENCE: 47
YINPSRGYTN YNQK                                                        14

SEQ ID NO: 48           moltype = AA  length = 8
FEATURE                 Location/Qualifiers
REGION                  1..8
                        note = CD3epsilon VH JA207 HCDR3
source                  1..8
                        mol_type = protein
                        organism = synthetic construct
SEQUENCE: 48
YDDDHYCL                                                                8

SEQ ID NO: 49           moltype = AA  length = 118
FEATURE                 Location/Qualifiers
REGION                  1..118
                        note = CD3epsilon VH 28F11
source                  1..118
                        mol_type = protein
                        organism = synthetic construct
SEQUENCE: 49
QVQLVESGGG VVQPGRSLRL SCAASGFKFS GYGMHWVRQA PGKGLEWVAV IWYDGSKKYY        60
VDSVKGRFTI SRDNSKNTLY LQMNSLRAED TAVYYCARQM GYWHFDLWGR GTLVTVSS         118

SEQ ID NO: 50           moltype = AA  length = 108
FEATURE                 Location/Qualifiers
REGION                  1..108
                        note = CD3epsilon VL
source                  1..108
                        mol_type = protein
                        organism = synthetic construct
SEQUENCE: 50
EIVLTQSPAT LSLSPGERAT LSCRASQSVS SYLAWYQQKP GQAPRLLIYD ASNRATGIPA        60
RFSGSGSGTD FTLTISSLEP EDFAVYYCQQ RSNWPPLTFG GGTKVEIK                   108

SEQ ID NO: 51           moltype = AA  length = 5
FEATURE                 Location/Qualifiers
REGION                  1..5
                        note = CD3epsilon VH 28F11 HCDR1
source                  1..5
                        mol_type = protein
                        organism = synthetic construct
SEQUENCE: 51
GYGMH                                                                   5

SEQ ID NO: 52           moltype = AA  length = 17
FEATURE                 Location/Qualifiers
REGION                  1..17
                        note = CD3epsilon VH 28F11 HCDR2
source                  1..17
                        mol_type = protein
                        organism = synthetic construct
SEQUENCE: 52
VIWYDGSKKY YVDSVKG                                                     17

SEQ ID NO: 53           moltype = AA  length = 9
FEATURE                 Location/Qualifiers
REGION                  1..9
                        note = CD3epsilon VH 28F11 HCDR3
source                  1..9
                        mol_type = protein
                        organism = synthetic construct
SEQUENCE: 53
QMGYWHFDL                                                               9

SEQ ID NO: 54           moltype = AA  length = 11
FEATURE                 Location/Qualifiers
REGION                  1..11
                        note = CD3epsilon VL LCDR1
source                  1..11
                        mol_type = protein
                        organism = synthetic construct
SEQUENCE: 54
RASQSVSSYL A                                                           11

SEQ ID NO: 55           moltype = AA  length = 7
FEATURE                 Location/Qualifiers
REGION                  1..7
                        note = CD3epsilon VL LCDR2
```

```
source                      1..7
                            mol_type = protein
                            organism = synthetic construct
SEQUENCE: 55
DASNRAT                                                                      7

SEQ ID NO: 56               moltype = AA   length = 10
FEATURE                     Location/Qualifiers
REGION                      1..10
                            note = CD3epsilon VL LCDR3
source                      1..10
                            mol_type = protein
                            organism = synthetic construct
SEQUENCE: 56
QQRSNWPPLT                                                                  10

SEQ ID NO: 57               moltype = AA   length = 118
FEATURE                     Location/Qualifiers
REGION                      1..118
                            note = CD3epsilon VH 27H5
source                      1..118
                            mol_type = protein
                            organism = synthetic construct
SEQUENCE: 57
QVQLVESGGG VVQPGRSLRL SCAASGFTFR SYGMHWVRQA PGKGLEWVAI IWYDGSKKNY  60
ADSVKGRFTI SRDNSKNTLY LQMNSLRAED TAVYYCARGT GYNWFDPWGQ GTLVTVSS   118

SEQ ID NO: 58               moltype = AA   length = 108
FEATURE                     Location/Qualifiers
REGION                      1..108
                            note = CD3epsilon VL
source                      1..108
                            mol_type = protein
                            organism = synthetic construct
SEQUENCE: 58
EIVLTQSPRT LSLSPGERAT LSCRASQSVS SSYLAWYQQK PGQAPRLLIY GASSRATGIP  60
DRFSGSGSGT DFTLTISRLD PEDFAVYYCQ QYGSSPITFG QGTRLEIK              108

SEQ ID NO: 59               moltype = AA   length = 5
FEATURE                     Location/Qualifiers
REGION                      1..5
                            note = CD3epsilon VH 27H5 HCDR1
source                      1..5
                            mol_type = protein
                            organism = synthetic construct
SEQUENCE: 59
SYGMH                                                                        5

SEQ ID NO: 60               moltype = AA   length = 17
FEATURE                     Location/Qualifiers
REGION                      1..17
                            note = CD3epsilon VH 27H5 HCDR2
source                      1..17
                            mol_type = protein
                            organism = synthetic construct
SEQUENCE: 60
IIWYDGSKKN YADSVKG                                                          17

SEQ ID NO: 61               moltype = AA   length = 9
FEATURE                     Location/Qualifiers
REGION                      1..9
                            note = CD3epsilon VH 27H5 HCDR3
source                      1..9
                            mol_type = protein
                            organism = synthetic construct
SEQUENCE: 61
GTGYNWFDP                                                                    9

SEQ ID NO: 62               moltype = AA   length = 12
FEATURE                     Location/Qualifiers
REGION                      1..12
                            note = CD3epsilon VL LCDR1
source                      1..12
                            mol_type = protein
                            organism = synthetic construct
SEQUENCE: 62
RASQSVSSSY LA                                                               12

SEQ ID NO: 63               moltype = AA   length = 7
```

```
FEATURE              Location/Qualifiers
REGION               1..7
                     note = CD3epsilon VL LCDR2
source               1..7
                     mol_type = protein
                     organism = synthetic construct
SEQUENCE: 63
GASSRAT                                                                   7

SEQ ID NO: 64        moltype = AA  length = 9
FEATURE              Location/Qualifiers
REGION               1..9
                     note = CD3epsilon VL LCDR3
source               1..9
                     mol_type = protein
                     organism = synthetic construct
SEQUENCE: 64
QQYGSSPIT                                                                 9

SEQ ID NO: 65        moltype = AA  length = 118
FEATURE              Location/Qualifiers
REGION               1..118
                     note = CD3epsilon VH 15C3
source               1..118
                     mol_type = protein
                     organism = synthetic construct
SEQUENCE: 65
QVQLVQSGGG VVQPGRSLRL SCVASGFTFS SYGMHWVRQA PGKGLEWVAA IWYNGRKQDY    60
ADSVKGRFTI SRDNSKNTLY LQMNSLRAED TAVYYCTRGT GYNWFDPWGQ GTLVTVSS    118

SEQ ID NO: 66        moltype = AA  length = 107
FEATURE              Location/Qualifiers
REGION               1..107
                     note = CD3epsilon VL2 15C3
source               1..107
                     mol_type = protein
                     organism = synthetic construct
SEQUENCE: 66
AIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPITFGQ GTRLEIK                107

SEQ ID NO: 67        moltype = AA  length = 5
FEATURE              Location/Qualifiers
REGION               1..5
                     note = CD3epsilon VH 15C3 HCDR1
source               1..5
                     mol_type = protein
                     organism = synthetic construct
SEQUENCE: 67
SYGMH                                                                     5

SEQ ID NO: 68        moltype = AA  length = 17
FEATURE              Location/Qualifiers
REGION               1..17
                     note = CD3epsilon VH 15C3 HCDR2
source               1..17
                     mol_type = protein
                     organism = synthetic construct
SEQUENCE: 68
AIWYNGRKQD YADSVKG                                                       17

SEQ ID NO: 69        moltype = AA  length = 9
FEATURE              Location/Qualifiers
REGION               1..9
                     note = CD3epsilon VH 15C3 HCDR3
source               1..9
                     mol_type = protein
                     organism = synthetic construct
SEQUENCE: 69
GTGYNWFDP                                                                 9

SEQ ID NO: 70        moltype = AA  length = 11
FEATURE              Location/Qualifiers
REGION               1..11
                     note = CD3epsilon VL2 15C3 LCDR1
source               1..11
                     mol_type = protein
                     organism = synthetic construct
SEQUENCE: 70
```

```
RASQGISSAL A                                                              11

SEQ ID NO: 71             moltype = AA  length = 7
FEATURE                   Location/Qualifiers
REGION                    1..7
                          note = CD3epsilon VL2 15C3 LCDR2
source                    1..7
                          mol_type = protein
                          organism = synthetic construct
SEQUENCE: 71
DASSLES                                                                   7

SEQ ID NO: 72             moltype = AA  length = 9
FEATURE                   Location/Qualifiers
REGION                    1..9
                          note = CD3epsilon VL2 15C3 LCDR3
source                    1..9
                          mol_type = protein
                          organism = synthetic construct
SEQUENCE: 72
QQFNSYPIT                                                                 9

SEQ ID NO: 73             moltype = AA  length = 118
FEATURE                   Location/Qualifiers
REGION                    1..118
                          note = CD8alpha VH Mb1a
source                    1..118
                          mol_type = protein
                          organism = synthetic construct
SEQUENCE: 73
EVQLVESGGG LVQPGGSLRL SCAASGFNIK DTYIHFVRQA PGKGLEWIGR IDPANDNTLY          60
ASKFQGKATI SADTSKNTAY LQMNSLRAGD TAVYYCGRGY GYYVFDHWGQ GTLVTVSS           118

SEQ ID NO: 74             moltype = AA  length = 107
FEATURE                   Location/Qualifiers
REGION                    1..107
                          note = CD8alpha VL
source                    1..107
                          mol_type = protein
                          organism = synthetic construct
SEQUENCE: 74
DVQITQSPSS LSASVGDRVT ITCRTSRSIS QYLAWYQQKP GKVPKLLIYS GSTLQSGVPS          60
RFSGSGSGTD FTLTISSLQP EDVATYYCQQ HNENPLTFGG GTKVEIK                       107

SEQ ID NO: 75             moltype = AA  length = 7
FEATURE                   Location/Qualifiers
REGION                    1..7
                          note = CD8alpha VH Mb1a HCDR1
source                    1..7
                          mol_type = protein
                          organism = synthetic construct
SEQUENCE: 75
GFNIKDT                                                                   7

SEQ ID NO: 76             moltype = AA  length = 9
FEATURE                   Location/Qualifiers
REGION                    1..9
                          note = CD8alpha VH Mb1a HCDR2
source                    1..9
                          mol_type = protein
                          organism = synthetic construct
SEQUENCE: 76
RIDPANDNT                                                                 9

SEQ ID NO: 77             moltype = AA  length = 7
FEATURE                   Location/Qualifiers
REGION                    1..7
                          note = CD8alpha VH Mb1a HCDR3
source                    1..7
                          mol_type = protein
                          organism = synthetic construct
SEQUENCE: 77
GYYVFDH                                                                   7

SEQ ID NO: 78             moltype = AA  length = 11
FEATURE                   Location/Qualifiers
REGION                    1..11
                          note = CD8alpha VL LCDR1
source                    1..11
```

```
                        mol_type = protein
                        organism = synthetic construct
SEQUENCE: 78
RTSRSISQYL A                                                            11

SEQ ID NO: 79           moltype = AA  length = 7
FEATURE                 Location/Qualifiers
REGION                  1..7
                        note = CD8alpha VL LCDR2
source                  1..7
                        mol_type = protein
                        organism = synthetic construct
SEQUENCE: 79
SGSTLQS                                                                 7

SEQ ID NO: 80           moltype = AA  length = 9
FEATURE                 Location/Qualifiers
REGION                  1..9
                        note = CD8alpha VL LCDR3
source                  1..9
                        mol_type = protein
                        organism = synthetic construct
SEQUENCE: 80
QQHNENPLT                                                               9

SEQ ID NO: 81           moltype = AA  length = 118
FEATURE                 Location/Qualifiers
REGION                  1..118
                        note = CD8alpha VH Mb1b
source                  1..118
                        mol_type = protein
                        organism = synthetic construct
SEQUENCE: 81
EVQLVESGGG LVQPGGSLRL SCAASGFNIK DTYIHFVRQA PGKGLEWIGR IDPANDNTLY        60
ASKFQGKATI SADTSKNTAY LQMNSLRAED TAVYYCGRGY GYYVFDHWGQ GTLVTVSS         118

SEQ ID NO: 82           moltype = AA  length = 107
FEATURE                 Location/Qualifiers
REGION                  1..107
                        note = CD8alpha VL
source                  1..107
                        mol_type = protein
                        organism = synthetic construct
SEQUENCE: 82
DVQITQSPSS LSASVGDRVT ITCRTSRSIS QYLAWYQQKP GKVPKLLIYS GSTLQSGVPS        60
RFSGSGSGTD FTLTISSLQP EDVATYYCQQ HNENPLTFGG GTKVEIK                    107

SEQ ID NO: 83           moltype = AA  length = 7
FEATURE                 Location/Qualifiers
REGION                  1..7
                        note = CD8alpha VH Mb1b HCDR1
source                  1..7
                        mol_type = protein
                        organism = synthetic construct
SEQUENCE: 83
GFNIKDT                                                                 7

SEQ ID NO: 84           moltype = AA  length = 9
FEATURE                 Location/Qualifiers
REGION                  1..9
                        note = CD8alpha VH Mb1b HCDR2
source                  1..9
                        mol_type = protein
                        organism = synthetic construct
SEQUENCE: 84
RIDPANDNT                                                               9

SEQ ID NO: 85           moltype = AA  length = 7
FEATURE                 Location/Qualifiers
REGION                  1..7
                        note = CD8alpha VH Mb1b HCDR3
source                  1..7
                        mol_type = protein
                        organism = synthetic construct
SEQUENCE: 85
GYYVFDH                                                                 7

SEQ ID NO: 86           moltype = AA  length = 11
FEATURE                 Location/Qualifiers
```

```
REGION                  1..11
                        note = CD8alpha VL LCDR1
source                  1..11
                        mol_type = protein
                        organism = synthetic construct
SEQUENCE: 86
RTSRSISQYL A                                                            11

SEQ ID NO: 87           moltype = AA   length = 7
FEATURE                 Location/Qualifiers
REGION                  1..7
                        note = CD8alpha VL LCDR2
source                  1..7
                        mol_type = protein
                        organism = synthetic construct
SEQUENCE: 87
SGSTLQS                                                                 7

SEQ ID NO: 88           moltype = AA   length = 9
FEATURE                 Location/Qualifiers
REGION                  1..9
                        note = CD8alpha VL LCDR3
source                  1..9
                        mol_type = protein
                        organism = synthetic construct
SEQUENCE: 88
QQHNENPLT                                                               9

SEQ ID NO: 89           moltype = AA   length = 145
FEATURE                 Location/Qualifiers
REGION                  1..145
                        note = CD8alpha R2HCD26 VHH
source                  1..145
                        mol_type = protein
                        organism = synthetic construct
SEQUENCE: 89
QVQLQESGGG LVQAGGSLRL SCAASGFTFD DYAIGWFRQA PGKEREGVSC IRVSDGSTYY       60
ADPVKGRFTI SSDNAKNTVY LQMNSLKPED AAVYYCAAGS LYTCVQSIVV VPARPYYDMD      120
YWGKGTQVTV SSAAAYPYDV PDYGS                                            145

SEQ ID NO: 90           moltype = AA   length = 10
FEATURE                 Location/Qualifiers
REGION                  1..10
                        note = CD8alpha R2HCD26 VHH HCDR1
source                  1..10
                        mol_type = protein
                        organism = synthetic construct
SEQUENCE: 90
GFTFDDYAIG                                                              10

SEQ ID NO: 91           moltype = AA   length = 17
FEATURE                 Location/Qualifiers
REGION                  1..17
                        note = CD8alpha R2HCD26 VHH HCDR2
source                  1..17
                        mol_type = protein
                        organism = synthetic construct
SEQUENCE: 91
CIRVSDGSTY YADPVKG                                                      17

SEQ ID NO: 92           moltype = AA   length = 24
FEATURE                 Location/Qualifiers
REGION                  1..24
                        note = CD8alpha R2HCD26 VHH HCDR3
source                  1..24
                        mol_type = protein
                        organism = synthetic construct
SEQUENCE: 92
AGSLYTCVQS IVVVPARPYY DMDY                                              24

SEQ ID NO: 93           moltype = AA   length = 132
FEATURE                 Location/Qualifiers
REGION                  1..132
                        note = CD8alpha R3HCD27 VHH
source                  1..132
                        mol_type = protein
                        organism = synthetic construct
SEQUENCE: 93
QVQLQESGGG SVQPGGSLRL SCAASGFTFD DYAMSWVRQV PGKGLEWVST INWNGGSAEY       60
```

```
AEPVKGRFTI SRDNAKNTVY LQMNSLKLED TAVYYCAKDA DLVWYNLSTG QGTQVTVSSA    120
AAYPYDVPDY GS                                                       132

SEQ ID NO: 94              moltype = AA  length = 10
FEATURE                    Location/Qualifiers
REGION                     1..10
                           note = CD8alpha R3HCD27 VHH HCDR1
source                     1..10
                           mol_type = protein
                           organism = synthetic construct
SEQUENCE: 94
GFTFDDYAMS                                                          10

SEQ ID NO: 95              moltype = AA  length = 17
FEATURE                    Location/Qualifiers
REGION                     1..17
                           note = CD8alpha R3HCD27 VHH HCDR2
source                     1..17
                           mol_type = protein
                           organism = synthetic construct
SEQUENCE: 95
TINWNGGSAE YAEPVKG                                                  17

SEQ ID NO: 96              moltype = AA  length = 11
FEATURE                    Location/Qualifiers
REGION                     1..11
                           note = CD8alpha R3HCD27 VHH HCDR3
source                     1..11
                           mol_type = protein
                           organism = synthetic construct
SEQUENCE: 96
KDADLVWYNL S                                                        11

SEQ ID NO: 97              moltype = AA  length = 132
FEATURE                    Location/Qualifiers
REGION                     1..132
                           note = CD8alpha R3HCD29 VHH
source                     1..132
                           mol_type = protein
                           organism = synthetic construct
SEQUENCE: 97
QVQLQESGGG LVQPGGSLRL SCAASGFTFD DYAMSWVRQV PGKGLEWVST INWNGGSAEY    60
AEPVKGRFTI SRDNAKNTVY LQMNSLKLED TAVYYCAKDA DLVWYNLRTG QGTQVTVSSA    120
AAYPYDVPDY GS                                                       132

SEQ ID NO: 98              moltype = AA  length = 10
FEATURE                    Location/Qualifiers
REGION                     1..10
                           note = CD8alpha R3HCD29 VHH HCDR1
source                     1..10
                           mol_type = protein
                           organism = synthetic construct
SEQUENCE: 98
GFTFDDYAMS                                                          10

SEQ ID NO: 99              moltype = AA  length = 17
FEATURE                    Location/Qualifiers
REGION                     1..17
                           note = CD8alpha R3HCD29 VHH HCDR2
source                     1..17
                           mol_type = protein
                           organism = synthetic construct
SEQUENCE: 99
TINWNGGSAE YAEPVKG                                                  17

SEQ ID NO: 100             moltype = AA  length = 11
FEATURE                    Location/Qualifiers
REGION                     1..11
                           note = CD8alpha R3HCD29 VHH HCDR3
source                     1..11
                           mol_type = protein
                           organism = synthetic construct
SEQUENCE: 100
KDADLVWYNL R                                                        11

SEQ ID NO: 101             moltype = AA  length = 123
FEATURE                    Location/Qualifiers
REGION                     1..123
                           note = KIR2DL1/2/3 VH IPH2102
```

```
source                  1..123
                        mol_type = protein
                        organism = synthetic construct
SEQUENCE: 101
QVQLVQSGAE VKKPGSSVKV SCKASGGTFS FYAISWVRQA PGQGLEWMGG FIPIFGAANY      60
AQKFQGRVTI TADESTSTAY MELSSLRSDD TAVYYCARIP SGSYYYDYDM DVWGQGTTVT     120
VSS                                                                   123

SEQ ID NO: 102          moltype = AA  length = 107
FEATURE                 Location/Qualifiers
REGION                  1..107
                        note = KIR2DL1/2/3 VL
source                  1..107
                        mol_type = protein
                        organism = synthetic construct
SEQUENCE: 102
EIVLTQSPVT LSLSPGERAT LSCRASQSVS SYLAWYQQKP GQAPRLLIYD ASNRATGIPA      60
RFSGSGSGTD FTLTISSLEP EDFAVYYCQQ RSNWMYTFGQ GTKLEIK                   107

SEQ ID NO: 103          moltype = AA  length = 5
FEATURE                 Location/Qualifiers
REGION                  1..5
                        note = KIR2DL1/2/3 VH IPH2102 HCDR1
source                  1..5
                        mol_type = protein
                        organism = synthetic construct
SEQUENCE: 103
FYAIS                                                                   5

SEQ ID NO: 104          moltype = AA  length = 15
FEATURE                 Location/Qualifiers
REGION                  1..15
                        note = KIR2DL1/2/3 VH IPH2102 HCDR2
source                  1..15
                        mol_type = protein
                        organism = synthetic construct
SEQUENCE: 104
GFIPIFGAAN YAQKF                                                       15

SEQ ID NO: 105          moltype = AA  length = 14
FEATURE                 Location/Qualifiers
REGION                  1..14
                        note = KIR2DL1/2/3 VH IPH2102 HCDR3
source                  1..14
                        mol_type = protein
                        organism = synthetic construct
SEQUENCE: 105
IPSGSYYYDY DMDV                                                        14

SEQ ID NO: 106          moltype = AA  length = 11
FEATURE                 Location/Qualifiers
REGION                  1..11
                        note = KIR2DL1/2/3 VL LCDR1
source                  1..11
                        mol_type = protein
                        organism = synthetic construct
SEQUENCE: 106
RASQSVSSYL A                                                           11

SEQ ID NO: 107          moltype = AA  length = 7
FEATURE                 Location/Qualifiers
REGION                  1..7
                        note = KIR2DL1/2/3 VL LCDR2
source                  1..7
                        mol_type = protein
                        organism = synthetic construct
SEQUENCE: 107
DASNRAT                                                                 7

SEQ ID NO: 108          moltype = AA  length = 10
FEATURE                 Location/Qualifiers
REGION                  1..10
                        note = KIR2DL1/2/3 VL LCDR3
source                  1..10
                        mol_type = protein
                        organism = synthetic construct
SEQUENCE: 108
QQRSNWMYTF                                                             10
```

-continued

| | | |
|---|---|---|
| SEQ ID NO: 109<br>FEATURE<br>REGION<br>source | moltype = AA   length = 123<br>Location/Qualifiers<br>1..123<br>note = KIR2DL1/2/3 VH IPH2102-1<br>1..123<br>mol_type = protein<br>organism = synthetic construct | |
| SEQUENCE: 109<br>QVQLVQSGAE VKKPGSSVKV SCKASGGTFS FYAISWVRQA PGQGLEWMGG FIPIFGAANY<br>AQKFQGRVTI TADESTSTAY MELSSLRSDD TAVYYCARIP SGSYYYDYDM DVWGQGTTVT<br>VSS | | 60<br>120<br>123 |
| SEQ ID NO: 110<br>FEATURE<br>REGION<br>source | moltype = AA   length = 107<br>Location/Qualifiers<br>1..107<br>note = KIR2DL1/2/3 VL<br>1..107<br>mol_type = protein<br>organism = synthetic construct | |
| SEQUENCE: 110<br>EIVLIQSPVT LSLSPGERAT LSCRASQSVS SYLAWYQQKP GQAPRLLIYD ASNRATGIPA<br>RFSGSGSGTD FTLTISSLEP EDFAVYYCQQ RSNWMYTFGQ GTKLEIK | | 60<br>107 |
| SEQ ID NO: 111<br>FEATURE<br>REGION<br>source | moltype = AA   length = 5<br>Location/Qualifiers<br>1..5<br>note = KIR2DL1/2/3 VH IPH2102-1 HCDR1<br>1..5<br>mol_type = protein<br>organism = synthetic construct | |
| SEQUENCE: 111<br>FYAIS | | 5 |
| SEQ ID NO: 112<br>FEATURE<br>REGION<br>source | moltype = AA   length = 15<br>Location/Qualifiers<br>1..15<br>note = KIR2DL1/2/3 VH IPH2102-1 HCDR2<br>1..15<br>mol_type = protein<br>organism = synthetic construct | |
| SEQUENCE: 112<br>GFIPIFGAAN YAQKF | | 15 |
| SEQ ID NO: 113<br>FEATURE<br>REGION<br>source | moltype = AA   length = 14<br>Location/Qualifiers<br>1..14<br>note = KIR2DL1/2/3 VH IPH2102-1 HCDR3<br>1..14<br>mol_type = protein<br>organism = synthetic construct | |
| SEQUENCE: 113<br>IPSGSYYYDY DMDV | | 14 |
| SEQ ID NO: 114<br>FEATURE<br>REGION<br>source | moltype = AA   length = 10<br>Location/Qualifiers<br>1..10<br>note = KIR2DL1/2/3 VL LCDR1<br>1..10<br>mol_type = protein<br>organism = synthetic construct | |
| SEQUENCE: 114<br>RASQSVSSYL | | 10 |
| SEQ ID NO: 115<br>FEATURE<br>REGION<br>source | moltype = AA   length = 7<br>Location/Qualifiers<br>1..7<br>note = KIR2DL1/2/3 VL LCDR2<br>1..7<br>mol_type = protein<br>organism = synthetic construct | |
| SEQUENCE: 115<br>DASNRAT | | 7 |
| SEQ ID NO: 116<br>FEATURE<br>REGION<br>source | moltype = AA   length = 10<br>Location/Qualifiers<br>1..10<br>note = KIR2DL1/2/3 VL LCDR3<br>1..10<br>mol_type = protein | |

```
                                    organism = synthetic construct
SEQUENCE: 116
QQRSNWMYTF                                                                     10

SEQ ID NO: 117          moltype = AA   length = 121
FEATURE                 Location/Qualifiers
REGION                  1..121
                        note = KIR2DL1/2/3 VH DF200
source                  1..121
                        mol_type = protein
                        organism = synthetic construct
SEQUENCE: 117
QVQLEQSGPG LVQPSQSLSI TCTVSGFSFT PYGVHWVRQS PGKGLEWLGV IWSGGNTDYN              60
AAFISRLSIN KDNSKSQVFF KMNSLQVNDT AIYYCARNPR PGNYPYGMDY WGQGTSVTVS              120
S                                                                              121

SEQ ID NO: 118          moltype = AA   length = 107
FEATURE                 Location/Qualifiers
REGION                  1..107
                        note = KIR2DL1/2/3 VL
source                  1..107
                        mol_type = protein
                        organism = synthetic construct
SEQUENCE: 118
NIVMTQSPKS MSMSVGERVT LTCKASENVV TYVSWYQQKP EQSPKLLIYG ASNRYTGVPD              60
RFTGSGSATD FTLTISSVQA EDLADYHCGQ GYSYPYTFGG GTKLEIK                            107

SEQ ID NO: 119          moltype = AA   length = 10
FEATURE                 Location/Qualifiers
REGION                  1..10
                        note = KIR2DL1/2/3 VH DF200 HCDR1
source                  1..10
                        mol_type = protein
                        organism = synthetic construct
SEQUENCE: 119
GFSFTPYGVH                                                                     10

SEQ ID NO: 120          moltype = AA   length = 16
FEATURE                 Location/Qualifiers
REGION                  1..16
                        note = KIR2DL1/2/3 VH DF200 HCDR2
source                  1..16
                        mol_type = protein
                        organism = synthetic construct
SEQUENCE: 120
VIWSGGNTDY NAAFIS                                                              16

SEQ ID NO: 121          moltype = AA   length = 13
FEATURE                 Location/Qualifiers
REGION                  1..13
                        note = KIR2DL1/2/3 VH DF200 HCDR3
source                  1..13
                        mol_type = protein
                        organism = synthetic construct
SEQUENCE: 121
NPRPGNYPYG MDY                                                                 13

SEQ ID NO: 122          moltype = AA   length = 11
FEATURE                 Location/Qualifiers
REGION                  1..11
                        note = KIR2DL1/2/3 VL LCDR1
source                  1..11
                        mol_type = protein
                        organism = synthetic construct
SEQUENCE: 122
KASENVVTYV S                                                                   11

SEQ ID NO: 123          moltype = AA   length = 7
FEATURE                 Location/Qualifiers
REGION                  1..7
                        note = KIR2DL1/2/3 VL LCDR2
source                  1..7
                        mol_type = protein
                        organism = synthetic construct
SEQUENCE: 123
GASNRYT                                                                        7

SEQ ID NO: 124          moltype = AA   length = 9
FEATURE                 Location/Qualifiers
```

```
REGION                  1..9
                        note = KIR2DL1/2/3 VL LCDR3
source                  1..9
                        mol_type = protein
                        organism = synthetic construct
SEQUENCE: 124
GQGYSYPYT                                                                 9

SEQ ID NO: 125          moltype = AA  length = 121
FEATURE                 Location/Qualifiers
REGION                  1..121
                        note = KIR2DL1/2/3 VH PAN2D
source                  1..121
                        mol_type = protein
                        organism = synthetic construct
SEQUENCE: 125
EVQLQQSGTV LARPGASVKM SCKASGYTFT SYWMHWMKQR PGQGLEWIGT IYPGNSDTNY          60
NQKFKGKAKL TAVTSTNTAY MELSSLTNED SAVYYCSRPT TATRSSAMDY WGQGTSVTVS         120
S                                                                       121

SEQ ID NO: 126          moltype = AA  length = 108
FEATURE                 Location/Qualifiers
REGION                  1..108
                        note = KIR2DL1/2/3 VL
source                  1..108
                        mol_type = protein
                        organism = synthetic construct
SEQUENCE: 126
QIVLTQSPAS MSASLGERVT MTCTASSSVS SSYLYWYQQK PGSSPKLWIY STSNLASGVP          60
ARFSGSGSGT SYSLTISSME AEDAATYYCH QYHRSPPTFG GGTKLEIK                     108

SEQ ID NO: 127          moltype = AA  length = 5
FEATURE                 Location/Qualifiers
REGION                  1..5
                        note = KIR2DL1/2/3 VH PAN2D HCDR1
source                  1..5
                        mol_type = protein
                        organism = synthetic construct
SEQUENCE: 127
SYWMH                                                                     5

SEQ ID NO: 128          moltype = AA  length = 16
FEATURE                 Location/Qualifiers
REGION                  1..16
                        note = KIR2DL1/2/3 VH PAN2D HCDR2
source                  1..16
                        mol_type = protein
                        organism = synthetic construct
SEQUENCE: 128
TIYPGNSDTN YNQKFK                                                        16

SEQ ID NO: 129          moltype = AA  length = 12
FEATURE                 Location/Qualifiers
REGION                  1..12
                        note = KIR2DL1/2/3 VH PAN2D HCDR3
source                  1..12
                        mol_type = protein
                        organism = synthetic construct
SEQUENCE: 129
PTTATRSSAM DY                                                            12

SEQ ID NO: 130          moltype = AA  length = 12
FEATURE                 Location/Qualifiers
REGION                  1..12
                        note = KIR2DL1/2/3 VL LCDR1
source                  1..12
                        mol_type = protein
                        organism = synthetic construct
SEQUENCE: 130
TASSSVSSSY LY                                                            12

SEQ ID NO: 131          moltype = AA  length = 7
FEATURE                 Location/Qualifiers
REGION                  1..7
                        note = KIR2DL1/2/3 VL LCDR2
source                  1..7
                        mol_type = protein
                        organism = synthetic construct
SEQUENCE: 131
```

```
STSNLAS                                                                    7

SEQ ID NO: 132          moltype = AA   length = 9
FEATURE                 Location/Qualifiers
REGION                  1..9
                        note = KIR2DL1/2/3 VL LCDR3
source                  1..9
                        mol_type = protein
                        organism = synthetic construct
SEQUENCE: 132
HQYHRSPPT                                                                  9

SEQ ID NO: 133          moltype = AA   length = 112
FEATURE                 Location/Qualifiers
REGION                  1..112
                        note = KIR3DL1 VH ET160-42
source                  1..112
                        mol_type = protein
                        organism = synthetic construct
SEQUENCE: 133
QVQLVQSGAE VKKPGASVKV SCKASGYTFT GYYMHWVRQA PGQGLEWMGW INPNSGGTNY    60
AQKFQGRVTM TRDTSISTAY MELSRLRSDD TAVYYCADLF YWGQGTLVTV SS            112

SEQ ID NO: 134          moltype = AA   length = 110
FEATURE                 Location/Qualifiers
REGION                  1..110
                        note = KIR3DL1 VL
source                  1..110
                        mol_type = protein
                        organism = synthetic construct
SEQUENCE: 134
QSALTQPASV SGSPGQSITI SCTGTSSDVG GYNYVSWYQQ HPGKAPKLMI YDVSNRPSGV    60
SNRFSGSKSG NTASLTISGL QAEDEADYYC SSYTSSNTLV FGTGTKVTVL               110

SEQ ID NO: 135          moltype = AA   length = 9
FEATURE                 Location/Qualifiers
REGION                  1..9
                        note = KIR3DL1 VH ET160-42 HCDR1
source                  1..9
                        mol_type = protein
                        organism = synthetic construct
SEQUENCE: 135
GYTFTGYYM                                                                  9

SEQ ID NO: 136          moltype = AA   length = 9
FEATURE                 Location/Qualifiers
REGION                  1..9
                        note = KIR3DL1 VH ET160-42 HCDR2
source                  1..9
                        mol_type = protein
                        organism = synthetic construct
SEQUENCE: 136
INPNSGGTN                                                                  9

SEQ ID NO: 137          moltype = AA   length = 6
FEATURE                 Location/Qualifiers
REGION                  1..6
                        note = KIR3DL1 VH ET160-42 HCDR3
source                  1..6
                        mol_type = protein
                        organism = synthetic construct
SEQUENCE: 137
ADLFYW                                                                     6

SEQ ID NO: 138          moltype = AA   length = 9
FEATURE                 Location/Qualifiers
REGION                  1..9
                        note = KIR3DL1 VL LCDR1
source                  1..9
                        mol_type = protein
                        organism = synthetic construct
SEQUENCE: 138
SSDVGGYNY                                                                  9

SEQ ID NO: 139          moltype =      length =
SEQUENCE: 139
000

SEQ ID NO: 140          moltype = AA   length = 11
```

```
FEATURE                 Location/Qualifiers
REGION                  1..11
                        note = KIR3DL1 VL LCDR3
source                  1..11
                        mol_type = protein
                        organism = synthetic construct
SEQUENCE: 140
SSYTSSNTLV F                                                             11

SEQ ID NO: 141          moltype = AA   length = 120
FEATURE                 Location/Qualifiers
REGION                  1..120
                        note = KIR3DL1 VH ET160-61
source                  1..120
                        mol_type = protein
                        organism = synthetic construct
SEQUENCE: 141
QVQLVESGGG LVQPGRSLRL SCAASGFTFD DYAMHWVRQA PGKGLEWVSG ISWNSGSIGY         60
ADSVKGRFTI SRDNAKNSLY LQMNSLRAED TAVYYCASSL RYFEWPIDYW GQGTLVTVSS       120

SEQ ID NO: 142          moltype = AA   length = 110
FEATURE                 Location/Qualifiers
REGION                  1..110
                        note = KIR3DL1 VL
source                  1..110
                        mol_type = protein
                        organism = synthetic construct
SEQUENCE: 142
NFMLTQPLSV SESPGKTVTI SCTANGGSLA SKYVQWFQQR PGSSPTTVIY DDNLRPSGVP         60
DRFSGSIDTS SNSAALTISG LKTEDEADYY CQSYDNSSVV FGGGTKLTVL                  110

SEQ ID NO: 143          moltype = AA   length = 8
FEATURE                 Location/Qualifiers
REGION                  1..8
                        note = KIR3DL1 VH ET160-61 HCDR1
source                  1..8
                        mol_type = protein
                        organism = synthetic construct
SEQUENCE: 143
GFTFDDYA                                                                  8

SEQ ID NO: 144          moltype = AA   length = 7
FEATURE                 Location/Qualifiers
REGION                  1..7
                        note = KIR3DL1 VH ET160-61 HCDR2
source                  1..7
                        mol_type = protein
                        organism = synthetic construct
SEQUENCE: 144
SWNSGSI                                                                   7

SEQ ID NO: 145          moltype = AA   length = 14
FEATURE                 Location/Qualifiers
REGION                  1..14
                        note = KIR3DL1 VH ET160-61 HCDR3
source                  1..14
                        mol_type = protein
                        organism = synthetic construct
SEQUENCE: 145
ASSLRYFEWP IDYW                                                          14

SEQ ID NO: 146          moltype = AA   length = 8
FEATURE                 Location/Qualifiers
REGION                  1..8
                        note = KIR3DL1 VL LCDR1
source                  1..8
                        mol_type = protein
                        organism = synthetic construct
SEQUENCE: 146
GGSLASKY                                                                  8

SEQ ID NO: 147          moltype = AA   length = 4
FEATURE                 Location/Qualifiers
REGION                  1..4
                        note = KIR3DL1 VL LCDR2
source                  1..4
                        mol_type = protein
                        organism = synthetic construct
SEQUENCE: 147
```

```
DDNL                                                                                     4

SEQ ID NO: 148           moltype = AA  length = 10
FEATURE                  Location/Qualifiers
REGION                   1..10
                         note = KIR3DL1 VL LCDR3
source                   1..10
                         mol_type = protein
                         organism = synthetic construct
SEQUENCE: 148
QSYDNSSVVF                                                                              10

SEQ ID NO: 149           moltype = AA  length = 116
FEATURE                  Location/Qualifiers
REGION                   1..116
                         note = KIR3DL1 VH ET160-74
source                   1..116
                         mol_type = protein
                         organism = synthetic construct
SEQUENCE: 149
QVQLVQSGAE VKKPGSSVKV SCKASGGTFS SYAISWVRQA PGQGLEWMGW MNPNSGNTGY                        60
AQKFQGRVTM TRNTSISTAY MELSSLRSED TAVYYCARYS FHLDGWGQGT LVTVSS                           116

SEQ ID NO: 150           moltype = AA  length = 110
FEATURE                  Location/Qualifiers
REGION                   1..110
                         note = KIR3DL1 VL
source                   1..110
                         mol_type = protein
                         organism = synthetic construct
SEQUENCE: 150
QSVLTQPPSV SAAPGQKVTI SCSGSSSNVG NNYVSWYQQV PGTAPKLLIY DNNRRPSGIP                        60
DRFSGSKSGT SATLGITGLQ TGDEADYYCG TWDNSLRVEL FGGGTKVTVL                                  110

SEQ ID NO: 151           moltype = AA  length = 8
FEATURE                  Location/Qualifiers
REGION                   1..8
                         note = KIR3DL1 VH ET160-74 HCDR1
source                   1..8
                         mol_type = protein
                         organism = synthetic construct
SEQUENCE: 151
GGTFSSYA                                                                                 8

SEQ ID NO: 152           moltype = AA  length = 8
FEATURE                  Location/Qualifiers
REGION                   1..8
                         note = KIR3DL1 VH ET160-74 HCDR2
source                   1..8
                         mol_type = protein
                         organism = synthetic construct
SEQUENCE: 152
MNPNSGNT                                                                                 8

SEQ ID NO: 153           moltype = AA  length = 8
FEATURE                  Location/Qualifiers
REGION                   1..8
                         note = KIR3DL1 VH ET160-74 HCDR3
source                   1..8
                         mol_type = protein
                         organism = synthetic construct
SEQUENCE: 153
ARYSFHLD                                                                                 8

SEQ ID NO: 154           moltype = AA  length = 8
FEATURE                  Location/Qualifiers
REGION                   1..8
                         note = KIR3DL1 VL LCDR1
source                   1..8
                         mol_type = protein
                         organism = synthetic construct
SEQUENCE: 154
SSNVGNNY                                                                                 8

SEQ ID NO: 155           moltype =   length =
SEQUENCE: 155
000

SEQ ID NO: 156           moltype = AA  length = 14
```

```
FEATURE                 Location/Qualifiers
REGION                  1..14
                        note = KIR3DL1 VL LCDR3
source                  1..14
                        mol_type = protein
                        organism = synthetic construct
SEQUENCE: 156
YCGTWDNSLR VELF                                                       14

SEQ ID NO: 157          moltype = AA  length = 123
FEATURE                 Location/Qualifiers
REGION                  1..123
                        note = KIR3DL2 VH AZ158
source                  1..123
                        mol_type = protein
                        organism = synthetic construct
SEQUENCE: 157
QVQLKESGPG LVAPSQSLSI TCTVSGFSLT SFGVHWVRQP PGKGLEWLGV IWAGGSTNYN      60
SALMSRLSIS KDNSKSQVFL KMNSLQNDDT AMYYCARGNS NHYVSSFYYF DYWGQGTTLT     120
VSS                                                                  123

SEQ ID NO: 158          moltype = AA  length = 106
FEATURE                 Location/Qualifiers
REGION                  1..106
                        note = KIR3DL2 VL
source                  1..106
                        mol_type = protein
                        organism = synthetic construct
SEQUENCE: 158
DIQMTQSPSS LSASLGGKVT ITCKASQDIN KYIAWYQHKP GKGPRLLIHY TSTLQPGIPS      60
RFSGSGSGRD YSFSISNLEP EDITTYYCLQ YDNLWTFGGG TKLEIK                    106

SEQ ID NO: 159          moltype = AA  length = 10
FEATURE                 Location/Qualifiers
REGION                  1..10
                        note = KIR3DL2 VH AZ158 HCDR1
source                  1..10
                        mol_type = protein
                        organism = synthetic construct
SEQUENCE: 159
GFSLTSFGVH                                                            10

SEQ ID NO: 160          moltype = AA  length = 16
FEATURE                 Location/Qualifiers
REGION                  1..16
                        note = KIR3DL2 VH AZ158 HCDR2
source                  1..16
                        mol_type = protein
                        organism = synthetic construct
SEQUENCE: 160
VIWAGGSTNY NSALMS                                                     16

SEQ ID NO: 161          moltype = AA  length = 15
FEATURE                 Location/Qualifiers
REGION                  1..15
                        note = KIR3DL2 VH AZ158 HCDR3
source                  1..15
                        mol_type = protein
                        organism = synthetic construct
SEQUENCE: 161
GNSNHYVSSF YYFDY                                                      15

SEQ ID NO: 162          moltype = AA  length = 11
FEATURE                 Location/Qualifiers
REGION                  1..11
                        note = KIR3DL2 VL LCDR1
source                  1..11
                        mol_type = protein
                        organism = synthetic construct
SEQUENCE: 162
KASQDINKYI A                                                          11

SEQ ID NO: 163          moltype = AA  length = 7
FEATURE                 Location/Qualifiers
REGION                  1..7
                        note = KIR3DL2 VL LCDR2
source                  1..7
                        mol_type = protein
                        organism = synthetic construct
```

```
SEQUENCE: 163
YTSTLQP                                                                 7

SEQ ID NO: 164          moltype = AA  length = 8
FEATURE                 Location/Qualifiers
REGION                  1..8
                        note = KIR3DL2 VL LCDR3
source                  1..8
                        mol_type = protein
                        organism = synthetic construct
SEQUENCE: 164
LQYDNLWT                                                                8

SEQ ID NO: 165          moltype = AA  length = 25
FEATURE                 Location/Qualifiers
REGION                  1..25
                        note = Linker
VARIANT                 6..25
                        note = amino acids 6-25, 11-25, 16-25, or 21-25 may be
                         present or absent
source                  1..25
                        mol_type = protein
                        organism = synthetic construct
SEQUENCE: 165
GGGGSGGGGS GGGGSGGGGS GGGGS                                             25

SEQ ID NO: 166          moltype = AA  length = 107
FEATURE                 Location/Qualifiers
REGION                  1..107
                        note = CD3epsilon VL1 15C3
source                  1..107
                        mol_type = protein
                        organism = synthetic construct
SEQUENCE: 166
EIVLTQSPAT LSLSPGERAT LSCRASQSVS SYLAWYQQKP GQAPRLLIYD ASNRATGIPA        60
RFSGSGSGTD FTLTISSLEP EDFAVYYCQQ RSNWPWTFGQ GTKVEIK                     107

SEQ ID NO: 167          moltype = AA  length = 11
FEATURE                 Location/Qualifiers
REGION                  1..11
                        note = CD3epsilon VL1 15C3 LCDR1
source                  1..11
                        mol_type = protein
                        organism = synthetic construct
SEQUENCE: 167
RASQSVSSYL A                                                            11

SEQ ID NO: 168          moltype = AA  length = 7
FEATURE                 Location/Qualifiers
REGION                  1..7
                        note = CD3epsilon VL1 15C3 LCDR2
source                  1..7
                        mol_type = protein
                        organism = synthetic construct
SEQUENCE: 168
DASNRAT                                                                 7

SEQ ID NO: 169          moltype = AA  length = 9
FEATURE                 Location/Qualifiers
REGION                  1..9
                        note = CD3epsilon VL1 15C3 LCDR3
source                  1..9
                        mol_type = protein
                        organism = synthetic construct
SEQUENCE: 169
QQRSNWPWT                                                               9

SEQ ID NO: 170          moltype = AA  length = 121
FEATURE                 Location/Qualifiers
REGION                  1..121
                        note = ICOS VH 422 H2L5
source                  1..121
                        mol_type = protein
                        organism = synthetic construct
SEQUENCE: 170
QVQLVQSGAE VKKPGSSVKV SCKASGYTFT DYAMHWVRQA PGQGLEWMGL ISIYSDHTNY        60
NQKFQGRVTI TADKSTSTAY MELSSLRSED TAVYYCGRNN YGNYGWYFDV WGQGTTVTVS       120
S                                                                      121
```

```
SEQ ID NO: 171         moltype = AA  length = 106
FEATURE                Location/Qualifiers
REGION                 1..106
                       note = ICOS VL
source                 1..106
                       mol_type = protein
                       organism = synthetic construct
SEQUENCE: 171
EIVLTQSPAT LSLSPGERAT LSCSASSSVS YMHWYQQKPG QAPRLLIYDT SKLASGIPAR    60
FSGSGSGTDY TLTISSLEPE DFAVYYCFQG SGYPYTFGQG TKLEIK                  106

SEQ ID NO: 172         moltype = AA  length = 5
FEATURE                Location/Qualifiers
REGION                 1..5
                       note = ICOS VH 422 H2L5 HCDR1
source                 1..5
                       mol_type = protein
                       organism = synthetic construct
SEQUENCE: 172
DYAMH                                                                 5

SEQ ID NO: 173         moltype = AA  length = 17
FEATURE                Location/Qualifiers
REGION                 1..17
                       note = ICOS VH 422 H2L5 HCDR2
source                 1..17
                       mol_type = protein
                       organism = synthetic construct
SEQUENCE: 173
LISIYSDHTN YNQKFQG                                                   17

SEQ ID NO: 174         moltype = AA  length = 12
FEATURE                Location/Qualifiers
REGION                 1..12
                       note = ICOS VH 422 H2L5 HCDR3
source                 1..12
                       mol_type = protein
                       organism = synthetic construct
SEQUENCE: 174
NNYGNYGWYF DV                                                        12

SEQ ID NO: 175         moltype = AA  length = 10
FEATURE                Location/Qualifiers
REGION                 1..10
                       note = ICOS VL LCDR1
source                 1..10
                       mol_type = protein
                       organism = synthetic construct
SEQUENCE: 175
SASSSVSYMH                                                           10

SEQ ID NO: 176         moltype = AA  length = 7
FEATURE                Location/Qualifiers
REGION                 1..7
                       note = ICOS VL LCDR2
source                 1..7
                       mol_type = protein
                       organism = synthetic construct
SEQUENCE: 176
DTSKLAS                                                               7

SEQ ID NO: 177         moltype = AA  length = 9
FEATURE                Location/Qualifiers
REGION                 1..9
                       note = ICOS VL LCDR3
source                 1..9
                       mol_type = protein
                       organism = synthetic construct
SEQUENCE: 177
FQGSGYPYT                                                             9

SEQ ID NO: 178         moltype = AA  length = 120
FEATURE                Location/Qualifiers
REGION                 1..120
                       note = PD-1 VH Pembrolizumab
source                 1..120
                       mol_type = protein
                       organism = synthetic construct
SEQUENCE: 178
```

```
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120

SEQ ID NO: 179          moltype = AA  length = 111
FEATURE                 Location/Qualifiers
REGION                  1..111
                        note = PD-1 VL
source                  1..111
                        mol_type = protein
                        organism = synthetic construct
SEQUENCE: 179
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI K            111

SEQ ID NO: 180          moltype = AA  length = 5
FEATURE                 Location/Qualifiers
REGION                  1..5
                        note = PD-1 VH Pembrolizumab HCDR1
source                  1..5
                        mol_type = protein
                        organism = synthetic construct
SEQUENCE: 180
NYYMY                                                                5

SEQ ID NO: 181          moltype = AA  length = 17
FEATURE                 Location/Qualifiers
REGION                  1..17
                        note = PD-1 VH Pembrolizumab HCDR2
source                  1..17
                        mol_type = protein
                        organism = synthetic construct
SEQUENCE: 181
GINPSNGGTN FNEKFKN                                                  17

SEQ ID NO: 182          moltype = AA  length = 11
FEATURE                 Location/Qualifiers
REGION                  1..11
                        note = PD-1 VH Pembrolizumab HCDR3
source                  1..11
                        mol_type = protein
                        organism = synthetic construct
SEQUENCE: 182
RDYRFDMGFD Y                                                        11

SEQ ID NO: 183          moltype = AA  length = 15
FEATURE                 Location/Qualifiers
REGION                  1..15
                        note = PD-1 VL LCDR1
source                  1..15
                        mol_type = protein
                        organism = synthetic construct
SEQUENCE: 183
RASKGVSTSG YSYLH                                                    15

SEQ ID NO: 184          moltype = AA  length = 7
FEATURE                 Location/Qualifiers
REGION                  1..7
                        note = PD-1 VL LCDR2
source                  1..7
                        mol_type = protein
                        organism = synthetic construct
SEQUENCE: 184
LASYLES                                                              7

SEQ ID NO: 185          moltype = AA  length = 9
FEATURE                 Location/Qualifiers
REGION                  1..9
                        note = PD-1 VL LCDR3
source                  1..9
                        mol_type = protein
                        organism = synthetic construct
SEQUENCE: 185
QHSRDLPLT                                                            9

SEQ ID NO: 186          moltype = AA  length = 124
FEATURE                 Location/Qualifiers
REGION                  1..124
                        note = CXCR3 VH 4Hu7
source                  1..124
```

```
                            mol_type = protein
                            organism = synthetic construct
SEQUENCE: 186
EVQLVESGGG VKKPGGSLKL SCAASGFTFS NYAMSWVRQT PGKGLEWVAT ISNGGSYTYY    60
PDSFQGRFTI SRDNAKSTLS LQMSSLKSED TAMYYCSRPS ERSHYYATSQ FAYWGQGTLV   120
TVSA                                                                124

SEQ ID NO: 187          moltype = AA  length = 106
FEATURE                 Location/Qualifiers
REGION                  1..106
                            note = CXCR3 VL
source                  1..106
                            mol_type = protein
                            organism = synthetic construct
SEQUENCE: 187
DIQLTQSPGS LSASVGDRVT MTCSASSSVS YMHWYQQKPG TSPKRWIYDT SKLASGVPAR    60
FSGSGSGTSY SLTISSLQPE DAATYYCQQW SSSPLTFGAG TKVELK                  106

SEQ ID NO: 188          moltype = AA  length = 8
FEATURE                 Location/Qualifiers
REGION                  1..8
                            note = CXCR3 VH 4Hu7 HCDR1
source                  1..8
                            mol_type = protein
                            organism = synthetic construct
SEQUENCE: 188
GFTFSNYA                                                              8

SEQ ID NO: 189          moltype = AA  length = 8
FEATURE                 Location/Qualifiers
REGION                  1..8
                            note = CXCR3 VH 4Hu7 HCDR2
source                  1..8
                            mol_type = protein
                            organism = synthetic construct
SEQUENCE: 189
ISNGGSYT                                                              8

SEQ ID NO: 190          moltype = AA  length = 17
FEATURE                 Location/Qualifiers
REGION                  1..17
                            note = CXCR3 VH 4Hu7 HCDR3
source                  1..17
                            mol_type = protein
                            organism = synthetic construct
SEQUENCE: 190
SRPSERSHYY ATSQFAY                                                   17

SEQ ID NO: 191          moltype = AA  length = 5
FEATURE                 Location/Qualifiers
REGION                  1..5
                            note = CXCR3 VL LCDR1
source                  1..5
                            mol_type = protein
                            organism = synthetic construct
SEQUENCE: 191
SSVSY                                                                 5

SEQ ID NO: 192          moltype =     length =
SEQUENCE: 192
000

SEQ ID NO: 193          moltype = AA  length = 9
FEATURE                 Location/Qualifiers
REGION                  1..9
                            note = CXCR3 VL LCDR3
source                  1..9
                            mol_type = protein
                            organism = synthetic construct
SEQUENCE: 193
QQWSSSPLT                                                             9

SEQ ID NO: 194          moltype = AA  length = 120
FEATURE                 Location/Qualifiers
REGION                  1..120
                            note = CD5 VH 5D7 H1L1
source                  1..120
                            mol_type = protein
                            organism = synthetic construct
```

```
SEQUENCE: 194
EVQLVESGGG VVQPGRSLRL SCTFSGFSLS TSGMGVGWIR QAPGKGLEWV AHIWWDDDVY     60
YNPSLKSRLT ITKDASTDTV YMELSSLRSE DTAVYYCVRR RATGTGFDYW GQGTLVTVSS    120

SEQ ID NO: 195          moltype = AA  length = 106
FEATURE                 Location/Qualifiers
REGION                  1..106
                        note = CD5 VL
source                  1..106
                        mol_type = protein
                        organism = synthetic construct
SEQUENCE: 195
NIVMTQSPSS LSASVGDRVT ITCQASQDVG TAVAWYQQKP DQSPKLLIYW TSTRHTGVPD     60
RFTGSGSGTD FTLTISSLQP EDIATYFCHQ YNSYNTFGSG TKLEIK                  106

SEQ ID NO: 196          moltype = AA  length = 9
FEATURE                 Location/Qualifiers
REGION                  1..9
                        note = CD5 VH 5D7 H1L1 HCDR1
source                  1..9
                        mol_type = protein
                        organism = synthetic construct
SEQUENCE: 196
FSLSTSGMG                                                              9

SEQ ID NO: 197          moltype = AA  length = 5
FEATURE                 Location/Qualifiers
REGION                  1..5
                        note = CD5 VH 5D7 H1L1 HCDR2
source                  1..5
                        mol_type = protein
                        organism = synthetic construct
SEQUENCE: 197
WWDDD                                                                  5

SEQ ID NO: 198          moltype = AA  length = 10
FEATURE                 Location/Qualifiers
REGION                  1..10
                        note = CD5 VH 5D7 H1L1 HCDR3
source                  1..10
                        mol_type = protein
                        organism = synthetic construct
SEQUENCE: 198
RRATGTGFDY                                                            10

SEQ ID NO: 199          moltype = AA  length = 6
FEATURE                 Location/Qualifiers
REGION                  1..6
                        note = CD5 VL LCDR1
source                  1..6
                        mol_type = protein
                        organism = synthetic construct
SEQUENCE: 199
QDVGTA                                                                 6

SEQ ID NO: 200          moltype = AA  length = 7
FEATURE                 Location/Qualifiers
REGION                  1..7
                        note = CD5 VL LCDR2
source                  1..7
                        mol_type = protein
                        organism = synthetic construct
SEQUENCE: 200
WTSTRHT                                                                7

SEQ ID NO: 201          moltype = AA  length = 6
FEATURE                 Location/Qualifiers
REGION                  1..6
                        note = CD5 VL LCDR3
source                  1..6
                        mol_type = protein
                        organism = synthetic construct
SEQUENCE: 201
YNSYNT                                                                 6
```

What is claimed is:

1. A binding agent comprising:
   a first binding domain that specifically binds to CD8 or a subunit of CD8 and comprises a heavy chain variable region (VH) comprising an hCDR1, an hCDR2, and an hCDR3 and a light chain variable region (VL) comprising an lCDR1, an lCDR2, and an lCDR3, wherein the hCDR1, hCDR2, hCDR3, lCDR1, lCDR2, and lCDR3 have amino acid sequences of SEQ ID NO: 83 to SEQ ID NO:88, respectively;
   a second binding domain that specifically binds to an inhibitory killer-cell immunoglobulin-like receptor (KIR) protein expressed on CD8+KIR+ T regulatory cells (Tregs), wherein the second binding domain comprises a VH comprising an hCDR1, an hCDR2, and an hCDR3 and a VL comprising an lCDR1, an lCDR2, and an lCDR3, wherein the hCDR1, hCDR2, hCDR3, lCDR1, lCDR2, and lCDR3 have amino acid sequences of SEQ ID NO: 103 to SEQ ID NO:108, respectively; and
   an IgG Fc domain.

2. The binding agent of claim 1, wherein the IgG domain is selected from an IgG1 domain and an IgG4 domain.

3. The binding agent of claim 1, wherein the first and second binding domains each comprise an antibody fragment selected from the group consisting of a Fab, Fab', F(ab')2, Fv, and scFv.

4. The binding agent of claim 3, wherein the first binding domain comprises an scFv and the second binding domain comprises a Fab.

5. A method of reducing the number or activity of autoreactive CD4+ T cells present in a subject in need thereof, comprising administering a binding agent to the subject in an amount effective to decrease the number or activity of autoreactive CD4+ T cells, wherein the binding agent binds to CD8+ killer-cell immunoglobulin-like receptor (KIR)+ regulatory T cells (Tregs) and comprises:
   a first binding domain that specifically binds to CD8 or a subunit of CD8 and comprises a heavy chain variable region (VH) comprising an hCDR1, an hCDR2, and an hCDR3 and a light chain variable region (VL) comprising an lCDR1, an lCDR2, and an lCDR3, wherein the hCDR1, hCDR2, hCDR3, lCDR1, lCDR2, and lCDR3 have amino acid sequences of SEQ ID NO: 83 to SEQ ID NO:88, respectively; and
   a second binding domain that specifically binds to an inhibitory KIR protein expressed on CD8+KIR+ T regulatory cells (Tregs), wherein the second binding domain of the binding agent comprises a VH comprising an hCDR1, an hCDR2, and an hCDR3 and a VL comprising an lCDR1, an lCDR2, and an lCDR3, wherein the hCDR1, hCDR2, hCDR3, lCDR1, lCDR2, and lCDR3 have amino acid sequences of SEQ ID NO: 103 to SEQ ID NO: 108, respectively; and
   an IgG Fc domain.

6. The method of claim 5, wherein the subject has been diagnosed with an autoimmune disease selected from celiac disease, Crohn's disease, juvenile idiopathic arthritis, inflammatory bowel disease (IBD), insulin-dependent diabetes mellitus (IDDM or type 1 diabetes), lupus nephritis, myasthenia gravis, myocarditis, multiple sclerosis (MS), pemphigus/pemphigoid, rheumatoid arthritis (RA), scleroderma/systemic sclerosis, Sjögren's syndrome (SjS), systemic lupus erythematosus (SLE), or ulcerative colitis.

7. The method of claim 5, wherein the first and second binding domains of the binding agent each comprise an antibody fragment selected from the group consisting of a Fab, Fab', F(ab')$_2$, Fv, and scFv.

8. The method of claim 7, wherein the first binding domain comprises an scFv and the second binding domain comprises a Fab.

* * * * *